US012742015B2

(12) United States Patent
Macoin et al.

(10) Patent No.: US 12,742,015 B2
(45) Date of Patent: Sep. 22, 2026

(54) AFFINITY MATURED ANTI-OX40 ANTIBODIES AND USE THEREOF

(71) Applicants: Astria Therapeutics, Inc., Boston, MA (US); Ichnos Sciences SA, La Chaux-de-Fonds (CH)

(72) Inventors: Julie Macoin, La Chaux-de-Fonds (CH); Thierry Monney, La Chaux-de-Fonds (CH); Nikolaos Biris, Westborough, MA (US); Jill C. Milne, Boston, MA (US); Christopher J. Morabito, Lexington, MA (US); Chunxia Zhao, Boston, MA (US)

(73) Assignees: Ichnos Sciences SA, La Chaux-de-Fonds (CH); Astria Therapeutics, Inc., Boston, MA (US)

( * ) Notice: Subject to any disclaimer, the term of this patent is extended or adjusted under 35 U.S.C. 154(b) by 0 days.

(21) Appl. No.: 19/283,716

(22) Filed: Jul. 29, 2025

(65) Prior Publication Data

US 2025/0353921 A1 Nov. 20, 2025

Related U.S. Application Data

(63) Continuation of application No. PCT/US2024/050127, filed on Oct. 4, 2024.

(60) Provisional application No. 63/645,656, filed on May 10, 2024, provisional application No. 63/588,662, filed on Oct. 6, 2023.

(51) Int. Cl.
*C07K 16/28* (2006.01)

(52) U.S. Cl.
CPC ...... *C07K 16/2878* (2013.01); *C07K 2317/33* (2013.01); *C07K 2317/732* (2013.01); *C07K 2317/92* (2013.01)

(58) Field of Classification Search
None
See application file for complete search history.

(56) References Cited

U.S. PATENT DOCUMENTS 6,875,433 B2 4/2005 Hart et al.
7,083,784 B2 8/2006 Dall'Acqua et al.
7,531,170 B1 5/2009 Croft et al.
7,605,237 B2 10/2009 Stevens et al.
7,635,167 B2 12/2009 Okazaki
7,670,600 B2 3/2010 Dall'Acqua et al.
7,722,876 B2 5/2010 Polonelli et al.
7,807,156 B1 10/2010 Croft et al.
7,928,074 B2 4/2011 Khare
8,110,664 B2 2/2012 Sanders et al.
8,283,450 B2 10/2012 Kato et al.
8,614,295 B2 12/2013 Lawson et al.
8,748,585 B2 6/2014 Attinger et al.
8,956,615 B1 2/2015 Croft et al.
8,962,807 B2 2/2015 Verdonck et al.
9,040,048 B2 5/2015 Adams et al.
9,139,653 B1 9/2015 Campbell et al.
9,200,060 B2 12/2015 Kannan et al.
9,428,570 B2 8/2016 Lawson et al.
9,475,848 B2 10/2016 Dehottay et al.
9,493,563 B2 11/2016 Blein et al.
9,803,023 B2 10/2017 Chamberlain et al.
9,834,611 B2 12/2017 Verdonck et al.
9,873,735 B2 1/2018 Adams et al.
9,969,810 B2 5/2018 Kato et al.
10,017,575 B2 7/2018 Lawson et al.
10,106,619 B2 10/2018 Croft et al.
10,822,425 B2 11/2020 Verdonck et al.
11,117,972 B2 9/2021 Eckelman et al.
11,192,953 B2 12/2021 Kato et al.
11,407,839 B2 8/2022 Attinger et al.
11,779,604 B2 10/2023 Bland-Ward et al.
12,281,169 B2 4/2025 Attinger et al.
2009/0041770 A1 2/2009 Chamberlain et al.
2016/0355597 A1 12/2016 Rhee et al.
2021/0206864 A1 7/2021 Back et al.
2021/0214453 A1 7/2021 Back et al.
2022/0251138 A1 8/2022 Giovannini et al.
2022/0273796 A1 9/2022 Dubey et al.
2025/0051468 A1 2/2025 Qiu et al.

FOREIGN PATENT DOCUMENTS

EP 4450522 A2 10/2024
WO WO-2007062245 A2 5/2007
WO WO-2008106116 A2 9/2008
WO WO-2010096418 A2 8/2010
WO WO-2013/008171 A1 1/2013
WO WO-2013084157 A1 6/2013
WO WO-2016022468 A1 2/2016
WO WO-2016179517 A1 11/2016
WO WO-2017096182 A1 6/2017
WO WO-2017134292 A1 8/2017
WO WO-2018089628 A1 5/2018

(Continued)

OTHER PUBLICATIONS

Genbank "HQ680975" accessed from uniprot.org on Dec. 8, 2025 (Year: 2011).*
Kussie "A Single Engineered Amino Acid Substitution Changes Antibody Fine Specificity" J immunol 152(1):146-52 (Year: 1994).*
Reitz "Toward precision medicine in Alzheimer's disease" Ann transl med 4(6):107 (Year: 2016).*
Stanford "Alzheimer's prevention, treatment and research—A Q and A with Dr Frank Longo" accessed from Stanfordhealthcare.org on May 3, 2016 (Year: 2016).*
Phase 2b Study to Evaluate Efficacy and Safety of ISB 830 in Adults with Moderate to Severe Atopic Dermatitis, ClinicalTrials.gov ID NCT03568162, Sponsor: Ichnos Sciences, SA; Aug. 8, 2022 (77 pages).

(Continued)

*Primary Examiner* — Adam Weidner
(74) *Attorney, Agent, or Firm* — Goodwin Procter LLP

(57) ABSTRACT

Provided herein are high affinity antagonistic anti-OX40 antibodies, methods of making such antibodies, and methods of using such antibodies to treat OX40-mediated disorders.

18 Claims, 30 Drawing Sheets

Specification includes a Sequence Listing.

(56) References Cited

FOREIGN PATENT DOCUMENTS

| | | | |
|---|---|---|---|
| WO | WO-2018112346 | A1 | 6/2018 |
| WO | WO-2019038742 | A1 | 2/2019 |
| WO | WO-2019223733 | A1 | 11/2019 |
| WO | WO-2019229155 | A1 | 12/2019 |
| WO | WO-2020011759 | A1 | 1/2020 |
| WO | WO-2020016417 | A1 | 1/2020 |
| WO | WO-2021013372 | A1 | 1/2021 |
| WO | WO-2021013385 | A1 | 1/2021 |
| WO | WO-2022029447 | A1 | 2/2022 |
| WO | WO-2022075476 | A1 | 4/2022 |
| WO | WO-2022198055 | A1 | 9/2022 |
| WO | WO-2022250502 | A1 | 12/2022 |
| WO | WO-2023017252 | A1 | 2/2023 |
| WO | WO-2023061424 | A1 | 4/2023 |
| WO | WO-2023109976 | A2 | 6/2023 |
| WO | WO-2023152486 | A1 | 8/2023 |

OTHER PUBLICATIONS

To Assess the Safety and Activity of GBR 830, Compared to Placebo, in Adults with Moderate-to-Severe Atopic Dermatitis, ClinicalTrials.gov ID NCT02683928, Sponsor: Ichnos Sciences SA; May 18, 2020 (54 pages).
Akiba, H et al. "CD28-independent costimulation of T cells by OX40 ligand and CD70 on activated B cells." Journal of immunology (Baltimore, Md. : 1950) vol. 162, 12 (1999): 7058-66.
Astria Therapeutics, Inc. "Annual Report" (Form 10-K) filed with the U.S. Securities & Exchange Commission on Mar. 4, 2024 (302 pages).
Astria Therapeutics, Inc. "Prospecuts Supplement" (Form 424B-B5) filed with the U.S. Securities & Exchange Commission on Mar. 4, 2024 (46 pages).
Astria Therapeutics, Inc. "Quarterly Report" (Form 10-Q) filed with the U.S. Securities & Exchange Commission on Aug. 12, 2024 (48 pages).
Astria Therapeutics, Inc. "Quarterly Report" (Form 10-Q) filed with the U.S. Securities & Exchange Commission on May 9, 2024 (34 pages).
Astria Therapeutics, Inc. "Quarterly Report" (Form 10-Q) filed with the U.S. Securities & Exchange Commission on Nov. 13, 2023 (90 pages).
Astria Therapeutics, Inc. "Registration Statement" (Form S-3) filed with the U.S. Securities & Exchange Commission on Dec. 15, 2023 (78 pages).
Astria Therapeutics, Inc. Prospectus Supplement (Form 424-B5) filed with the U.S. Securities & Exchange Commission on Oct. 12, 2023 (65 pages).
Astria Therapeutics, Inc., "Astria Corporate Presentation Aug. 2024," published Aug. 12, 2024 (26 pages).
Astria Therapeutics, Inc., "Astria Corporate Presentation Feb. 2024," published Feb. 8, 2024, (29 pages).
Astria Therapeutics, Inc., "Astria Corporate Presentation Jeffries London Nov. 2023," published Nov. 15, 2023 (21 pages).
Astria Therapeutics, Inc., "Astria Corporate Presentation Jun. 2024," published Jun. 3, 2024, (27 pages).
Astria Therapeutics, Inc., "Astria Corporate Presentation Mar. 2024", published Mar. 4, 2024 (23 pages).
Astria Therapeutics, Inc., "Astria Corporate Presentation May 2024", published May 9, 2024 (25 pages).
Astria Therapeutics, Inc., "Astria Corporate Presentation Nov. 2023" published Nov. 13, 2023 (29 pages).
Astria Therapeutics, Inc., "Astria Therapeutics Oct. 2023," published Oct. 12, 2023 (28 pages).
Astria Therapeutics, Inc., "Corporate Presentation Dec. 2024," published Dec. 11, 2024 (28 pages).
Astria Therapeutics, Inc., "STAR-0310," accessed at https://astriatx.com/our-science/star-0310 on Aug. 21, 2024 (3 pages).
Astria Therapeutics, Inc., Press Release entitled "Astria Therapeutics Announces Exclusive Worldwide Licensed Agreement with Ichnos Sciences for OX40 Portfolio," dated Oct. 11, 2023 (2 pages).
Astria Therapeutics, Inc., Press Release entitled "Astria Therapeutics Announces FDA Clearance of IND Application for STAR-0310, A monoclonal Antibody OX40 Antagonist for the Treatment of Atopic Dermatitis," dated Dec. 10, 2024 (2 pages).
Astria Therapeutics, Inc., Press Release entitled "Astria Therapeutics Reports First Quarter 2024 Financial Results and Provides a Corporate Update," dated May 9, 2024 (4 pages).
Astria Therapeutics, Inc., Press Release entitled "Astria Therapeutics Reports Fourth Quarter and Full 2023 Financial Results and Provides a Corporate Update," dated Mar. 4, 2024 (4 pages).
Astria Therapeutics, Inc., Press Release entitled "Astria Therapeutics Reports Second Quarter 2024 Financial Results and Provides a Corporate Update," dated Aug. 12, 2024 (4 pages).
Astria Therapeutics, Inc., Press Release entitled "Astria Therapeutics Reports Third Quarter Financial Results and Provides a Corporate Update," dated Nov. 13, 2023 (4 pages).
Biris et al., "Development and characterization of STAR-0310: a novel OX40 antagonistic monoclonal antibody"—Abstract—European Academy of Allergy and Clinical Immunology (EAACI) Congress, May 31-Jun. 1, 2024, Valencia, Spain.
Biris et al., "Development and characterization of STAR-0310: a novel OX40 antagonistic monoclonal antibody"—Poster presented at European Academy of Allergy and Clinical Immunology (EAACI) Congress, Jun. 1, 2024, Valencia, Spain.
Blauvelt, Andrew et al. "Long-term management of moderate-to-severe atopic dermatitis with dupilumab and concomitant topical corticosteroids (Liberty Ad Chronos): a 1-year, randomised, double-blinded, placebo-controlled, phase 3 trial." Lancet (London, England) vol. 389, 10086 (2017): 2287-2303. doi:10.1016/S0140-6736(17)31191-1.
Booth, Brian J et al. "Extending human IgG half-life using structure-guided design." mAbs vol. 10,7 (2018): 1098-1110. doi:10.1080/19420862.2018.1490119.
Calderhead, D M et al. "Cloning of mouse Ox40: a T cell activation marker that may mediate T-B cell interactions." Journal of immunology (Baltimore, Md. : 1950) vol. 151, 10 (1993): 5261-71.
Croft, Michael et al. "OX40 in the Pathogenesis of Atopic Dermatitis—A New Therapeutic Target." American journal of clinical dermatology vol. 25,3 (2024): 447-461. doi:10.1007/s40257-023-00838-9.
Croft, Michael et al. "The significance of OX40 and OX40L to T-cell biology and immune disease." Immunological reviews vol. 229,1 (2009): 173-91. doi:10.1111/j.1600-065X.2009.00766.x.
Dall'Acqua, William F et al. "Increasing the affinity of a human IgG1 for the neonatal Fc receptor: biological consequences." Journal of immunology (Baltimore, Md. : 1950) vol. 169,9 (2002): 5171-80. doi:10.4049/jimmunol.169.9.5171.
Dall'Acqua, William F et al. "Properties of human IgG1s engineered for enhanced binding to the neonatal Fc receptor (FcRn)." The Journal of biological chemistry vol. 281,33 (2006): 23514-24. doi:10.1074/jbc.M604292200.
Facheris, Paola et al. "The translational revolution in atopic dermatitis: the paradigm shift from pathogenesis to treatment." Cellular & molecular immunology vol. 20,5 (2023): 448-474. doi:10.1038/s41423-023-00992-4.
Gramaglia, I et al. "Ox-40 ligand: a potent costimulatory molecule for sustaining primary CD4 T cell responses." Journal of immunology (Baltimore, Md. : 1950) vol. 161,12 (1998): 6510-7.
Griffin, M Pamela et al. "Safety, Tolerability, and Pharmacokinetics of MEDI8897, the Respiratory Syncytial Virus Prefusion F-Targeting Monoclonal Antibody with an Extended Half-Life, in Healthy Adults." Antimicrobial agents and chemotherapy vol. 61,3 e01714-16. Feb. 23, 2017, doi:10.1128/AAC.01714-16.
Guttman-Yassky, Emma et al. "An anti-OX40 antibody to treat moderate-to-severe atopic dermatitis: a multicentre, double-blind, placebo-controlled phase 2b study." Lancet (London, England) vol. 401,10372 (2023): 204-214. doi:10.1016/S0140-6736(22)02037-2.
Guttman-Yassky, Emma et al. "GBR 830, an anti-OX40, improves skin gene signatures and clinical scores in patients with atopic

(56) References Cited

OTHER PUBLICATIONS dermatitis." The Journal of allergy and clinical immunology vol. 144,2 (2019): 482-493.e7. doi:10.1016/j.jaci.2018.11.053.
International Search Report for International Patent Application No. PCT/US2024/050127 by Ichnos Sciences SA mailed Dec. 23, 2024, from the International Searching Authority/Australian Patent Office (7 pages).
Kondělková, Katerina et al. "Regulatory T cells (TREG) and their roles in immune system with respect to immunopathological disorders." Acta medica (Hradec Kralove) vol. 53,2 (2010): 73-7. doi:10.14712/18059694.2016.63.
Lé, Ana Maria, and Tiago Torres. "OX40-OX40L Inhibition for the Treatment of Atopic Dermatitis-Focus on Rocatinlimab and Amlitelimab." Pharmaceutics vol. 14, 12 2753. Dec. 8, 2022, doi:10.3390/pharmaceutics14122753.
Lobefaro, Fabio et al. "Atopic Dermatitis: Clinical Aspects and Unmet Needs." Biomedicines vol. 10,11 2927. Nov. 14, 2022, doi:10.3390/biomedicines10112927.
Miyano, Takuya et al. "A mathematical model to identify optimal combinations of drug targets for dupilumab poor responders in atopic dermatitis." Allergy vol. 77,2 (2022): 582-594. doi:10.1111/all. 14870.
Ohshima, Y et al. "OX40 costimulation enhances interleukin-4 (IL-4) expression at priming and promotes the differentiation of naive human CD4(+) T cells into high IL-4-producing effectors." Blood vol. 92,9 (1998): 3338-45.
Picone, Vincenzo et al. "An overview of new and emerging antibody therapies for moderate-severe atopic dermatitis in adults." Expert review of clinical pharmacology vol. 16, 12 (2023): 1239-1248. doi:10.1080/17512433.2023.2292615.
Ralph, Kerry et al., "Identification and characterization of an antagonistic anti-mouse CD40 antibody." The Journal of Immunology, vol. 196, Issue 1 Supplement, May 2016, p. 70.19, https://doi.org/10.4049/jimmunol.196.Supp.70.19.
Ratchataswan, Thanaporn et al. "Biologics for Treatment of Atopic Dermatitis: Current Status and Future Prospect." The journal of allergy and clinical immunology. In practice vol. 9,3 (2021): 1053-1065. doi:10.1016/j.jaip.2020.11.034.
Renert-Yuval, Yael, and Emma Guttman-Yassky. "What's New in Atopic Dermatitis." Dermatologic clinics vol. 37,2 (2019): 205-213. doi:10.1016/j.det.2018.12.007.
Rewerska, Barbara et al. "Phase 2b randomized trial of OX40 inhibitor telazorlimab for moderate- to-severe atopic dermatitis." The journal of allergy and clinical immunology. Global vol. 3,1 100195. Nov. 22, 2023, doi:10.1016/j.jacig.2023.100195.
Sadrolashrafi, Kaviyon et al. "An OX-Tra'Ordinary Tale: The Role of OX40 and OX40L in Atopic Dermatitis." Cells vol. 13,7 587. Mar. 28, 2024, doi:10.3390/cells13070587.
Silverberg, Jonathan I. "Comorbidities and the impact of atopic dermatitis." Annals of allergy, asthma & immunology : official publication of the American College of Allergy, Asthma, & Immunology vol. 123,2 (2019): 144-151. doi:10.1016/j.anai.2019.04.020.
Sroka-Tomaszewska, Jowita, and Magdalena Trzeciak. "Molecular Mechanisms of Atopic Dermatitis Pathogenesis." International journal of molecular sciences vol. 22,8 4130. Apr. 16, 2021, doi:10.3390/ijms22084130.
Tidwell, W James, and Joseph F Fowler Jr. "T-cell inhibitors for atopic dermatitis." Journal of the American Academy of Dermatology vol. 78,3 Suppl 1 (2018): S67-S70. doi:10.1016/j.jaad.2017.12.020.
Uppal, Shelley K et al. "Review and analysis of biologic therapies currently in phase II and phase III clinical trials for atopic dermatitis." The Journal of dermatological treatment vol. 33,2 (2022): 626-636. doi:10.1080/09546634.2020.1775775.
Voo, Kui S et al. "Antibodies targeting human OX40 expand effector T cells and block inducible and natural regulatory T cell function." Journal of immunology (Baltimore, Md. : 1950) vol. 191,7 (2013): 3641-50. doi:10.4049/jimmunol.1202752.
Weidinger, Stephan et al. "Safety and efficacy of amlitelimab, a fully human nondepleting, noncytotoxic anti-OX40 ligand monoclonal antibody, in atopic dermatitis: results of a phase IIa randomized placebo-controlled trial." The British journal of dermatology vol. 189,5 (2023): 531-539. doi:10.1093/bjd/ljad240.
Written Opinion for International Patent Application No. PCT/US2024/050127 by Ichnos Sciences SA mailed Dec. 23, 2024, from the International Searching Authority/Australian Patent Office (6 pages).
Yang, Nan et al. "Novel Targeted Biological Agents for the Treatment of Atopic Dermatitis." BioDrugs : clinical immunotherapeutics, biopharmaceuticals and gene therapy vol. 35,4 (2021): 401-415. doi:10.1007/s40259-021-00490-x.
Zahavi, David et al. "Enhancing antibody-dependent cell-mediated cytotoxicity: a strategy for improving antibody-based immunotherapy." Antibody therapeutics vol. 1,1 7-12. Jun. 24, 2018, doi:10.1093/abt/tby002.
Zhang, Di et al. "Fc Engineering Approaches to Enhance the Agonism and Effector Functions of an Anti-OX40 Antibody." The Journal of biological chemistry vol. 291,53 (2016): 27134-27146. doi:10.1074/jbc.M116.757773.
Zhao et al., "Preclinical Profile of STAR-0310, a novel OX40 antagonistic monoclonal antibody"—Abstract 558, Journal of Investigative Dermatology, vol. 144, Issue 8, Supplement, S97, Aug. 2024 (Abstract initially published for Society for Investigative Dermatology meeting in Dallas, Texas, USA, from May 15-18, 2024).
Zhao et al., "Preclinical Profile of STAR-0310, a novel OX40 antagonistic monoclonal antibody"—Poster presented at Society for Investigative Dermatology on May 16, 2024, in Dallas, Texas, USA.
"Telazorlimab," International Nonproprietary Names for Pharmaceutical Substances (INN) Recommended INN: List 84, WHO Drug Information, vol. 34, No. 3, 2020, p. 687, 776, 777.

* cited by examiner

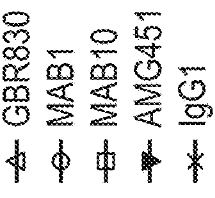
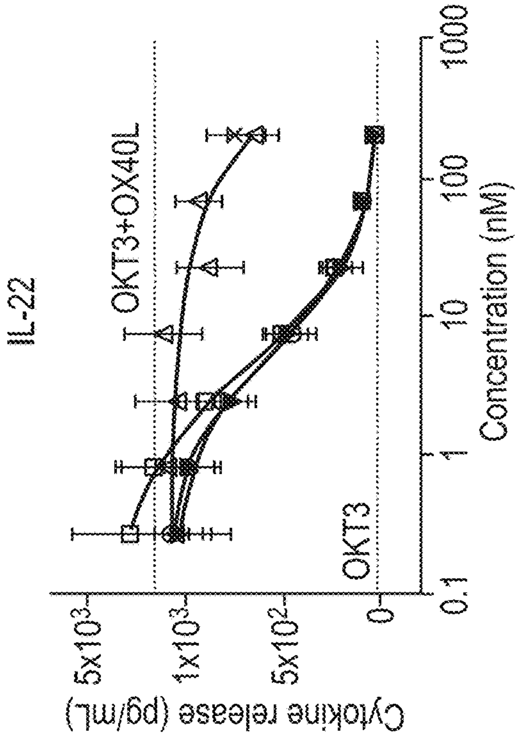
FIG. 14J
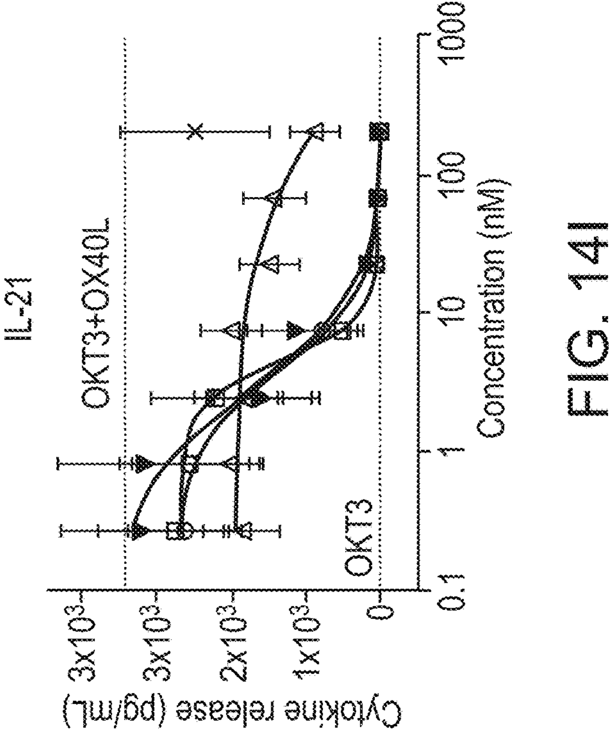
FIG. 14I

FIG. 21

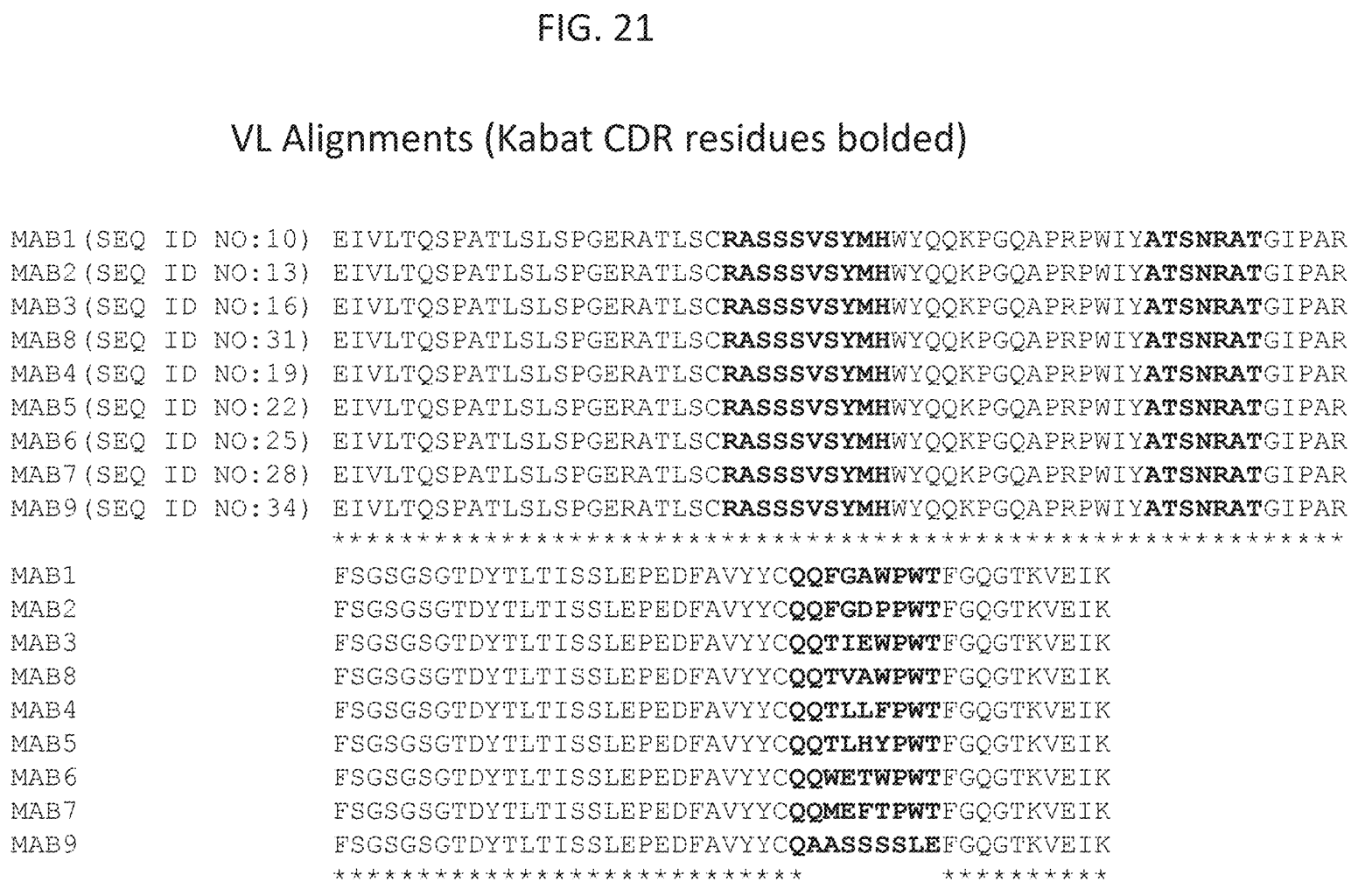

VL Alignments (Kabat CDR residues bolded)

MAB1(SEQ ID NO:10) EIVLTQSPATLSLSPGERATLSCRASSSVSYMHWYQQKPGQAPRPWIYATSNRATGIPAR
MAB2(SEQ ID NO:13) EIVLTQSPATLSLSPGERATLSCRASSSVSYMHWYQQKPGQAPRPWIYATSNRATGIPAR
MAB3(SEQ ID NO:16) EIVLTQSPATLSLSPGERATLSCRASSSVSYMHWYQQKPGQAPRPWIYATSNRATGIPAR
MAB8(SEQ ID NO:31) EIVLTQSPATLSLSPGERATLSCRASSSVSYMHWYQQKPGQAPRPWIYATSNRATGIPAR
MAB4(SEQ ID NO:19) EIVLTQSPATLSLSPGERATLSCRASSSVSYMHWYQQKPGQAPRPWIYATSNRATGIPAR
MAB5(SEQ ID NO:22) EIVLTQSPATLSLSPGERATLSCRASSSVSYMHWYQQKPGQAPRPWIYATSNRATGIPAR
MAB6(SEQ ID NO:25) EIVLTQSPATLSLSPGERATLSCRASSSVSYMHWYQQKPGQAPRPWIYATSNRATGIPAR
MAB7(SEQ ID NO:28) EIVLTQSPATLSLSPGERATLSCRASSSVSYMHWYQQKPGQAPRPWIYATSNRATGIPAR
MAB9(SEQ ID NO:34) EIVLTQSPATLSLSPGERATLSCRASSSVSYMHWYQQKPGQAPRPWIYATSNRATGIPAR
************************************************************

MAB1 FSGSGSGTDYTLTISSLEPEDFAVYYCQQFGAWPWTFGQGTKVEIK
MAB2 FSGSGSGTDYTLTISSLEPEDFAVYYCQQFGDPPWTFGQGTKVEIK
MAB3 FSGSGSGTDYTLTISSLEPEDFAVYYCQQTIEWPWTFGQGTKVEIK
MAB8 FSGSGSGTDYTLTISSLEPEDFAVYYCQQTVAWPWTFGQGTKVEIK
MAB4 FSGSGSGTDYTLTISSLEPEDFAVYYCQQTLLFPWTFGQGTKVEIK
MAB5 FSGSGSGTDYTLTISSLEPEDFAVYYCQQTLHYPWTFGQGTKVEIK
MAB6 FSGSGSGTDYTLTISSLEPEDFAVYYCQQWETWPWTFGQGTKVEIK
MAB7 FSGSGSGTDYTLTISSLEPEDFAVYYCQQMEFTPWTFGQGTKVEIK
MAB9 FSGSGSGTDYTLTISSLEPEDFAVYYCQAASSSSLEFGQGTKVEIK
*************************          ********

FIG. 22

Heavy Chain Alignments

```
MAB1    QVTLKESGPALVKPTQTLTLTCSFSGFSLSTSGMGVGWIRQPPGKALEWIAHIWWDDDKY
MAB10   QVTLKESGPALVKPTQTLTLTCSFSGFSLSTSGMGVGWIRQPPGKALEWIAHIWWDDDKY
MAB11   QVTLKESGPALVKPTQTLTLTCSFSGFSLSTSGMGVGWIRQPPGKALEWIAHIWWDDDKY
        ************************************************************

MAB1    YNTALKTRLTISKDTSKNQVVLTMTNMDPVDTATYYCARIDWDGFAYWGQGTLVTVSSAS
MAB10   YNTALKTRLTISKDTSKNQVVLTMTNMDPVDTATYYCARIDWDGFAYWGQGTLVTVSSAS
MAB11   YNTALKTRLTISKDTSKNQVVLTMTNMDPVDTATYYCARIDWDGFAYWGQGTLVTVSSAS
        ************************************************************

MAB1    TKGPSVFPLAPSSKSTSGGTAALGCLVKDYFPEPVTVSWNSGALTSGVHTFPAVLQSSGL
MAB10   TKGPSVFPLAPSSKSTSGGTAALGCLVKDYFPEPVTVSWNSGALTSGVHTFPAVLQSSGL
MAB11   TKGPSVFPLAPSSKSTSGGTAALGCLVKDYFPEPVTVSWNSGALTSGVHTFPAVLQSSGL
        ************************************************************

MAB1    YSLSSVVTVPSSSLGTQTYICNVNHKPSNTKVDKKVEPKSCDKTHTCPPCPAPELLGGPS
MAB10   YSLSSVVTVPSSSLGTQTYICNVNHKPSNTKVDKKVEPKSCDKTHTCPPCPAPELLGGPS
MAB11   YSLSSVVTVPSSSLGTQTYICNVNHKPSNTKVDKKVEPKSCDKTHTCPPCPAPELLGGPS
        ************************************************************

MAB1    VFLFPPKPKDTLMISRTPEVTCVVVDVSHEDPEVKFNWYVDGVEVHNAKTKPREEQYNST
MAB10   VFLFPPKPKDTLYITREPEVTCVVVDVSHEDPEVKFNWYVDGVEVHNAKTKPREEQYNST
MAB11   VFLFPPKPKDTLMISRTPEVTCVVVDVSHEDPEVKFNWYVDGVEVHNAKTKPREEQYNST
        ************ *:* *******************************************

MAB1    YRVVSVLTVLHQDWLNGKEYKCKVSNKALPAPIEKTISKAKGQPREPQVYTLPPSRDELT
MAB10   YRVVSVLTVLHQDWLNGKEYKCKVSNKALPAPIEKTISKAKGQPREPQVYTLPPSRDELT
MAB11   YRVVSVLTVLHQDWLNGKEYKCKVSNKALPAPIEKTISKAKGQPREPQVYTLPPSRDELT
        ************************************************************

MAB1    KNQVSLTCLVKGFYPSDIAVEWESNGQPENNYKTTPPVLDSDGSFFLYSKLTVDKSRWQQ
MAB10   KNQVSLTCLVKGFYPSDIAVEWESNGQPENNYKTTPPVLDSDGSFFLYSKLTVDKSRWQQ
MAB11   KNQVSLTCLVKGFYPSDIAVEWESNGQPENNYKTTPPVLDSDGSFFLYSKLTVDKSRWQQ
        ************************************************************

MAB1    GNVFSCSVMHEALHNHYTQKSLSLSPGK (SEQ ID NO:9)
MAB10   GNVFSCSVMHEALHNHYTQKSLSLSPGK (SEQ ID NO:73)
MAB11   GNVFSCSVLHEALHSHYTQKSLSLSPGK (SEQ ID NO:74)
        ********:*****.*************
```

AFFINITY MATURED ANTI-OX40 ANTIBODIES AND USE THEREOF

CROSS-REFERENCE TO RELATED APPLICATIONS

This application is a continuation of International Patent Application No. PCT/US2024/050127 filed Oct. 4, 2024, which claims priority to and the benefit of U.S. Provisional Patent Application No. 63/588,662 filed Oct. 6, 2023, and U.S. Provisional Patent Application No. 63/645,656 filed May 10, 2024, the contents of each which are incorporated by reference herein in their entireties.

REFERENCE TO SEQUENCE LISTING XML

This application contains a Sequence Listing which has been submitted electronically in XML format. The Sequence Listing XML is incorporated herein by reference. Said XML file, created on Apr. 14, 2026, is named AST-003US_SL.xml and is 84,808 bytes in size.

FIELD

The disclosure relates generally to affinity matured anti-OX40 antibodies, and their manufacture and use in the treatment of various OX40-mediated disorders, including inflammatory and autoimmune disorders.

BACKGROUND

OX40 (TNFRSF4, CD134) is a costimulatory receptor member of the NGFR/TNFR superfamily, expressed predominantly on activated T lymphocytes including CD4 and CD8 T cells, T helper cells (type 1, type 2, and type 3: Th1, Th2, and Th17) and Forkhead box P3 positive (Foxp3+) CD4+ regulatory T cells (Tregs). Unlike CD28, which is a classic constitutively expressed T cell costimulatory receptor, OX40 is not expressed on naïve T lymphocytes. Rather, OX40 expression is transiently induced on CD4 and CD8 T cells from 24 hours to 5 days after initial TCR stimulation (Calderhead et al. (1993), J. Immunol. 151(1):5261-71; Gramaglia et al. (1998), J. Immunol., 161(12):6510-6517; Akiba et al. (1999), J. Immunol., 162(12):7058-7066). In addition, OX40 appears to be up-regulated on Tregs, a population of T cells that is critical at maintaining immune tolerance and fine-tuning T cell activity (Kondelkova et al. (2010), Acta Medica, 53(2):73-77). In general, the binding of OX40L expressed on antigen presenting cells (APCs) to OX40 on T cells facilitates the effector function of the T cells.

OX40 and CD30 are believed to be crucial for the late phases of, or long-lasting, T cell responses. Binding to OX40 by its ligand OX40L (TNFSF4-CD252) leads to enhanced T cell survival and proliferation which can lead to autoimmune diseases. Certain OX40 therapeutic antibodies in development for autoimmune disorders generally exhibit some level of residual agonistic activity that results in T cell activation and proliferation. Thus, despite the advances that have been made to date in treating OX40 mediated disorders, there is still a need for additional anti-OX40 therapeutics.

SUMMARY

The present disclosure is based, in part, upon the discovery of high affinity, antagonistic anti-OX40 antibodies, their manufacture and use in the treatment OX40 mediated disorders, including inflammatory and autoimmune disorders. Certain of the high affinity antibodies disclosed herein do not exhibit detectable agonistic activity (e.g., T cell activation and proliferation) making them particularly useful in the treatment of inflammatory and autoimmune disorders.

Certain of the antibodies disclosed herein, including MAB1 and MAB10, exhibit increased affinity for OX40 as compared to the parental antibody telazorlimab (referred to herein as GBR 830, and also known as ISB830). MAB1 and MAB10 also lack agonistic activity compared to benchmark antibodies such as rocatinlimab (also known as KHK4083 or AMG451) which retain residual agonistic activity. In vitro, MAB1 and MAB10 show stronger potency than telazorlimab (GBR 830) to inhibit T cell proliferation. Furthermore, MAB1 and MAB10 also show reduced ADCC-mediated depletion of T cells as compared to rocatinlimab and a unique potential for limiting Treg depletion via ADCC. These and other pharmacological properties support the potential efficacy of MAB1 and MAB10 in the field of OX40 therapy for autoimmune disease.

In one aspect, the disclosure provides an antibody or antigen binding fragment thereof that binds to OX40, e.g., human OX40. In one example, the antibody or antigen binding fragment thereof comprises three heavy chain complementarity determining regions (CDRs) (CDR-H1, CDR-H2, and CDR-H3) of a heavy chain variable domain (VH) comprising the amino acid sequence set forth in SEQ ID NO:7, and three light chain CDRs (CDR-L1, CDR-L2, and CDR-L3) of a light chain variable domain (VL) comprising the amino acid sequence set forth in SEQ ID NO:8. In other examples, the antibody or antigen binding fragment thereof comprises three heavy chain complementarity determining regions (CDRs) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:12, SEQ ID NO:15, SEQ ID NO:18, SEQ ID NO:21, SEQ ID NO:24, SEQ ID NO:27, SEQ ID NO:30, or SEQ ID NO:33. The CDR-H1, CDR-H2, and CDR-H3, and the CDR-L1, CDR-L2, and CDR-L3 may be defined according to the Kabat, Chothia, IMGT, AbM, Contact or Honneger (AHo) CDR numbering systems as discussed herein, or other numbering systems known in the art. The antibody or antigen binding fragment thereof may be an isolated antibody or antigen binding fragment.

In another aspect, the disclosure provides an antibody or antigen binding fragment thereof, that binds to OX40, e.g., human OX40. The antibody or antigen binding fragment thereof comprises a heavy chain variable region comprising a CDR-H1 comprising the amino acid sequence set forth in SEQ ID NO:1, a CDR-H2 comprising the amino acid sequence set forth in SEQ ID NO:2, a CDR-H3 comprising the amino acid sequence set forth in SEQ ID NO:3; and a light chain variable region comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:38 or 71, where $X_1$ is F, T, W, or M; where $X_2$ is G, I, V, L, or E; where $X_3$ is A, D, E, L, H, T, or F; and where X4 is W, P, F, Y, or T. For example, the CDR-L3 comprises the amino acid sequence set forth in SEQ ID NO:38. For example, the CDR-L3 comprises the amino acid sequence set forth in SEQ ID NO:71. In some examples, $X_1$ is F or T, $X_2$ is L, G, or E, $X_3$ is A, and $X_4$ is W. The antibody or antigen binding fragment thereof may be an isolated antibody or antigen binding fragment.

In a further aspect, the disclosure provides an antibody, or antigen binding fragment thereof, that binds to OX40. The antibody or antigen binding fragment thereof comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3; and a light chain variable region comprising a CDR-L1 comprising the amino acid sequence set forth in SEQ ID NO:4, a CDR-L2 comprising the amino acid sequence set forth in SEQ ID NO:5, and a CDR-L3 comprising an amino acid sequence as set forth in SEQ ID NO:6, SEQ ID NO:11, SEQ ID NO:14, SEQ ID NO:17, SEQ ID NO:20, SEQ ID NO:23, SEQ ID NO:26, SEQ ID NO:29, or SEQ ID NO:32. The antibody or antigen binding fragment thereof may be an isolated antibody or antigen binding fragment.

In yet another aspect, the disclosure provides an antibody or antigen binding fragment thereof, that binds to OX40, e.g., human OX40. The antibody or antigen binding fragment thereof includes a heavy chain variable region comprising (a) a heavy chain CDR1 comprising the amino acid sequence of SEQ ID NO:1, SEQ ID NO:41, SEQ ID NO:47, SEQ ID NO:53, SEQ ID NO:59, or SEQ ID NO:65; a heavy chain CDR2 comprising the amino acid sequence of SEQ ID NO:2, SEQ ID NO:42, SEQ ID NO:48, SEQ ID NO:54, SEQ ID NO:60, or SEQ ID NO:66; and a heavy chain CDR3 comprising the amino acid sequence of SEQ ID NO:3, SEQ ID NO:55, SEQ ID NO:61, or SEQ ID NO:67; and (b) comprising a light chain variable region comprising a light chain CDR1 comprising the amino acid sequence of SEQ ID NO:4, SEQ ID NO:56, SEQ ID NO:62, or SEQ ID NO:68; a light chain CDR2 comprising the amino acid sequence of SEQ ID NO:5, SEQ ID NO:57, the amino acid sequence AT, or SEQ ID NO:69; and a light chain CDR3 comprising the amino acid sequence of SEQ ID NO:6, SEQ ID NO:58, or SEQ ID NO:70. The antibody or antigen binding fragment thereof may be an isolated antibody or antigen binding fragment.

For example, the antibody or antigen binding fragment thereof that binds OX40, e.g., human OX40, may include a heavy chain variable region comprising a heavy chain CDR1 having the amino acid sequence of SEQ ID NO:1, a heavy chain CDR2 having the amino acid sequence of SEQ ID NO:2, and a heavy chain CDR3 having the amino acid sequence of SEQ ID NO:3, and a light chain variable region comprising light chain CDR1 having the amino acid sequence of SEQ ID NO:4, a light chain CDR 2 having the amino acid sequence of SEQ ID NO:5, and a light chain CDR3 having the amino acid sequence of SEQ ID NO:6.

For example, the antibody or antigen binding fragment thereof that binds OX40, e.g., human OX40, may include a heavy chain variable region comprising a heavy chain CDR1 having the amino acid sequence of SEQ ID NO:41, a heavy chain CDR2 having the amino acid sequence of SEQ ID NO:42, and a heavy chain CDR3 having the amino acid sequence of SEQ ID NO:3, and a light chain variable region comprising a light chain CDR1 having the amino acid sequence of SEQ ID NO:4, a light chain CDR 2 having the amino acid sequence of SEQ ID NO:5, and a light chain CDR3 having the amino acid sequence of SEQ ID NO:6.

For example, the antibody or antigen binding fragment thereof that binds OX40, e.g., human OX40, may include a heavy chain variable region comprising a heavy chain CDR1 having the amino acid sequence of SEQ ID NO:47, a heavy chain CDR2 having the amino acid sequence of SEQ ID NO:48, a heavy chain CDR3 having the amino acid sequence of SEQ ID NO:3, and a light chain variable region comprising light chain CDR1 having the amino acid sequence of SEQ ID NO:4, a light chain CDR 2 having the amino acid sequence of SEQ ID NO:5, and a light chain CDR3 having the amino acid sequence of SEQ ID NO:6.

For example, the antibody or antigen binding fragment thereof that binds OX40, e.g., human OX40, may include a heavy chain variable region comprising a heavy chain CDR1 having the amino acid sequence of SEQ ID NO:53, a heavy chain CDR2 having the amino acid sequence of SEQ ID NO:54, a heavy chain CDR3 having the amino acid sequence of SEQ ID NO:55, and a light chain variable region comprising a light chain CDR1 having the amino acid sequence of SEQ ID NO:56, a light chain CDR 2 having the amino acid sequence of SEQ ID NO:57, and a light chain CDR3 having the amino acid sequence of SEQ ID NO:58.

For example, the antibody or antigen binding fragment thereof that binds OX40, e.g., human OX40, may include a heavy chain variable region comprising a heavy chain CDR1 having the amino acid sequence of SEQ ID NO:59, a heavy chain CDR2 having the amino acid sequence of SEQ ID NO:60, a heavy chain CDR3 having the amino acid sequence of SEQ ID NO:61, and a light chain variable region comprising a light chain CDR1 having the amino acid sequence of SEQ ID NO:62, a light chain CDR 2 having the amino acid sequence AT, and a light chain CDR3 having the amino acid sequence of SEQ ID NO:6.

For example, the antibody or antigen binding fragment thereof that binds OX40, e.g., human OX40, may include a heavy chain variable region comprising a heavy chain CDR1 having the amino acid sequence of SEQ ID NO:65, a heavy chain CDR2 having the amino acid sequence of SEQ ID NO:66, a heavy chain CDR3 having the amino acid sequence of SEQ ID NO:67, and a light chain variable region comprising a light chain CDR1 having the amino acid sequence of SEQ ID NO:68, a light chain CDR 2 having the amino acid sequence of SEQ ID NO:69, and a light chain CDR3 having the amino acid sequence of SEQ ID NO:70.

In certain examples, the OX40 is human OX40. Accordingly, in some examples, the antibody or antigen binding fragment thereof that binds OX40 is an antibody or antigen fragment thereof that binds human OX40.

In certain examples, the antibody or antigen binding fragment thereof that binds OX40, e.g., human OX40, is an antagonist of OX40. Furthermore, the antibody or antigen binding fragment thereof that binds OX40 can be a humanized antibody. The CDRs of the antibody or antigen binding fragment thereof may be interposed between human or humanized framework sequences. The antibody or antigen binding fragment thereof may include a heavy chain having an Fc region with an amino acid modification that increases the serum half-life of the antibody or antigen binding fragment. For example, the antibody or antigen binding fragment thereof may include an IgG1 heavy chain, e.g., with an Fc region having the mutations M252Y, S254T, and T256E as numbered according to EU numbering.

In certain examples, the antibody or antigen binding fragment thereof that binds OX40, e.g., human OX40, includes a heavy chain variable region having the amino acid sequence of SEQ ID NO:7. In other examples, the antibody or antigen binding fragment thereof that binds OX40, e.g., human OX40, and includes a light chain variable region having the amino acid sequence of SEQ ID NO:8. In yet further examples, the antibody or antigen binding fragment thereof that binds OX40, e.g., human OX40, includes a heavy chain variable region having the amino acid sequence of SEQ ID NO:7, and includes a light chain variable region having the amino acid sequence of SEQ ID NO:8. In still further examples, the antibody or antigen binding fragment thereof that binds OX40, e.g., human OX40, includes a heavy chain variable region having the amino acid sequence of SEQ ID NO:7, and includes a light chain variable region having an amino acid sequence selected from SEQ ID NO:12, 15, 18, 21, 24, 27, 30, or 33.

In certain other examples, the antibody or antigen binding fragment thereof that binds OX40, e.g., human OX40, includes a heavy chain having the amino acid sequence of SEQ ID NO:9, while in other examples, the antibody or antigen binding fragment thereof includes a heavy chain having the amino acid sequence of SEQ ID NO:73. In some examples, the antibody or antigen binding fragment thereof that binds OX40, e.g., human OX40, includes a light chain having the amino acid sequence of SEQ ID NO:10. In one particular case, the antibody or antigen binding fragment thereof that binds OX40, e.g., human OX40, includes a heavy chain having the amino acid sequence of SEQ ID NO:73, and a light chain having the amino acid sequence of SEQ ID NO:10. In another particular case, the antibody or antigen binding fragment thereof that binds OX40, e.g., human OX40, includes a heavy chain having the amino acid sequence of SEQ ID NO:9, and a light chain having the amino acid sequence of SEQ ID NO:10.

In further examples, the antibody or antigen binding fragment thereof that binds OX40, e.g., human OX40, includes a heavy chain having the amino acid sequence of SEQ ID NO:9, and a light chain comprising the amino acid sequence of SEQ ID NO:13, 16, 19, 22, 25, 28, 31, or 34. In still further examples, the antibody or antigen binding fragment thereof that binds OX40, e.g., human OX40, includes a heavy chain having the amino acid sequence of SEQ ID NO:73, and a light chain comprising the amino acid sequence of SEQ ID NO:13, 16, 19, 22, 25, 28, 31, or 34.

In certain examples, the antibody or antigen binding fragment thereof that binds OX40, e.g., human OX40, as disclosed herein increases inhibition of T cell proliferation as compared to telazorlimab.

In other examples, the antibody or antigen binding fragment thereof that binds OX40, e.g., human OX40, as disclosed herein is formulated in a pharmaceutical composition with a pharmaceutically acceptable carrier.

In another aspect, the disclosure provides nucleic acids encoding the light chain CDRs, light chain variable region, or light chain of the antibody or antigen binding fragment thereof that binds OX40, e.g., human OX40, as disclosed herein. The nucleic acid may be contained in an expression vector. The expression vector may further include a nucleotide sequence encoding the heavy chain CDRs, heavy chain variable region, or heavy chain of the antibody or antigen binding fragment thereof that binds OX40, e.g., human OX40, as disclosed herein. The expression vector may further be contained in a host cell. In one example, a nucleic acid is provided that encodes the amino acid sequence of SEQ ID NO:7 and SEQ ID NO:8. In another example, a nucleic acid is provided that encodes the amino acid sequence of SEQ ID NO:9 and SEQ ID NO:10. In another example, a nucleic acid is provided that encodes the amino acid sequence of SEQ ID NO:73 and SEQ ID NO:10.

In addition, the disclosure provides a host cell including an expression vector having a nucleotide sequence encoding the amino acid sequence of SEQ ID NO:7 and an expression vector having a nucleotide sequence encoding the amino acid sequence of SEQ ID NO:8, while in another example, a host cell includes an expression vector having a nucleotide sequence encoding the amino acid sequence of SEQ ID NO:9 and an expression vector having a nucleotide sequence encoding the amino acid sequence of SEQ ID NO:10. In yet another example, a host cell includes an expression vector having a nucleotide sequence encoding the amino acid sequence of SEQ ID NO:73, and an expression vector having a nucleotide sequence encoding the amino acid sequence of SEQ ID NO:10. In yet another example, a host cell includes an expression vector having a nucleotide sequence encoding the amino acid sequence of SEQ ID NO:73 and of SEQ ID NO:10.

In another aspect, the disclosure provides a method of producing an antibody, or antigen binding fragment thereof, that binds to human OX40, e.g., human OX40. In this method, a host cell is grown under conditions so that the host cell expresses a polypeptide or polypeptides comprising the heavy chain or heavy chain variable region or heavy chain CDRs, and the light chain or light chain variable region or the light chain CDRs of an antibody or antigen fragment thereof that binds to human OX40, e.g., human OX40, as described herein, and then the antibody or the antigen-binding fragment of the antibody is purified therefrom.

In another aspect, the disclosure provides a method of treating an OX40 mediated disorder in a subject. The method includes administering to the subject (e.g., a human) a therapeutically effective amount of an antibody or antigen binding fragment thereof that binds OX40 (e.g., human OX40).

In yet another aspect, the disclosure provides a method of reducing or inhibiting T cell proliferation in a subject (e.g., a human) in need thereof. The method includes administering to the subject (e.g., a human) a therapeutically effective amount of an antibody or antigen binding fragment thereof that binds OX40 (e.g., human OX40). The subject may, for example, have an OX40 mediated disorder.

In such aspects, the OX40 mediated disorder may be arthritis, rheumatoid arthritis, psoriatic arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, prurigo nodularis, vasculitis, surgical adhesions, stroke, Type I Diabetes, Lyme disease, meningoencephalitis, autoimmune uveitis, immune mediated inflammatory disorders of the central and peripheral nervous system such as multiple sclerosis, lupus (such as systemic lupus erythematosus or lupus nephritis) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, chronic spontaneous urticaria (CSU), chronic inducible urticaria (CIU), Wegener's granulomatosis, pancreatitis, trauma (surgery), graft-versus-host disease (GVHD), transplant rejection, cardiovascular disease including ischemic diseases such as myocardial infarction as well as atherosclerosis, intravascular coagulation, bone resorption, osteoporosis, osteoarthritis, periodontitis, hypochlorhydria and neuromyelitis optica. In certain examples, the OX40 mediated disorder is Atopic Dermatitis, Prurigo Nodularis, Alopecia Areata, Chronic Spontaneous Urticaria (CSU) and Chronic Inducible Urticaria (CIU), Asthma, Hidradenitis Suppurativa, Lupus Nephritis, Systemic Lupus Erythematosus, Pemphigus Vulgaris, Psoriatic Arthritis, Vasculitis, Hashimoto Thyroiditis, Systemic Sclerosis, Cutaneous Sclerosis, Scleroderma, Chronic Pruritus from Unknown Origin, Ankylosing Spondylitis, Sjogren's Syndrome, Psoriasis, or Vitiligo.

In certain examples, the OX40 mediated disorder is atopic dermatitis. In other examples, the OX40 mediated disorder is urticaria, e.g., chronic spontaneous urticaria or, e.g., chronic inducible urticaria. In yet other examples, the OX40 mediated disorder is an autoimmune disorder such as lupus erythematosus or rheumatoid arthritis. In still other examples, the OX40 mediated disorder is asthma. In yet other disorders, the OX40 mediated disorder is alopecia areata, scleroderma, or hidradenitis suppurativa.

BRIEF DESCRIPTION OF THE DRAWINGS

These and other features, aspects, and advantages of the present disclosure will become better understood with regard to the following description, and accompanying drawings, where:

FIG. 2A shows binding to OX40-HRRR-Fc. FIG. 2B shows binding to OX40-RHRR-Fc. FIG. 2C shows binding to OX40-HHHR-Fc. FIG. 2D shows binding to OX40-HHRH-Fc. Three concentrations of the indicated anti-OX40 antibodies were used (1, 3, and 10 μg/mL) to confirm the binding at low concentration on the OX40 chimeric constructs. (R=rat module, H=Human module in the OX40-Fc constructs). The graphs show the OD at 450 nm measured for each condition.

FIG. 14I shows the dose-dependent curve of IL-21 release (pg/mL) inhibition in a T cell proliferation assay after incubation with GBR830, MAB1, MAB10, AMG451, and IgG1. FIG. 14J shows the dose-dependent curve of IL-22 release (pg/mL) inhibition in a T cell proliferation assay after incubation with GBR830, MAB1, MAB10, AMG451, and IgG1. The legend appearing to the right of each of FIGS. 14B, 14F, and 14J also applies to each of FIGS. 14A, 14C, 14D, 14E, 14G, 14H, and 14I.

FIG. 21 shows an alignment of the VL domains of MAB1-9. The CDR residues according to the Kabat numbering scheme are shown in bold.

FIG. 22 shows an alignment of the heavy chain of MAB1, MAB10, and MAB11. The YTE and LS changes in MAB10 and MAB11, respectively, are shown in bold and underlined.

FIG. 25A shows 0.07 μg/mL OX40L. FIG. 25B shows 0.3 μg/mL OX40L. FIG. 25C shows 5 μg/mL OX40L.

FIG. 26A shows no OX40L. FIG. 26B shows 0.07 μg/mL OX40L. FIG. 26C shows 0.3 μg/mL OX40L. FIG. 26D shows 5 μg/mL OX40L.

DETAILED DESCRIPTION

Figure 1:
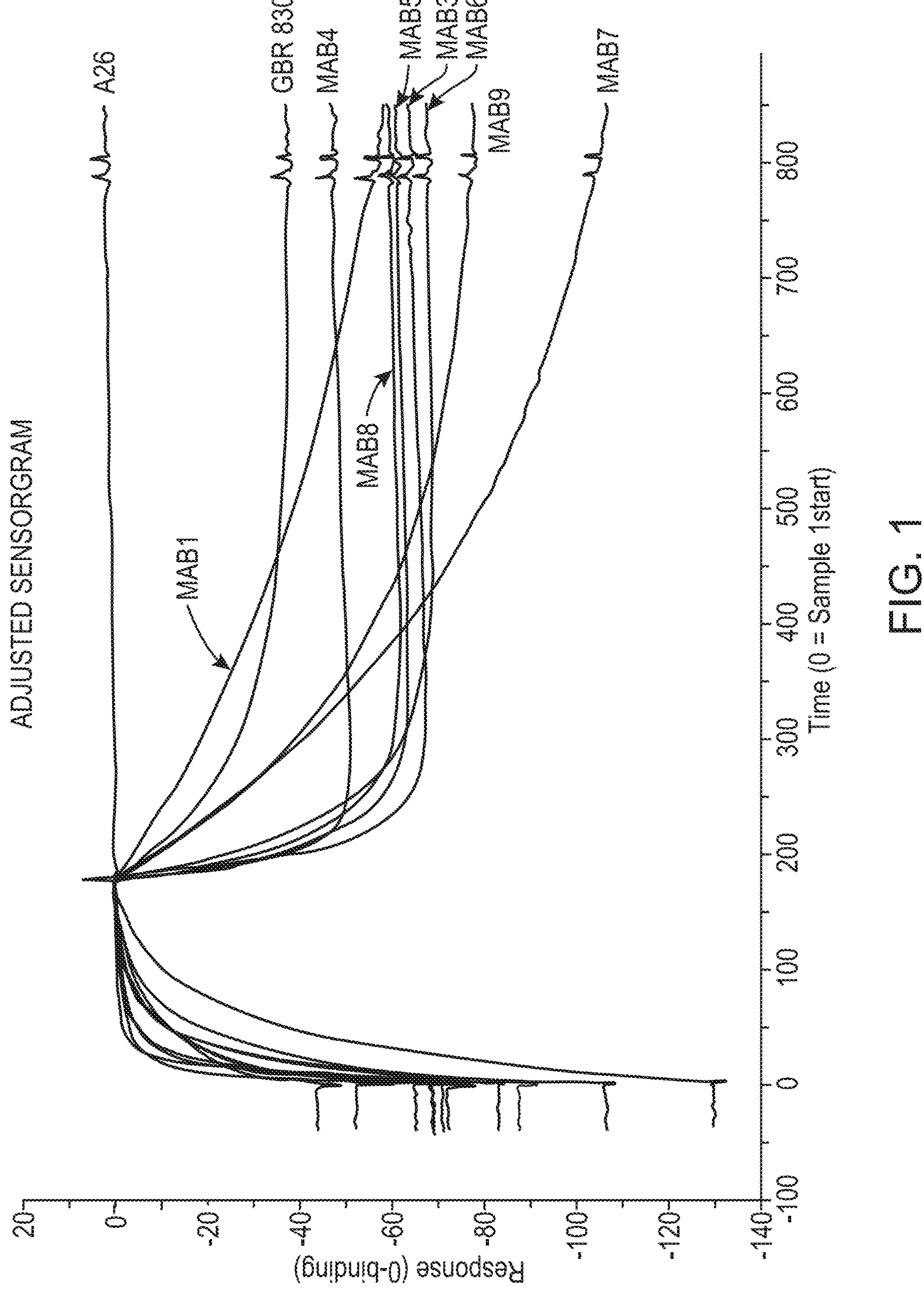
FIG. 1 is a graph showing affinity measurements (binding versus time) for GBR 830 and nine GBR 830 variants (denoted as MAB1 to MAB9) for human OX40-CRD-avihis.

The present disclosure is based, in part, upon the discovery of a high affinity, antagonistic anti-OX40 antibodies, their manufacture and use in the treatment OX40 mediated disorders, including inflammatory and autoimmune disorders. Certain of the high affinity antibodies do not have any detectable agonistic properties making them particularly useful in the treatment of inflammatory and autoimmune disorders.

I. Definitions

Unless defined otherwise, technical and scientific terms used herein have the same meaning as is commonly understood by one of skill in the art to which the claimed subject matter belongs. For example, nomenclatures utilized in connection with, and techniques of, e.g., polypeptide and polynucleotide chemistry and synthesis, molecular and cellular biology, protein biology and biochemistry, immunology, etc. described herein are those well-known and commonly used in the art.

The articles "a," "an," and "the" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise. The expression "and/or" in connection with three or more recited objects should be understood to have the same meaning unless otherwise understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

The term "in combination with" as used herein means that the described agents can be administered to a subject together in a mixture, concurrently as single agents or sequentially as single agents in any order. The term "ameliorating" refers to any therapeutically beneficial result in the treatment of a OX40-mediated disease state, e.g., an allergy, asthma, COPD, rheumatoid arthritis, dermatitis, or psoriasis disease state, including prophylaxis, lessening in the severity of symptoms or lessening progression of the disease, or inducing remission of the disease, or cure thereof.

The term "isolated," for example, in reference to antibody or antigen binding fragment refers to an antibody or antigen binding fragment that has been removed, for example, by purification, from its natural environment, for example, inside a living cell, body fluid, tissue, or animal.

The term "OX40" as used herein includes naturally occurring variants, isoforms, and species homologs of OX40, and the term "human OX40" as used herein includes naturally occurring variants, isoforms, and species homologs of human OX40. Antibodies of this disclosure may, in certain cases, cross-react with OX40 from species other than human. In certain embodiments, the antibodies may be completely specific for one or more human OX40 proteins and may not exhibit species or other types of non-human cross-reactivity. The complete amino acid sequence of an exemplary human OX40 has Swiss-Prot accession number P43489 (TNR4—HUMAN; SEQ ID NO:72). OX40 is also known as CD134, TNFRSF4, ACT35 or TXGP1 L. Human OX40 is designated GeneID: 7293 by Entrez Gene, and HGNC: 11918 by HGNC. OX40 has also been designated CD134 (cluster of differentiation 134). OX40 can be encoded by the gene designated TNFRSF4/OX40. The term "human OX40" encompasses all known or as yet undiscovered alleles and polymorphic forms of human OX40. The terms "human OX40", "OX40" or "OX40 Receptor" are used interchangeably herein.

As used herein, the terms "OX40 ligand" or "OX40L" are used interchangeably and include OX40 ligand, specifically human OX40 ligand. OX40L is a member of the TNF superfamily and is also known as gp34 or CD252. OX40L has also been designated CD252 (cluster of differentiation 252) and has the sequence database accession number P23510 (Swiss-Prot) or Q6FGS4 (Uniprot). OX40L is expressed on the surface of activated B cells, T cells, dendritic cells and endothelial cells.

As used herein, the term "OX40-mediated disorder" includes conditions that involve the OX40 signaling pathway (e.g., activation of the OX40 signaling pathway) such as allergy, asthma, COPD, rheumatoid arthritis, psoriasis, atopic dermatitis, urticarias such as chronic spontaneous urticaria (CSU) or chronic inducible urticaria (CIU), and diseases associated with autoimmunity and inflammation. For an OX40-mediated disorder where activation of the OX40 signaling pathway contributes to the disorder's pathology, OX40 antagonism may be therapeutically useful to treat that OX40-mediated disorder. Other OX40-mediated disorders are disclosed herein.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically acceptable carrier" as used herein refers to an agent (e.g., excipient, carrier, buffer, etc.) suitable for use in contact with the tissues of human beings and animals without excessive toxicity, irritation, allergic response, or other problem or complication, commensurate with a reasonable benefit/risk ratio. Pharmaceutically acceptable carriers include any and all solvents, dispersion media, coatings, antibacterial and antifungal agents, isotonic and absorption delaying agents, and the like, compatible with pharmaceutical administration. Standard pharmaceutical carriers may include, for example a phosphate buffered saline solution, water, emulsions (e.g., such as an oil/water or water/oil emulsions), and various types of wetting agents. The compositions also can include stabilizers and preservatives. For examples of carriers, stabilizers, and adjuvants, see e.g., Adeboye Adejare, REMINGTON: THE SCIENCE AND PRACTICE OF PHARMACY (23rd ed. 2020).

As used herein, the terms "subject" and "patient" are used interchangeably and refer to an organism to be treated by the methods and compositions described herein. Such organisms preferably include, but are not limited to, mammals (e.g., murines, simians, equines, bovines, porcines, canines, felines, and the like), and more preferably includes humans. The antibodies disclosed herein have both human therapy and veterinary applications. In certain examples, the subjects disclosed herein are human and the disclosed antibodies are used for human therapy.

As used herein, the terms "treat," "treating," and "treatment" refer to the treatment of a disease, disorder, or symptom or manifestation of such in a subject, e.g., in a human. This includes: (a) preventing a disease or disorder, (b) inhibiting the disease, disorder, etc., i.e., slowing or arresting its progress or development; and (b) relieving the disease, disorder, etc., e.g., causing regression of the disease state or ameliorating at least one symptom of the disorder. As used herein, "prevent", "preventing" and "prevention" refer to causing a disease, disorder, or symptom or manifestation of such not to occur for at least a period of time in at least some subjects. Those "in need of treatment" include mammals already having the disease or disorder, such as humans, as well as those prone to having the disease or disorder, including those in which the disease or disorder is to be prevented.

As used herein, the phrase "therapeutically effective amount" refers to the amount of an active agent (e.g., an anti-OX40 antibody or antigen binding fragment thereof disclosed herein) sufficient to effect beneficial or desired results. An effective amount can be administered in one or more administrations, applications, or dosages and is not intended to be limited to a particular formulation or administration route. A therapeutically effective amount can be a "prophylactically effective amount" as prophylaxis can be considered therapy.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (ncbi.nlm.nih.gov/blast).

It should be understood that the expression "at least one of" includes individually each of the recited objects after the expression and the various combinations of two or more of the recited objects unless otherwise understood from the context and use.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where a molecular weight is provided and not an absolute value, for example, of a polymer, then the molecular weight should be understood to be an average molecule weight, unless otherwise stated or understood from the context.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

It should be understood that the order of steps or order for performing certain actions is immaterial so long as the present invention remains operable. Moreover, two or more steps or actions may be conducted simultaneously.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s).

For example, it will be appreciated that all features described and depicted herein can be applicable to all aspects of the invention(s) described and depicted herein.

II. OX40 Antibodies

Figures 20A, 20B:
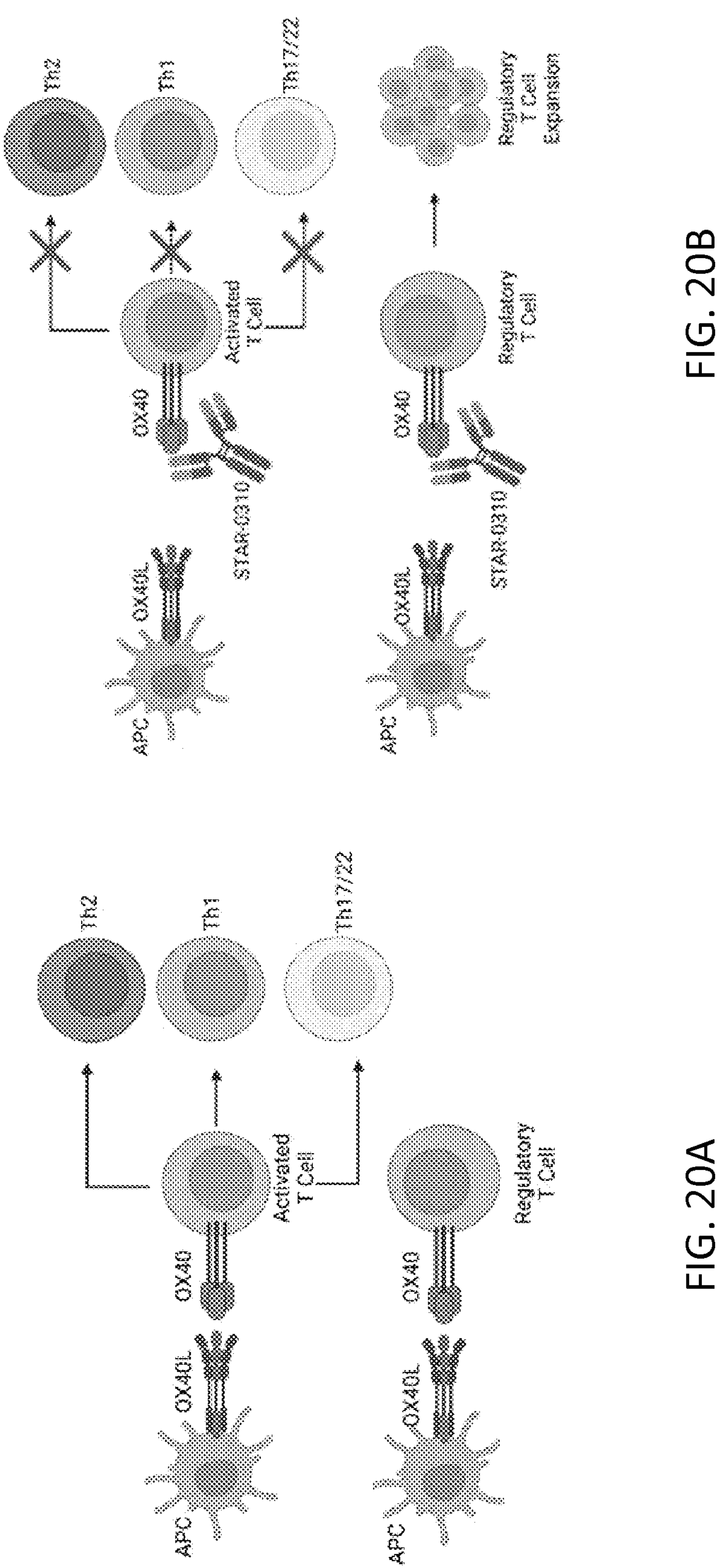
FIG. 20A shows a schematic of the OX40-OX40L costimulation signaling pathway and its effect on activated T cells and regulatory T cells.
FIG. 20B provides a schematic of how MAB10 may target the OX40 receptor, impacting Th1, Th2 and Th17/22 pathways, and preserving the regulatory T cells.

The co-stimulatory T-cell receptor OX40 is predominantly expressed on effector and regulatory T-cells. Its ligand, OX40L, is expressed on activated antigen-presenting cells, including dendritic cells, endothelial cells, macrophages, and activated B-cells. OX40-OX40L engagement is key to potentiating the expansion of effector T-cells and the prolongation of their survival by suppressing apoptosis, enhancing T-cell effector functions, such as cytokine production, and generating T helper memory cells. OX40 co-stimulation inhibits regulatory T cell induction via multiple mechanisms (FIG. 20A). Without wishing to be bound by theory, the antibodies provided herein, such as MAB1 and MAB10, target the OX40 receptor, impacting Th1, Th2 and Th17/22 pathways and preserving the regulatory T cells (FIG. 20B).

In general, an antibody is a glycoprotein comprising at least two heavy (H) chains and two light (L) chains interconnected by disulfide bonds. Each heavy chain is comprised of a heavy chain variable region (abbreviated herein as VH) and a heavy chain constant region. The heavy chain constant region comprises three domains, CH1, CH2 and CH3. Each light chain is comprised of a light chain variable region (abbreviated herein as VL) and a light chain constant region. The light chain constant region comprises one domain, CL. The VH and VL regions can be further subdivided into regions of hypervariability, termed complementarity determining regions (CDRs), which are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Heavy chain CDRs 1, 2, and 3 may be referred to herein as HCDR1, HCDR2, and HCDR3, respectively, for example, or CDR-H1, CDR-H2, and CDR-H3, respectively, for example. Light chain CDRs 1, 2, and 3 may be referred to herein as LCDR1, LCDR2, and LCDR3, respectively, for example, or CDR-L1, CDR-L2, and CDR-L3, respectively, for example. The amino acid sequences of FR1, FR2, FR3, and FR4 all together constitute the "non-CDR region" or "non-extended CDR region" of VH or VL as referred to herein. The VH and VL regions together define an antigen binding site.

A "heavy chain variable framework region" as referred herein may comprise one or more (e.g., one, two, three and/or four, preferably four) heavy chain variable framework region sequences (e.g., framework 1 (FR1), framework 2 (FR2), framework 3 (FR3) and/or framework 4 (FR4)). A "light chain variable framework region" as referred herein may comprise one or more (e.g., one, two, three and/or four, preferably four) light chain framework region sequences (e.g., framework 1 (FR1), framework 2 (FR2), framework 3 (FR3) and/or framework 4 (FR4)).

The variable regions of the heavy and light chains contain a binding site or binding domain that interacts with an antigen. The constant regions of the antibodies may mediate the binding of the immunoglobulin to host tissues or factors, including various cells of the immune system (e.g., effector cells) and the First component (C1q) of the classical complement system.

The phrases "full length antibody" and "intact antibody" include a structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region. It is contemplated that antigen-binding fragments of a given antibody include, for example, a Fab fragment, a Fab' fragment, a $(Fab')_2$ fragment, a Fv fragment, a single chain Fv molecule (e.g., scFv), minibody, diabody, and triabody.

An antibody or antigen binding fragment thereof that binds to OX40 refers to an intact antibody or an antigen binding fragment thereof that binds to OX40, e.g., human OX40. The antibody or antigen binding fragment thereof preferably has a binding affinity ($K_D$) for OX40, e.g., human OX40, of 500 nM or stronger, 200 nM or stronger, 150 nM or stronger, 125 nM or stronger, 100 nM, 75 nM, 50 nM, 25 nM, 10 nM, 6 nM or stronger.

The phrase "antagonistic antibody and antigen binding fragments thereof," and similar phrases, in the context of the specification refers to an antibody or antigen binding fragment capable of inhibiting and/or neutralizing the biological signaling activity of OX40, e.g., by blocking binding or substantially reducing the binding of OX40 to OX40 ligand and thus inhibiting or reducing the signalization pathway triggered by OX40 and/or inhibiting or reducing an OX40-mediated cell response like lymphocyte proliferation, cytokine expression, or lymphocyte survival.

A "chimeric antibody" refers to an antibody in which the variable region sequences are derived from one species and the constant region sequences are derived from another species, such as an antibody in which the variable region sequences are derived from a mouse antibody and the constant region sequences are derived from a human antibody.

A "humanized antibody" refers to antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

Antibodies or antigen binding fragments of antibodies as disclosed herein may be isolated antibodies or antigen binding fragments, e.g., removed from their natural environment. For example, antibodies or binding fragments thereof may be removed from, for example, a cell, tissue, body fluid, or animal body, for example, by various purification techniques.

For all human immunoglobulins, the heavy chain constant domains and the human kappa immunoglobulin light chain constant domain numbering is according to the "EU numbering system" (Edelman et al. (1969) Proc. Natl. Acad. Sci. USA, 63(1): 78-85). For the human lambda immunoglobulin light chain constant domains (IGLC1, IGLC2, IGLC3, IGLC6, and IGLC7), numbering is according to the "Kabat numbering system" (Kabat et al. (1991) Sequences of Proteins of Immunological Interest. 5th Edition—US Department of Health and Human Services, NIH publication n°

91-3242) as described by Dariavach et al. (1987) Proc. Natl. Acad. Sci. USA, 84(24): 9074-8 and Frangione et al. (1985) Proc. Natl. Acad. Sci. USA, 82(10): 3415-9.

In naturally occurring antibodies, the antigen-binding site typically consists of two variable domains that define specificity: one located in the heavy chain (VH) and the other located in the light chain (VL). In some cases, specificity may exclusively reside in only one variable domain as in single-domain antibodies from heavy-chain antibodies found in camelids. The amino acid sequence boundaries of the CDRs in the VH and VL domains can be determined by one of skill in the art using any of a number of known numbering schemes, including those described by Kabat et al., supra ("Kabat" numbering scheme); Al-Lazikani et al. (1997) J. Mol. Biol., 273: 927-948 ("Chothia" numbering scheme); Martin (Enhanced Chothia or AbM) Abhinandan and Martin (2008) Mol. Immunol., 45(14): 3832-9; MacCallum et al. (1996) J. Mol. Biol., 262: 732-745 ("Contact" numbering scheme); Lefranc et al. (2003) Dev. Comp. Immunol., 27: 55-77 ("IMGT" numbering scheme); and Honegger and Pluckthun (2001) J. Mol. Biol., 309: 657-70 ("AHo" numbering scheme).

The Kabat defined CDRs are based on sequence variability and is the most commonly used (Kabat et al., supra). The Chothia defined CDRs instead are based on the location of the structural loops (Chothia & Lesk (1987) J. Mol. Biol., 196: 901-917). The AbM defined CDRs are a compromise between the Kabat and Chothia numbering schemes and are used by Oxford Molecular's AbM antibody modelling software (Martin et al. (1989) Proc. Natl. Acad. Sci. USA, 86: 9268-72; Martin et al. (1991) Methods Enzymol., 203: 121-153; Pedersen et al. (1992) Immunomethods, 1: 126-136; Rees et al. (1996) In Sternberg M. J. E. (ed.), Protein Structure Prediction. Oxford University Press, Oxford, 141-172). The contact defined CDRs are based on an analysis of the available complex structures available in the Protein Databank (MacCallum et al. (1996) J. Mol. Biol., 262: 732-745). The IMGT®, the "international ImMunoGeneTics information System®" (www.imgt.org) defined CDRs are based on the IMGT numbering for all immunoglobulin and T cell receptor V-REGIONs of all species (IMGT®, the international ImMunoGeneTics information System®; Lefranc et al. (1991) Nucleic Acids Res., 27(1): 209-12; Ruiz et al. (2000) Nucleic Acids Res., 28(1): 219-21; Lefranc (2001) Nucleic Acids Res., 29(1): 207-9; Lefranc (2003) Nucleic Acids Res., 31(1): 307-10; Lefranc et al. (2005) Dev. Comp. Immunol., 29(3): 185-203; Kaas et al. (2007) Briefings in Functional Genomics & Proteomics, 6(4): 253-64). Alternatively, the CDRs can be defined according to Honegger's numbering scheme that is based on structural alignment of an antibody's three dimensional features (AHo; Honegger et al. (2001) J. Mol. Biol., 309: 657-70). A comparison of the various numbering systems is described in Dondelinger et al. (2018) Front. Immunol., 9: 2278. Table 1 provides the positions of CDR-L1, CDR-L2, CDR-L3, CDR-H1, CDR-H2, and CDR-H3 as identified by the Kabat, Chothia, AbM, Contact, and IMGT schemes. For CDR-H1, residue numbering is provided using both the Kabat and Chothia numbering schemes.

Antibody sequences, domain numbering, and CDRs may be assigned, for example, using antibody numbering software, such as Abnum, available at bioinf.org.uk/abs/abnum/, and described in Abhinandan and Martin (2008) Immunology, 45: 3832-3839; AbYsis available at abysis.org/abysis/index.html; or ANARCI, available at opig.stats.ox.ac.uk/webapps/sabdab-sabpred/sabpred/anarci/and described in Dunbar et al. (2016) Nucleic Acids Res., 44: W474-W478. Descriptions of the various antibody numbering schemes are also available at bioinf.org.uk/abs/info.html.

TABLE 1

Residues in CDRs according to the indicated numbering schemes

| CDR | Kabat | Chothia | AbM | Contact | IMGT | AHo |
|---|---|---|---|---|---|---|
| L1 | L24-L34 | L24-L34 | L24-L34 | L30-L36 | L27-L32 | L25-40 |
| L2 | L50-L56 | L50-L56 | L50-L56 | L46-L55 | L50-L51 | L58-77 |
| L3 | L89-L97 | L89-L97 | L89-L97 | L89-L96 | L89-L97 | L109-137 |
| H1 (Kabat Numbering) | H31-H35B | H26-H32 or H34* | H26-H35B | H30-H35B | H26-H35B | H25-40 |
| H1 (Chothia/Martin Numbering) | H31-H35 | H26-H32 | H26-H35 | H30-H35 | H26-H33 | H25-40 |
| H2 | H50-H65 | H52-H56 | H50-H58 | H47-H58 | H51-H56 | H58-77 |
| H3 | H95-H102 | H95-H102 | H95-H102 | H93-H101 | H93-H102 | H109-137 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

Antibodies are grouped into classes, also referred to as isotypes, as determined genetically by the constant region. Human constant light chains are classified as kappa (CK) and lambda (Cλ) light chains. Heavy chains are classified as mu (μ) delta (δ), gamma (γ), alpha (α), or epsilon (ε), and define the antibody's isotype as IgM, IgD, IgG, IgA, and IgE, respectively. Thus, "isotype" as used herein is meant any of the classes and/or subclasses of immunoglobulins defined by the chemical and antigenic characteristics of their constant regions.

As used herein, unless otherwise indicated, the terms "immunoglobulin Fc domain", "Fc," "Fc domain," "Fc region" refers to a fragment of an immunoglobulin heavy chain constant region which, either alone or in combination with a second immunoglobulin Fc domain, is capable of binding to an Fc receptor. An immunoglobulin Fc domain may include, e.g., immunoglobulin CH2 and CH3 domains. An immunoglobulin Fc domain may include, e.g., immunoglobulin CH2 and CH3 domains and an immunoglobulin hinge region. Boundaries between immunoglobulin hinge regions, CH2, and CH3 domains are well known in the art, and can be found, e.g., in the PROSITE database (available on the world wide web at prosite.expasy.org). Unless otherwise specified herein, numbering of amino acid residues in the Fc region or constant region is according to the EU numbering system, also called the EU index, as described in Kabat et al., SEQUENCES OF PROTEINS OF IMMUNOLOGICAL INTEREST, 5TH ED. Public Health Service, National Institutes of Health, Bethesda, MD, 1991 and Edelman et al. (1969) PROC NATL ACAD SCI USA, 63(1): 78-85. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. Fc can refer to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. The IgG class is the most commonly used for therapeutic purposes. In humans this class comprises subclasses IgG1, IgG2, IgG3 and IgG4. In mice this class comprises subclasses IgG1, IgG2a, IgG2b, IgG2c and IgG3.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., IMMUNO BIOLOGY: THE IMMUNE SYSTEM IN HEALTH AND DISEASE, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daeron (1997) ANNU. REV. IMMUNOL., 15: 203-234). FcRs are reviewed in Ravetch and Kinet (1991) ANNU. REV. IMMUNOL., 9: 457-92; Capel et al. (1994) IMMUNOMETHODS, 4: 25-34; and de Haas et al. (1995) J. LAB. CLIN. MED., 126: 330-41.

The IgG Fc region can further comprise one or more mutations that modulates (e.g., increases) its binding to the Neonatal Fc Receptor (FcRn), thereby to extend the serum half-life of the OX40 antibody. Such mutations are known in the art and reviewed by Ramdani et al. (2022) INT. J. MOL. SCI., 23(17): 9604, as well as U.S. Pat. Nos. 9,803,023, and 8,394,925. In certain embodiments, the one or more mutations comprise M252Y, S254T, and T256E ("YTE"); M428L and N434S (Xtend™, "LS"); H433K and N434F (NHance®); M252Y and T256D; T250Q and M428L; T307A, E380A, and N434A; T256D and T307Q, or T256D and T307W. These residues are according to the EU numbering index. Modifications that extend the serum half-life of the OX40 antibody (e.g., YTE mutations) may permit less frequent dosing of the antibody as a therapeutic and/or more durable inhibition of undesirable T cell activation and/or proliferation, as well as promote reductions in ADCC (antibody dependent cell-mediated cytotoxicity) (Dall'Acqua, et al. (2006) J. BIOL. CHEM 281(33): 23514-23524). Less frequent dosing with an antibody that comprises a serum half-life extension modification as compared to the parental antibody or a control antibody can be, for example, every two to three months.

The term "effector function" as used herein includes a biochemical event that results from the interaction of an antibody Fc region with an Fc receptor or ligand. Effector functions include FcγR-mediated effector functions such as ADCC (antibody dependent cell-mediated cytotoxicity) and ADCP (antibody dependent cell-mediated phagocytosis), and complement-mediated effector functions such as CDC (complement dependent cytotoxicity). Depending upon the circumstances, ADCC-mediated killing of immune cells (e.g., T cells) can result in release of cytokines and other immune modulatory molecules. This release can cause pyrexia and chills in the subject. An effector function of an antibody may be altered by altering, i.e., enhancing or reducing, preferably enhancing, the affinity of the antibody for an effector molecule such as an Fc receptor (FcR) or a complement component. Binding affinity will generally be varied by modifying the effector molecule binding site, and in this case, it is appropriate to locate the site of interest and modify at least part of the site in a suitable way. It is also envisaged that an alteration in the binding site on the antibody for the effector molecule need not alter significantly the overall binding affinity but may alter the geometry of the interaction rendering the effector mechanism ineffective as in non-productive binding. It is further envisaged that an effector function may also be altered by modifying a site not directly involved in effector molecule binding, but otherwise involved in performance of the effector function. By altering an effector function of an antibody it may be possible to control various aspects of the immune response, e.g., enhancing or suppressing various reactions of the immune system, with possible beneficial effects in diagnosis and therapy.

It is understood that modifications in the CH2 domain can affect the binding of FcRs to the Fc. A number of amino acid modifications in the Fc region are known in the art for selectively altering the affinity of the Fc for different Fc-gamma (Fcγ) receptors (FcγR or FcR).

Exemplary mutations that alter the binding of FcRs to the Fc are listed below:

i. S298A/E333A/K334A, S298A/E333A/K334A/K326A (Lu et al. (2011) J. IMMUNOL. METHODS, 365(1-2): 132-41);
ii. F243L/R292P/Y300L/V305I/P396L, F243L/R292P/Y300L/L235V/P396L (Stavenhagen et al. (2007) Cancer Res., 67(18): 8882-90; Nordstrom et al. (2011) Breast Cancer Res., 13(6): R123);
iii. F243L (Stewart et al. (2011) Protein Eng Des Sel., 24(9): 671-8.), S298A/E333A/K334A (Shields et al. (2001) J. Biol. Chem., 276(9): 6591-604);
iv. S239D/I332E/A330L, S239D/I332E (Lazar et al. (2006) Proc. Natl. Acad. Sci. USA, 103(11): 4005-10);
v. S239D/S267E, S267E/L328F (Chu et al. (2008) Mol. Immunol., 45(15): 3926-33);
vi. S239D/D265S/S298A/I332E, S239E/S298A/K326A/A327H, G237F/S298A/A33 OL/I332E, S239D/I332E/S298A, S239D/K326E/A330L/I332E/S298A, G236A/S239D/D270L/I332E, S239E/S267E/H268D, L234F/S267E/N325L, G237F/V266L/S267D and other mutations listed in WO2011/120134 and WO2011/120135. THERAPEUTIC ANTIBODY ENGINEERING (by William R. Strohl and Lila M. Strohl, Woodhead Publishing series in Biomedicine No 11, ISBN 1 907568 37 9, October 2012) lists mutations on page 283;
vii. M252Y, S254T, and T256E ("YTE"; Dall'Acqua, et al. (2002), J. IMMUNOL., 169: 5171-5180 and Dall'Acqua, et al. (2006) J. BIOL. CHEM 281(33): 23514-23524); and
viii. M428L and N434S ("LS"; Zalevsky, et al. (2010) Nat BIOTECHNOL 28: 157-159).

Fc modifications reducing FcγR and/or complement binding and/or effector function are known in the art. Strategies that have been used to engineer antibodies with reduced or silenced effector activity are discussed in Strohl (2009) Curr. Opin. Biotech., 20: 685-691, and Strohl, W R and Strohl L M (2012) "Antibody Fc engineering for optimal antibody performance" In Therapeutic Antibody Engineering, Cambridge: Woodhead Publishing, pp 225-249. These strategies include reduction of effector function through modification of glycosylation, use of IgG2/IgG4 scaffolds, or the introduction of mutations in the hinge or CH2 regions of the Fc. For example, U.S. Patent Publication No. 2011/0212087 (Strohl), International Patent Publication No. WO 2006/105338 (Xencor), U.S. Patent Publication No. 2012/0225058 (Xencor), U.S. Patent Publication No. 2012/0251531 (Genentech), International Application Publication No. WO1999/051642, and Strop et al. (2012) J. Mol. Biol., 420: 204-219), describe exemplary specific Fc modifications to reduce FcγR or complement binding to the Fc. For example, in certain embodiments, the one or more mutations comprise N297A, N297G, or N297Q mutation. In certain embodiments, the one or more mutations comprises or further comprises L234A and L235A (LALA) mutations, L234A, L235A, and P329A (LALAPA) mutations, L234A, L235A, and P329G (LALAPG) mutations, or L234A, L235E, G237A, A330S, and P331S (LALEGAASPS) mutations.

Specific, non-limiting examples of known amino acid modifications to reduce FcγR or complement binding to the Fc include those identified in the following Table 2:

TABLE 2

| Modifications to reduce FcγR or complement binding to the Fc Mutations |
| --- |
| N297A |
| L234A/L235A |
| IgG2 V234A/G237A |
| IgG4 L235A/G237A/E318A |
| IgG4 S228P/L236E |
| IgG2 H268Q/V309L/A330S/A331S |
| C220S/C226S/C229S/P238S |
| C226S/C229S/E3233P/L235V/L235A |
| L234F/L235E/P331S |
| Hinge mutant, C226S/P230S |
| M252Y, S254T, and T256E ("YTE") |
| M428L and N434S ("LS") |

Methods of producing antibodies with little or no fucose on the Fc glycosylation site (Asn 297 EU numbering, N297) without altering the amino acid sequence are well known in the art. The GlymaxX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology, 20(12): 1607-1618.) Examples of cell lines capable of producing defucosylated antibody include CHO-DG44 with stable overexpression of the bacterial oxidoreductase GDP-6-deoxy-D-lyxo-4-hexylose reductase (RMD) (see von Horsten et al., supra) or Lec13 CHO cells, which are deficient in protein fucosylation (see Ripka et al. (1986) Arch. Biochem. Biophys., 249: 533-545; U.S. Patent Publication No. 2003/0157108; WO 2004/056312), and knockout cell lines, such as alpha-1,6-fucosyltransferase gene or FUT8 knockout CHO cells (see Yamane-Ohnuki et al. (2004) Biotech. Bioeng., 87: 614-622; Kanda et al. (2006) Biotechnol. Bioeng., 94: 680-688; and WO 2003/085107). Another approach to obtaining antibodies with lowered levels of fucosylation can be found in U.S. Pat. No. 8,409,572, which teaches selecting cell lines for antibody production for their ability to yield lower levels of fucosylation on antibodies.

Antibodies can be fully afucosylated (meaning they contain no detectable fucose) or they can be partially afucosylated, meaning that the antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

Antibodies described herein can be engineered to contain an IgG1 domain with reduced levels of, or no, fucose at position Asn 297 (N297) compared to a naturally occurring IgG1 domain. Such Fc domains are known to have improved ADCC. See Shields et al. (2002) J. Biol. Chem., 277:26733-26740. The amount of fucose may be determined using any suitable method, for example as described in WO 2008/077546.

Antibody Variable Regions and Heavy and Light Chains

In one aspect, the disclosure provides an OX40 antibody or antigen-binding fragment thereof that comprises a variable heavy (VH) chain sequence comprising the amino acid sequence set forth in SEQ ID NO:7, and/or a variable light (VL) chain sequence comprising the amino acid sequence set forth in SEQ ID NO:8, 12, 15, 18, 21, 24, 27, 30, or 33.

In one aspect, the disclosure provides an OX40 antibody or antigen-binding fragment thereof that comprises a variable heavy (VH) chain sequence comprising the amino acid sequence set forth in SEQ ID NO:7, and a variable light (VL) chain sequence comprising the amino acid sequence set forth in SEQ ID NO:8, 12, 15, 18, 21, 24, 27, 30, or 33.

In certain embodiments, the disclosure provides an OX40 antibody or antigen-binding fragment thereof comprising a variable heavy (VH) chain sequence comprising the amino acid sequence set forth in SEQ ID NO:7.

In certain embodiments, the disclosure provides an OX40 antibody or antigen-binding fragment thereof comprising a variable light (VL) chain sequence comprising the amino acid sequence set forth in SEQ ID NO:8.

In certain embodiments, the disclosure provides an OX40 antibody or antigen-binding fragment thereof comprising a variable light (VL) chain sequence comprising the amino acid sequence set forth in SEQ ID NO:12.

In certain embodiments, the disclosure provides an OX40 antibody or antigen-binding fragment thereof comprising a variable light (VL) chain sequence comprising the amino acid sequence set forth in SEQ ID NO:15.

In certain embodiments, the disclosure provides an OX40 antibody or antigen-binding fragment thereof comprising a variable light (VL) chain sequence comprising the amino acid sequence set forth in SEQ ID NO:18.

In certain embodiments, the disclosure provides an OX40 antibody or antigen-binding fragment thereof comprising a variable light (VL) chain sequence comprising the amino acid sequence set forth in SEQ ID NO:21.

In certain embodiments, the disclosure provides an OX40 antibody or antigen-binding fragment thereof comprising a variable light (VL) chain sequence comprising the amino acid sequence set forth in SEQ ID NO:24.

In certain embodiments, the disclosure provides an OX40 antibody or antigen-binding fragment thereof comprising a variable light (VL) chain sequence comprising the amino acid sequence set forth in SEQ ID NO:27.

In certain embodiments, the disclosure provides an OX40 antibody or antigen-binding fragment thereof comprising a variable light (VL) chain sequence comprising the amino acid sequence set forth in SEQ ID NO:30.

In certain embodiments, the disclosure provides an OX40 antibody or antigen-binding fragment thereof comprising a variable light (VL) chain sequence comprising the amino acid sequence set forth in SEQ ID NO:33.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:8.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:12.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:15.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:18.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:21.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:24.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:27.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:30.

In certain embodiments, the disclosure provides an OX40 antibody or antigen-binding fragment thereof comprising a variable heavy (VH) chain sequence comprising the amino acid sequence set forth in SEQ ID NO:7, and a variable light (VL) chain sequence comprising the amino acid sequence set forth in SEQ ID NO:33.

In another aspect, the disclosure provides variants of the OX40 antibodies disclosed herein where amino acid alterations (e.g., 1, 2, 3, 4, 5, 6, 7, 8, 9, or 10 total amino acid alterations) are present across the framework regions of the variable heavy (VH) chain sequence as compared to a variable heavy (VH) chain sequence disclosed herein, e.g., SEQ ID NO:7, and/or where amino acid alterations (e.g., 1, 2, 3, 4, 5, 6, 7, 8, 9, or 10 total amino acid alterations) are present across the framework regions of the variable light (VL) chain sequence as compared to a variable light (VL) chain sequence disclosed herein, e.g., SEQ ID NO:8. The alterations may be conservative substitutions of amino acids in the framework regions, or non-conservative substitutions of amino acids in the framework regions, or amino acid deletions in the framework regions, or amino acid insertions in the framework regions, or combinations thereof. For example, there may be 1-10, e.g., 1-5, e.g., 1 or 2, total amino acid alterations, e.g., substitutions, across the framework regions of the variable heavy (VH) chain sequence. For example, there may be 1-10, e.g., 1-5, e.g., 1 or 2, total amino acid alterations across the framework regions of the variable light (VL) chain. Pairwise alignment using the default settings of the AlignX module of Vector NTI v.9.0.0 (Invitrogen Corp., Carlsbad, Calif.) or other suitable alignment software, such as BLAST, CLUSTAL, or BLOSUM, may be used to identify the number of amino acid alterations that have been made in frameworks regions of a variable heavy or variable light chain as compared to a variable heavy (VH) or variable light (VL) chain reference sequence.

In certain embodiments, the disclosure provides an OX40 antibody or antigen-binding fragment thereof that comprises a variable heavy (VH) chain comprising the amino acid sequence set forth in SEQ ID NO:7, except that the variable heavy (VH) chain contains 1, 2, 3, 4, or 5, total amino acid modifications (e.g., 1 or 2 total modifications, e.g., substitutions) across the variable heavy chain framework regions, and a variable light (VL) chain comprising the amino acid sequence set forth in SEQ ID NO:8.

In certain embodiments, the disclosure provides an OX40 antibody or antigen-binding fragment thereof that comprises a variable heavy (VH) chain comprising the amino acid sequence set forth in SEQ ID NO:7, and comprises a variable light (VL) chain comprising the amino acid sequence set forth in SEQ ID NO:8, except that the light chain contains 1, 2, 3, 4, or 5 total amino acid modifications (e.g., 1 or 2 total modifications, e.g., substitutions) across the light chain framework regions.

In certain embodiments, the disclosure provides an OX40 antibody or antigen-binding fragment thereof that comprises a variable heavy (VH) chain comprising the amino acid sequence set forth in SEQ ID NO:7, except that the variable heavy (VH) chain contains 1, 2, 3, 4, or 5, total amino acid modifications (e.g., 1 or 2 total modifications, e.g., substitutions) across the variable heavy chain framework regions, and a variable light (VL) chain comprising the amino acid sequence set forth in SEQ ID NO:8, except that the light chain contains 1, 2, 3, 4, or 5 total amino acid modifications (e.g., 1 or 2 total modifications, e.g., substitutions) across the light chain framework regions.

In certain embodiments, the disclosure provides an OX40 antibody or antigen-binding fragment thereof that comprises a variable heavy (VH) chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:7, where the sequence variation is limited to the heavy chain framework regions, and a variable light (VL) chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:8, where the sequence variation is limited to the light chain framework and constant regions.

In certain embodiments, the disclosure provides an OX40 antibody or antigen-binding fragment thereof that comprises a variable heavy (VH) chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:7, where the sequence variation is limited to the heavy chain framework regions, and a variable light (VL) chain comprising the amino acid sequence set forth in SEQ ID NO:8.

In certain embodiments, the disclosure provides an OX40 antibody or antigen-binding fragment thereof that comprises a variable heavy (VH) chain comprising the amino acid sequence set forth in SEQ ID NO:7, and a variable light (VL) chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:8, where the sequence variation is limited to the light chain framework and constant regions.

In certain embodiments, the disclosure provides an OX40 antibody or antigen-binding fragment thereof that comprises a variable heavy (VH) chain sequence comprising the heavy chain CDR1, the heavy chain CDR2, and the heavy chain CDR3 of the amino acid sequence set forth in SEQ ID NO:7, and the light chain CDR1, the light chain CDR2, and the light chain CDR3 of a variable light (VL) chain sequence comprising the amino acid sequence set forth in SEQ ID NO:8, 12, 15, 18, 21, 24, 27, 30, or 33, e.g., SEQ ID NO:8. In some embodiments, the variable heavy chain sequence may further comprise at least 90%, at least 91%, at least 92%, at least 93%, at least 94%, at least 95%, at least 96%, at least 97%, at least 98%, at least 99%, greater than 99% but less than 100%, or 100% sequence identity, e.g., at least 99%, with the amino acid sequence of the heavy chain variable region set forth in SEQ ID NO:7, wherein any sequence variation is found in the framework regions, and/or the light chain variable region may further comprise an amino acid sequence having at least 95%, at least 96%, at least 97%, at least 98%, at least 99%, or greater than 99% but less than 100%, or 100% sequence identity, e.g., at least 99% with the amino acid sequence of the light chain variable region set forth in SEQ ID NO: 8, 12, 15, 18, 21, 24, 27, 30, or 33, e.g., SEQ ID NO:8, wherein any sequence variation is found in the framework regions. In other embodiments, the heavy chain variable region further comprises the amino acid sequence of the heavy chain variable region set forth in SEQ ID NO:7 except that there is/are 1, 2, 3, 4, 5, 6, 7, 8, 9, or 10 total amino acid modifications (e.g., substitutions, e.g., conservative substitutions, e.g., deletions) in the heavy chain variable framework regions, e.g., 1 or 2 modifications, and/or the light chain variable region further comprises the amino acid sequence of the light chain variable region set forth in SEQ ID NO: 8, 12, 15, 18, 21, 24, 27, 30, or 33, e.g., SEQ ID NO:8, except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the light chain variable framework regions. The CDRs may be defined by the Kabat definition. The CDRs may be defined by the Chothia definition. The CDRs may be defined by the AbM definition. The CDRs may be defined by the IMGT definition. The CDRs may be defined by the Contact definition. The CDRs may be defined by the AHo definition.

In another aspect, the disclosure provides an OX40 antibody or antigen-binding fragment thereof that comprises a heavy chain sequence comprising the amino acid sequence set forth in SEQ ID NO:9, and/or a light chain sequence comprising the amino acid sequence set forth in SEQ ID NO:10, 13, 16, 19, 22, 25, 28, 31 or 34.

In another aspect, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:10, 13, 16, 19, 22, 25, 28, 31 or 34.

In certain embodiments, the disclosure provides an OX40 antibody or antigen-binding fragment thereof that comprises a heavy chain sequence comprising the amino acid sequence set forth in SEQ ID NO:9.

In certain embodiments, the disclosure provides an OX40 antibody or antigen-binding fragment thereof that comprises a light chain sequence comprising the amino acid sequence set forth in SEQ ID NO:10.

In certain embodiments, the disclosure provides an OX40 antibody or antigen-binding fragment thereof that comprises a light chain sequence comprising the amino acid sequence set forth in SEQ ID NO:13.

In certain embodiments, the disclosure provides an OX40 antibody or antigen-binding fragment thereof that comprises a light chain sequence comprising the amino acid sequence set forth in SEQ ID NO:16.

In certain embodiments, the disclosure provides an OX40 antibody or antigen-binding fragment thereof that comprises a light chain sequence comprising the amino acid sequence set forth in SEQ ID NO:19.

In certain embodiments, the disclosure provides an OX40 antibody or antigen-binding fragment thereof that comprises a light chain sequence comprising the amino acid sequence set forth in SEQ ID NO:22.

In certain embodiments, the disclosure provides an OX40 antibody or antigen-binding fragment thereof that comprises a light chain sequence comprising the amino acid sequence set forth in SEQ ID NO:25.

In certain embodiments, the disclosure provides an OX40 antibody or antigen-binding fragment thereof that comprises a light chain sequence comprising the amino acid sequence set forth in SEQ ID NO:28.

In certain embodiments, the disclosure provides an OX40 antibody or antigen-binding fragment thereof that comprises a light chain sequence comprising the amino acid sequence set forth in SEQ ID NO:31.

In certain embodiments, the disclosure provides an OX40 antibody or antigen-binding fragment thereof that comprises a light chain sequence comprising the amino acid sequence set forth in SEQ ID NO:34.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:10.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:13.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:16.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:19.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:22.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:25.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:28.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:31.

In certain embodiments, the disclosure provides an OX40 antibody or antigen-binding fragment thereof that comprises a heavy chain sequence comprising the amino acid sequence set forth in SEQ ID NO:9, and a light chain sequence comprising the amino acid sequence set forth in SEQ ID NO:34.

In another aspect, the disclosure provides an OX40 antibody or antigen-binding fragment thereof that comprises a heavy chain sequence comprising the amino acid sequence set forth in SEQ ID NO:73, and/or a light chain sequence comprising the amino acid sequence set forth in SEQ ID NO:10, 13, 16, 19, 22, 25, 28, 31 or 34.

In another aspect, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:10, 13, 16, 19, 22, 25, 28, 31 or 34.

In certain embodiments, the disclosure provides an OX40 antibody or antigen-binding fragment thereof that comprises a heavy chain sequence comprising the amino acid sequence set forth in SEQ ID NO:73.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:10.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:13.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:16.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:19.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:22.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:25.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:28.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:31.

In certain embodiments, the disclosure provides an OX40 antibody or antigen-binding fragment thereof that comprises a heavy chain sequence comprising the amino acid sequence set forth in SEQ ID NO:73, and a light chain sequence comprising the amino acid sequence set forth in SEQ ID NO:34.

In another aspect, the disclosure provides variants of the OX40 antibodies disclosed herein where amino acid alterations (e.g., 1, 2, 3, 4, 5, 6, 7, 8, 9, or 10 total amino acid alterations) are present across the framework and constant region of the heavy chain as compared to a heavy chain sequence disclosed herein, e.g., SEQ ID NO:73 or SEQ ID NO:9; and/or where amino acid alterations (e.g., 1, 2, 3, 4, 5, 6, 7, 8, 9, or 10 total amino acid alterations) are present across the framework and constant regions of the light chain as compared to a light chain sequence disclosed herein, e.g., SEQ ID NO:10. The alterations may be conservative substitutions of amino acids in the framework or constant regions, or non-conservative substitutions of amino acids in the framework or constant regions, or amino acid deletions in the framework or constant regions, or amino acid insertions in the framework or constant regions, or combinations thereof. For example, there may be 1-10, e.g., 1-5, total amino acid alterations, e.g., substitutions, across the framework and constant regions of the heavy chain. For example, there may be 1-10, e.g., 1-5, total amino acid alterations across the framework and constant region of the light chain. Pair wise alignment using the default settings of the AlignX module of Vector NTI v.9.0.0 (Invitrogen Corp., Carlsbad, Calif.) or other suitable alignment software, such as BLAST, CLUSTAL, or BLOSUM, may be used to identify the number of amino alterations that have been made in a heavy or light chain sequence as compared to a heavy or light chain reference sequence.

In certain embodiments, the disclosure provides an OX40 antibody or antigen-binding fragment thereof that comprises a heavy chain comprising the amino acid sequence set forth in SEQ ID NO:73, except that the heavy chain contains 1, 2, 3, 4, 5, 6, 7, 8, 9, or 10 total amino acid modifications (e.g., 1, 2, 3, 4, or 5 total modifications, e.g., substitutions) across the heavy chain framework and constant regions, and a light chain comprising the amino acid sequence set forth in SEQ ID NO:10.

In certain embodiments, the disclosure provides an OX40 antibody or antigen-binding fragment thereof that comprises a heavy chain comprising the amino acid sequence set forth in SEQ ID NO:73, and comprises a light chain sequence comprising the amino acid sequence set forth in SEQ ID NO:10, except that the light chain contains 1, 2, 3, 4, 5, 6, 7, 8, 9, or 10 total amino acid modifications (e.g., 1, 2, 3, 4, or 5 total modifications, e.g., substitutions) across the light chain framework and constant regions.

In certain embodiments, the disclosure provides an OX40 antibody or antigen-binding fragment thereof that comprises a heavy chain comprising the amino acid sequence set forth in SEQ ID NO:73, except that the heavy chain contains 1, 2, 3, 4, 5, 6, 7, 8, 9, or 10 total amino acid modifications (e.g., 1, 2, 3, 4, or 5 total modifications, e.g., substitutions) across the heavy chain framework and constant regions, and comprises a light chain comprising the amino acid sequence set forth in SEQ ID NO:10, except that the light chain contains 1, 2, 3, 4, 5, 6, 7, 8, 9, or 10 total amino acid modifications (e.g., 1, 2, 3, 4, or 5 total modifications, e.g., substitutions) across the light chain framework and constant regions.

In certain embodiments, the disclosure provides an OX40 antibody or antigen-binding fragment thereof that comprises a heavy chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:73, where the sequence variation is limited to the heavy chain framework and constant regions, and a light chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:10, where the sequence variation is limited to the light chain framework and constant regions.

In certain embodiments, the disclosure provides an OX40 antibody or antigen-binding fragment thereof that comprises a heavy chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:73, where the sequence variation is limited to the heavy chain framework and constant regions, and a light chain comprising the amino acid sequence set forth in SEQ ID NO:10.

In certain embodiments, the disclosure provides an OX40 antibody or antigen-binding fragment thereof that comprises a heavy chain comprising the amino acid sequence set forth in SEQ ID NO:73, and a light chain comprising at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% amino acid sequence identity, e.g., 99% or greater, with the amino acid sequence set forth in SEQ ID NO:10, where the sequence variation is limited to the light chain framework and constant regions.

Variant OX40 antibody or antigen-binding fragments thereof disclosed herein may retain substantial biological activity, e.g., to specifically bind to OX40. For example, such variants may retain similar nanomolar affinity ($K_D$) for OX40 as compared to the unmodified reference antibody.

Antibody CDRs

The antibodies, or binding fragments thereof, that bind OX40, e.g., human OX40, disclosed herein may be defined by the CDR sequences of their variable regions. The CDR sequences are interposed between framework sequences which may be human or humanized, for example.

For example, the disclosure provides an antibody or antigen binding fragment thereof that binds to OX40, e.g., human OX40, that includes three heavy chain complementarity determining regions (CDRs) (CDR-H1, CDR-H2, and CDR-H3) and, three light chain CDRs (CDR-L1, CDR-L2, and CDR-L3), wherein the CDR-H1, CDR-H2, and CDR-H3 are present in a heavy chain variable domain (VH) comprising the amino acid sequence set forth in SEQ ID NO:7 and wherein the CDR-L1, CDR-L2, and CDR-L3 are present in a light chain variable domain (VL) comprising the amino acid sequence set forth in SEQ ID NO:8. The CDR-H1, CDR-H2, and CDR-H3, and the CDR-L1, CDR-L2, and CDR-L3 may be defined according to the Kabat, Chothia, IMGT, AbM, Contact or Honneger (AHo) CDR numbering systems as discussed herein, or other numbering systems known in the art.

In addition, the disclosure provides an antibody or antigen-binding fragment thereof that binds OX40, e.g., human OX40, that comprises three heavy chain CDR sequences (CDRs) (CDR-H1, CDR-H2, and CDR-H3) of a heavy chain variable domain (VH) comprising the amino acid sequence set forth in SEQ ID NO:7, and/or three light chain complementarity determining regions (CDRs) (CDR-L1, CDR-L2, and CDR-L3) of a light chain variable domain (VL) comprising the amino acid sequence set forth in SEQ ID NOs: 8, 12, 15, 18, 21, 24, 27, 30, or 33. In certain embodiments, an antibody or antigen-binding fragment thereof that binds OX40, e.g., human OX40, that comprises three heavy chain CDR sequences (CDRs) (CDR-H1, CDR-H2, and CDR-H3) of a heavy chain variable domain (VH) comprising the amino acid sequence set forth in SEQ ID NO:7, and three light chain complementarity determining regions (CDRs) (CDR-L1, CDR-L2, and CDR-L3) of a light chain variable domain (VL) comprising the amino acid sequence set forth in SEQ ID NOs: 8, 12, 15, 18, 21, 24, 27, 30, or 33. In certain embodiments, the CDRs are defined according to Kabat. In certain embodiments, the CDRs are defined according to Chothia. In certain embodiments, the CDRs are defined according to AbM. In certain embodiments, the CDRs are defined according to Contact. In certain embodiments, the CDRs are defined according to IMGT. In certain embodiments, the CDRs are defined according to AHo.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:8.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:12.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:15.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:18.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:21.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:24.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:27.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:30.

For example, the disclosure provides an antibody or antigen-binding fragment thereof that binds OX40, e.g., human OX40, that comprises three heavy chain complementarity determining sequences (CDRs) (CDR-H1, CDR-H2, and CDR-H3) of a heavy chain variable domain (VH) comprising the amino acid sequence set forth in SEQ ID NO:7, and three light chain complementarity determining sequences (CDRs) (CDR-L1, CDR-L2, and CDR-L3) of a light chain variable domain (VL) comprising the amino acid sequence set forth in SEQ ID NO:33.

In certain embodiments, the CDRs of the aforementioned antibodies are defined according to Kabat. In certain embodiments, the CDRs are defined according to Chothia. In certain embodiments, the CDRs are defined according to AbM. In certain embodiments, the CDRs are defined according to Contact. In certain embodiments, the CDRs are defined according to IMGT. In certain embodiments, the CDRs are defined according to AHo.

The disclosure also provides an antibody or antigen binding fragment thereof that binds to OX40, e.g., human OX40, that comprises a heavy chain variable region comprising a CDR-H1 comprising the amino acid sequence set forth in SEQ ID NO:1, CDR-H2 comprises the amino acid sequence set forth in SEQ ID NO:2, and a CDR-H3 comprising the amino acid sequence set forth in SEQ ID NO:3; and a light chain variable region comprising a CDR-L1 comprises the amino acid sequence set forth in SEQ ID NO:4, a CDR-L2 comprising the amino acid sequence set forth in SEQ ID NO:5, and a CDR-L3 comprising an amino acid sequence as set forth in SEQ ID NO:38, where $X_1$ is F, T, W or M; where $X_2$ is G, I, V, L, or E; where $X_3$ is A, D, E, L, H, T, or F; and where $X_4$ is W, P, F, Y, or T. In some embodiments, $X_1$ is F or T, $X_2$ is L, G, or E, $X_3$ is A, and $X_4$ is W. In some embodiments, $X_1$ is F or T. In some embodiments, $X_1$ is F. In some embodiments, $X_1$ is T. In some embodiments, $X_2$ is L, G, or E. In some embodiments, $X_2$ is G. In some embodiments, $X_2$ is L. In some embodiments, $X_3$ is A. In some embodiments, and $X_4$ is W.

The disclosure also provides an antibody or antigen binding fragment thereof that binds to OX40, e.g., human OX40, that comprises a heavy chain variable region comprising a CDR-H1 comprising the amino acid sequence set forth in SEQ ID NO:1, CDR-H2 comprises the amino acid sequence set forth in SEQ ID NO:2, and a CDR-H3 comprising the amino acid sequence set forth in SEQ ID NO:3; and a light chain variable region comprising a CDR-L1 comprises the amino acid sequence set forth in SEQ ID NO:4, a CDR-L2 comprising the amino acid sequence set forth in SEQ ID NO:5, and a CDR-L3 comprising an amino acid sequence as set forth in SEQ ID NO:71, where $X_1$ is F, T, W or M; where $X_2$ is G, I, V, L, or E; where $X_3$ is A, D, E, L, H, T, or F; and where $X_4$ is W, P, F, Y, or T. In some embodiments, $X_1$ is F or T, $X_2$ is L, G, or E, $X_3$ is A, and $X_4$ is W. In some embodiments, $X_1$ is F or T. In some embodiments, $X_1$ is F. In some embodiments, $X_1$ is T. In some embodiments, $X_2$ is L, G, or E. In some embodiments, $X_2$ is G. In some embodiments, $X_2$ is L. In some embodiments, $X_3$ is A. In some embodiments, and $X_4$ is W.

In some examples, the disclosed antibody or antigen binding fragment that binds OX40, e.g., human OX40, may include one or more of the amino acid sequences provided in Table 3, which are CDRs of the antibody or antigen binding fragment as defined by Kabat numbering. For example, the antibody or antigen binding fragment thereof may include a heavy chain variable region comprising heavy chain complementarity determining regions HCDR1, HCDR2, HCDR3, and/or a light chain variable region comprising the light chain complementarity determining regions LCDR1, LCDR2, and LCDR3 of an antibody as provided in Table 3.

TABLE 3

CDRs Defined by Kabat

| Antibody Name | HCDR1 | HCDR2 | HCDR3 | LCDR1 | LCDR2 | LCDR3 |
|---|---|---|---|---|---|---|
| MAB1 MAB10 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QQFGAWPWT (SEQ ID NO: 6) |
| MAB2 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QOFGDPPWT (SEQ ID NO: 11) |
| MAB3 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QQTIEWPWT (SEQ ID NO: 14) |
| MAB4 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QQTLLFPWT (SEQ ID NO: 17) |
| MAB5 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QQTLHYPWT (SEQ ID NO: 20) |
| MAB6 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QQWETWPWT (SEQ ID NO: 23) |
| MAB7 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QQMEFTPWT (SEQ ID NO: 26) |
| MAB8 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QQTVAWPWT (SEQ ID NO: 29) |
| MAB9 | TSGMGVG (SEQ ID NO: 1) | HIWWDDDKYYNTALKT (SEQ ID NO: 2) | IDWDGFAY (SEQ ID NO: 3) | RASSSVSYMH (SEQ ID NO: 4) | ATSNRAT (SEQ ID NO: 5) | QAASSSSLE (SEQ ID NO: 32) |

sequence having at least 95%, at least 96%, at least 97%, at least 98%, at least 99%, or greater than 99% but less than 100%, or 100% sequence identity, e.g., at least 99% with the amino acid sequence of the light chain variable region set forth in SEQ ID NO: 8, 12, 15, 18, 21, 24, 27, 30, or 33, wherein any sequence variation is found in the framework regions. In some embodiments, the heavy chain variable region further comprises the amino acid sequence of the heavy chain variable region set forth in SEQ ID NO:7 except that there is/are 1, 2, 3, 4, 5, 6, 7, 8, 9, or 10 total amino acid modifications (e.g., substitutions, e.g., conservative substitutions, e.g., deletions) across the heavy chain variable framework regions, e.g., 1 or 2 modifications, and/or the light chain variable region further comprises the amino acid sequence of the light chain variable region set forth in SEQ ID NO: 8, 12, 15, 18, 21, 24, 27, 30, or 33, except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the light chain variable framework regions.

For example, in certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3; and a light chain variable region sequence comprising a CDR-L1 comprising the amino acid sequence set forth in SEQ ID NO:4, CDR-L2 comprises the amino acid sequence set forth in SEQ ID NO:5, and CDR-L3 comprising a sequence as set forth in SEQ ID NO: 6, 11, 14, 17, 20, 23, 26, 29, or 32. In some embodiments, the heavy chain variable region may further comprise an amino acid sequence having at least 90%, at least 91%, at least 92%, at least 93%, at least 94%, at least 95%, at least 96%, at least 97%, at least 98%, at least 99%, greater than 99% but less than 100%, or 100% sequence identity, e.g., at least 99%, with the amino acid sequence of the heavy chain variable region set forth in SEQ ID NO:7, wherein any sequence variation is found in the framework regions, and/or the light chain variable region may further comprise an amino acid In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:6. In some embodiments, the heavy chain variable region may further comprise an amino acid sequence having at least 90%, at least 91%, at least 92%, at least 93%, at least 94%, at least 95%, at least 96%, at least 97%, at least 98%, at least 99%, greater than 99% but less than 100%, or 100% sequence identity, e.g., at least 99%, with the amino acid sequence of the heavy chain variable region set forth in SEQ ID NO:7, wherein any sequence variation is found in the framework regions, and the light chain variable region may further comprise an amino acid sequence having at least 95%, at least 96%, at least 97%, at least 98%, at least 99%, or greater than 99% but less than 100%, or 100% sequence identity, e.g., at least 99%, with the amino acid sequence of the light chain variable region set forth in SEQ ID NO:8, wherein any sequence variation is found in the framework regions. In some embodiments, the heavy chain variable region further comprises the amino acid sequence of the heavy chain variable region set forth in SEQ ID NO:7 except that there is/are 1, 2, 3, 4, 5, 6, 7, 8, 9, or 10 total amino acid modifications (e.g., substitutions, e.g., conservative substitutions, e.g., deletions), e.g., 1 or 2 modification, across the heavy chain variable framework regions, and/or the light chain variable region further comprises the amino acid sequence of the light chain variable region set forth in SEQ ID NO: 8 except that there is/are 1, 2, 3, 4, 5, 6, 7, 8, 9, or 10 total amino acid modifications (e.g., substitutions, e.g., conservative substitutions, e.g., deletions), e.g., 1 or 2 modification, across the light chain variable framework regions.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:11.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:14.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:17.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:20.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:23.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:26.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:29.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:32.

In some examples, the disclosed antibody or antigen binding fragment that binds OX40, e.g., human OX40, may include one or more of the amino acid sequences provided in Table 4, which are CDRs of the antibody or antigen binding fragment as defined by Chothia numbering. For example, the antibody or antigen binding fragment thereof may include a heavy chain variable region comprising heavy chain complementarity determining regions HCDR1, HCDR2, HCDR3, and/or a light chain variable region comprising the light chain complementarity determining regions LCDR1, LCDR2, and LCDR3 of an antibody as provided in Table 4.

TABLE 4

CDRs Defined by Chothia

| Antibody Name | HCDR1 | HCDR2 | HCDR3 | LCDR1 | LCDR2 | LCDR3 |
|---|---|---|---|---|---|---|
| MAB1 MAB10 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQFGAWPWT (SEQ ID NO: 6) |
| MAB2 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQFGDPPWT (SEQ ID NO: 11) |
| MAB3 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQTIEWPWT (SEQ ID NO: 14) |
| MAB4 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQTLLFPWT (SEQ ID NO: 17) |
| MAB5 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQTLHYPWT (SEQ ID NO: 20) |
| MAB6 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQWETWPWT (SEQ ID NO: 23) |
| MAB7 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQMEFTPWT (SEQ ID NO: 26) |
| MAB8 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QQTVAWPWT (SEQ ID NO: 29) |
| MAB9 | GFSLSTSGM (SEQ ID NO: 41) | WWDDD (SEQ ID NO: 42) | IDWDGFAY (SEQ ID NO: 3) | RASSSVSYMH (SEQ ID NO: 4) | ATSNRAT (SEQ ID NO: 5) | QAASSSSLE (SEQ ID NO: 32) |

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:41, a CDR-H2 comprising the amino acid sequence set forth in SEQ ID NO:42, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:6.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:41, a CDR-H2 comprising the amino acid sequence set forth in SEQ ID NO:42, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising an amino acid sequence set forth in one of SEQ ID NOs: 6, 11, 14, 17, 20, 23, 26, 29, or 32. In some embodiments, the heavy chain variable region may further comprise an amino acid sequence having at least 90%, at least 91%, at least 92%, at least 93%, at least 94%, at least 95%, at least 96%, at least 97%, at least 98%, at least 99%, greater than 99% but less than 100%, or 100% sequence identity, e.g., at least 99%, with the amino acid sequence of the heavy chain variable region set forth in SEQ ID NO:7, wherein any sequence variation is found in the framework regions, and/or the light chain variable region may further comprise an amino acid sequence having at least 95%, at least 96%, at least 97%, at least 98%, at least 99%, or greater than 99% but less than 100%, or 100% sequence identity, at least 99%, with the amino acid sequence of the light chain variable region set forth in SEQ ID NO: 8, 12, 15, 18, 21, 24, 27, 30, or 33, e.g., SEQ ID NO:8, wherein any sequence variation is found in the framework regions. In some embodiments, the heavy chain variable region further comprises the amino acid sequence of the heavy chain variable region set forth in SEQ ID NO:7 except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the heavy chain variable framework regions, and/or the light chain variable region further comprises the amino acid sequence of the light chain variable region set forth in SEQ ID NO: 8, 12, 15, 18, 21, 24, 27, 30, or 33, e.g., SEQ ID NO:8, except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the light chain variable framework regions. The CDR-L3 may be SEQ ID NO:6. The sequence identity may be at least 99%.

In some examples, the disclosed antibody or antigen binding fragment that binds OX40, e.g., human OX40, may include one or more of the amino acid sequences provided in Table 5, which are CDRs of the antibody or antigen binding fragment as defined by AbM numbering. For example, the antibody or antigen binding fragment thereof may include a heavy chain variable region comprising heavy chain complementarity determining regions HCDR1, HCDR2, HCDR3, and/or a light chain variable region comprising the light chain complementarity determining regions LCDR1, LCDR2, and LCDR3 of an antibody as provided in Table 5.

TABLE 5

| CDRs Defined by AbM | | | | | | |
|---|---|---|---|---|---|---|
| Antibody Name | HCDR1 | HCDR2 | HCDR3 | LCDR1 | LCDR2 | LCDR3 |
| MAB1 MAB10 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQFGAWPWT (SEQ ID NO: 6) |
| MAB2 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQFGDPPWT (SEQ ID NO: 11) |
| MAB3 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQTIEWPWT (SEQ ID NO: 14) |
| MAB4 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQTLLFPWT (SEQ ID NO: 17) |
| MAB5 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQTLHYPWT (SEQ ID NO: 20) |
| MAB6 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQWETWPWT (SEQ ID NO: 23) |
| MAB7 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQMEFTPWT (SEQ ID NO: 26) |
| MAB8 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QQTVAWPWT (SEQ ID NO: 29) |
| MAB9 | GFSLSTSGM GVG (SEQ ID NO: 47) | HIWWDDDKY (SEQ ID NO: 48) | IDWDGFAY (SEQ ID NO: 3) | RASSSVSYMH (SEQ ID NO: 4) | ATSNRAT (SEQ ID NO: 5) | QAASSSSLE (SEQ ID NO: 32) |

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:47, a CDR-H2 comprising the amino acid sequence set forth in SEQ ID NO:48, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:6.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:47, a CDR-H2 comprising the amino acid sequence set forth in SEQ ID NO:48, and a CDR-H3 comprising the amino acid sequence set forth in SEQ ID NO:3, and a light chain variable region sequence comprising a CDR-L1 comprising the amino acid sequence set forth in SEQ ID NO:4, a CDR-L2 comprising the amino acid sequence set forth in SEQ ID NO:5, and a CDR-L3 comprising an amino acid sequence set forth in one of SEQ ID NOs: 6, 11, 14, 17, 20, 23, 26, 29, or 32. In some embodiments, the heavy chain variable region may further comprise an amino acid sequence having at least 90%, at least 91%, at least 92%, at least 93%, at least 94%, at least 95%, at least 96%, at least 97%, at least 98%, at least 99%, greater than 99% but less than 100%, or 100% sequence identity, e.g., at least 99%, with the amino acid sequence of the heavy chain variable region set forth in SEQ ID NO:7, wherein any sequence variation is found in the framework regions, and/or the light chain variable region may further comprise an amino acid sequence having at least 95%, at least 96%, at least 97%, at least 98%, at least 99%, or greater than 99% but less than 100%, or 100% sequence identity, at least 99%, with the amino acid sequence of the light chain variable region set forth in SEQ ID NO: 8, 12, 15, 18, 21, 24, 27, 30, or 33, e.g., SEQ ID NO:8, wherein any sequence variation is found in the framework regions. In some embodiments, the heavy chain variable region further comprises the amino acid sequence of the heavy chain variable region set forth in SEQ ID NO:7 except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the heavy chain variable framework regions, and/or the light chain variable region further comprises the amino acid sequence of the light chain variable region set forth in SEQ ID NO: 8, 12, 15, 18, 21, 24, 27, 30, or 33, e.g., SEQ ID NO:8, except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the light chain variable framework regions. The CDR-L3 may be SEQ ID NO:6. The sequence identity may be at least 99%.

In some examples, the disclosed antibody or antigen binding fragment that binds OX40, e.g., human OX40, may include one or more of the amino acid sequences provided in Table 6, which are CDRs of the antibody or antigen binding fragment as defined by IMGT numbering. For example, the antibody or antigen binding fragment thereof may include a heavy chain variable region comprising heavy chain complementarity determining regions HCDR1, HCDR2, HCDR3, and/or a light chain variable region comprising the light chain complementarity determining regions LCDR1, LCDR2, and LCDR3 of an antibody as provided in Table 6.

comprising the amino acid sequence AT, and a CDR-L3 comprising the amino acid sequence set forth in SEQ ID NO:6.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:59, a CDR-H2 comprising the amino acid sequence set forth in SEQ ID NO:60, and a CDR-H3 comprising the amino acid sequence set forth in SEQ ID NO:61, and a light chain variable region comprising a CDR-L1 comprising the amino acid sequence set forth in SEQ ID NO:62, a CDR-L2 comprising the amino acid sequence AT, and a CDR-L3 comprising an amino acid sequence set forth in one of SEQ ID NOs: 6, 11, 14, 17, 20, 23, 26, 29, or 32. In some embodiments, the heavy chain variable region may further comprise an amino acid sequence having at least 90%, at least 91%, at least 92%, at least 93%, at least 94%, at least 95%, at least 96%, at least 97%, at least 98%, at least 99%, greater than 99% but less than 100%, or 100% sequence

TABLE 6

CDRs Defined by IMGT

| Antibody Name | HCDR1 | HCDR2 | HCDR3 | LCDR1 | LCDR2 | LCDR3 |
|---|---|---|---|---|---|---|
| MAB1 MAB10 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQFGAWPWT (SEQ ID NO: 6) |
| MAB2 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQFGDPPWT (SEQ ID NO: 11) |
| MAB3 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQTIEWPWT (SEQ ID NO: 14) |
| MAB4 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQTLLFPWT (SEQ ID NO: 17) |
| MAB5 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQTLHYPWT (SEQ ID NO: 20) |
| MAB6 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQWETWPWT (SEQ ID NO: 23) |
| MAB7 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQMEFTPWT (SEQ ID NO: 26) |
| MAB8 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QQTVAWPWT (SEQ ID NO: 29) |
| MAB9 | GFSLSTSGMG (SEQ ID NO: 59) | IWWDDDK (SEQ ID NO: 60) | ARIDWDGFAY (SEQ ID NO: 61) | SSVSY (SEQ ID NO: 62) | AT | QAASSSSLE (SEQ ID NO: 32) |

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:59, a CDR-H2 comprising the amino acid sequence set forth in SEQ ID NO:60, and a CDR-H3 comprising the amino acid sequence set forth in SEQ ID NO:61, and a light chain variable region comprising a CDR-L1 comprising the amino acid sequence set forth in SEQ ID NO:62, a CDR-L2 identity, e.g., at least 99%, with the amino acid sequence of the heavy chain variable region set forth in SEQ ID NO:7, wherein any sequence variation is found in the framework regions, and/or the light chain variable region may further comprise an amino acid sequence having at least 95%, at least 96%, at least 97%, at least 98%, at least 99%, or greater than 99% but less than 100%, or 100% sequence identity, at least 99%, with the amino acid sequence of the light chain variable region set forth in SEQ ID NO: 8, 12, 15, 18, 21, 24, 27, 30, or 33, e.g., SEQ ID NO:8, wherein any sequence variation is found in the framework regions. In some embodiments, the heavy chain variable region further comprises the amino acid sequence of the heavy chain variable region set forth in SEQ ID NO:7 except that there is/are to 1, 2, 3, 4, 5, 6, 7, 8, 9, or 10 total amino acid modifications (e.g., substitutions, e.g., conservative substitutions, e.g., deletions), e.g., 1 or 2 modifications, across the heavy chain variable framework regions, and/or the light chain variable region further comprises the amino acid sequence of the light chain variable region set forth in SEQ ID NO: 8, 12, 15, 18, 21, 24, 27, 30, or 33, e.g., SEQ ID NO:8, except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the light chain variable framework regions. The CDR-L3 may be SEQ ID NO:6. The sequence identity may be at least 99%.

In some examples, the disclosed antibody or antigen binding fragment that binds OX40, e.g., human OX40, may include one or more of the amino acid sequences provided in Table 7, which are CDRs of the antibody or antigen binding fragment as defined by Contact numbering. For example, the antibody or antigen binding fragment thereof may include a heavy chain variable region comprising heavy chain complementarity determining regions HCDR1, HCDR2, HCDR3, and/or a light chain variable region comprising the light chain complementarity determining regions LCDR1, LCDR2, and LCDR3 of an antibody as provided in Table 7.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:53, a CDR-H2 comprising the amino acid sequence set forth in SEQ ID NO:54, and a CDR-H3 comprising the amino acid sequence set forth in SEQ ID NO:55, and a light chain variable region comprising a CDR-L1 comprising the amino acid sequence set forth in SEQ ID NO:56, a CDR-L2 comprising the amino acid sequence set forth in SEQ ID NO:57, and a CDR-L3 comprising the amino acid sequence set forth in SEQ ID NO:58.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:53, a CDR-H2 comprising the amino acid sequence set forth in SEQ ID NO:54, and a CDR-H3 comprising the amino acid sequence set forth in SEQ ID NO:55, and a light chain variable region comprising a CDR-L1 comprising the amino acid sequence set forth in SEQ ID NO:56, a CDR-L2 comprising the amino acid sequence set forth in SEQ ID NO:57, and a CDR-L3 comprising an amino acid sequence set forth in one of SEQ ID NOs: 58, 75, 77, 79, 81, 83, 85, 87, or 89. In some embodiments, the heavy chain variable region may further comprise an amino acid sequence having at least 90%, at least 91%, at least 92%, at least 93%, at least 94%, at least 95%, at least 96%, at least 97%, at least 98%, at least 99%, greater than 99% but less than 100%, or 100%

TABLE 7

CDRs Defined by Contact

| Antibody Name | HCDR1 | HCDR2 | HCDR3 | LCDR1 | LCDR2 | LCDR3 |
|---|---|---|---|---|---|---|
| MAB1 MAB10 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQFGAWPW (SEQ ID NO: 58) |
| MAB2 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQFGDPPW (SEQ ID NO: 75) |
| MAB3 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQTIEWPW (SEQ ID NO: 77) |
| MAB4 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQTLLFPW (SEQ ID NO: 79) |
| MAB5 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQTLHYPW (SEQ ID NO: 81) |
| MAB6 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQWETWPW (SEQ ID NO: 83) |
| MAB7 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQMEFTPW (SEQ ID NO: 85) |
| MAB8 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QQTVAWPW (SEQ ID NO: 87) |
| MAB9 | STSGMGVG (SEQ ID NO: 53) | WIAHIWWDDDKY (SEQ ID NO: 54) | ARIDWDGFA (SEQ ID NO: 55) | SYMHWY (SEQ ID NO: 56) | PWIYATSNRA (SEQ ID NO: 57) | QAASSSSL (SEQ ID NO: 89) |

sequence identity, e.g., at least 99%, with the amino acid sequence of the heavy chain variable region set forth in SEQ ID NO:7, wherein any sequence variation is found in the framework regions, and/or the light chain variable region may further comprise an amino acid sequence having at least 95%, at least 96%, at least 97%, at least 98%, at least 99%, or greater than 99% but less than 100%, or 100% sequence identity, at least 99%, with the amino acid sequence of the light chain variable region set forth in SEQ ID NO: 8, 12, 15, 18, 21, 24, 27, 30, or 33, e.g., SEQ ID NO:8, wherein any sequence variation is found in the framework regions. In some embodiments, the heavy chain variable region further comprises the amino acid sequence of the heavy chain variable region set forth in SEQ ID NO:7 except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the heavy chain variable framework regions, and/or the light chain variable region further comprises the amino acid sequence of the light chain variable region set forth in SEQ ID NO: 8, 12, 15, 18, 21, 24, 27, 30, or 33, e.g., SEQ ID NO:8, except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the light chain variable framework regions. The CDR-L3 may be SEQ ID NO:58. The sequence identity may be at least 99%.

In some examples, the disclosed antibody or antigen binding fragment that binds OX40, e.g., human OX40, may include one or more of the amino acid sequences provided in Table 8, which are CDRs of the antibody or antigen binding fragment as defined by AHo numbering. For example, the antibody or antigen binding fragment thereof may include a heavy chain variable region comprising heavy chain complementarity determining regions HCDR1, HCDR2, HCDR3, and/or a light chain variable region comprising the light chain complementarity determining regions LCDR1, LCDR2, and LCDR3 of an antibody as provided in Table 8.

TABLE 8

CDRs Defined by AHo

| Antibody Name | HCDR1 | HCDR2 | HCDR3 | LCDR1 | LCDR2 | LCDR3 |
|---|---|---|---|---|---|---|
| MAB1 MAB10 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | FGAWPW (SEQ ID NO: 70) |
| MAB2 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | FGDPPW (SEQ ID NO: 76) |
| MAB3 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | TIEWPW (SEQ ID NO: 78) |
| MAB4 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | TLLFPW (SEQ ID NO: 80) |
| MAB5 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | TLHYPW (SEQ ID NO: 82) |
| MAB6 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | WETWPW (SEQ ID NO: 84) |
| MAB7 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | MEFTPW (SEQ ID NO: 86) |
| MAB8 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | TVAWPW (SEQ ID NO: 88) |
| MAB9 | FSGFSLSTSGMG (SEQ ID NO: 65) | IWWDDDKYYNTALKTR (SEQ ID NO: 66) | IDWDGFA (SEQ ID NO: 67) | ASSSVSY (SEQ ID NO: 68) | ATSNRATGIPAR (SEQ ID NO: 69) | ASSSSL (SEQ ID NO: 90) |

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:65, a CDR-H2 comprising the amino acid sequence set forth in SEQ ID NO:66, and a CDR-H3 comprising the amino acid sequence set forth in SEQ ID NO:67, and a light chain variable region comprising a CDR-L1 comprising the amino acid sequence set forth in SEQ ID NO:68, a CDR-L2 comprising the amino acid sequence set forth in SEQ ID NO:69, and a CDR-L3 comprising the amino acid sequence set forth in SEQ ID NO:70.

In certain embodiments, the antibody, or antigen binding fragment thereof, that binds OX40, e.g., human OX40 comprises a heavy chain variable region comprising a CDR-H1 comprising the amino acid sequence set forth in SEQ ID NO:65, a CDR-H2 comprising the amino acid sequence set forth in SEQ ID NO:66, and a CDR-H3 comprising the amino acid sequence set forth in SEQ ID NO:67, and a light chain variable region comprising a CDR-L1 comprising the amino acid sequence set forth in SEQ ID NO:68, a CDR-L2 comprising the amino acid sequence set forth in SEQ ID NO:69, and a CDR-L3 comprising an amino acid sequence set forth in one of SEQ ID NOs: 70, 76, 78, 80, 82, 84, 86, 88, or 90. In some embodiments, the heavy chain variable region may further comprise an amino acid sequence having at least 90%, at least 91%, at least 92%, at least 93%, at least 94%, at least 95%, at least 96%, at least 97%, at least 98%, at least 99%, greater than 99% but less than 100%, or 100% sequence identity, e.g., at least 99%, with the amino acid sequence of the heavy chain variable region set forth in SEQ ID NO:7, wherein any sequence variation is found in the framework regions, and/or the light chain variable region may further comprise an amino acid sequence having at least 95%, at least 96%, at least 97%, at least 98%, at least 99%, or greater than 99% but less than 100%, or 100% sequence identity, at least 99%, with the amino acid sequence of the light chain variable region set forth in SEQ ID NO: 8, 12, 15, 18, 21, 24, 27, 30, or 33, e.g., SEQ ID NO:8, wherein any sequence variation is found in the framework regions. In some embodiments, the heavy chain variable region further comprises the amino acid sequence of the heavy chain variable region set forth in SEQ ID NO:7 except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the heavy chain variable framework regions, and/or the light chain variable region further comprises the amino acid sequence of the light chain variable region set forth in SEQ ID NO: 8, 12, 15, 18, 21, 24, 27, 30, or 33, e.g., SEQ ID NO:8, except that there is/are 1, 2, 3, 4, 5, 6, 7, 8, 9, or 10 total amino acid modifications (e.g., substitutions, e.g., conservative substitutions, e.g., deletions), e.g., 1 or 2 modifications, across the light chain variable framework regions. The CDR-L3 may be SEQ ID NO:70. The sequence identity may be at least 99%.

In other examples, the antibody, or antigen binding fragment thereof, that binds to OX40, e.g., human OX40, comprises:

(a) a heavy chain variable region comprising:
- a heavy chain CDR1 comprising the amino acid sequence of SEQ ID NO:1, SEQ ID NO:41, SEQ ID NO:47, SEQ ID NO:53, SEQ ID NO:59, or SEQ ID NO:65;
- a heavy chain CDR2 comprising the amino acid sequence of SEQ ID NO:2, SEQ ID NO:42, SEQ ID NO:48, SEQ ID NO:54, SEQ ID NO:60, or SEQ ID NO:66; and
- a heavy chain CDR3 comprising the amino acid sequence of SEQ ID NO:3, SEQ ID NO:55, SEQ ID NO:61, or SEQ ID NO:67; and (b) a light chain variable region comprising:
- a light chain CDR1 comprising the amino acid sequence of SEQ ID NO:4, SEQ ID SEQ ID NO:56, SEQ ID NO:62, or SEQ ID NO:68;
- a light chain CDR2 comprising the amino acid sequence of SEQ ID NO:5, SEQ ID SEQ ID NO:57, the amino acid sequence AT, or SEQ ID NO:69; and
- a light chain CDR3 comprising the amino acid sequence of SEQ ID NO:6, SEQ ID NO:58, and SEQ ID NO:70.

III. Methods of Making Anti-OX40 Antibodies

Methods for producing anti-OX40 antibodies and antigen binding fragments thereof, e.g., those disclosed herein, are known in the art. For example, DNA molecules encoding light chain variable regions and/or heavy chain variable regions can be synthesized chemically or by recombinant DNA methodologies. For example, the sequences of the antibodies can be cloned from hybridomas by conventional hybridization techniques or polymerase chain reaction (PCR) techniques, using the appropriate synthetic nucleic acid primers. The resulting DNA molecules encoding the variable regions of interest can be ligated to other appropriate nucleotide sequences, including, for example, constant region coding sequences, and expression control sequences, to produce conventional gene expression constructs (i.e., expression vectors) encoding the desired antibodies. Production of defined gene constructs is within routine skill in the art.

The disclosure provides a polynucleotide or sets of polynucleotides that encode the OX40 antibodies or antigen binding fragments disclosed herein.

In certain embodiments, the polynucleotide or sets of polynucleotides comprises a sequence as set forth in SEQ ID NO:39 and/or 40. In certain embodiments, the polynucleotide or sets of polynucleotides encodes an amino acid sequence comprising the amino acid sequences set forth in SEQ ID NOs: 1, 2, 3, 4, 5, and 6. In certain embodiments, the polynucleotide or sets of polynucleotides encodes an amino acid sequence as set forth in SEQ ID NO:7 and/or SEQ ID NO:8. In certain embodiments, the polynucleotide or sets of polynucleotides encodes an amino acid sequence as set forth in SEQ ID NO:9 and/or 10.

In certain embodiments, a set of polynucleotides is provided where one polynucleotide comprises the sequence as set forth in SEQ ID NO:39, and a separate polynucleotide encodes the sequence as set forth in SEQ ID NO:40. In certain embodiments, a set of polynucleotides is provided where one polynucleotide encodes an amino acid sequence comprising the amino acid sequences set forth in SEQ ID NOs: 1, 2, 3, and a separate polynucleotide encodes an amino acid sequence comprising the amino acid sequences set forth in SEQ ID Nos: 4, 5, and 6. In certain embodiments, a set of polynucleotides is provided where one polynucleotide encodes an amino acid sequence as set forth in SEQ ID NO:7 and a separate polynucleotide encodes an amino acid sequence as set forth in SEQ ID NO:8. In certain embodiments, a set of polynucleotides is provided where one a polynucleotide encodes an amino acid sequence as set forth in SEQ ID NO:9 and a separate polynucleotide encodes an amino acid sequence set forth in SEQ ID NO:10.

In certain embodiments, the polynucleotide or sets of polynucleotides encodes an amino acid sequence as set forth in SEQ ID NO:7 and as set forth in one of SEQ ID NOs: 8, 12, 15, 18, 21, 24, 27, 30, or 33. In certain embodiments, the polynucleotide or sets of polynucleotides encodes an amino acid sequence as set forth in SEQ ID NO:9 and as set forth in one of SEQ ID NOs: 10, 13, 16, 19, 22, 25, 28, 31 or 34. In one specific example, the polynucleotide or sets of polynucleotides encodes an amino acid sequence as set forth in SEQ ID NO:9 and as set forth in SEQ ID NO:10.

In certain embodiments, a set of polynucleotides is provided where one polynucleotide encodes an amino acid sequence as set forth in SEQ ID NO:7 and a separate a polynucleotide encodes an amino acid sequence as set forth in one of SEQ ID NOs: 8, 12, 15, 18, 21, 24, 27, 30, or 33. In certain embodiments, a set of polynucleotides is provided where one polynucleotide encodes an amino acid sequence as set forth in SEQ ID NO:9 and a separate polynucleotide encodes an amino acid sequence as set forth in one of SEQ ID NOs: 10, 13, 16, 19, 22, 25, 28, 31 or 34. In one specific example, a polynucleotide encodes an amino acid sequence as set forth in SEQ ID NO:9 and a separate a polynucleotide encodes an amino acid sequence as set forth in SEQ ID NO:10.

In yet further embodiments, the polynucleotide or sets of polynucleotides encodes an amino acid sequence as set forth in SEQ ID NO:73 and as set forth in one of SEQ ID NOs: 10, 13, 16, 19, 22, 25, 28, 31 or 34. In one specific example, the polynucleotide or sets of polynucleotides encodes an amino acid sequence as set forth in SEQ ID NO:73 and as set forth in SEQ ID NO:10.

In yet further embodiments, a set of polynucleotides is provided where one polynucleotide encodes an amino acid sequence as set forth in SEQ ID NO:73 and a separate polynucleotide encodes an amino acid as set forth in one of SEQ ID NOs: 10, 13, 16, 19, 22, 25, 28, 31 or 34. In one specific example, a set of polynucleotides is provided where one polynucleotide encodes an amino acid sequence as set forth in SEQ ID NO:73 and a separate polynucleotide encodes an amino acid sequence as set forth in SEQ ID NO:10.

In another aspect, the disclosure provides vectors (e.g., expression vectors) comprising the polynucleotide or sets of polynucleotides as described herein. In another aspect, the disclosure provides a host cell (e.g., an expression host cell) comprising the polynucleotide or sets of polynucleotides, or the vectors as described herein.

The polynucleotides or sets of polynucleotides described herein can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an antibody or portion thereof, the expression vector optionally contains sequences encoding all or part of a constant region, enabling an entire, or a part of, a heavy or light chain to be expressed. The gene construct can be introduced into eukaryotic host cells using conventional techniques.

The host cells can express a recombinant antibody or antigen binding fragment comprising $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof. In some embodiments, a host cell is transfected with a single vector expressing the antibody or antigen binding fragment thereof. Alternatively, a host cell can be co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

The antibodies or antigen binding fragments thereof can be produced by growing (culturing) a host cell transfected with an expression vector encoding such a variable region, under conditions that permit expression of the polypeptide. It is within ordinary skill in the art to express immunoglobulin heavy chain and the light chains from a single expression vector or from two separate expression vectors. Following expression, the expression product can be harvested and purified or isolated using techniques known in the art, e.g., Protein A, Protein G, affinity tags such as glutathione-S-transferase (GST) or histidine tags.

IV. Pharmaceutical Compositions

Once produced, the antibodies or antigen binding fragments thereof can be formulated into a pharmaceutical composition.

For therapeutic use, an antibody or antigen binding fragment thereof is combined with a pharmaceutically acceptable carrier. Various carriers (e.g., diluents, excipients, etc.) used in formulating and preparing pharmaceutical compositions are known and/or readily accessible to those of skill in the art. Depending upon the circumstances, a carrier can include a liquid (e.g., a sterile liquid) or a solid. A carrier may be selected from or comprise water, aqueous solvents, non-aqueous solvents, dispersion media, surfactants, antioxidants, buffers, adjuvants, tonicity agents, stabilizers, bulking agents, lyoprotectants, metal ions, chelating agents, isotonic and absorption delaying agents, and the like, that are compatible with pharmaceutical administration. The use of such media and agents for pharmaceutically active substances is known in the art. Typically a carrier is approved by United States Food and Drug Administration and meets the standards of the United States Pharmacopoeia (USP), the European Pharmacopoeia (EP), the British Pharmacopoeia, and/or other International Pharmacopoeia. Suitable formulations for use in the present disclosure are found in see, e.g., Adeboye Adejare, Remington: the Science and Practice of Pharmacy ($23^{rd}$ ed. 2020). For a brief review of methods for drug delivery, see, e.g., Langer (1990) Science, 249: 1527-1533. The resulting pharmaceutical compositions are suitable for administration to a subject (e.g., an animal, e.g., a mammal, e.g., a human).

A pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, e.g., Adeboye Adejare, REMINGTON: THE SCIENCE AND PRACTICE OF PHARMACY ($23^{rd}$ ed. 2020)).

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semi-permeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate, or poly-D (−)-3-hydroxybutyric acid. Sustained release compositions may also include liposomes that can be prepared by any of several methods known in the art.

Depending upon the circumstances, a pharmaceutical composition may contain nanoparticles, or lipid droplets, e.g., polymeric nanoparticles, liposomes, or micelles (see Anselmo et al. (2016) BIOENG. TRANSL. MED., 1: 10-29).

Pharmaceutical compositions containing an antibody or antigen binding fragment thereof can be presented in a dosage unit form and can be prepared by any suitable method. A pharmaceutical composition should be formulated to be compatible with its intended route of administration. Examples of routes of administration are intravenous (IV), subcutaneous or intramuscular, for example. Other routes may include intraperitoneal, intradermal, inhalation, transdermal, topical, transmucosal, intrathecal and rectal administration. In certain embodiments, the antibody or antigen binding fragment is administered by subcutaneous administration.

Useful formulations can be prepared by methods known in the pharmaceutical art. For example, see e.g., Adeboye Adejare, REMINGTON: THE SCIENCE AND PRACTICE OF PHARMACY ($23^{rd}$ ed. 2020). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, polyethoxylated castor oil or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Formulations can be sterilized, for example, by methods appropriate to retain activity and stability of the antibody or antigen binding fragment thereof. Sterilization can be accomplished by any suitable method, e.g., filtration through sterile filtration membranes. Where the composition is lyophilized, filter sterilization can be conducted prior to or following lyophilization and reconstitution.

Depending upon the drug substance and formulation, the resulting dosage forms can be stable for extended periods of time, such as 1 month, 3 months, 6 months, 1 year, 2 years, 3 years, or more, when the dosage form is a liquid or solid. The formulations can be stable at room temperature or higher. It is contemplated that the dosage form is stable at ambient conditions in PBS. Alternatively the dosage form is frozen (e.g., a liquid or a lyophilizate) and stable under appropriate temperatures such as, e.g., −20° C., −80° C.).

Depending upon the circumstances, the dosage forms can be formulated as a unit dose, which can include, for example, about 10 mg, 25 mg, 50 mg, 100 mg, 250 mg, 500 mg, 1 g, 1.5 g, 2.5 g, 5 g, or 10 g of the drug substance. The dosage may be found in a suitable liquid carrier, e.g., for intravenous, intramuscular, or subcutaneous administration.

The compositions described herein may be administered locally or systemically. It is contemplated that the compositions described herein are generally administered by parenteral administration. Preparations for parenteral administration include sterile aqueous or non-aqueous solutions, suspensions, and emulsions. In certain embodiments, the pharmaceutical composition is administered subcutaneously or may be administered intravenously, e.g., via intravenous infusion. In certain embodiments, it is contemplated that the synthetic constructs disclosed herein can be administered by systemic administration.

Generally, a therapeutically effective amount of active component, for example, an antibody or antigen binding fragment disclosed herein, is in the range of 0.1 mg/kg to 1000 mg/kg, e.g., 1 mg/kg to 100 mg/kg, e.g., 10 mg/kg to 500 mg/kg, e.g., 500 mg/kg to 1000 mg/kg. In certain embodiments, the effective amount is in the range of 15 to 50 mg/kg. In certain embodiments, the effective amount is 15 mg/kg. In certain embodiments, the effective amount is 30 mg/kg. In certain embodiments, the effective amount is 50 mg/kg. The amount administered will depend on variables such as the type and extent of disease or indication to be treated, the overall health of the patient, the in vivo potency of the active component, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study. Dosing frequency can vary, depending on factors such as route of administration, dosage amount, serum half-life of the synthetic peptide, and the disease, disorder, or condition being treated. Exemplary dosing frequencies are once per day, once per week and once every two weeks.

V. Methods of Treatment

The antagonist antibodies disclosed herein have numerous in vitro and in vivo diagnostic and therapeutic utilities involving the diagnosis and treatment of OX40 mediated disorders. For example, these molecules can be administered to cells in culture, in vitro or ex vivo, or to human subjects, to treat, prevent and to diagnose a variety of OX40-mediated disorders. Preferred subjects are human and include subject having disorders mediated by OX40 activity (OX40 mediated disorders). The antagonist antibodies or antibody binding fragments thereof of the present disclosure can be effective in treating subjects independent of their OX40 costimulatory status. In some embodiments, the subjects are human subjects expressing a low level of OX40.

In a particular embodiment, the antagonist antibodies are used to treat, prevent or diagnose a variety of OX40-mediated disorders. Thus the disclosure provides a method for treating an OX40 mediated disorder in a subject, the method comprising administering to the subject a therapeutically effective amount of the antagonist antibody or antigen binding fragment thereof.

In a particular embodiment, the OX40 antibody disclosed herein bind to T cells. In some embodiments, the T cells are T regulatory (Treg) cells. In some embodiments, the T cells are Th1, Th2, or Th17/22 cells. In some embodiments, the T cells are T memory cells. Depending upon the circumstances, the OX40 antibody can inhibit effector T cells. Such inhibition can be silencing or reducing activation of the T cell that is not dependent on ADCC-mediated killing of the T cell. Inhibition of the OX40 pathway can silence effector T cells such as Th1, Th2, and Th17/22 cells as well as T memory cells, while resulting in less effect on Treg cells. See, e.g., Guttman-Yassky E, et al., (2019) J. Allergy Clin. Immunol. August; 144(2):482-493.e7.

In some embodiments, the OX40 antibody disclosed herein has reduced adverse effects due to ADCC, such as pyrexia and chills, as compared to a control OX40 antibody. For example, the antibody is MAB10.

Exemplary OX40 mediated disorders include infections (viral, bacterial, fungal and parasitic), endotoxic shock associated with infection, arthritis, rheumatoid arthritis, psoriatic arthritis, asthma, bronchitis, influenza, respiratory syncytial virus, pneumonia, chronic obstructive pulmonary disease (COPD), idiopathic pulmonary fibrosis (IPF), Hashimoto's Thyroiditis, cryptogenic fibrosing alveolitis (CFA), idiopathic fibrosing interstitial pneumonia, emphysema, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, prurigo nodularis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus or lupus nephritis) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, urticaria such as chronic spontaneous urticaria (CSU) or chronic inducible urticaria (CIU), Wegener's granulomatosis, systemic sclerosis, cutaneous sclerosis, chronic pruritis (e.g., of unknown origin), Vitiligo, Sjogren's syndrome, ankylosing spondylitis, pancreatitis, trauma (surgery), graft-versus-host disease (GVHD), transplant rejection, cardiovascular disease including ischemic diseases such as myocardial infarction as well as atherosclerosis, intravascular coagulation, bone resorption, osteoporosis, osteoarthritis, periodontitis, hypochlorhydria, neuromyelitis optica, alopecia areata, scleroderma, or hidradenitis suppurativa. These exemplary OX40 mediated disorders may be treated with the antibodies, or binding fragments thereof that bind OX40, e.g., human OX40, as disclosed herein, In selected examples, OX40 mediated disorders to be treated with the antibodies, or binding fragments thereof that bind OX40, e.g., human OX40, disclosed herein are selected from multiple sclerosis, rheumatoid arthritis, colitis, psoriasis, asthma, COPD, idiopathic pulmonary fibrosis (IPF), graft-versus-host-disease (GVHD), atherosclerosis and diabetes. In other selected examples, the OX40-mediated disorder is Atopic Dermatitis, Prurigo Nodularis, Alopecia Areata, Chronic Spontaneous Urticaria and Chronic Inducible Urticaria, Asthma, Hidradenitis Suppurativa, Lupus Nephritis, Systemic Lupus Erythematosus, Pemphigus Vulgaris, Psoriatic Arthritis, Vasculitis, Hashimoto Thyroiditis, Systemic Sclerosis, Cutaneous Sclerosis, Scleroderma, Chronic Pruritus from Unknown Origin, Ankylosing Spondylitis, Sjogren's Syndrome, Psoriasis, or Vitiligo.

In certain examples, the OX40 mediated disorder to be treated with the antibody is graft-versus-host-disease (GVHD). In yet other examples, the OX40 mediated disorder is atopic dermatitis. In still other examples the OX40 mediated disorder is urticaria, e.g., chronic spontaneous urticaria (CSU), or e.g., chronic inducible urticaria (CIU). In yet other examples, the OX40 mediated disorder is an autoimmune disorder such as lupus erythematosus or rheumatoid arthritis. In still other examples, the OX40 mediated disorder is asthma. In other examples, the OX40 mediated disorder is alopecia areata, scleroderma, or hidradenitis suppurativa.

The present disclosure also provides an antibody for use in the treatment of pain, particularly pain associated with inflammation.

In addition, the antibodies can be used to detect levels of OX40, or levels of cells which contain OX40 on their membrane surface, which levels can then be linked to certain disease symptoms. Alternatively, the antibodies can be used to inhibit or block OX40 function which, in turn, can be linked to the prevention or amelioration of certain disease symptoms, thereby implicating OX40 as a mediator of the disease. This can be achieved by contacting a sample and a control sample with the OX40 antibody under conditions that allow for the formation of a complex between the antibody and OX40. Any complexes formed between the antibody and OX40 are detected and compared in the sample and the control. In view of the specific binding of the antibodies for OX40, the antibodies can be used to specifically detect OX40 expression on the surface of cells, e.g., can be used to detect a subject having low expression level of OX40.

The present disclosure further provides the use of an antagonist antibody or fragment thereof as a medicament and the use of an antagonist antibody or fragment thereof in the preparation of a medicament for the treatment of an OX40 mediated disorder. Also provided is the antagonist antibody or antigen biding fragment thereof for use in a method for treating an OX40 mediated disorder such as the disorders described herein.

Depending upon the circumstances, the antagonist antibody disclosed herein may be particularly useful for treating OX40 mediated disorders independent of the OX40 costimulatory status of a subject. Furthermore, the antagonist antibody or fragment thereof can be used for treating an OX40 mediated disorder wherein a subject expresses a low level of OX40.

Further, as disclosed herein, the antibodies, or binding fragments thereof, that bind OX40, e.g., human OX40 may be administered to a subject in need of reduction or inhibition of T cell proliferation. The antibody or binding fragment thereof may be administered in a therapeutically effective amount to reduce or inhibit T cell proliferation in the subject. The subject may have an OX40 mediated disorder as described herein above.

EXAMPLES

The subject matter is now described with reference to the following examples. These examples are provided for the purpose of illustration only and the claims should in no way be construed as being limited to these examples, but rather should be construed to encompass any and all variations which become evident as a result of the teaching provided herein.

Below are examples of specific embodiments for carrying out the present invention. The examples are offered for illustrative purposes only, and are not intended to limit the scope of the present invention in any way.

Example 1: Generation of Antibodies Via Affinity Maturation

Materials and Methods

Affinity Maturation Library Generation

The library was designed in the scFv format with diversity restricted to the CDR-3 of the variable light chain of GBR 830 (telazorlimab, described in U.S. Pat. No. 8,748,585) (SEQ ID NO:37). CDR diversification was achieved by synthesis of random sequences using nucleotide mixtures. All 20 amino acids plus the amber stop codon (TAG) were encoded by the NNK degenerate codon (wherein N is any of the four deoxyribonucleotides and K is G or T). A flexible linker based on three Gly4Ser peptide repeats was used for assembling the two variable domains. The resulting library contained GBR 830 variable domains having a CDR-L3 with the following sequence CQQXXXXPWTF (Kabat residues 88-98, SEQ ID NO:71) wherein X is a random naturally occurring amino acid (encoded by the NNK degenerate codon). Diversified scFv fragments were cloned into pGLEN8, a modified pHEN1 phagemid vector (Hoogenboom (1991) Nucleic Acids Res., 19(15): 4133-7) and the resulting ligation reaction electroporated into *E. coli* XL-1 blue cells. Transformed cells were spread on 2YT-100 μg/mL ampicillin-5% glucose (2YTAG) plates and incubated overnight (O/N) at 30° C. Colonies were scraped off into 10 mL of 2YT medium and 15% glycerol (final concentration) was added for storage at −80° C. Dilutions of transformed cells were spread on 2YTAG plates and incubated overnight at 37° C. for titration. The final library of scFv fragments reached a total diversity of $6.7\times10^6$. Phage were produced by infection of transfected cells culture with $>10^{10}$ plaque forming units (pfu) helper phage (M13K07) for 30 min at 37° C. and subsequent culture of cells O/N at 30° C., after replacement of medium with 2YT medium supplemented with ampicillin (100 μg/mL) and kanamycin (25 μg/mL). Phage purification was achieved by two precipitations steps with one-third v/v of 20% PEG-6000, 2.5 M NaCl. Post precipitation, phage were resuspended in phosphate buffer saline (PBS).

Recombinant Antigens

Recombinant antigens were expressed and purified at Glenmark Pharmaceuticals S.A. Human and cynomolgus OX40 ECDs were expressed with a poly-histidine sequence fused to their C-termini or as Fc fusions (human IgG1 isotype). Library selections were performed on cynomolgus OX40-ECD-Fc and human OX40-ECD-his. Kinetic screen was performed on human OX40-ECD-his and cynomolgus OX40-ECD-his. KD measurements on cynomolgus OX40 were performed with the cynomolgus OX40-ECD-his protein. A human OX40 protein encompassing only the cysteine rich (CRD) region of the ECD fused to an avi-tag and a poly-histidine sequence at the C-terminus was found to be more homogenous and monomeric than the human OX40-ECD-his and was used for KD measurements.

Library Selection

A Nunc MaxiSorp 5 ml immunotube was coated with 80 μg of cynomolgus OX40-ECD-Fc solubilized in 4 mL PBS. Purified phage particles ($10^{10}$ plaque-forming units) and immunotubes were blocked with PBS containing 3% (w/v) skimmed milk (3% MPBS). Blocked phages were then added to the blocked immunotube and incubated for 2 hrs at room temperature (RT). Unbound phages were discarded with supernatant and immunotube was washed twenty times with PBS containing 0.1% (v/v) Tween 20 (PBS-Tween 0.1%) and a further twenty times with PBS. Phage were eluted with 100 mM triethylamine for 10 min at RT and neutralized using 1 M Tris-HCl pH 8 (10% v/v). Eluted phage were used to infect 10 mL of exponentially growing *E. coli* XL-1 blue cells. Infected cells were grown in 2YT medium for 30 min at 37° C., then spread on 2YTAG (2TY medium supplemented with 100 μg/mL ampicillin and 5% glucose) agar plates and incubated overnight at 30° C. Colonies were scraped off into 10 mL of 2YT and 15% glycerol (v/v) was added for storage at −80° C. XL-1 cells from glycerol stocks were grown at 37° C. and 240 RPM in 2YTAG medium until OD at 600 nm reached 0.5. Cells were then superinfected with the M13K07 helper phage using a multiplicity of infection (MOI) of ten for 30 min at 37° C. Culture medium was then changed for 2YTAK (2YT medium supplemented with 100 μg/mL ampicillin and 25 μg/mL kanamycin) and cells were further cultured overnight at 30° C. and 280 RPM. The next day, phages were precipitated from cell supernatant using two precipitations steps with one-third v/v of 20% PEG-6000, 2.5 M NaCl and resuspended in 1.5 ml PBS. A second round of selection was carried out using 1.4 mL of phage rescued from first round. The same experimental setup was used, with the exception of changing the coating of the immunotube to 80 μg of human OX40-ECD-his instead of cynomolgus OX40-ECD-Fc.

ScFv Clone Screening

The binding of scFv clones was assessed by ELISA. Individual *E. coli* colonies from the second round of selection were picked and grown in 2YT ampicillin medium (96-well deep well plates). ScFv expression was induced by addition of 1 mM of IPTG and incubation ON at 30° C. and 250 RPM. Cells were centrifuged and culture supernatant were used for screening. RIA/EIA plates were coated with either 200 ng/well of human OX40-ECD-his or cynomolgus OX40-ECD-Fc. In order to discriminate potential antibodies selected against the Fc fragment, a plate was also coated with an irrelevant Fc fused antigen. The plates were then blocked with PBS supplemented with 3% Bovine Serum Albumin (BSA). 80 μL of bacteria culture supernatants were then mixed with 20 μl of 3% BSA and added to the blocked plates for 1 hr at room temperature. Bound scFvs were detected using a biotinylated chicken anti-c-myc antibody diluted 1:5000 in PBS-0.3% BSA incubated for 1 hr at RT, followed by staining with the Pierce High Sensitivity Streptavidin-HRP reagent diluted 1:8000 in PBS-0.3% BSA for 30 min at RT. Plates were extensively washed using PBS supplemented with 0.05% Tween 20 between each incubation step. Finally, bound scFvs were revealed using 100 μL per well of TMB peroxidase EIA for 5 min at RT. Enzymatic activity was stopped by addition of 50 μL of 2N $H_2SO_4$ and OD at 405 nm was measured. Clones that bound specifically to both human and cynomolgus OX40 but not to irrelevant antigen-Fc fusion protein were DNA sequenced.

Expression and Purification of Recombinant Antibody Fragments cDNAs encoding the different antibody constant regions were gene synthetized by GENEART AG (Regensburg, Germany) and modified using standard molecular biology techniques. PCR products were digested with appropriate DNA restriction enzymes, purified and ligated in modified pcDNA3.1 plasmids (Invitrogen) which carried a CMV promoter and the bovine growth hormone poly-adenylation signal sequence. The expression vectors also carried oriP, which is the origin of plasmid replication of Epstein-Barr virus, and the murine VJ2C leader peptide for secretion of the encoded polypeptide chain. For reformatting in the scFv-Fc format, each scFv cDNA was amplified by PCR from its phage library vector and cloned in the modified pcDNA 3.1 vector described above upstream of a cDNA encoding small four Gly linker sequence and a human IgG1 Fc region (human IgG1 hinge, CH2 and CH3 domains).

For reformatting scFv library clones into human IgG1, each scFv clone in its phage library vector was used to amplify its individual VH and VL cDNAs by PCR, next the VH PCR product was cloned in the modified pcDNA 3.1 vector described above upstream of a cDNA encoding a human IgG1 heavy chain (CH1, hinge, CH2 and CH3 domains), whereas the VL PCR product was cloned in the modified pcDNA 3.1 vector described above upstream of a cDNA encoding a human kappa constant light chain domain.

For transient expression, recombinant scFv-Fc vectors were directly transfected to express scFv-Fc fusion proteins. For antibody expression, equal quantities of heavy chain and light chain vectors were co-transfected into suspension-adapted HEK293-EBNA cells using PEI. Typically, cells were prepared at 8 million cells per ml in RPMI supplemented with 0.1% Pluronic F-68. Cells were then transfected with a DNA-PEI mixture. Four hours post-transfection, the cell culture was diluted 1:1 in EX-CELL® 293 supplemented with Phenol Red and 4 mM L-Glutamine and incubated for five days with orbital shaking at 37° C., 5% $CO_2$ and 80% humidity. Cell-free culture supernatants containing the recombinant proteins were prepared by centrifugation followed by filtration, and used for further purification. scFv-Fc fusion proteins and antibodies were purified using the CaptivA™ PriMAB resin (rproteinA Affinity Resin). Affinity resin was added to each filtered culture supernatant and incubated overnight at 4° C. with gentle mixing. The next day, resin beads were collected into Poly-Prep columns, washed with PBS, and the recombinant proteins eluted with an acidic buffer (typically glycine 0.1 M pH 3). After neutralization with 1/10 volume of 1M Tris-HCl pH 8, preparations were buffer-exchanged into PBS.

Kinetic Screening

The binding kinetics screen was performed on a Biacore T200 instrument at room temperature. A sensor chip (Series S CM5) previously coupled with a capture antibody (Human antibody capture kit) was used to capture about 500 response units (RUs) of test protein (scFv-Fc or antibody), previously diluted at a final concentration of 50 nM in HBS-EP+ buffer (running buffer) on flow cell (fc) No 2 at 10 μL/min. Human OX40-ECD-his or cynomolgus OX40-ECD-his previously diluted at 1 μM were injected on fc No1 and fc No2 (fc No1 being used as reference) for 3 min followed by a 10 min dissociation period in running buffer at a flow rate of 30 μl/min. Regeneration was performed after the end of each cycle using a 1 min injection of 3 M $MgCl_2$. Following completion of the run, raw data was analyzed in the Biacore Evaluation Software (v3.0). Blank subtracted and reference subtracted binding curves were normalized on the binding event time point and off-rates were compared.

Affinity Measurement of MAB1 IgG1 to Human and Cynomolgus OX40

Surface Plasmon Resonance (SPR) analysis was used to measure the association and dissociation rate constants for the binding kinetics of MAB1 IgG1 and GBR 830. The binding kinetics were measured on a Biacore T200 instrument at RT and analyzed with the Biacore T200 Evaluation Software (v3.0). Analyzed data were exported using the Biacore T200 Kinetics Summary software (v3.0). A Series S sensor chip previously coupled with an anti-human capture antibody (human antibody capture kit) was used to capture 200 RU of MAB1 antibody or GBR 830 on fc No2, both previously diluted at 5 μg/ml final concentration in HBS-EP+ buffer (running buffer). Human OX40-CRD-avi-his or cynomolgus OX40-ECD-his previously diluted in HBS-EP+ buffer was injected on fc No1 and fc No2 (fc1 being used as reference); a three-fold dilution series of Human OX40-CRD-avi-his and Cynomolgus OX40-ECD-his from 1000 nM to 1.37 nM and a blank control (0 nM) was flowed across the captured GBR 830 or MAB1 IgG. Experimental data were processed using a 1:1 Langmuir model with global Rmax.

Results

Antibody 830 (GBR 830) was affinity matured by phage display. Nine clones were generated and characterized. The affinity maturation process focused on CDR-L3 diversification. One clone, MAB1, was selected for additional characterization. The MAB1 amino acid sequence differs from the GBR 830 antibody in the CDR3 of its variable light chain domain by four amino acids. The GBR 830 LCDR3 sequence is QQWSSNPWT (SEQ ID NO:35) compared to the MAB1 LCDR3 sequence of QQFGAWPWT (SEQ ID NO:6).

ScFv Clone Screening

Supernatants from 88 clones were screened by ELISA with 33 clones showing a specific binding to both human and cynomolgus OX40, but not to the irrelevant antigen-Fc fusion protein. Among these 33 clones, 21 had a unique CDR-L3 amino acid sequence. Unique clones with the highest binding signals were reformatted as scFv-Fc fusion proteins for further assessment by SPR. Clones were randomly named MAB1 to MAB9. Variable light chain, light chain, and L3 CDR sequences of MAB1 to MAB9 are provided in SEQ ID NOs: 6, 8, and 10-34.

Kinetic Screening

MAB1 to MAB9 scFv clones were reformatted as scFv-Fc fusion proteins following the procedure described above. Binding kinetics were assessed by SPR (FIG. 1). Only one clone, MAB1, showed a significantly slower off-rate than the parental clone GBR 830 on human OX40 (FIG. 1) and a slightly better or comparable off rate on cyno OX40 (data not shown).

Affinity Measurement of MAB1 IgG1 to Human and Cynomolgus OX40

GBR 830 and MAB1 binding affinities to human and cynomolgus OX40 ECDs were measured using a 1:1 Langmuir binding model. This model assumes a 1:1 interaction between the ligand and analyte and determines the association rate (Ka), dissociation rate (Kd) and affinity (KD) for each sample. Using this model, the KD is defined as the ratio between the dissociation rate and the association rate, i.e. KD=Kd/Ka.

In addition to KD values, the relative affinity of MAB1 to the parental clone GBR 830 was determined using the calculation: relative affinity=($KD_{GBR\ 830}/KD_{MAB1}$).

Affinity of MAB1 to human OX40-CRD-avi-his and cynomolgus OX40-ECD-his was measured at 6 nM and 557 nM, respectively; while affinity of GBR 830 for these two antigens was measured at 80 nM and 3 μM, respectively using the same experimental setup (Table 9).

TABLE 9

Summary of characterization of MAB1 IgG1

| Sample | Human OX40 Ka (1/Ms) | Human OX40 Kd (1/s) | Human OX40 KD (nM) | Cyno OX40 Ka (1/Ms) | Cyno OX40 Kd (1/s) | Cynomolgus OX40 KD (nM) |
|---|---|---|---|---|---|---|
| GBR 830 | 8.13E+04 | 6.54E−03 | 80.4 ± 2.4 | N/A | N/A | 3040 ± 1870 |
| MAB1 | 2.74E+05 | 1.63E−03 | 6.0 ± 0.2 | 7.27E+04 | 4.05E−02 | 557 ± 31 |
| MAB1 fold increase in affinity for | | | 13.4x | | | 5.5x |

GBR 830 affinity for the extracellular domain (ECD) of OX40 was measured at 100-80 nM and 5-3 μM for human and cynomolgus monkey, respectively. MAB1 exhibited about 13 fold improvement in affinity for human OX40 with an average KD value of 6 nM. MAB1's affinity for cynomolgus monkey OX40 was also improved by about fivefold with an average KD value of 0.55 μM.

Example 2: In Vitro Characterization of MAB1 Antagonism

Surface plasmon resonance (SPR) studies showed that GBR 830 displayed a monovalent affinity for OX40 of 80-100 nM, however cell-based apparent affinity was measured in the low nM range: 1.25±0.41 nM on CD4+ T cells and 3.46±0.47 nM on CD8+ T cells. GBR 830 also displayed a lack of OX40 agonism. One hypothesis for the lack of agonism by GBR 830 was that its monovalent affinity limited the crosslinking potency required for agonistic activity. The affinity matured variant, MAB1, showed a 13 fold higher monovalent affinity for OX40 than GBR 830. Thus, there was a possibility that affinity matured antibodies based on GBR 830 could result in increased agonism of OX40, resulting in a trade off between better antibody binding and increased agonistic activity. To assess the possibility of increased agonism due to increased affinity, the MAB1 antibody was tested in agonism assays, discussed below.

Materials and Methods

Epitope Mapping by ELISA

Epitope mapping was performed using binding ELISA. In order to verify epitope conservation by MAB1, MAB1 binding to human-rat OX40 CRD chimeric proteins was tested by ELISA. Briefly, RHHH for example, represents an OX40 in which the CRD1 is of rat origin and CRD2, 3 and 4 are of human origin, RHRR corresponds to an OX40 in which the CRD1, 3 and 4 are of rat origin and CRD2 is from human. HHHR corresponds to an OX40 in which CRD1, 2, and 3 are of human origin and CRD4 is rat. HRRR corresponds to an OX40 in which CRD1 is of human origin and CRD2, 3, and 4 are rat. HHRH corresponds to an OX40 in which CRD1, 2, and 4 are of human origin and CRD3 is rat. Human-rat chimeric OX40 extracellular domain proteins were coated at 2 μg/mL in DPBS. Serial dilutions (1/3) of GBR 830, MAB1 and 7H11 antibodies starting from 10 μg/mL were added on OX40 coated plates. HRP-labeled goat anti human Fab antibody (Jackson ImmunoResearch) was used at a dilution of 1:2,000 as the detection antibody. Plates were blocked and washed respectively with ELISA Blocking buffer and ELISA Washing buffer.

Data (absorbance units) were then plotted against antibody concentrations and analyzed using Prism (GraphPad) software.

Blocking FACS

Comparison of GBR 830 and MAB1 cross-blocking was performed on HPB-ALL. HPB-ALL cells were incubated with serial dilutions of cold GBR 830 or MAB1 (starting from g/mL and diluted 1/3) for 30 minutes on ice and in the dark. After a washing step (2 rounds of centrifugation with in-between resuspension with Flow Cytometry Buffer), cells were suspended with single dose of labeled-MAB1 (for GBR 830 dose-response) and labeled-GBR 830 for MAB1 dose-response. Plates were incubated for 30 minutes on ice and in the dark. After a washing step, cells were resuspended in 200 μL FACS buffer and immediately acquired using flow cytometer.

Data (Geometric Mean of Fluorescence Intensity) were then plotted against antibody concentrations and analyzed using Prism (GraphPad) software. A non-linear regression fitting was applied after X=Log(X) transformation and sigmoidal dose-response fitting was applied to all data-sets to determine the EC50 values. The data are presented as the mean±SD in all the graphs.

Jurkat-OX40-NFκB Signaling Assay

The assay was performed with test antibodies as soluble agents or coated.

Procedure with antibodies as soluble agents: Sterile 96 well flat bottom, chimney well, CLEAR microplates were coated overnight with OKT3 (5 μg/ml). Control wells without coated OKT3 were included. Jurkat-NFκB cells were plated at $5\times10^4$ cells/well (50 μL) on OKT3 pre-coated plates. Serial dilutions of test antibodies or OX40L were added to the cells and the plates were incubated for 5 hours at 37° C. in a cell culture incubator. After the incubation, 75 μL of Bio-Glo solution (Promega) were placed into the wells and luminescence was measured on Synergy Neo plate Reader (Biotek) using the following settings: read tape—endpoint; integration time—1 minute; emission—hole; optics position—top; gain 135; read height—1.00 mm. Data (luminescence units) were then plotted against antibody concentrations and analyzed using Prism (GraphPad) software. A non-linear regression fitting was applied after X=Log(X) transformation and sigmoidal dose-response fitting was applied to all data-sets to determine the EC50 values. Each condition was performed in duplicate.

Procedure with coated antibodies: Sterile 96 well flat bottom, chimney well, CLEAR microplates were coated overnight with OKT3 (5 μg/mL) or a mix of OKT3 (5 μg/mL) and anti-OX40 antibodies (10 μg/mL and serial dilutions 1/4). Control wells without coated antibodies were included. Jurkat-NFκB cells were plated at $5\times10^4$ cells/well (50 μL) on antibody pre-coated plates and incubated for 5 hours at 37° C. in a cell culture incubator. The readout procedure was the same than described above.

T Cell Agonism Assay

Human T cells were purified from PBMCs using EasySep™ Human T Cell Isolation Kit (StemCell Technologies) following manufacturer's instructions.

Flow cytometry staining to check T cell purity was performed on an aliquot of freshly purified T cells. The purity was consistently above 95%.

Mouse anti-Human CD3 (OKT3) solution was prepared at 4 μg/mL, this solution was distributed in Deep-well plate. Other treatments (OX40L, anti-OX40 antibodies, IgG control) were diluted at 5 or 10 μg/mL in the relevant wells of OKT3 solution in order to prepare co-coating solution. One hundred L of treatment solutions were transferred to 96-well plates for overnight coating at 4° C.

Purified T cells (105 T cell/well) were added to pre-coated plates. Plates were incubated at 37° C. for three days and 0.5 μCu/well of $^3$H-Thymidine was added to the wells. Plates were further incubated for 15-24 hrs. Plates were harvested using a Filtermate 196 harvester on Filtermat A filters and the radioactivity was counted on a MicroBeta Trilux Counter (Wallac). A proliferation index was calculated according to the following formula:

$$\text{Proliferation Index} = CPM_{Sample}/CPM_{OKT3\ only}$$

CPM was the radioactivity count per minute.

Data (Proliferation Indexes) were then plotted against antibody (categorical) and analyzed using JMP (SAS) software.

Statistical Analysis

Statistical analyses were performed using JMP software (SAS Institute Inc) on the T cell proliferation assay data. A donor-paired analysis was performed to take into account inter-donor variability.

The statistical analysis was conducted to compare the effect of the various treatments vs IgG1 control condition. For each T cell donor, the difference of proliferation index (PI) [Treatment X–Hu IgG1 control] was calculated, where treatment X represents a test condition (OX40L, anti-OX40 antibody, anti-CD28 antibody). For each treatment, the PI difference was analyzed using a one-tail paired student's t-test against the following null hypothesis (H0): the mean of the PI difference for all tested donors is equal to 0. H0 was rejected (and therefore the tested treatment was considered significantly different from the control condition) if $p<0.05$.

Results

GBR 830 and MAB1 Binding on OX40 Receptor

MAB1 is a variant of GBR 830 that has over 10-fold enhanced affinity for OX40. The affinity of MAB1 (6 nM) is very close to the affinity of humanized 7H11 (5.4 nM), which exhibits agonistic activity.

Figures 2A, 2B, 2C, 2D:
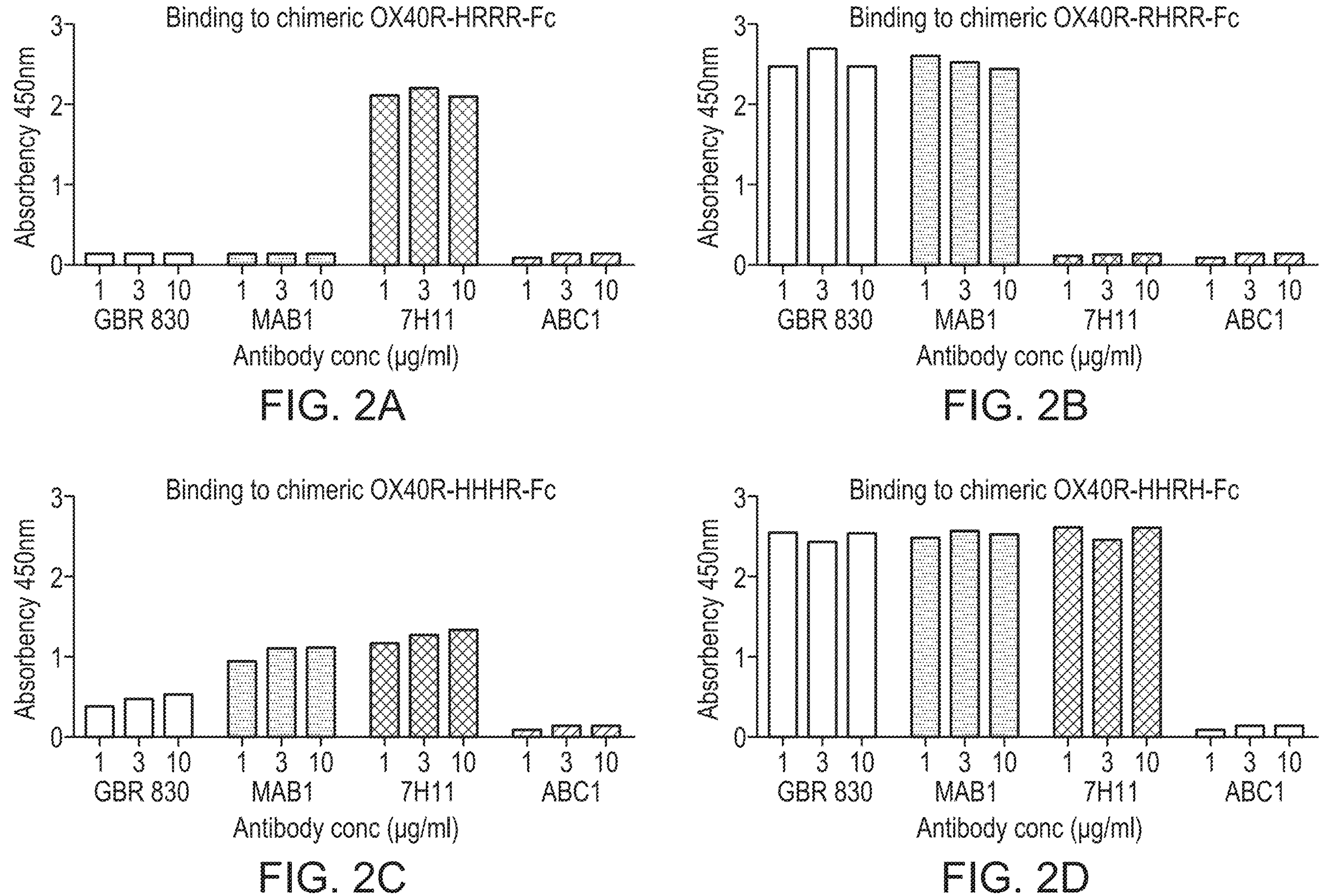
FIGS. 2A-2D are bar charts showing direct binding ELISA data for epitope mapping using the indicated human/rat chimeric OX40 constructs.

GBR 830 epitope was previously characterized to be within cysteine rich domain (CRD) 2 of OX40 (see e.g., U.S. Pat. No. 8,748,585). FIG. 2 provides direct binding ELISA data using the indicated human/rat chimeric OX40 constructs. 7H11 bound to HRRR, HHRH and HHHR proteins, but not on RHRR protein. 7H11 antibody is thus a CRD1 domain specific binder. GBR 830 and MAB1 bound to RHRR, HHHR and HHRH proteins, not on HRRR protein. GBR 830 and MAB1 are therefore CRD2 domain specific binders. Isotype control antibody did not bind to any recombinant chimeric proteins. Thus, MAB1 bound the same CRD2 epitope as GBR 830. Therefore, the affinity maturation did not change the OX40 epitope on CDR2.

Figure 3:
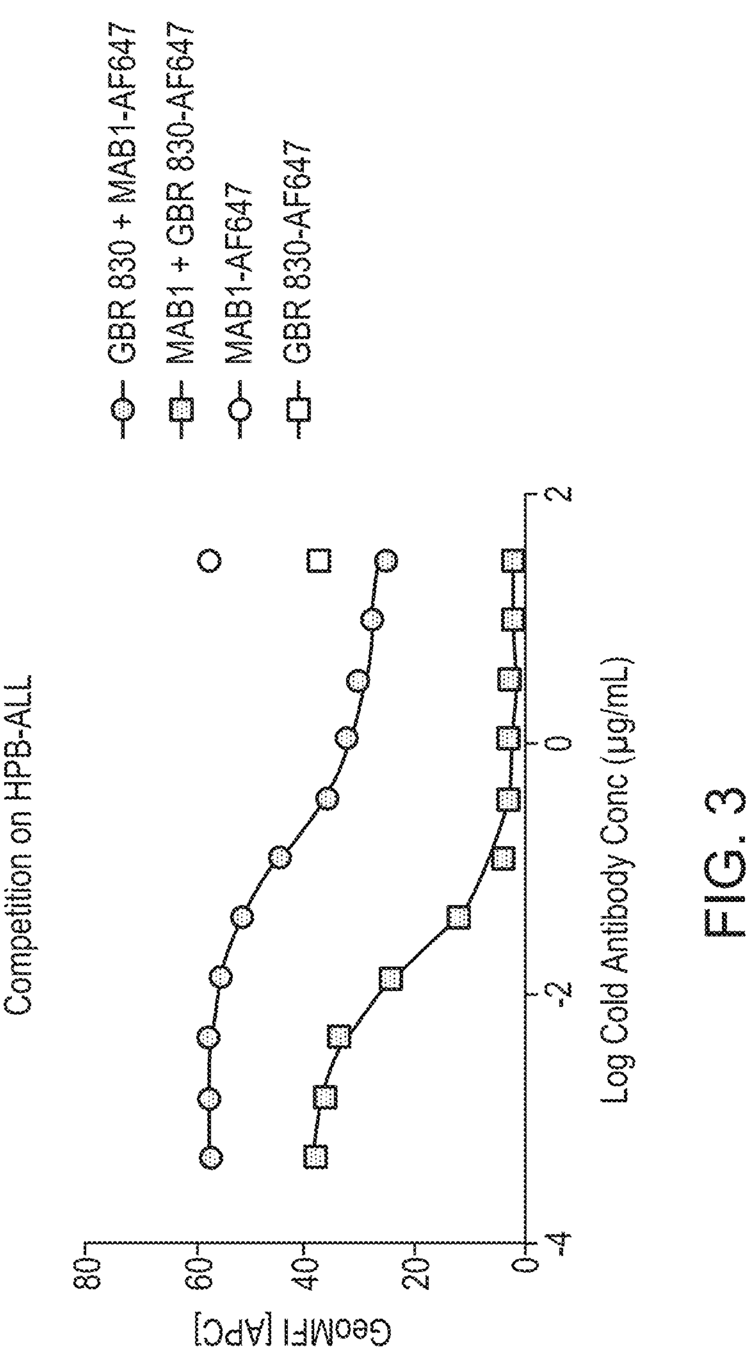
FIG. 3 is a graph showing the cross-blocking activity of GBR830 and MAB1, using the geometric mean fluorescence intensity (GeoMFI) of AF647 fluorescence (APC channel) on OX40-expressing HPB-ALL cells. The top curve shows the blocking effect of cold GBR 830 pre-incubation to the binding of labeled MAB1. The bottom curve shows the blocking effect of MAB1 pre-incubation on the binding of GBR 830-AF647. An IgG4-AF647 showed no background staining (not shown). The single points indicate binding of MAB1-AF647 and GBR 830-AF647 at the highest antibody concentration used.

GBR 830 and MAB1 were also tested for cross-blocking ability, using a flow cytometry staining on OX40-expressing HPB-ALL cell line. Labeled-GBR830 (GBR830-AF647) binding was blocked in a dose-dependent manner by MAB1 as indicated by the reduced geoMFI as cold antibody (MAB1) concentration increased. Similarly, labeled-MAB1 (MAB1-AF647) binding was partially blocked by GBR 830 (FIG. 3). The partial block may be due to MAB1-AF647 displacement of GBR 830 on the cell due to its higher affinity. This result further indicates that GBR 830 and MAB1 share the same epitope, and that MAB1 displays enhanced binding to cells expressing OX40 over GBR 830.

T Cell Agonism Assay with Coated Antibodies

Purified T cells from different donors were incubated in cell culture plates pre-coated with anti-CD3 (OKT3, to induce OX40 expression on T cells) and anti-OX40 or control antibodies. Agonism was assessed by T cell proliferation detected by incorporation of 3H-thymidine. A proliferation index (PI) superior to 2 between the OX40 antibody plus OKT3 and the OKT3-only conditions was considered as reflecting agonism since this threshold discriminated well between the positive controls and the negative IgG1 control. A PI superior to 2 was also previously used to characterize agonism for other TNFR targeting antibodies (Ralph, Panzenbeck et al. 2016).

OX40L and 7H11 were used as agonistic positive controls. Additional OX40 antagonists were also included: A26 (UCB pharma), A10 (Genentech) and 112V8 (corresponding to the sequence of the rocatinlimab antibody (also known as KHK4083 or AMG451) Kirin Pharma). The OX40 agonistic antibody MEDI0562 (humanized 9B12, tavolixizumab, Medimmune) was also included.

A donor was excluded from the analysis if: the sample showed agonism (PI>2) with the IgG1 control antibody or it showed no agonism with both positive controls OX40L and 7H11. If one positive control showed agonism the donor was included in the final analysis. A total of 5 out of 23 donors were excluded. Therefore, 18 donors were included in the final analysis.

Table 10 summarizes the proportion of responders and gives the average PI. The data indicate that the positive controls OX40L and 7H11, as well as the OX40 agonist antibody MEDI0562 (humanized 9B12) showed an average PI significantly superior to the IgG1 control antibody ($p<0.05$). In contrast, the average PI of GBR 830 and MAB1 were not different from the control, indicating that neither antibody induced activation of OX40, and thus did not display detectable agonism.

TABLE 10

Summary of agonism in coated antibody T cell assay

| | OX40L | HuIgG1 | 7H11 | A10 | A26-IgG | 112V8 |
|---|---|---|---|---|---|---|
| Av | 5.61 | 1.16 | 8.36 | 3.05 | 2.59 | 9.56 |
| SD | 7.47 | 0.38 | 6.39 | 1.41 | 2.28 | 12.45 |

TABLE 10-continued

| Summary of agonism in coated antibody T cell assay | | | | | | |
|---|---|---|---|---|---|---|
| Resp | 11 of 18 | 0 of 15 | 17 of 18 | 9 of 11 | 5 of 14 | 7 of 9 |
| p | 0.0106 | Ref | 0.0008 | 0.0016 | 0.0101 | 0.0375 |
| | Ab131 | Ab315 | GBR830 | MAB1 | 9B12 | Anti-CD28 |
| Av | 5.47 | 2.27 | 0.98 | 0.97 | 3.41 | 22.57 |
| SD | 1.07 | 1.28 | 0.37 | 0.36 | 1.77 | 25.95 |
| Resp | 3 of 3 | 2 of 3 | 0 of 18 | 0 of 13 | 9 of 11 | 11 of 13 |
| p | NA | NA | 0.9821 | 0.9302 | 0.0005 | 0.0062 |

Legand:
Av is average stimulation index, calculated on all donors included in the final analysis.
SD is standard deviation.
Resp indicates the proportion of T cell donors showing a SI >2 out of total included donors, for each antibody.
P indicates the p value of a paired student t-test comparing each treatment to huIgG1 control.
NA: not applicable, no paired IgG control data.

Legend: Av is average stimulation index, calculated on all donors included in the final analysis. SD is standard deviation. Resp indicates the proportion of T cell donors showing a SI>2 out of total included donors, for each antibody. P indicates the p value of a paired student t-test comparing each treatment to huIgG1 control. NA: not applicable, no paired IgG control data.

The positive controls OX40L and 7H11 antibodies showed agonism in the majority of T cell donors (11 and 17 out 18 respectively) as defined by a PI>2. The OX40 agonist antibody MEDI0562 (humanized 9B12) also displayed agonism with 9 out of 11 donors. Interestingly, the A26, as well as the 112V8 and A10 antibodies, which are described as OX40 antagonists also displayed agonism with a substantial proportion of T cell donors. Similarly the Ab 315 and Ab 131, two antibodies described to block OX40L-mediated adhesion of OX40 T cells (Imura, Hori et al. 1996) also showed agonism. In contrast, GBR 830 did not show any sign of agonism in any of the 18 T cell donor populations in which it was tested. Importantly, MAB1 did also not show agonism in any of the 13 donor cell populations in which it was tested.

Figure 7:
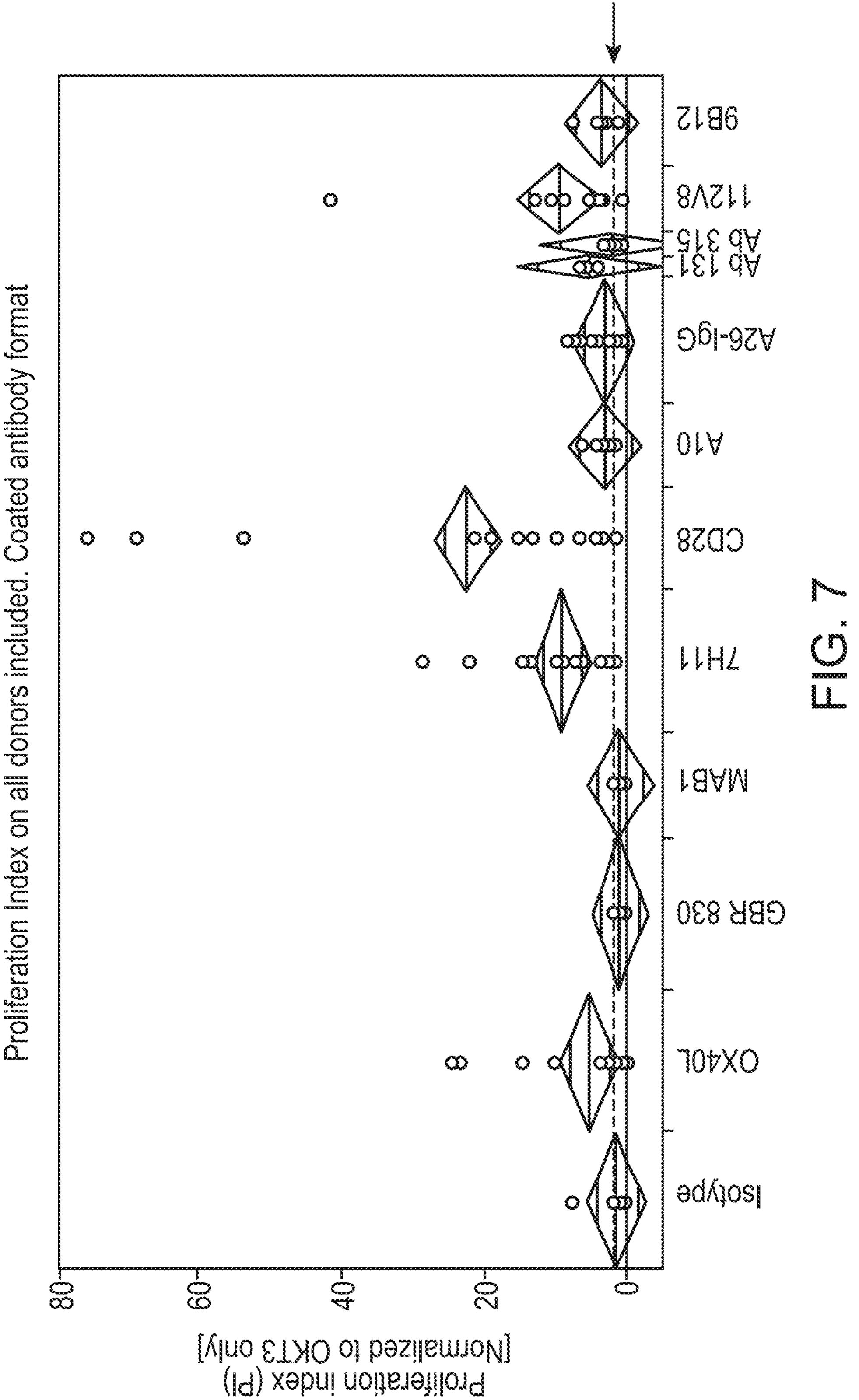
FIG. 7 is a chart showing T cell agonism measured by the proliferation indexes for the indicated antibodies at the highest concentration tested (5 or 10 μg/mL) for all T cell donors in the soluble antibody with no crosslinking assay. The horizontal line indicated with an arrow shows the threshold considered for agonism (PI>2). Each dot represents the average PI of a triplicate measurement. The diamond shaped green box shows the mean and 95% confidence intervals of the mean. CD28 indicates anti-CD28 used as a soluble agent. Isotype is an IgG1 isotype control.

FIG. 7 provides the proliferation index data on all donors included in the final analysis, with all antibodies tested. The horizontal line above zero represents the threshold for agonism (PI>2). As shown, MAB1 was below the threshold for agonism.

T Cell Agonism with Antibodies as Soluble Agents with or without Fc Crosslink

An assay with OX40 antibodies as soluble agent was also performed in parallel to the coated antibody format. Briefly, purified T cells from 6 donors were incubated in cell culture plates pre-coated with anti-CD3. OX40 or control antibodies were added as soluble agents (at 10, 1 and 0.1 μg/mL). In some conditions an anti-human IgG Fc fragment specific was added at 5 μg/mL. Agonism was assessed by calculating the PI as in the coated assay format.

Figure 8:
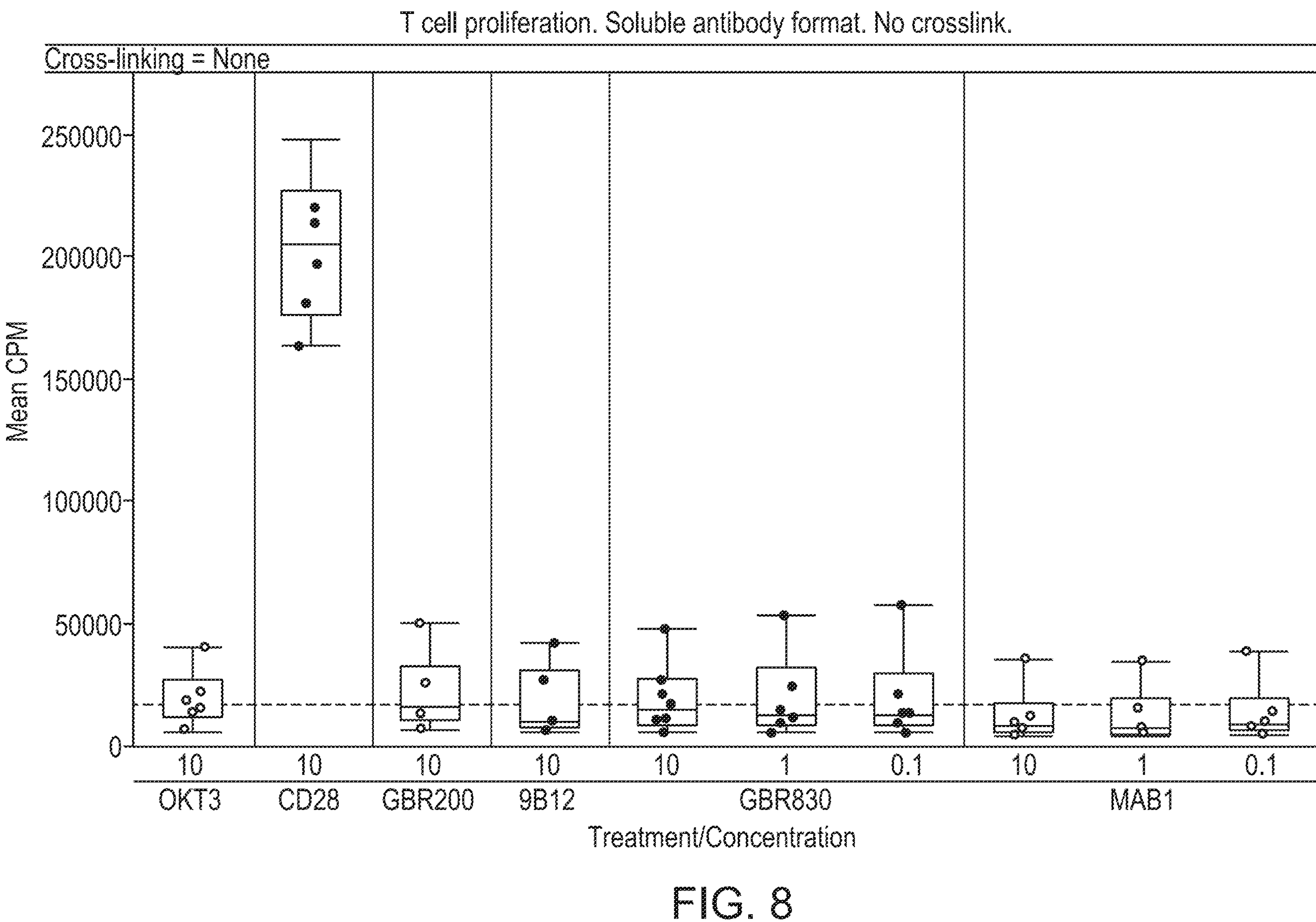
FIG. 8 is a chart showing T cell agonism, assessed by T cell proliferation measured by radioactivity counts per minute (CPM) for the indicated conditions in a soluble antibody no crosslinking assay. Each point represents the average CPM of a triplicate measurement. The boxes show the median, 25th and 75th quartile and the whiskers the lowest and highest measure. "OKT3 alone" is anti-CD3 only (OKT3) condition, and "GBR 200" is trastuzumab used as an IgG1 control, "CD28" is an anti-CD28 antibody and "9B12" is an OX40 agonistic antibody, each of which was used at 10 μg/mL. Soluble antibodies GBR 830 and MAB1 were used at 10, 1 and 0.1 μg/mL. The dashed line indicates the baseline level of anti-CD3 only.

No antibodies showed detectable agonism when added as soluble agents, except the positive control anti-CD28 antibody which showed strong agonism. (FIG. 8). These 6 donors all showed agonism with the positive control 7H11 and the OX40 agonist MEDI0562 (humanized 9B12) in the coated antibody format.

Figure 9:
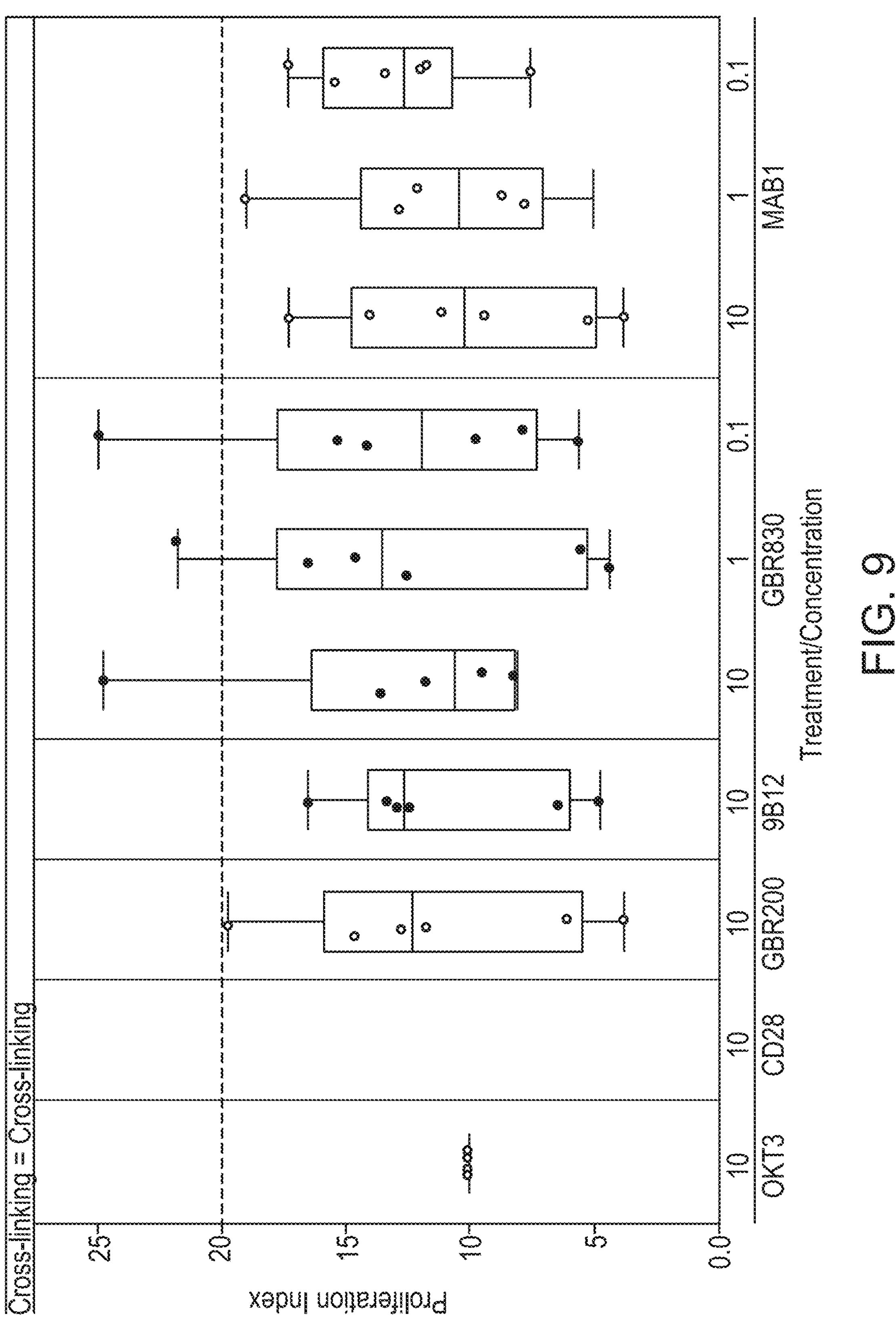
FIG. 9 is a chart showing T cell agonism, measured by the proliferation index for the indicated conditions in the soluble antibody with crosslinking assay. Each point represents the average PI of a triplicate measurement. The boxes show the median, 25th and 75th quartile and the whiskers the lowest and highest measure. "OKT3 alone" is anti-CD3 only (OKT3) condition, and "GBR 200" is trastuzumab used as an IgG1 control, "CD28" is anti-CD28 antibody and "9B12" is an OX40 agonistic antibody, each of which was used at 10 μg/mL. Soluble antibodies GBR 830 and MAB1 were used at 10, 1 and 0.1 μg/mL. The dashed line indicates the threshold considered for agonism (PI>2).

When an anti-human IgG-Fc specific crosslinker antibody was added to the soluble antibodies, the results were similar (FIG. 9). MAB1 showed no agonism in the 6 donors tested in this experiment.

Characterization of Agonism Activity in the Jurkat-NFκB Assay

A Jurkat-OX40-NFκB-signaling assay was used to test agonism of OX40 antibodies. The Jurkat-NFκB cells respond to OX40 signaling by producing luciferase. The cells response to OX40L and GBR 830 was to consistently inhibit OX40L-mediated luciferase production (data not shown). This type of assay was sensitive to detect agonism of OX40 antibodies and other TNFR antibodies (see, e.g., Voo et al. (2013) J. Immunol., 191(7): 3641-3650; Zhang et al. (2016) J. Biol. Chem., 291(53): 27134-27146; Ralph et al. (2016) J. Immunol., 196 (Suppl 1): 70.19-70.19).

Figure 4:
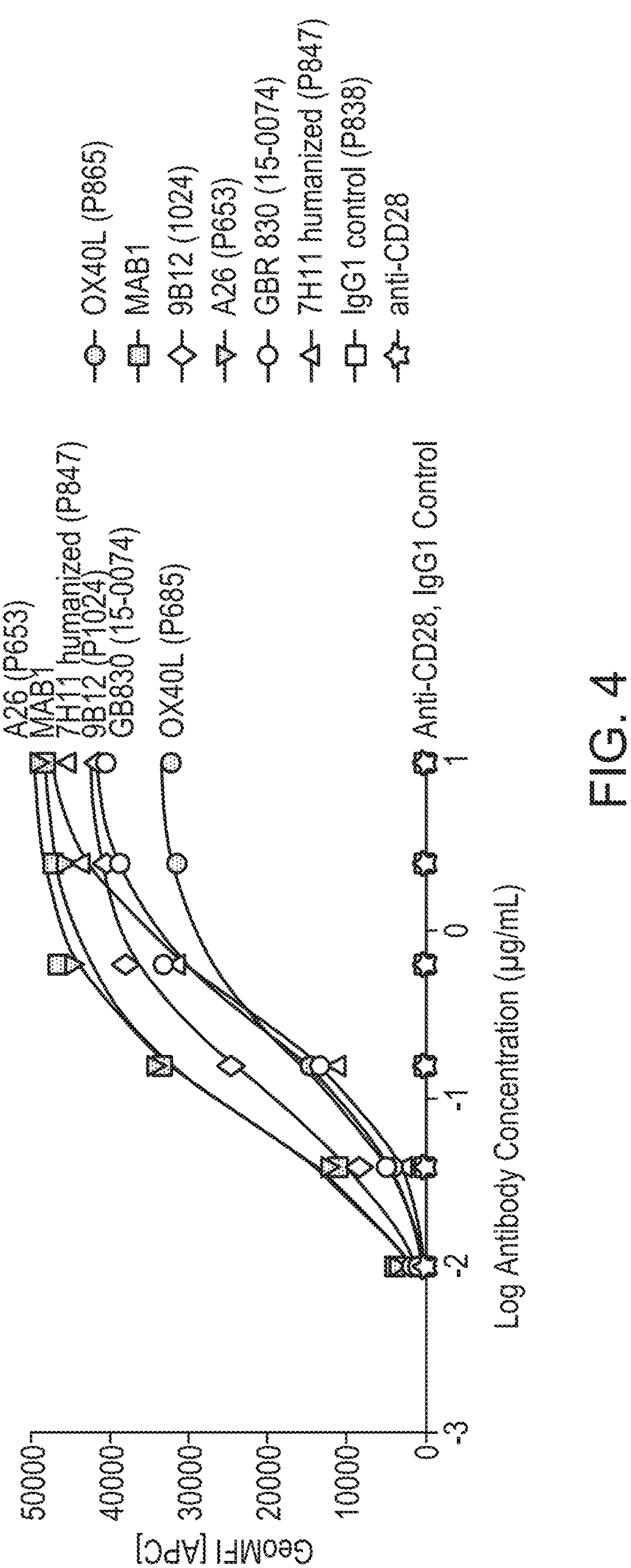
FIG. 4 is a graph showing FACS binding of anti-OX40 antibodies when Jurkat-NFκB cells were incubated with a dose response of OX40L-Fc or the indicated antibodies. Staining was detected with an anti-human IgG Fc-AF647 antibody. The graph shows the geometric mean fluorescence intensity (GeoMFI) of AF647 fluorescence (APC channel).

Antibodies used in this experiment were controlled for binding to Jurkat-NFκB cells (FIG. 4). As shown in FIG. 4, all antibodies except the anti-CD28 and the IgG1 control bound to the Jurkat-NFκB cells.

Figures 5A, 5B:
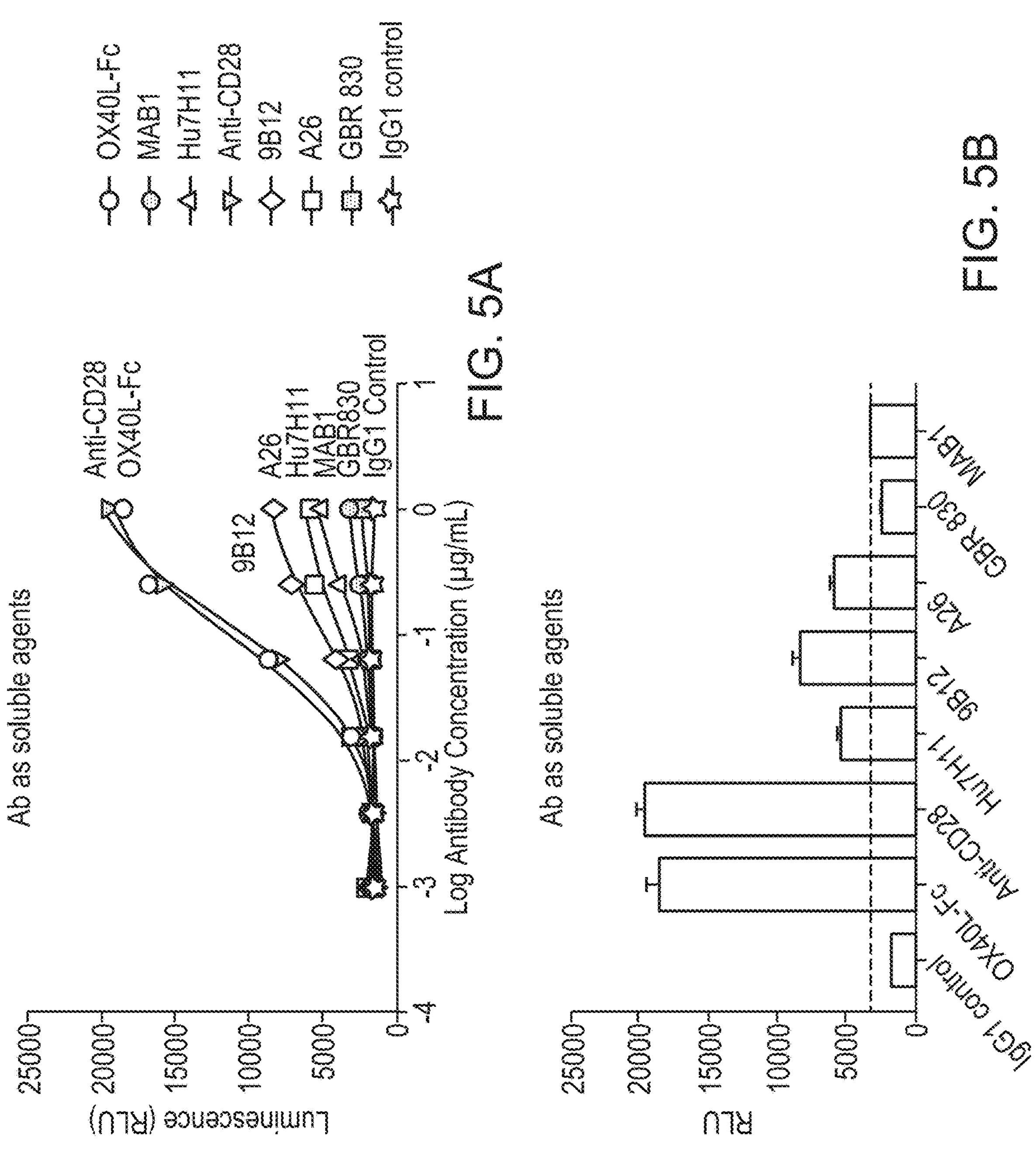
FIG. 5A is a graph showing dose response curves when Jurkat-NFκB cells were incubated with the indicated antibodies or OX40L on CD3 pre-coated plates. The graph shows the luminescence dose response for indicated antibodies. Each point shows the average of duplicates. The curve shows the non-linear regression fitting.
FIG. 5B is a bar chart showing the luminescence response at the highest tested concentration. The dotted line indicates the threshold of 2-fold over the IgG1 control.
Figures 23A, 23B:
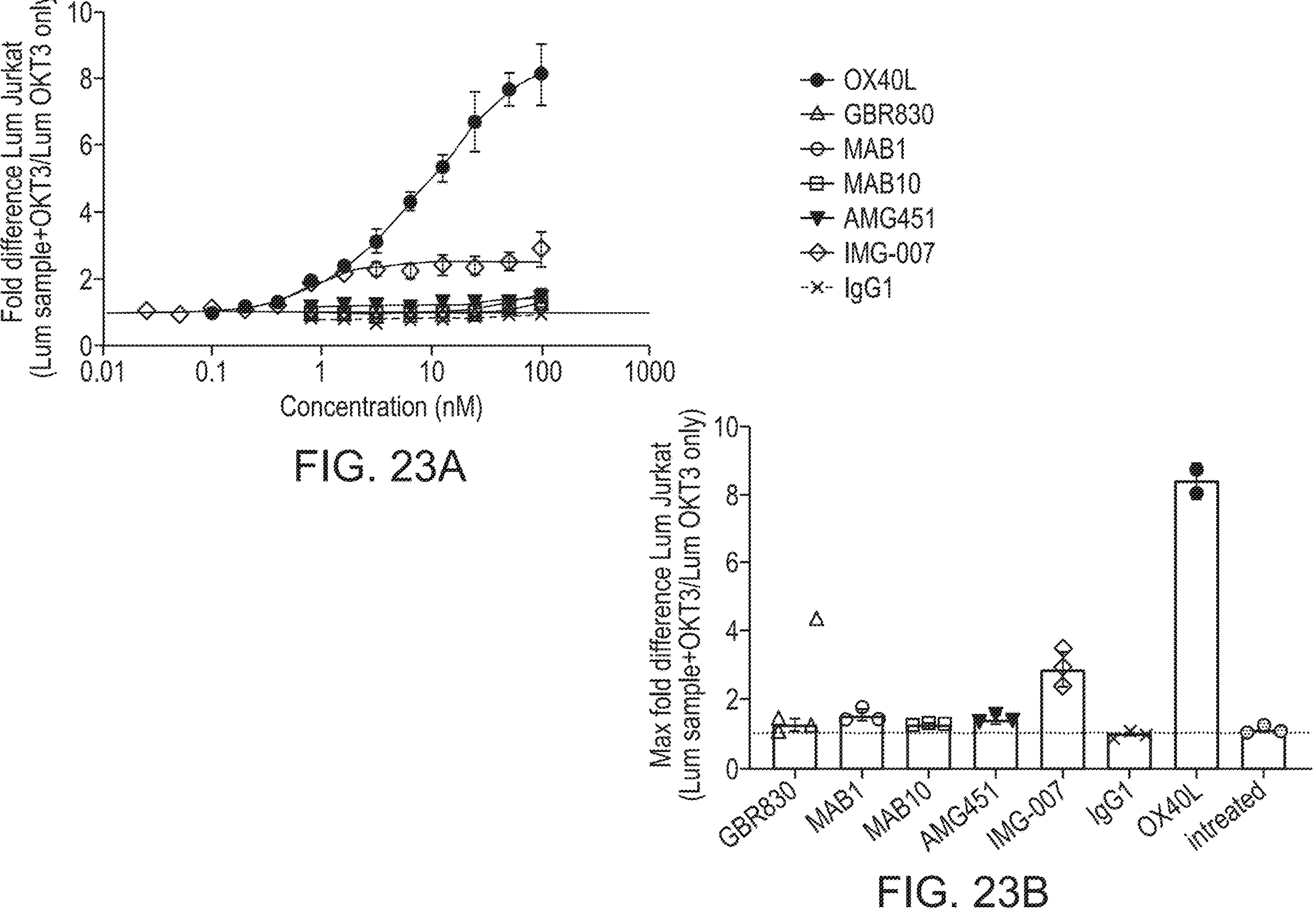
FIG. 23A is a graph showing dose response curves when Jurkat-NFκB cells were incubated with the indicated antibodies or OX40L on CD3 pre-coated plates. The graph shows the luminescence dose response for indicated antibodies. Each point shows the average of duplicates. The curve shows the non-linear regression fitting.
FIG. 23B is a bar chart showing the luminescence response for each of the indicated antibodies at the highest tested concentration. The dotted line indicates the threshold of 2-fold over the IgG1 control.

To render the system more sensitive, Jurkat-NFκB cells were stimulated by coated anti-CD3 during the assay. When no CD3 stimulation was applied, all signals, except OX40L were very weak (data not shown). Both OX40L and anti-CD28 triggered a strong signal (FIGS. 5A, 23A, 23B). In contrast, GBR 830, MAB1 and MAB10 triggered a signal similar to the IgG control even at the highest concentration (FIGS. 5B, 23A, 23B). MAB10 did not induce agonistic activity in the Jurkat-NFκB-OX40 cells and thus did not induce agonism of the OX40-OX-40L costimulatory pathway (FIGS. 23A and 23B). Similar results were obtained for GBR830, and MAB1, whereas IMG-007 induced a 3-fold increase in luminescence as compared to the untreated control. OX40L, used as a positive control, induced 8-fold higher luminescence than the untreated control (OKT3 coated without treatment). IgG1 was used as a negative control. Both MEDI0562 (humanized 9B12) OX40 agonist and 7H11 antibody, which showed consistent agonism in the T cell-based proliferation assay, triggered a signal more than 2 fold above the IgG control (FIG. 5A). Similarly, the A26 antibody also triggered a signal at least 2 fold above background, thus indicated agonism of the T cells.

Figures 6A, 6B:
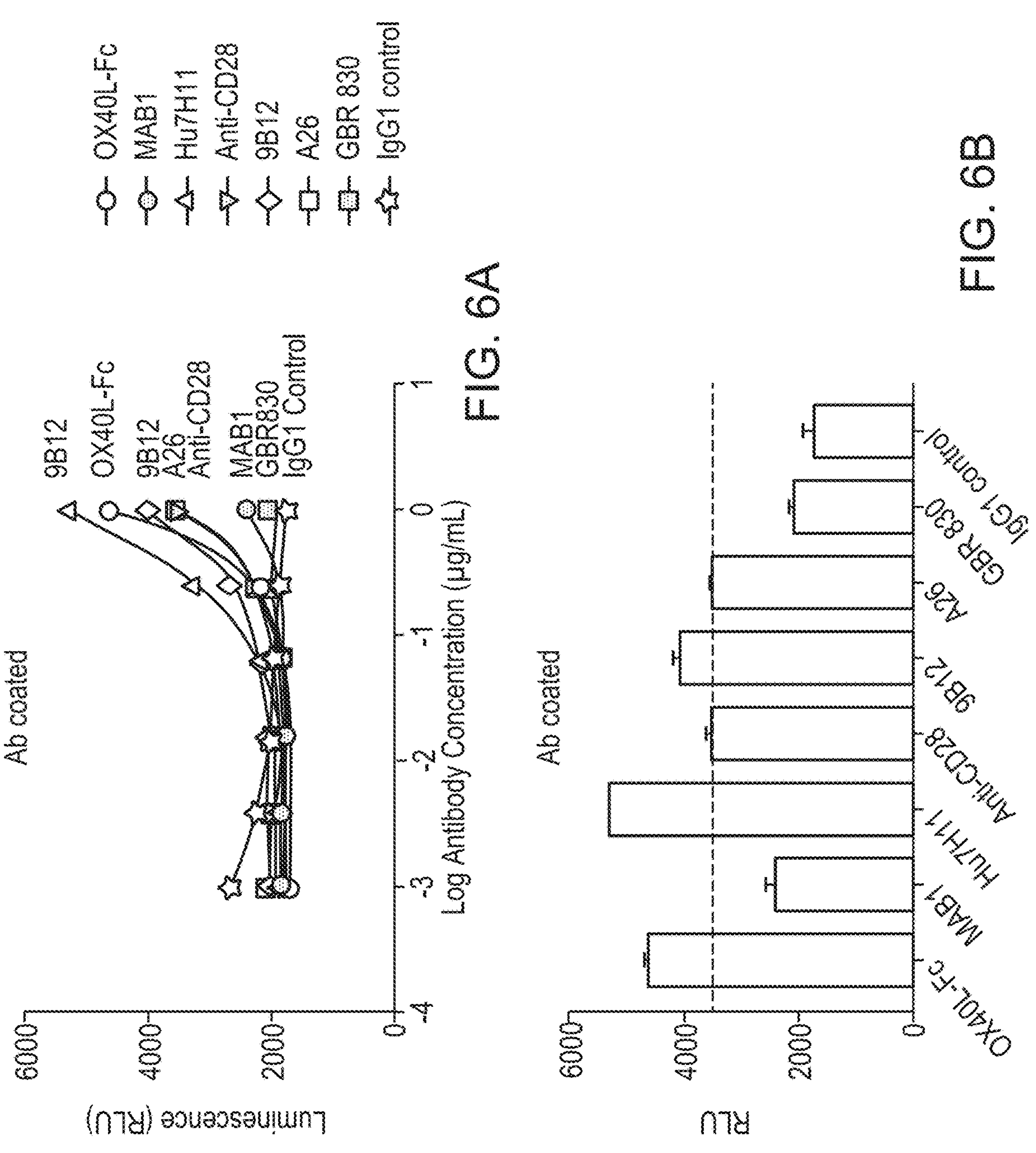
FIG. 6A is a graph showing dose response curves of the agonism activity when Jurkat-NFκB cells were incubated on plates co-coated with OKT3 plus the indicated antibodies. The graph shows the luminescence dose response for indicated antibodies. Each point shows the average of duplicates. The curve shows the non-linear regression fitting.
FIG. 6B is a bar chart showing the luminescence response at the highest tested concentration. The dotted line indicates the threshold of 2-fold over the IgG1 control.

The assay was also performed with coated antibodies. The signaling induced by the positive control OX40L was weaker but still present. However, similarly to the soluble condition, all antibodies, except GBR 830 and MAB1 triggered a signal above the IgG1 control (FIG. 6). Thus, GBR 830 and MAB1 did not induce OX40 signaling in the assay with the coated antibodies, in contrast to the other OX40 antibodies tested.

These data show that in the Jurkat-OX40-NFκB-signaling assay, GBR 830, the affinity matured MAB1, and the Fc modified MAB10 antibodies were not able to trigger signaling by OX40, either when used in solution or as coated agents.

In sum, GBR 830 and MAB1 did not display OX40 signaling (agonism) in a total of 18 and 13 human T cell donors, respectively, in the human T cell based assay, with coated antibodies. Thus, the affinity matured MAB1 antibody exhibited both a significant increase in affinity as compared to the parental clone GBR 830 and an absence of detectable agonism in vitro. In contrast, the positive control humanized 7H11 antibody showed agonism with 17 out of 18 human cell donors. Similarly, the OX40 agonist antibody MEDI0562 (humanized 9B12) displayed agonism in 9 out of 11 donors. Anti-OX40 antibodies described as antagonists, such as A26, A10, or 112V8 (KHK4083/AMG451) also revealed agonism with a significant proportion of human T cell donors. Thus, the coated antibody assay was able to detect agonism of OX40L and 7H11 anti-OX40 antibody, as well as other anti-OX40 antibodies.

In the Jurkat-based signaling assay, GBR 830, MAB1 and MAB10 did not induce a significant signal while control antibodies 7H11 and MEDI0562 did induce a signal at least 2 fold above the IgG control. In this assay the A26 "antagonist" antibody also revealed agonism. As shown in FIGS. 23A-B, the anti-OX40 antibody IMG-007 also induced agonism in the Jurkat cells.

These data indicate that an increase of over 10 fold in affinity by MAB1 antibody did not result in increased agonism of OX40 signaling as compared to the parental GBR 830 antibody. Thus, there was no observable tradeoff between better antibody binding and increased agonistic activity by the MAB1 and MAB10 antibodies. The increased affinity and lack of detectable agonism in vitro is a unique and unexpected property of MAB1 and MAB10 among anti-OX40 antibodies.

Example 3: In Vitro Characterization of MAB1 Pharmacology Profile

Materials and Methods

PBMC Isolation

Human peripheral blood mononuclear cells (PBMC) were harvested from apheresis filters using Ficoll gradient isolation. Briefly, the blood was diluted ½ with PBS and the cells suspension was layered on 50 ml Sepmate Tubes (StemCell Technologies) pre-filled with Ficoll. After centrifugation at 1200 g for 10 minutes with brake, the supernatants containing the mononuclear cells were collected and transferred into a tube. The PBMCs were washed 3 times with PBS by centrifugation for 10 minutes at 350 g and used immediately or frozen in CryoStorCS10 medium.

Activated T Cells Proliferation

T Cell Isolation and Purity Assessment

T cell isolation was performed following the indication of the Human Pan T cell isolation kit by Miltenyi. Briefly, human PBMC were counted and resuspended in the isolation buffer containing PBS+0.5% BSA+2 mM EDTA (40 μL per $10^7$ total cells). 10 μL of Pan T Cell Biotin-Antibody Cocktail per $10^7$ total cells was mixed with the cell suspension and incubated for 5 minutes at 4° C. After incubation, 30 μL of isolation buffer was added (per 107 total cells) and 20 μL of Pan T Cell MicroBead Cocktail was added. The cells were incubated 10 minutes at 4° C. and added to the LS column, which had been previously rinsed with 3 mL of isolation buffer. After further wash of the column with 3 mL of isolation buffer, all the flow-through, containing the purified enriched T cell population, was collected and used for subsequent assays.

The human CD3+ T cells purity was assessed by flow cytometry. Briefly, 100,000 isolated CD3+ T cells were seeded in a U-bottom p96 wells and washed once. Cells were then resuspended in flow cytometry buffer containing the following anti-human antibodies: CD3 APC-eF780 (clone SK7), CD4 PE-Cy7 (clone OKT4), CD8 AF700 (clone SK-1), CD33 PE-Cy5 (clone HIM3-4), CD56 PE-eF610 (clone CMSSB), CD19 AF488 (HIB19), CD45RA APC (clone HI100), CCR7 PE (clone 3D12), in the presence of Fc block. After 20 min in the fridge, the cells were washed with flow cytometry buffer and resuspended in DAPI solution and acquired with a Cytoflex-S(Coulter) instrument, using the following gating strategy: CD45, CD56, CD3, CD4 and CD8 specific antibodies were used to assess single viable cells for expression of CD45, CD3, CD4 and CD8 by flow cytometry. The fraction of CD3+ CD56− T cells was quantified in single viable cells as well as the relative fractions of CD4 and CD8 T cells. Only cell isolations that exceeded 90% of CD3+ T cells were used for the proliferation assay.

T Cell Activation

On the day of the T cell isolation, 6-well plates were pre-coated with anti-human CD3 Ab OKT3 (4 ug/mL in PBS), at 4° C. ON. The next day the wells were rinsed with sterile PBS and rested isolated T cells were seeded in the OKT3-coated wells at $5\times10^6$ cells/mL in complete RPMI medium with the addition of sCD28 (1 μg/mL). The cells were then incubated at 37° C. for 30 hrs.

Evaluation of OX40 Expression on Activated T Cells and Differentiated Tregs Populations Before performing the ADCC assay with activated T cells, the cells were tested for their surface expression of OX40, among other activation markers. Briefly, 100,000 activated T cells were collected and washed once before being resuspended in 50 μL flow cytometry buffer containing the following anti-human Abs: CD3 APC-eF780, CD4 PE-Cy7, CD8 BV421, CD25 AF700, CD69 SB600, CD107a AF488, CD134 PE. CD69 SB600, CD107a AF488, CD134 PE. After incubation at 4° C. for 20 min, cells were washed once and resuspended in Sytox Blue solution and acquired by a Cytoflex-S cytometer.

Proliferation Assay

The day of the T cell activation, 96-well plates were pre-coated with OX40L (5 g/mL in PBS) at 4° C. for 36 hrs. Thirty hours after incubation of T cells with OKT3 and sCD28, activated T cells were recovered and plated in U bottom 96-well plates $5\times10^6$ cells/mL in 200 μL of complete RPMI with serial dilution of GBR 830, MAB1, KHK4083 and control Ab (starting from 100 μg/mL, with 8 dilutions of 1/5) for 1 hr at 37° C. The cells were then transferred to the OX40L-coated plate and incubated for 3 days at 37° C. Eighteen hours prior the end of the assay, 0.5 Cu of Thymidine solution were added to each well. At the end of the incubation, Thymidine incorporation was measured by MicroBeta Trilux Counter (PerkinElmer). The percentage of inhibition of proliferation was calculated according to the following formula:

$$\%\ \text{Killing} = 100 - ((\text{Value} * 100/(\text{Max value}))$$

The percentage of inhibition of proliferation for each condition was then plotted using GraphPad Prism software. After logarithmic transformation, a non-linear regression was applied to all data sets, using a log (agonist) vs. response regression model to determine the EC50 values.

Antibody-Dependent Cell-Mediated Cytotoxicity (ADCC)-Mediated Killing of Activated T Cells by OX40 Antibodies and Differentiation of Tregs In Vitro T Cells Isolation and Activation PBMC were resuspended at $5\times10^7$ cells/ml in flow cytometry buffer and Enrichment Cocktail was added at 50 μl/mL of suspension. The cells were incubated at RT for 10 min and RapidSpheres were added at 40 μL/mL of suspension, mixed and incubated at RT for 5 min. The final volume of the suspension was brought at 10 mL with flow cytometry buffer and placed in the magnet for 3 minutes. The suspension was poured into a new tube and washed once. The T cells were plated at $1\times10^6$ cells/mL in complete RPMI with CD3/CD28 dynabeads ($1\times10^6$ beads/mL) and incubated for 40 hr at 37° C.

CD4+ T Cells Isolation and In Vitro Differentiation

The day before the selection, 6-well plates were coated with anti-human CD3 Ab (OKT3 at 5 μg/mL in PBS) for 18 hr at 37° C. PBMC were resuspended at $5\times10^7$ cells/mL in flow cytometry buffer and anti-CD45RO biotinylated Ab and Isolation Cocktail were added at 50μ/ml of suspension. The cells were incubated at RT for 5 min and RapidSpheres were added at 40 μL/mL of suspension, mixed and incubated at RT for 10 min. The final volume of the suspension was brought at 10 mL with flow cytometry buffer and placed in the magnet for 5 minutes. The suspension was poured into a new tube and the cells were washed once. The CD4+ T cells were plated at $1\times10^6$ cells/mL in complete RPMI with sCD28 (1 μg/mL), IL2 (100 IU/ml), Rapamycin (0.1 μg/mL), TGF-beta (0.005 μg/mL) and Retinoic acid (0.01 mM). The cells were incubated for 4 days in the incubator, then recovered and re-plated in new OKT3-pre-coated wells for 3 more days.

NK Cells Isolation

PBMC were resuspended at $5\times10^7$ cells/mL in flow cytometry buffer and Enrichment Cocktail was added at 50 μl/mL of suspension. The cells were incubated at RT for 10 min and magnetic particles were added at 100 μL/mL of suspension, mixed and incubated at RT for 5 min. The final volume of the suspension was brought at 10 ml with flow cytometry buffer and placed in the magnet for 2.5 minutes. The suspension was poured into a new tube and washed once. NK cells were plated at $1\times10^6$ cells/mL in complete RPMI and incubated for 24 hrs at 37° C. The next day, 100 IU/mL of IL2 were added and cells were incubated for an additional 24 hrs.

Evaluation of OX40 Expression on Activated T Cells and Differentiated Tregs Populations Before performing the ADCC assay with in vitro differentiated Tregs, the cells were tested for their surface expression of OX40, among other activation markers. For activated T cells, 100,000 activated T cells were collected and washed once before being resuspended in 50 μL flow cytometry buffer containing the following anti-human Abs: CD3 APC-eF780, CD4 PE-Cy7, CD8 BV421, CD25 AF700, CD69 SB600, CD107a AF488, CD134 PE. CD69 SB600, CD107a AF488, CD134 PE. After incubation at 4° C. for 20 min, cells were washed once and resuspended in Sytox Blue solution and acquired by a Cytoflex-S cytometer.

For the activated T cells, the following gating strategy was used: Following staining with viable dye, CD3, CD4, CD8 and CD134 specific antibodies, single viable activated CD3+ cells expressing CD4 or CD8 were gated and the fraction of CD134 positive cells evaluated.

For in vitro differentiated Tregs, 100,000 cells were collected and resuspended in PBS buffer in the presence of Fc blocking and fixable live/dead staining (L/D yellow) and incubated at 4° C. for 20 min. After incubation, cells were washed and resuspended in 50 μL flow cytometry buffer containing the following anti-human Abs: CD8 AF700, CD4 PE-eF610, CD25 SB645, CD127 APC, CD69 SB600, CD107a AF488, CD134 PE. After incubation at 4° C. for 20 min, cells were washed once and resuspended in 80 μL Fixation/Permeabilization buffer at 4° C. for 20 min. After wash with Permeabilization buffer, cells were stained with anti-Human FoxP3 PE-Cy7 at 4° C. for 30 min. After 2× wash with Permeabilization buffer, cells were resuspended in flow cytometry buffer and acquired by a Cytoflex-S cytometer.

For the in vitro differentiated Tregs, the following gating strategy was used: Following staining with viable dye, CD3, CD4, CD127, CD25, FOXP3 and CD134 specific antibodies, single viable cells co-expressing CD4 and CD25 were gated and the fraction of CD134 positive cells evaluated in $CD4^{Pos}CD25^{Pos}CD127^{Low}$FOXP3Pos cells.

ADCC-Mediated Killing of Activated T Cells by OX40 Antibodies

Activated T cells were collected and dynabeads were removed. Cells were counted and resuspended in PBS at $1\times10^6$ cells/mL in the presence of eF670 2 μM, for 15 min at 37° C. After wash, the cells were resuspended at $0.2\times10^6$ cells/mL and dispensed at 50 μL/well in a U bottom 96-well plate. GBR 830, MAB1, KHK4083 and isotype control were added at 20 nM, with serial dilutions of 1:5. NK cells were collected, washed and resuspended at $1\times10^6$ cells/mL and dispensed in wells. After 4.5 hrs of incubation, the plates were washed once and the cells were resuspended in Fixable L/D NIR dye and incubated for 30 min at 4° C. The cells were then washed and resuspended in flow cytometry buffer and acquired on a Cytoflex-S cytometer. For the analysis, the number of viable cells were extrapolated for each condition using FlowJo software (BD). For the % of ADCC, the following formula was used:

$$\% ADCC = \frac{\text{Samples Abs. count} - \text{Untreated Abs. count}}{0 - \text{Untreated Abs. count}} * 100$$

ADCC-Mediated Killing of In Vitro Differentiated Tregs by OX40 Antibodies

In vitro differentiated Tregs were collected and washed. Cells were counted and resuspended in PBS at $1\times10^6$ cells/mL in the presence of eF670 2 μM, for 15 min at 37° C. After wash, the cells were resuspended at $0.2\times10^6$ cells/mL and dispensed at 50 μL/well in a U bottom 96-well plate. GBR 830, MAB1, KHK4083 and isotype control were added at 20 nM, with serial dilutions of 1:5. NK cells were collected, washed and resuspended at $1\times10^6$ cells/mL and dispensed. After 4.5 hrs of incubation, the plates were washed once and the cells are resuspended in Fixable L/D NIR dye and incubated for 30 min at 4° C. The cells were then washed and resuspended in flow cytometry buffer and acquired on a Cytoflex-S cytometer.

For the analysis, the number of viable cells were extrapolated for each condition using FlowJo software (BD). For the % of ADCC, the following formula was used:

$$\% ADCC = \frac{\text{Samples Abs. count} - \text{Untreated Abs. count}}{0 - \text{Untreated Abs. count}} * 100$$

Results

T Cell Proliferation Assay and Purity

GBR 830 and MAB1 were first tested for their potency to inhibit the proliferation of activated purified T cells exposed to OX40 ligand. Their potency was compared to antibody KHK4083. The inhibition of T cell proliferation was evaluated by thymidine incorporation.

T cells were isolated from healthy donor PBMCs by negative immunomagnetic selection and the purity of the T cell fraction was assessed by flow cytometry using the gating strategy described above. Isolated T cell fractions that exceeded 90% of CD56− CD3+ cells in single viable cells were used for proliferation assay.

T cell proliferation inhibition as induced by antagonistic antibodies GBR 830, MAB1, and KHK4083 was assessed. To assess the potency of OX40 antagonistic antibodies to inhibit T cell activation, T cells purified from PBMCs were stimulated through TCR/CD3 and CD28 triggering with antibodies and exposed to OX40 ligand in the presence of increasing concentrations of anti-OX40 antibodies. TCR/CD3 and CD28 triggering induced OX40 expression at the surface of T cells, which were then incubated with OX40 blocking antibodies for one hour at 37° C. Activated T cells were then exposed to immobilized OX40 ligand for three days and their proliferation was measured by thymidine incorporation.

Figure 10:
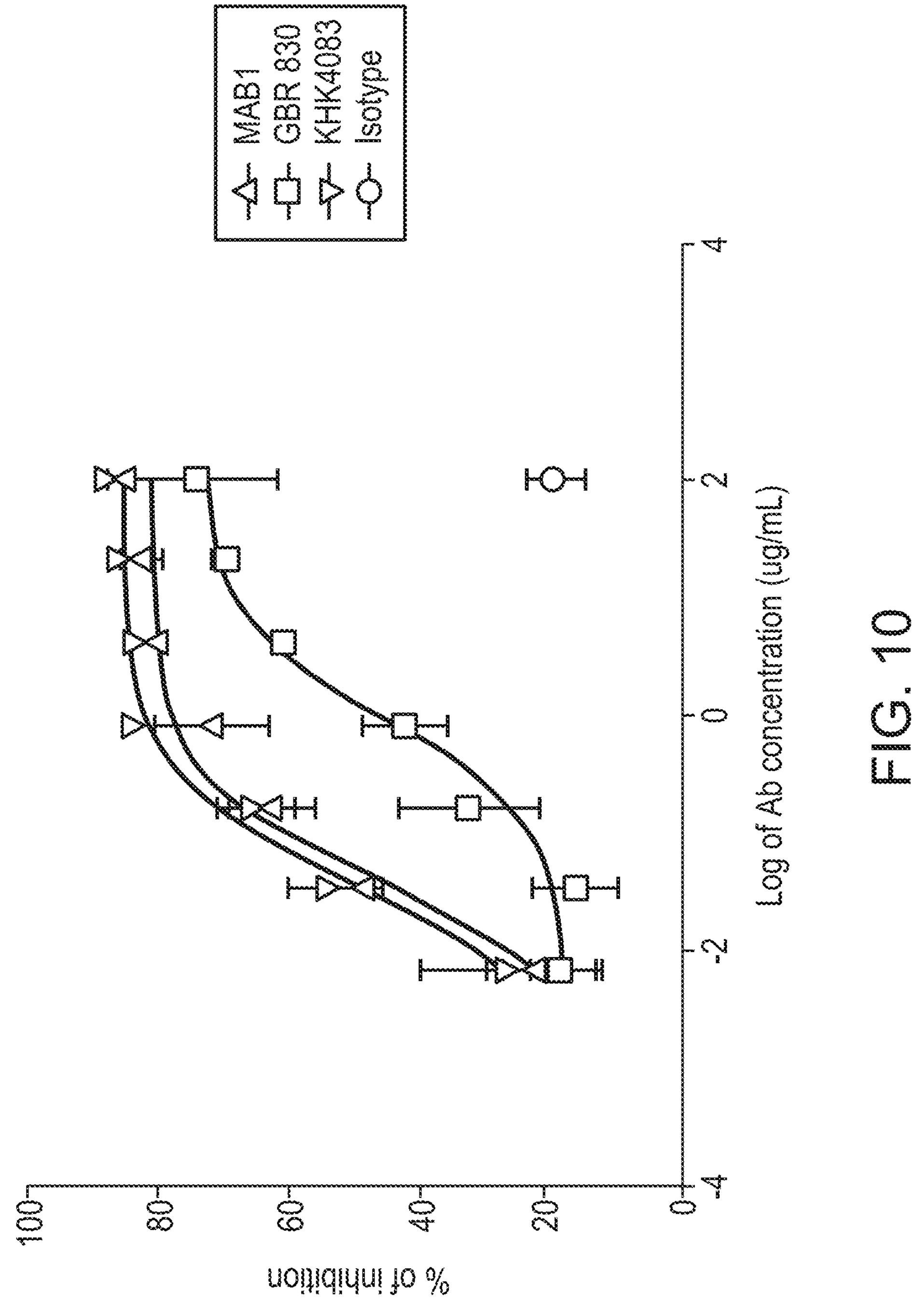
FIG. 10 is a graph showing the inhibition of T cell proliferation. Isolated T cells were activated via TCR and CD28 triggering, exposed to OX40L and treated with GBR 830, MAB1, KHK4083 and isotype control antibodies. The graph shows one example of dose response inhibition of T cell proliferation from one PBMC donor. Each data point is the mean of the percentage of inhibition of T cell proliferation from the same PBMC donor performed in triplicate, standard deviation to the mean is shown. Five independent experiments were performed.

Inhibition of T cell proliferation induced by GBR 830, MAB1 and KHK4083 in the T cell proliferation assay is provided in FIG. 10. Data from five independent experiments conducted with five distinct PBMC donors indicate that MAB1 is 33-fold more potent than GBR 830 to inhibit T cell proliferation (EC50 of inhibition of 0.17+/−0.01 and 5.67+/−2.1 nM, respectively; Tukey-HSD test, p=0.0014) and equally potent as KHK4083 (EC50 of inhibition of 0.17+/−0.01 and 0.15+/−0.01 nM, respectively; Tukey-HSD test, p>0.05). Table 11 provides a summary of the T cell proliferation inhibitory EC50 for MAB1, GBR 830, and KHK4083 and a statistical analysis of inhibition of T cell proliferation, including Half maximal effective concentration (EC50) of GBR 830, MAB1 and KHK4083 to induce inhibition of T cell proliferation in a thymidine proliferation assay and p value comparison of MAB1 to GBR 830 and KHK4083 (AMG451).

MAB1 T cell inhibition was compared to GBR 830 and KHK4083 (AMG451). A Tukey-HSD test was performed on the EC50 obtained from five independent experiments conducted with T cells from five healthy donors. MAB1 unexpectedly induced an inhibition of T cell proliferation statistically significantly higher than GBR 830, in fact, about 30 fold higher.

TABLE 11

Statistical Analysis of Inhibition of T Cell Proliferation

| EC50 Mean ± SD, five donors | | | P value, MAB1 vs other abs | Fold change to GBR 830 |
|---|---|---|---|---|
| GBR 830 | nM | 5.67 ± 2.1 | P = 0.0014 | — |
| | ug/ml | 0.833 ± 0.47 | | |
| MAB1 | nM | 0.17 ± 0.01 | — | 33 |
| | ug/ml | 0.24 ± 0.02 | | |
| KHK4083 | nM | 0.15 ± 0.01 | p > 0.05 | 38 |
| | ug/ml | 0.019 ± 0.02 | | |

Values are averages (±SD) from independent experiments. EC50=Half maximal effective concentration of inhibition of T cell proliferation from five independent experiments conducted with T cells from five healthy donors.

ADCC Assay

The potency of GBR 830 and MAB1 to kill T cells through ADCC in vitro was next assessed and compared to KHK4083. First, the expression level of OX40 at the surface of activated T cells and Tregs differentiated in vitro was determined, and the potency of OX40 antibodies to induce the killing of these T cell populations in vitro by ADCC was measured.

Quantification of OX40 Expression at the Surface of Activated T Cells and In Vitro Differentiated Tregs T cells isolated from PBMCs by immunomagnetic selection and activated through TCR and CD28 triggering for 40 hr were used as a source of activated T cells in this assay. Tregs were differentiated in vitro from immunomagnetically selected CD4 memory T cells that were activated through TCR/CD28 triggering and exposed to TGF-beta, IL-2, retinoic acid and rapamycin. The expression of OX40 (CD134) at the surface of activated T cells and Treg cell populations was measured by flow cytometry using the gating strategy described previously. A consistent and robust up-regulation of OX40 expression was observed at the surface of more than 63% of activated CD8+ T cells and 82% of activated CD4+ T cells (data not shown). OX40 expression at the surface of Tregs differentiated in vitro was evaluated with a comparable approach using the gating strategy described above. OX40 was up-regulated at the surface of more than 87% of Tregs (data not shown).

ADCC-Mediated Killing of Activated T Cells by OX40 Antibodies

In order to assess whether OX40 antagonistic antibodies induce the killing of OX40 expressing T cells, purified activated T cells and Tregs were co-cultured with human activated NK cells in the presence of increasing concentrations of GBR 830, MAB1, benchmark and control Ab. The fraction of T cells killed by ADCC was evaluated by flow cytometry 4.5 hours later.

Figure 11:
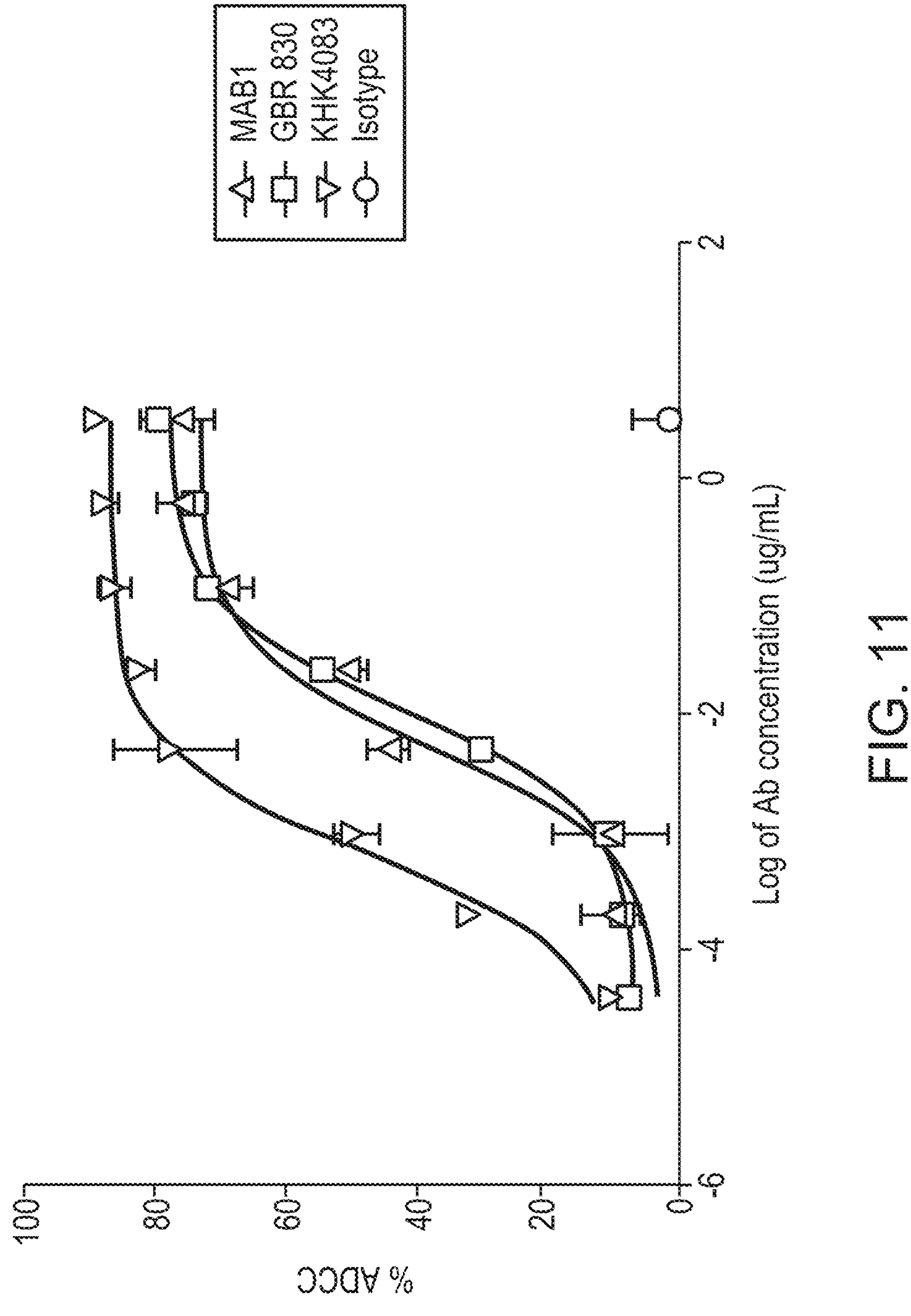
FIG. 11 is a graph showing ADCC-mediated killing of activated T cells by OX40 and isotype control antibodies. Isolated activated T cells were co-cultured with activated NK cells in the presence of GBR 830, MAB1, KHK4083 and isotype control antibodies. The graph shows one example of dose response of T cell killing through ADCC. Each data point is the mean of the percentage of T cell killing through ADCC from the same PBMC donor performed in triplicate, standard deviation to the mean is shown. Fifteen independent experiments were performed.

FIG. 11 shows T cell killing by ADCC induced by GBR 830, MAB1 and KHK4083. Data from two independent experiments conducted with six distinct PBMC donors indicate that MAB1 and KHK4083 were more potent than GBR 830 to kill activated T cells through ADCC, respectively. However, MAB1 induced 3-fold less ADCC than the KHK4083 antibody. Thus, while both KHK4083 and MAB1 show a higher T cell killing potency than GBR 830, KHK4083 also exhibited a higher T cell killing potency than MAB1. The comparatively reduced T-cell killing potentially of MAB1 suggests a superior safety profile as compared to KHK4083.

Table 12 provides a summary of the half maximal effective concentration (EC50) of GBR 830, MAB1 and KHK4083 to induce T cell killing through ADCC and a statistical analysis of the ADCC killing. All the values are averages (±SD) from different experiments. EC50=Half maximal effective concentration of T cell killing through ADCC from fifteen independent experiments conducted with T cells and NK cells from five healthy donors.

TABLE 12

| ADCC EC50 Mean ± SD, 15 donors | | | P value, MAB1 vs other abs | Fold Change to GBR 830 |
|---|---|---|---|---|
| GBR 830 | nM | 0.078 ± 0.02 | P = 0.0002 | — |
| | ug/ml | 0.13 ± 0.005 | | |
| MAB1 | nM | 0.026 ± 0.02 | — | 3.25 |
| | ug/ml | 0.004 ± 0.001 | | |

TABLE 12-continued

| ADCC EC50 Mean ± SD, 15 donors | | | P value, MAB1 vs other abs | Fold Change to GBR 830 |
|---|---|---|---|---|
| KHK4083 | nM | 0.008 ± 0.004 | p > 0.05 | 9.8 |
| | ug/ml | 0.001 ± 0.001 | | |

ADCC-Mediated Killing of In Vitro Differentiated Tregs by OX40 Antibodies

Figure 12:
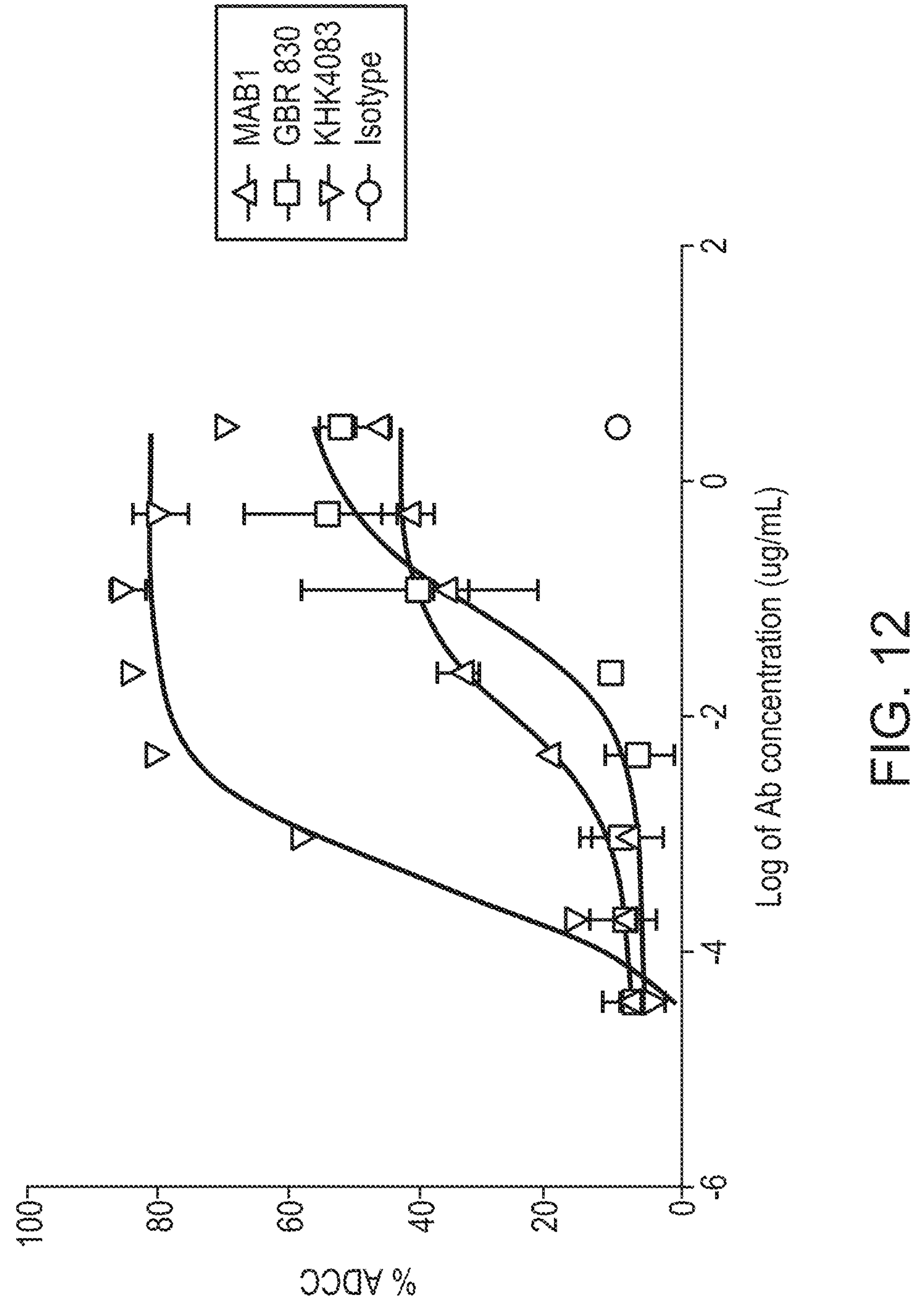
FIG. 12 is a graph showing ADCC-mediated killing of in vitro differentiated Tregs by OX40 and isotype control antibodies. In vitro differentiated Tregs were co-cultured with activated NK cells in the presence of GBR 830, MAB1, KHK4083 and isotype control antibodies. The graph shows one example of dose response of Treg killing by ADCC. Each data point is the mean of the percentage of T cell killing through ADCC from the same PBMC donor performed in triplicate, standard deviation to the mean is shown. Five independent experiments were performed.

Isolated human NK were incubated with in vitro differentiated human Tregs in the presence of GBR 830, MAB1, KHK4083 and isotype control Ab. A representative example of ADCC-mediated killing of in vitro differentiated Tregs by OX40 antibodies is shown in FIG. 12. Data from five independent experiments conducted with five distinct PBMC donors indicate that MAB1 and KHK4083 induced more ADCC-mediated killing of Tregs as compared to GBR 830 respectively. However, KHK4083 also shows a statistically higher ADCC potency than MAB1 (Tukey-HSD test, p=0.015). Thus, while both KHK4083 and MAB1 show a higher ADCC mediated T cell killing potency than GBR 830, KHK4083 also exhibited a higher T cell killing potency than MAB1.

Table 13 provides a summary of the half maximal effective concentration (EC50) of GBR 830, MAB1 and KHK4083 to induce T cell killing through ADCC in in vitro differentiated Tregs and a statistical analysis of the ADCC killing. All the values are averages (±SD) from different experiments. EC50=Half maximal effective concentration of T cell killing through ADCC from fifteen independent experiments conducted with T cells and NK cells from five healthy donors.

TABLE 13

| ADCC EC50 Mean ± SD, 15 donors | | | P value, MAB1 vs other abs | Fold Change to GBR 830 |
|---|---|---|---|---|
| GBR 830 | nM | 0.833 ± 0.25 | P = 0.009 | — |
| | ug/mL | 0.121 ± 0.05 | | |
| MAB1 | nM | 0.089 ± 0.01 | — | 74 |
| | ug/mL | 0.015 ± 0.005 | | |
| KHK4083 | nM | 0.005 ± 0.004 | P = 0.015 | 167 |
| | ug/mL | 0.001 ± 0.001 | | |

MAB1 proved to be as efficient as KHK4083 at blocking the proliferation of primary human T cells in vitro in an assay assessing proliferation of purified T cells induced by TCR/CD3 and CD28 triggering in the presence of immobilized purified OX40L (FIG. 10).

Further, in both assay settings, the potency of MAB1 to inhibit T cell proliferation was statistically significantly higher relative to GBR 830. While MAB1 also showed an increase in ADCC-mediated killing of T cells as compared to GBR 830, it also exhibited less ADCC-mediated killing of T cells as compared to KHK4083 (FIG. 11). Finally, under the same assay conditions, MAB1 also exhibited a lower ability than HKH4083 to kill in vitro differentiated Tregs. (FIG. 12). Taken together these results show that MAB1, besides showing a stronger potency at blocking T cell proliferation, can spare Tregs, suggesting a more favorable outcome in auto-immune disease, for which blocking of T cells but maintenance of Tregs viability are critical to restore immune tolerance.

In summary, GBR 830 and MAB1 were shown to be devoid of agonistic activity while benchmark KHK4083 showed residual agonistic activity. In vitro, MAB1 shows a stronger potency than GBR 830 to inhibit T cell proliferation. Furthermore, MAB1 also shows reduced potency as compared to KHK4083 to deplete activated T cells and a unique potential at limiting Tregs depletion. These and other pharmacological properties support the potential efficacy of MAB1 in the field of OX40 therapy for autoimmune disease.

Example 4: Characterization of MAB1 Binding

Materials and Methods

Fc Engineering of MAB1

YTE mutations (M252Y, S254T, and T256E according to EU numbering) were introduced into the MAB1 heavy chain Fc domain, resulting in MAB10 which comprises the heavy chain amino acid sequence of SEQ ID NO:73 paired with the MAB1 light chain amino acid sequence (SEQ ID NO:10) (FIG. 21). Accordingly, MAB1 and MAB10 have the same heavy chain variable region sequences; the only sequence differences between these two antibodies is the “YTE” mutation in the heavy chain constant region of MAB10. MAB1 and MAB10 have the same light chain sequence.

Affinity Determination to OX40

Surface Plasmon Resonance (SPR) analysis was used to determine the affinity of the MAB10 antibody as well as the AMG451 (rocatinlimab or KHK4083), GBR830, and MAB1 antibodies to the human OX40 protein, at different temperatures and pH's and using a single cycle kinetics (SCK) method.

Measurements were performed on a Biacore 8K+ instrument (Cytiva Life Sciences) the Biacore 8K+ Control Software and analyzed with the Biacore Insight Evaluation Software (v3.0). Briefly, a goat anti-human IgG (Fc specific) antibody (JIR, catalog NO: 109-005-098) was immobilized to around at ≈13,000-14,000 resonance units (abbreviated RU) on a Series S CM5 Sensor Chip (Cytiva Life Sciences, catalog NO: BR100530) using an amine coupling kit (Cytiva Life Sciences) in both flow cells. Triplicate samples of AMG451 huIgG1 afucosylated (FlowEighteen38, Lot NO: 230900054), GBR830 (FlowEighteen38, Lot NO: 230900056), MAB1 (FlowEighteen38, Lot NO: 231000022), MAB10 (FlowEighteen38, Lot NO: 230900169) and human isotype control (BioLegend, catalog NO: 403502) antibodies were diluted at 5 nM and injected in flow cell 2 at 25 or 37° C. Human OX40 (Acro Biosystems, catalog NO: OX0-H5224) protein was injected in both flow cells at two-fold dilutions from 100-6.25 nM at 25 or 37° C., with an off-rate measurement of 600 seconds. After each binding event, baseline levels were restored using a regeneration solution on both flow-paths. HBS-EP+pH 7.4 solution were used as running buffer. Data was analyzed using the SCK evaluation method of the Biacore Insight Evaluation Software and kinetic parameters were determined using the 1:1 binding fitting model.

Kinetic parameters generated at pH 7.4 and 25° C. are reported in Table 14. Each measurement is the mean of three identical replicate conditions.

SPR Epitope Binning Assay

Epitope binning experiments were conducted in a Biacore 8K+ instrument using the Biacore 8K+ Control Software and analyzed with the Biacore Insight Evaluation Software (v3.0). An epitope binning sandwich assay was used. Briefly, MAB10, MAB1 and GBR830, and AMG451 antibodies were immobilized to approximately 10,000-16,000 resonance units (RU) on a Series S CM5 Sensor Chip using an amine coupling kit in flow cell 2. As a control, an anti-His human isotype control antibodies were also immobilized. Antigen was injected in flow cells 1 and 2 followed by the injection of each one of the tested antibodies also in both flow cells. Baseline levels were restored using 10 mM Glycine-HCl pH 1.5 buffer as regeneration solution and HBS-EP+pH 7.4 solution was used as a running buffer. Data were analyzed using the epitope binning extension of the Biacore Insight Evaluation Software.

Affinity Determination to Fcγ Receptors

Surface Plasmon Resonance (SPR) analysis was used to determine the affinity of the MAB10 antibody as well as the AMG451, GBR830, and MAB1 antibodies to several Fc7 receptors, using a multi cycle kinetics (MCK) method.

Measurements were performed on a Biacore 8K+ instrument (Cytiva Life Sciences) using the Biacore 8K+ Control Software and analyzed with the Biacore Insight Evaluation Software (v3.0). Briefly, a mouse anti-tetra His antibody (Qiagen, catalog NO: 34670) was immobilized to around at ~6,000-7,000 resonance units (abbreviated RU) on a Series S CM5 Sensor Chip (Cytiva Life Sciences, catalog NO: BR100012) using an amine coupling kit (Cytiva Life Sciences) in both flow cells. Human CD64, CD32b, CD32a (167 His), CD32a (167 Arg), CD16b (NA2 allotype), CD16a (F176V), and CD16a (176F) proteins (Sino Biological, Cat. nr. 10256-H08H, 10259-H08H, 10374-H08H1, 10374-H08H, 11046-H08H, 10389-H08H1, and 10389-H08H) were injected in flow cell 2. AMG451 huIgG1 afucosylated (FlowEighteen38, Lot NO: 230900054), GBR830 (FlowEighteen38, Lot NO: 230900056), MAB1 (FlowEighteen38, Lot NO: 231000022), MAB10 (FlowEighteen38, Lot NO: 230900169) and human isotype control (BioLegend, catalog NO: 403502) antibodies were prepared as eleven-step two-fold diluted solutions (5,000-4.88 nM) and injected in both flow cells, with an off-rate measurement of 150 seconds. After each binding event, baseline levels were restored using a regeneration solution on both flow-paths. HBS-EP+pH 7.4 solution were used as running buffer. Data was analyzed using the MCK evaluation method of the Biacore Insight Evaluation Software and kinetic parameters were determined using the 1:1 binding and steady-state affinity methods.

Kinetic parameters are reported in Table 15. Each measurement is the mean of three identical replicate conditions.

Affinity Determination to FcRn

Surface Plasmon Resonance (SPR) analysis was used to determine the affinity of the MAB10 antibody as well as the AMG451, GBR830, and MAB1 antibodies to FcRn receptor, using a multi cycle kinetics (MCK) method.

Measurements were performed on a Biacore 8K+ instrument (Cytiva Life Sciences) using the Biacore 8K+ Control Software and analyzed with the Biacore Insight Evaluation Software (v3.0). Briefly, AMG451 huIgG1 afucosylated (FlowEighteen38, Lot NO: 230900054), GBR830 (FlowEighteen38, Lot NO: 230900056), MAB1 (FlowEighteen38, Lot NO: 231000022), Mab10 (FlowEighteen38, Lot NO: 230900169) and human isotype control (BioLegend, catalog NO: 403502) antibodies were immobilized to around at ≈180 resonance units (abbreviated RU) on a Series S CM5

Sensor Chip (Cytiva Life Sciences, catalog NO: BR100530) using an amine coupling kit (Cytiva Life Sciences) in flow cell 2. Human FcRn protein (Acro Biosystems, catalog NO: FCN-H52W7) was prepared as nine-step two-fold diluted solutions (500-1.95 nM) and injected in both flow cells with an off-rate measurement of 90 seconds. After each binding event, baseline levels were restored using a regeneration solution on both flow-paths. HBS-EP+pH 7.4 or 6.0 solution were used as running buffer. Data was analysed using the MCK evaluation method of the Biacore Insight Evaluation Software and kinetic parameters were determined using the 1:1 binding and steady-state affinity methods.

Figures 13A, 13B, 13C:
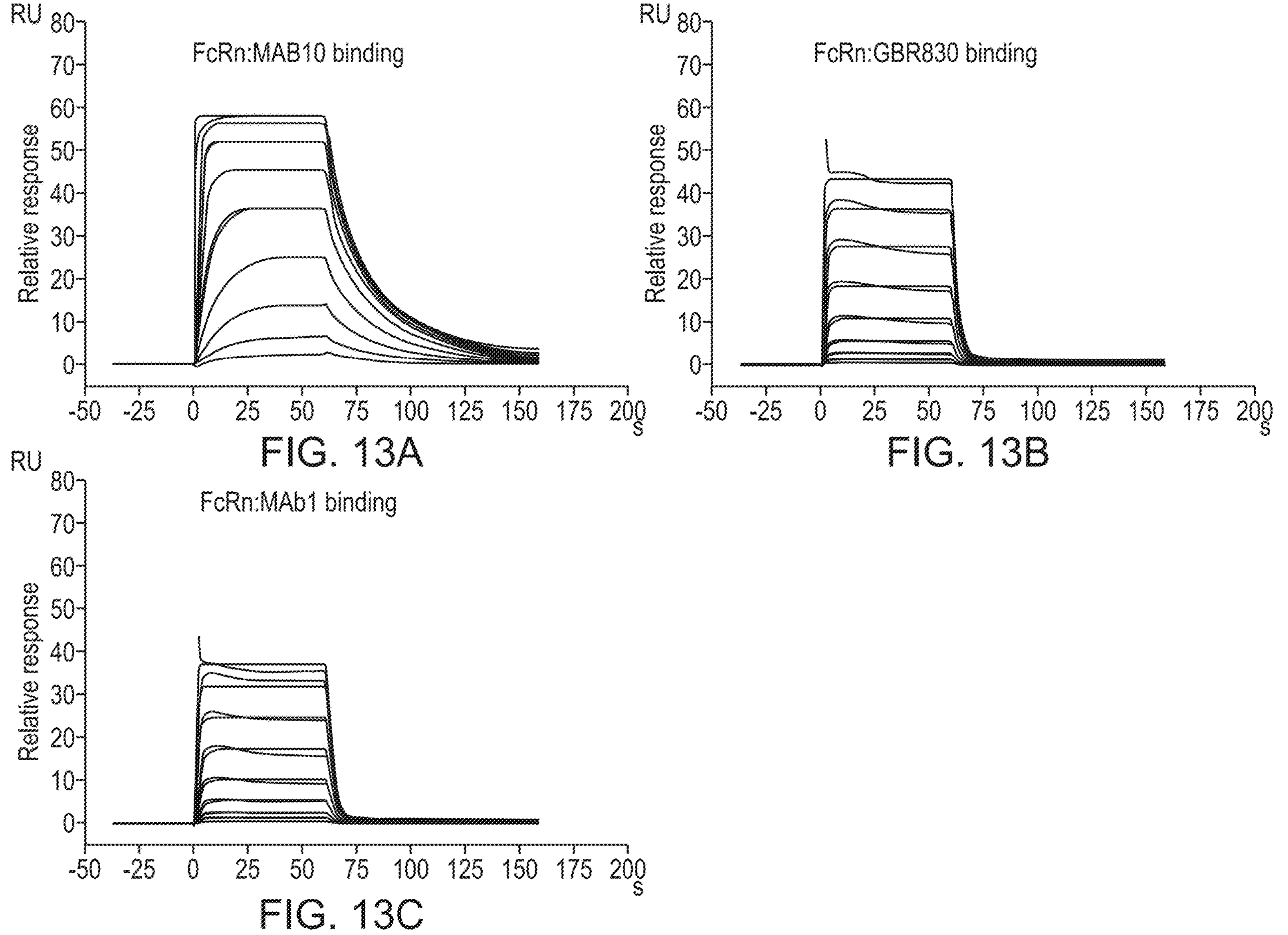
FIG. 13A shows the surface plasmon resonance (SPR) sensograms of MAB10 binding to FcRn.
FIG. 13B shows the SPR sensograms of GBR830 binding to FcRn.
FIG. 13C shows the SPR sensograms of MAB1 binding to FcRn.

Sensorgrams showing the association and dissociation of the huFcRn protein at pH 6.0 are presented in FIG. 13A-C and kinetic parameters are reported in Table 16. Each measurement is the mean of three identical replicate conditions.

Results

Affinity Determination to OX40

Surface Plasmon Resonance (SPR) results from Table 14 (below) show that all anti-OX40 antibodies bind to the recombinant human OX40 receptor, in particular MAB10, MAB1 and AMG451 shows similar nanomolar affinities to human OX40, while GBR830 shows the lowest affinity with a KD of 59.3 nM, and provides the mean+/−SD of association constant (ka), dissociation constant (kd) and binding affinity (KD) of each molecule to human OX40 determined from Surface Plasmon Resonance analyses. Each measurement is the mean of three identical replicate conditions.

GBR830 has been submitted to an affinity maturation process that has generated MAB1 with an 8-fold increase in binding affinity.

MAB10 and MAB1 that share the same binding arms (e.g., the same variable regions) show highly similar association constant (ka), dissociation constant (kd) and binding affinity (KD), demonstrating that the addition of YTE mutation on MAB10 did not impact the binding to human OX40 receptor.

TABLE 14

Overview of kinetic parameters for GBR830, MAB1, MAB10 and AMG451 to recombinant human OX40 protein at pH 7.4 and 25° C.

| Antibody | ka ($M^{-1}$ $s^{-1}$) ± S.D. | kd ($s^{-1}$) ± S.D. | KD (nM) ± S.D. |
|---|---|---|---|
| GBR830 | $1.5 \times 10^5 \pm 2.7 \times 10^3$ | $8.6 \times 10^{-3} \pm 1.9 \times 10^{-4}$ | 59.3 ± 2.0 |
| MAB1 | $2.3 \times 10^5 \pm 5.7 \times 10^3$ | $1.6 \times 10^{-3} \pm 2.0 \times 10^{-5}$ | 6.8 ± 0.2 |
| MAB10 | $2.3 \times 10^5 \pm 9.3 \times 10^3$ | $1.6 \times 10^{-3} \pm 3.5 \times 10^{-5}$ | 7.2 ± 0.4 |
| AMG451 | $1.7 \times 10^5 \pm 3.1 \times 10^4$ | $5.3 \times 10^{-4} \pm 1.4 \times 10^{-4}$ | 3.0 ± 0.4 |

SPR Binning Assay

Binding levels (RU) of each tested antibody to the antigen captured by the immobilized antibody were extracted from the binding curves using the Biacore Insight Evaluation Software. No binding response, defined as RU<10, indicated epitope overlap while binding response, defined as RU>10, indicated the presence of different epitope bins. MAB10 was confirmed to display epitope overlap with MAB1, and GBR830 as all of these antibodies were binned together. Further, no binding to GBR830, or MAB1 was observed when OX40 was captured by MAB10, thus confirming epitope overlap of these molecules. Further, no binding of the human isotype control to captured huOX40 was observed.

In contrast, AMG451 did not fall within the same bin as any of MAB1, MAB10, or GBR830. Thus, the epitope target of AMG451 is different than the epitope target of MAB1, MAB10, or GBR830.

Affinity Determination to Fcγ Receptors

Surface Plasmon Resonance (SPR) results from Table 15 show that MAB10 binds significantly weaker to all Fcγ receptors compared to GBR830 and MAB1 antibodies, indicating reduced effector functions.

The comparison between MAB1 and MAB10 demonstrates that the YTE mutation leads to a lower binding affinity to CD16a variants, CD16b, and CD32a (167H). MAB10 showed a similar profile to the remaining antibodies only for the CD64 protein. No binding of the MAB10 was observed for the CD32a (167R) and CD32b proteins. Further, the data from MAB11 (MAB9 with "LS" modification in the Fc heavy chain (SEQ ID NO:74)) showed that this Fc modification did not impact Fcγ receptor binding.

Table 15 shows the binding affinity (KD) of each molecule to human FcγRI, FcγRIIIa176F, FcγRIIIa176V, FcγRIIIb, FcγRIIa167R, FcγRIIa167H and FcγRIIb determined from Surface Plasmon Resonance analyses.

constant (kd) and binding affinity (KD), demonstrating that the addition of YTE mutation on MAB10 did not adversely impact the binding to human OX40 receptor.

The YTE mutation in MAB10 lead to a lower binding affinity of MAB10 to the Fcγ receptors as compared to GBR830 and MAB1, suggesting reduced Fc-mediated effector functions of MAB10, such as ADCC and ADCP.

The YTE mutation also significantly impacted the FcRn binding of MAB10, as an 8.8-fold higher affinity was measured for MAB10 compared to GBR830 and MAB1. Without wishing to be bound by theory, this increased affinity may indicate a potential longer half-life.

Example 5: In Vitro Characterization of MAB10 Pharmacology Profile

Materials and Methods

OX40/OX40L-Induced Cytokine Release in a T Cell Assay

To evaluate the potential of MAB10 to inhibit T cell activation in the presence of OX40L, and subsequent cytokine release, functional characterization was performed using a T cell activation assay.

TABLE 15

Overview of binding affinity (KD) for GBR830, MAB1, MAB11 and MAB10 to a set of Fcγ Receptors.

| Antibody | Binding affinity, KD (nM) | | | | | | |
|---|---|---|---|---|---|---|---|
| | FcγRI | FcγRIIIa176F | FcγRIIIa176V | FcγRIIIb | FcγRIIa167R | FcγRIIa167H | FcγRIIb |
| GBR830 | 6.2 | 365 | 330 | 3220 | 4690 | 3410 | 7260 |
| MAB1 | 5.4 | 334 | 297 | 3630 | 6140 | 4030 | 11600 |
| MAB11 | 6.3 | 246 | 221 | 2740 | 5430 | 3380 | 9880 |
| MAB10 | 8.7 | 992 | 816 | 15600 | NB | 12700 | NB |
| MAB10 fold-change relative to MAB1 | 1.6 | 3 | 2.7 | 4.3 | NB | 3.1 | NB |

Affinity Determination to FcRn

Surface Plasmon Resonance (SPR) results from FIG. 13A-C and Table 16 show that MAB10 (FIG. 13A) binds with a higher affinity to human FcRn compared to GBR830 (FIG. 13B) and MAB1 (FIG. 13C) antibodies, indicating potential longer half-life, demonstrating the impact of the YTE mutation, that increased by 8.8-fold the binding constant of MAB10 compared to MAB1.

Table 16 shows the binding affinity (KD) of each molecule to human FcRn from Surface Plasmon Resonance analyses. Each measurement is the mean of three identical replicate conditions.

TABLE 16

Overview of binding affinity (KD) for GBR830, MAB1, and MAB10 to the human FcRn.

| FcRn Binding affinity KD (nM) | GBR830 | MAB1 | MAB10 |
|---|---|---|---|
| pH 6.0 | 112.2 ± 13.6 | 101.7 ± 20.2 | 11.5 ± 0.5 |
| pH 7.4 | N/B | N/B | N/B |

All anti-OX40 antibodies bound to the recombinant human OX40 receptor. MAB10, MAB1 and AMG451 showed similar nanomolar affinities to human OX40, while GBR830 showed the lowest affinity with a KD of 59.3 nM. MAB1 and MAB10 bound to human OX40 with an 8-fold increase in binding affinity compared to GBR830.

MAB10 and MAB1 share the same variable domains and show highly similar association constant (ka), dissociation Human PBMC were harvested from buffy coats obtained from Biopole (Switzerland) Transfusion Center using ficoll density gradient isolation and rested overnight at 37° C. and 5% $CO_2$ in pre-warmed complete RPMI medium (RPMI supplemented with 10% non-heat inactivated fetal bovine serum, 1% Glutamine, 1% HEPES, 1% Non-essential Amino Acids, 1% Sodium Pyruvate, and 1% Penicillin/Streptomycin) at 1 million cells/ml. In parallel, 6-well plates (TPP, catalog NO: 92006) were coated with 1 μg/ml of recombinant OKT3, a human anti-CD3 antibody diluted in PBS and were then incubated overnight at 4° C. The next day, T cells were isolated from resting PBMC, and 100,000 cells were distributed per well on OKT3-coated plate (washed three times in PBS) with the addition of 1 μg/ml of soluble CD28 (sCD28). T cells were incubated at 37° C. and 5% $CO_2$ for 30 h. Additionally, 96-well flat-bottom plates (TPP, catalog NO: 92096) were pre-coated with recombinant OKT3 (1 μg/ml) and recombinant human OX40L (5 μg/ml) diluted in PBS and incubated overnight at 4° C. On the day of the assay, coated OKT3/OX40L plates were washed three times in PBS and hundred thousand activated T cells were labelled with 5 μM of Cell Proliferation Dye eFluor450 solution (ThermoFisher Scientific, catalog NO: 65-0842-85) and plated at 0.1 million per well. Serial dilutions of GBR830, MAB1, MAB10 and AMG451 starting from 200 nM and diluted by 3-fold, and control antibody were plated shortly after T cells. Plates were then incubated for 4 days at 370 C, 5% $CO_2$. After the incubation, T cell assay readout was evaluated by measuring the cytokine level in supernatants. Plates were centrifuged at 350 g for 3 min and supernatants kept at −80° C. until cytokine release assessment. Cytokines were quantified using Meso Scale Discovery U-PLEX TH1/TH2 Combo kit (MesoScale Discovery, K15010K; IFN-γ, IL-10, IL-2, IL-4, IL-5, IL-8, IL-10, IL-12p70, IL-13, TNF-α, IL-31, IL-17a, IL-21, and IL-22) following the manufacturer's instructions. Quantification values were plotted using Prism software (GraphPad).

Figures 14A, 14B, 14C, 14D:
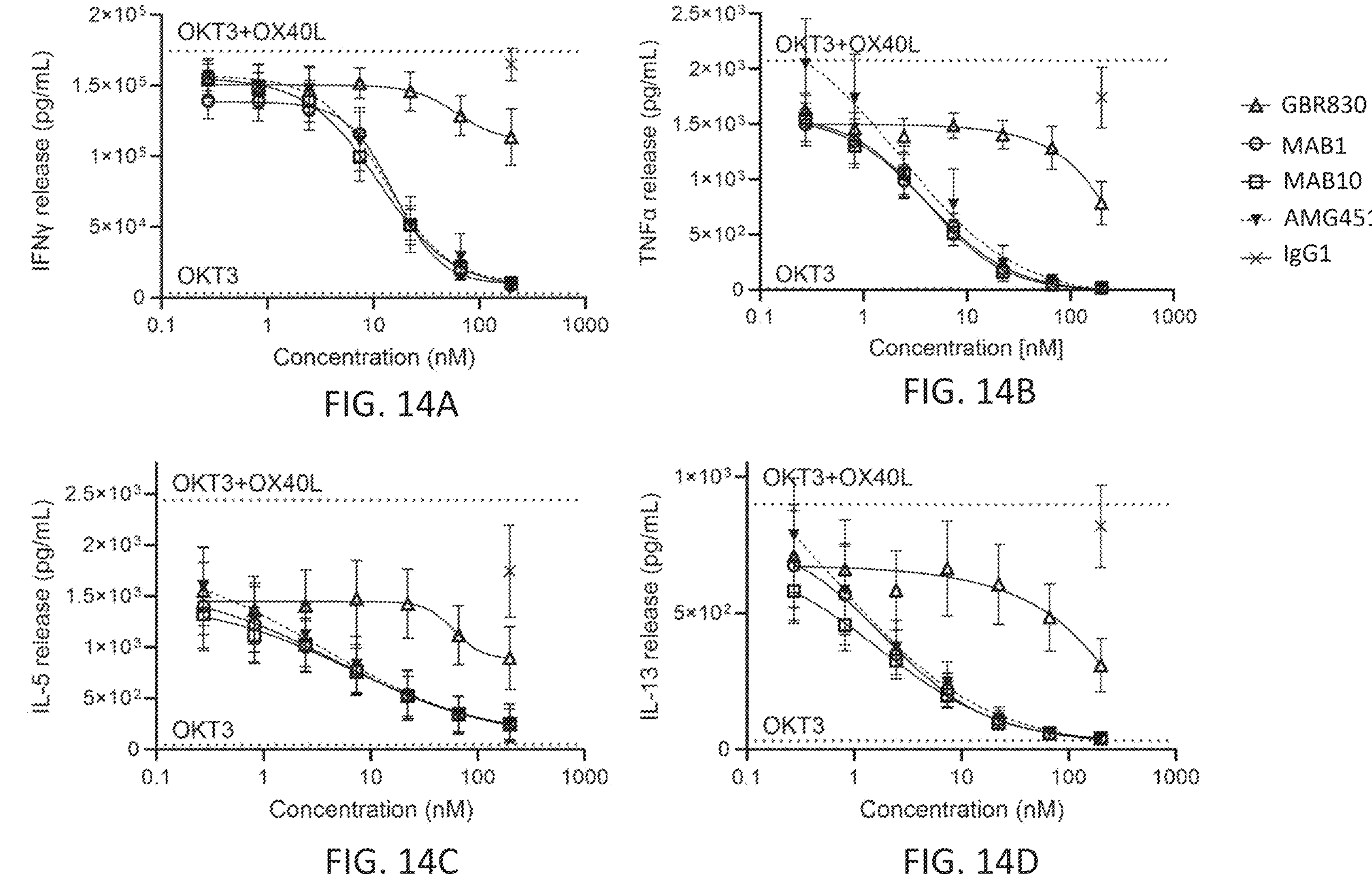
FIG. 14A shows the dose-dependent curve of IFNγ release (pg/mL) inhibition in a T cell proliferation assay after incubation with GBR830, MAB1, MAB10, AMG451 (KHK4083 or rocatinlimab), and IgG1.
FIG. 14B shows the dose-dependent curve of TNFα release (pg/mL) inhibition in a T cell proliferation assay after incubation with GBR830, MAB1, MAB10, AMG451, and IgG1.
FIG. 14C shows the dose-dependent curve of IL-5 release (pg/mL) inhibition in a T cell proliferation assay after incubation with GBR830, MAB1, MAB10, AMG451, and IgG1.
FIG. 14D shows the dose-dependent curve of IL-13 release (pg/mL) inhibition in a T cell proliferation assay after incubation with GBR830, MAB1, MAB10, AMG451, and IgG1.
Figures 14E, 14F, 14G, 14H:
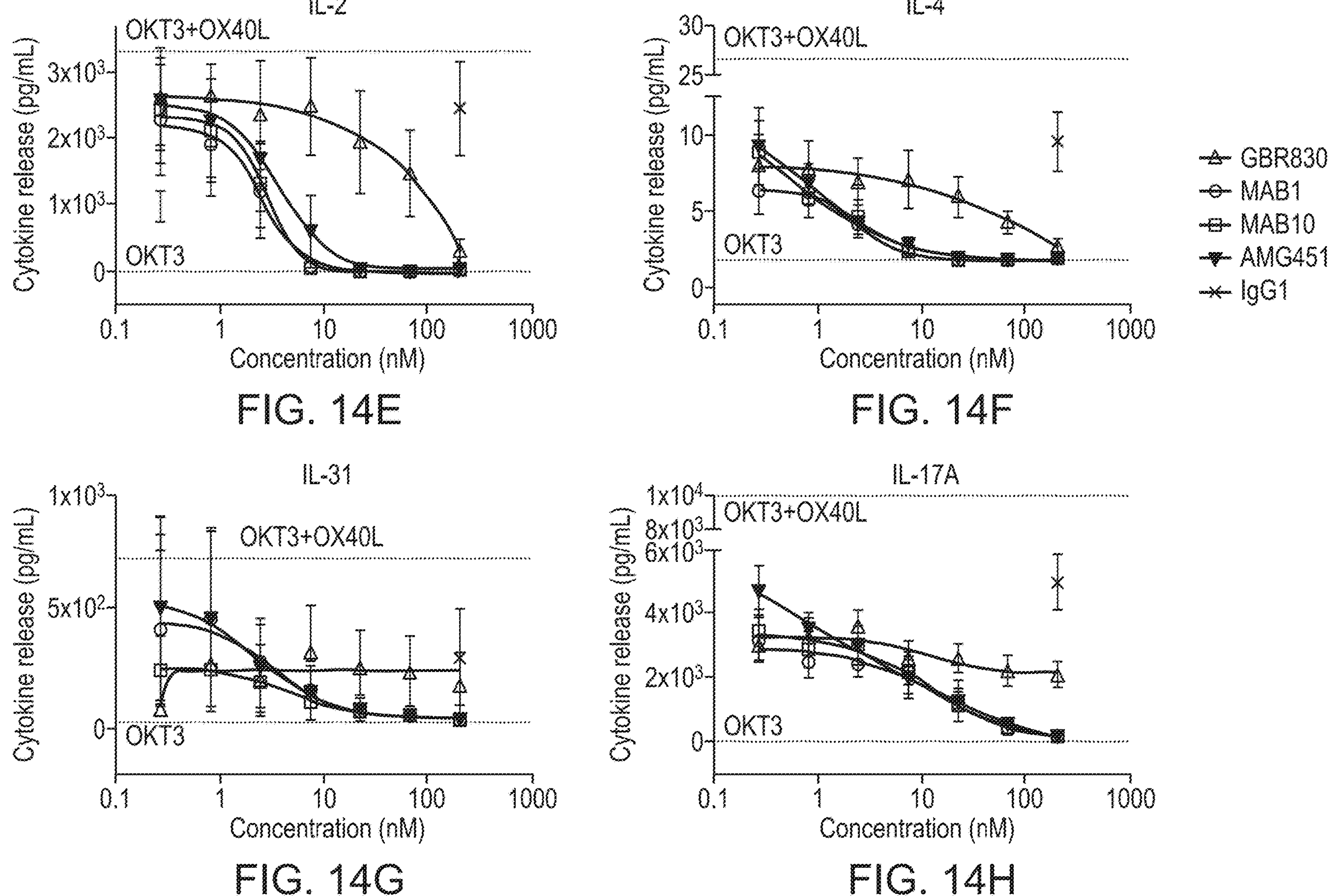
FIG. 14E shows the dose-dependent curve of IL-2 release (pg/mL) inhibition in a T cell proliferation assay after incubation with GBR830, MAB1, MAB10, AMG451, and IgG1.
FIG. 14F shows the dose-dependent curve of IL-4 release (pg/mL) inhibition in a T cell proliferation assay after incubation with GBR830, MAB1, MAB10, AMG451, and IgG1.
FIG. 14G shows the dose-dependent curve of IL-31 release (pg/mL) inhibition in a T cell proliferation assay after incubation with GBR830, MAB1, MAB10, AMG451, and IgG1.
FIG. 14H shows the dose-dependent curve of IL-17a release (pg/mL) inhibition in a T cell proliferation assay after incubation with GBR830, MAB1, MAB10, AMG451, and IgG1.
Figures 15A, 15B, 15C, 15D:
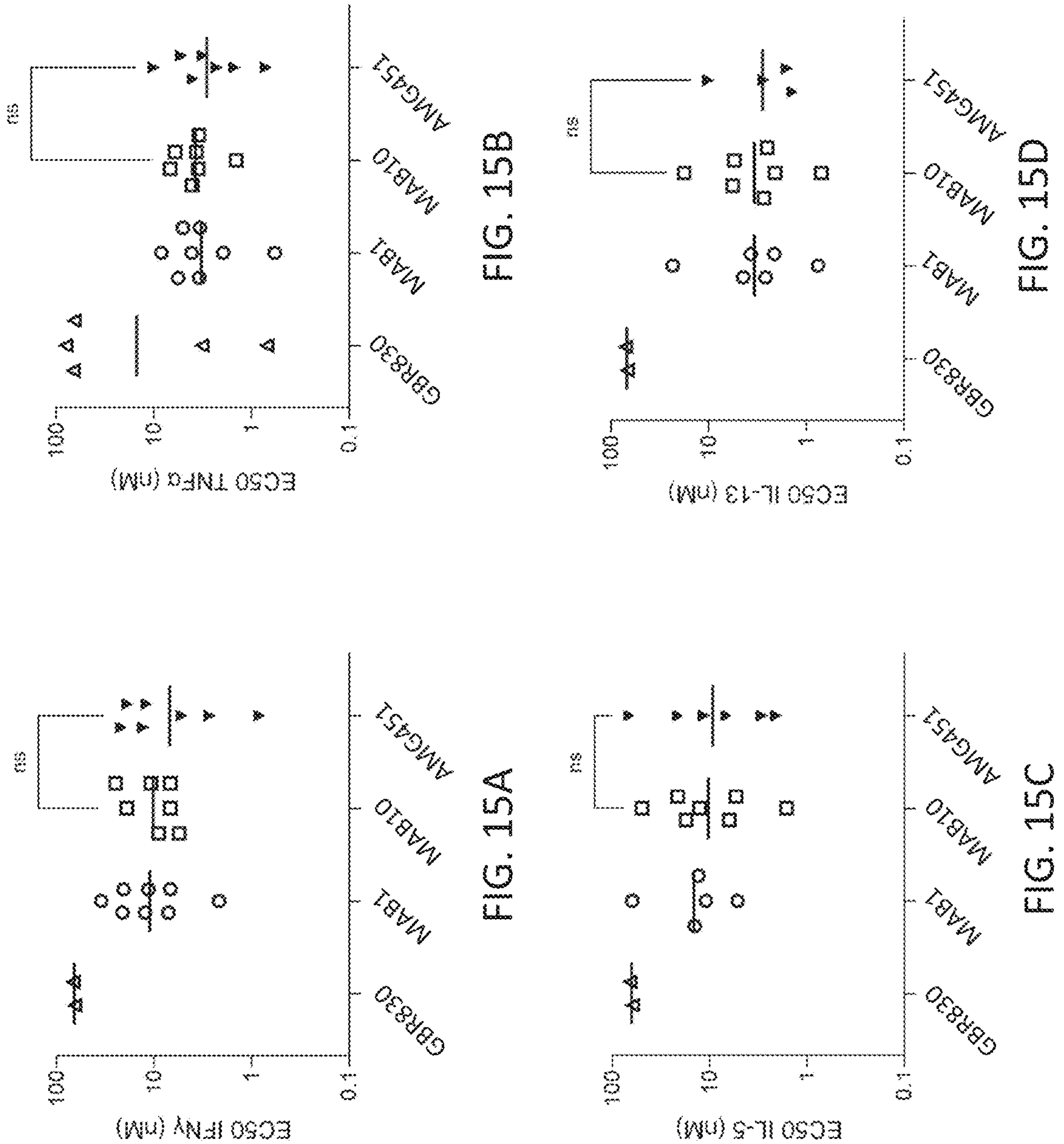
FIG. 15A shows the EC50 (nM) of the IFNγ release inhibition in a T cell proliferation assay after incubation with GBR830, MAB1, MAB10, AMG451, and IgG1.
FIG. 15B shows the EC50 (nM) of TNFα release inhibition in a T cell proliferation assay after incubation with GBR830, MAB1, MAB10, AMG451, and IgG1.
FIG. 15C shows the EC50 (nM) of IL-5 release inhibition in a T cell proliferation assay after incubation with GBR830, MAB1, MAB10, AMG451, and IgG1.
FIG. 15D shows the EC50 (nM) of IL-13 release inhibition in a T cell proliferation assay after incubation with GBR830, MAB1, MAB10, AMG451, and IgG1.
Figures 15E, 15F, 15G, 15H:
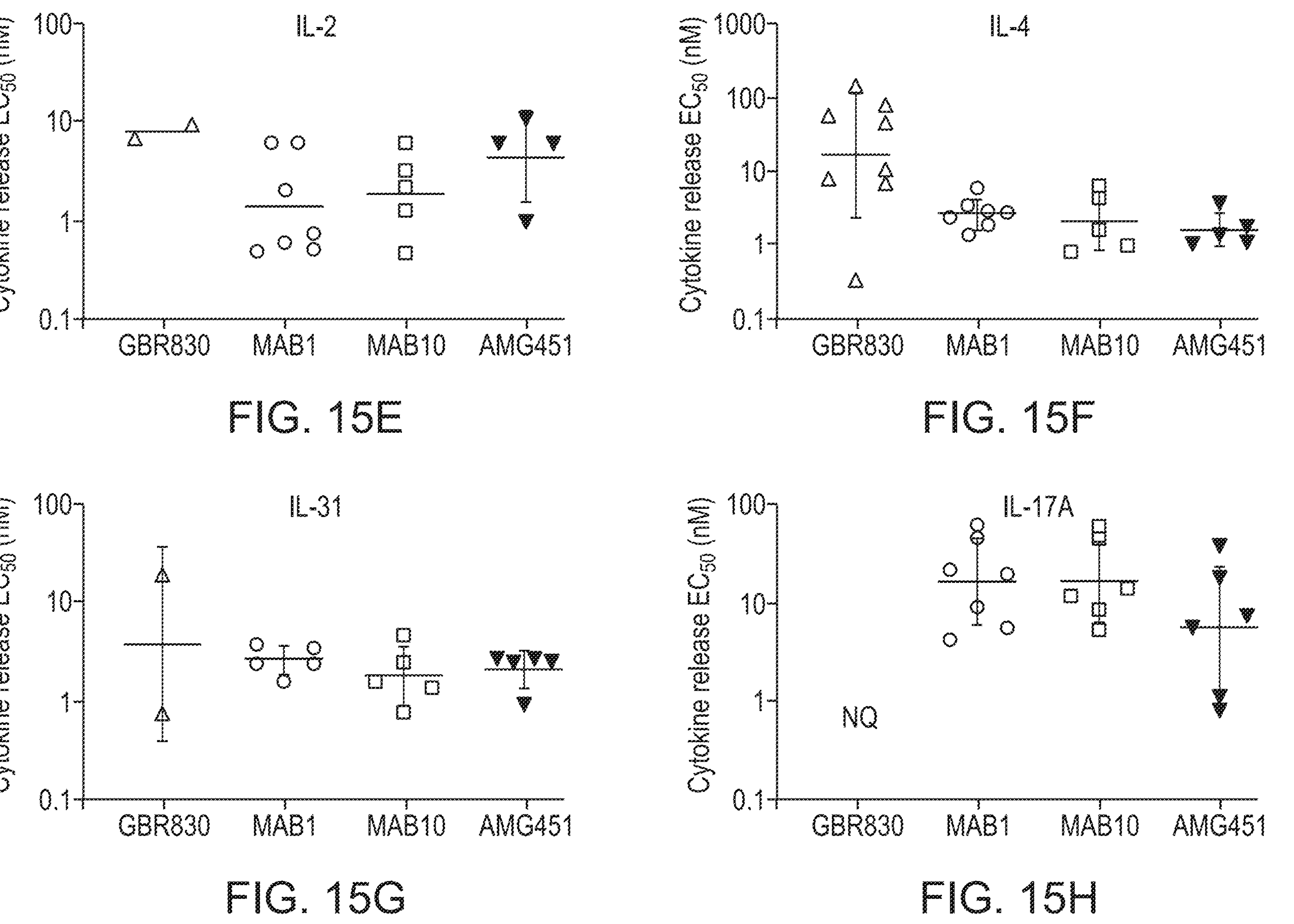
FIG. 15E shows the EC50 (nM) of IL-2 release inhibition in a T cell proliferation assay after incubation with GBR830, MAB1, MAB10, AMG451, and IgG1.
FIG. 15F shows the EC50 (nM) of IL-4 release inhibition in a T cell proliferation assay after incubation with GBR830, MAB1, MAB10, AMG451, and IgG1.
FIG. 15G shows the EC50 (nM) of IL-31 release inhibition in a T cell proliferation assay after incubation with GBR830, MAB1, MAB10, AMG451, and IgG1.
FIG. 15H shows the EC50 (nM) of IL-17a release inhibition in a T cell proliferation assay after incubation with GBR830, MAB1, MAB10, AMG451, and IgG1.
Figure 15J:
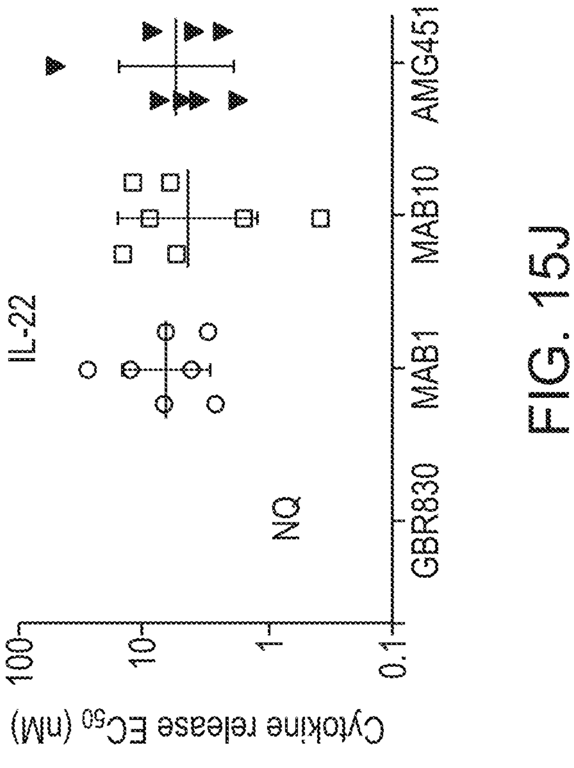
FIG. 15J shows the EC50 (nM) of IL-22 release inhibition in a T cell proliferation assay after incubation with GBR830, MAB1, MAB10, AMG451, and IgG1. Each symbol represents the EC50 value for one individual donor, among the eight individual T cell donors tested, from two independent experiments. Values were excluded based on goodness of fit ($R^2>0.7$), out-of-range EC50 values or if the curve was not reaching a plateau. EC50 values were compared using a paired One-way ANOVA test followed by Tukey's post-hoc comparison (ns $p>0.05$, *$p<0.05$, $0.01<p<0.05$, *$p<0.01$).
Figure 15I:
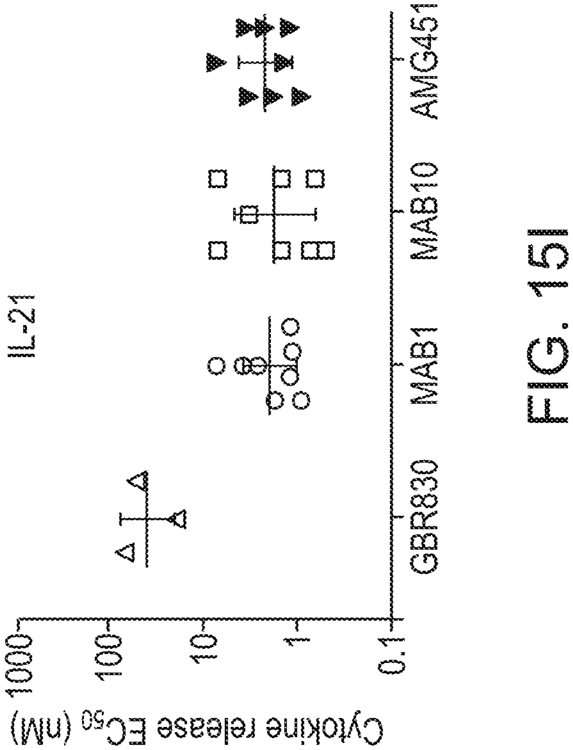
FIG. 15I shows the EC50 (nM) of IL-21 release inhibition in a T cell proliferation assay after incubation with GBR830, MAB1, MAB10, AMG451, and IgG1.
Figures 16A, 16B:
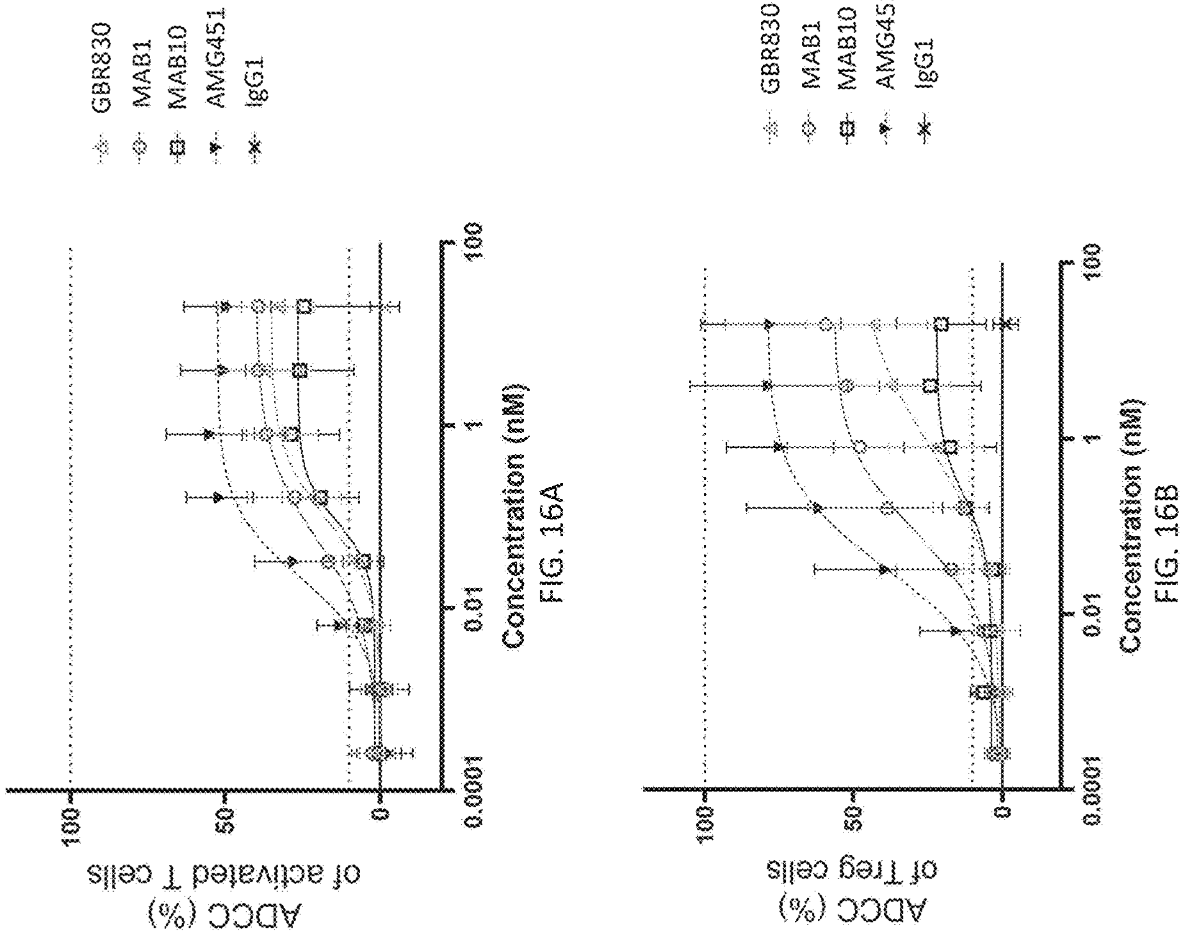
FIG. 16A shows the dose-dependent curve of the indicated anti-OX40 antibodies and benchmark antibody AMG451 to induce the killing of activated T cells assessed in a ADCC assay with a 5:1 Effector-to-target ratio and measured by LDH release after 4.5 hours.
FIG. 16B shows the dose-dependent curve of the indicated anti-OX40 antibodies and benchmark antibody AMG451 to induce the killing of regulatory T cells assessed in a ADCC assay with a 5:1 Effector-to-target ratio and measured by LDH release after 4.5 hours.

From those data, a subset of those cytokine quantification results was plotted using Prism software (GraphPad): IFN-γ (FIG. 14A), TNF-alpha (FIG. 14B), IL-5 (FIG. 14C) and IL-13 (FIG. 14D), IL-2 (FIG. 14E), IL-4 (FIG. 14F), IL-31 (FIG. 14G), IL-17a (FIG. 14H), IL-21 (FIG. 14I), and IL-22 (FIG. 14J). Half maximal effective concentration or EC50 values were calculated from the quantification dose-response curves using a logistic 4 parameter regression model with variable slope. Values were excluded based on goodness of fit ($R^2$>0.7), out-of-range EC50 values or if the curve was not reaching a plateau. Treatment groups were compared in statistical analyses performed on logarithmically transformed EC50 values, using a paired-one way ANOVA (donor as pairing factor) followed by post-hoc Tukey HSD comparison. EC50 values are provided in FIGS. 15A-J: IFN-γ (FIG. 15A), TNF-alpha (FIG. 15B), IL-5 (FIG. 15C), IL-13 (FIG. 15D), IL-2 (FIG. 15E), IL-4 (FIG. 15F), IL-31 (FIG. 15G), IL-17a (FIG. 15H), IL-21 (FIG. 15I), and IL-22 (FIG. 15J), and Mean EC50+/−Standard Deviation are reported in pM in Table 17.

OX40 Internalization Assay

Peripheral blood monocytes (PBMCs) from healthy volunteers were harvested from buffy coats (BC) using ficoll gradient isolation. T cell isolation from PBMCs was performed using EasySep™ Human T Cell Isolation kit (#17951, StemCell Technologies) following the manufacturer's instructions. In brief, PBMCs were resuspended at $5\times10^7$ cells/mL with cold EasySep buffer before proceeding to isolation using the Big Easy Magnet protocol. Isolated T cells were resuspended in complete medium at $10^6$ cells/mL and activated for 2 days with Dynabeads Human T-Activator CD3/CD28 ($10^6$ beads/mL) to obtain activated T cells.

The day of the experiment, Dynabeads were removed from the activated T cells media. Cells were resuspended at $0.8\times10^6$ cells/mL and seeded into a 96-well flat bottom black plate Clear without coating reagent (50 μl/well of cells suspension, $0.4\times10^5$ cells/well). The plate was left 1 hour at RT to allow the cells to settle. Tested molecules were labelled at 2× concentration with Fab-Fluor reagent by incubating the antibody with Fabfluor Dye at a molar ratio of 1:3 in internalization medium for 15 minutes at 37° C. 5% CO2. Fifty microliters of labelled antibodies were added on top of the cells to reach a final concentration of 8 μg/mL (1×) in the wells. Control wells without treatment (No Ab condition) or with T cells and Fab-Fluor reagent alone (Fabfluor condition) were added for background evaluation. Plates were immediately placed into the Incucyte Live-Cell Analysis System and images were acquired by scanning 4 fields per well every hour for 24 hours using Phase and Red channels with 20× magnification and non-adherent cell module.

The analysis procedure comprises a minimal area selection set at 79.22 $\mu m^2$ to detect T cells (called Total cells in the formula). T cells displaying red mean intensity (RCU) above 0.358 represented positive internalization of OX40 (called Red cells in the formula). The threshold for the RCU was determined based on the signal obtained from the isotype control and the experimental controls. The percentage internalization was obtained from the raw data Excel file using the following formula: % internalization=(Red cells/Total cells)×100

The % OX40 internalization over the incubation time was plotted using GraphPad prism software (version 10).

Cross Reactivity with Non-Human OX40

ELISA: Human (hu), cynomolgus monkey (cy), mouse (mo), rat (ra) and rabbit (rb) OX40 proteins were diluted at 2 μg/mL in Phosphate-buffered saline (PBS) (pH 7.4) and coated overnight at 4° C. in a volume of 100 μL in MaxiSorp™ high protein-binding capacity 96 well plates. The next day, the plates were washed 3 times with PBS-Tween 0.05%, pH 7.4 (PBS-T) using an automatic plate washer and blocked for 2 h at room temperature with 250 μL/well of 4% skimmed milk/PBS solution. After blocking, the plates were washed 3 times with PBS-T. Next, 100 μl μL of MAB10 antibody in eleven three-fold serial dilutions ranging from 50 to 0.001 nM in 1% skimmed milk in PBS were added to the wells and incubated for 1 h at room temperature. After washing 5 times with PBS-T, 100 μL of an anti-human IgG peroxidase conjugate antibody at a 1:5,000 dilution in 1% skimmed milk in PBS was added for detection. Plates were incubated for 1 h at room temperature, then washed 5 times with PBS-T and 3 times with PBS (pH 7.4). Signal development was performed by adding 100 μL of 3,3',5,5'-tetramethylbenzidine (TMB) to each well. Color development was allowed for 5 min, and the reaction was stopped by adding 100 μl of $H_2SO4$ solution. MAB10 binding levels to immobilized OX40 proteins were measured as the optical density (OD) at 450 nm using a microplate spectrophotometer. Titration curves of the MAB10 antibody for the human, cynomolgus monkey, mouse, rat and rabbit OX40 proteins were obtained using GraphPad Prism 7 software and applying the (agonist) vs. response—variable slope (four parameters) fitting model. Three identical replicates were run and the data averaged.

SPR: Surface Plasmon Resonance (SPR) analysis was used to determine the affinity of MAB10 antibody to the human (hu), cynomolgus monkey (cy), mouse (mo), rat (ra) and rabbit (rb) OX40 proteins, using the single cycle kinetics (SCK) method.

Measurements were performed on a Biacore 8K+ instrument using the Biacore 8K+ Control Software and analyzed with the Biacore Insight Evaluation Software (v3.0). Briefly, a goat anti-human IgG (Fc specific) antibody was immobilized to approximately 11,000-14,000 resonance units (RU) on a Series S CM5 Sensor Chip using an amine coupling kit in both flow cells. Triplicate samples of MAB10 and human isotype control antibody were diluted to 5 nM or 20 nM for affinity determination on hu/cy/mo/raOX40 and rbOX40, respectively, and injected in flow cell 2.

The OX40 proteins were injected in both flow cells at two-fold dilutions ranging from 100-6.25 nM (hu/mo/ra OX40), 500-31.25 nM (cyOX40) and 1000-62.5 nM (rbOX40) with an off-rate measurement period of 600 seconds. After each binding event, baseline levels were restored using 10 mM Glycine-HCl pH 1.5 as regeneration solution on both flow-paths. HBS-EP+pH 7.4 solution was used as running buffer. Data were analyzed using the SCK evaluation method of the Biacore Insight Evaluation Software and kinetic parameters were determined using the 1:1 binding fitting model. A threshold of 10 RU was established as the cut-off for detecting significant binding activity. Interactions resulting in a response of less than 10 RU were considered as no binding (NB).

Kinetic parameters are reported in Table 18. Each measurement represents the mean of three identical replicate conditions.

Signaling Inhibition and Receptor Occupancy in Jurkat-NFκB-OX40 Reporter Cells

The Jurkat-NFκB-OX40 cell line previously described was used to characterize the relationship between OX40 engagement at the surface of T cells by MAB10, GBR830, and MAB1, and their ability to inhibit the OX40-OX40L co-stimulation pathway.

To assess the inhibition of the OX40-OX40L costimulatory pathway in Jurkat-NFκB-OX40 cells, sterile 96-well CLEAR microplates were coated overnight at 4° C. with OKT3 (5 g/mL) diluted in PBS. The day of the experiment, coated plates were rinsed three times with PBS and Jurkat-NFκB-OX40 cells were plated at $0.1\times10^6$ cells/well (25 μL) in the OKT3 pre-coated plates. Anti-OX40 antibodies were prepared 3 times concentrated to reach a final concentration of 200 nM in the wells, with a serial dilution of 1/3 over 11 dilutions, resulting in a lowest concentration of 0.003 nM. IgG1 control antibody was added at the highest dose (200 nM). OX40L at 3 different final concentrations (5, 0.3 and 0.07 μg/mL) or medium only (condition without OX40L) was added on top of cells (25 μL), plus 25 μL of each of the antibodies. Control wells were included in order to calculate the percentage of inhibition of the OX40-OX40L signaling. The condition "OX40L OKT3" (in the calculation formula) represents the highest achievable costimulation of the OX40-OX40L pathway and was used as maximum to calculate the percentage of inhibition. The condition where cells were plated on top of wells coated with OKT3 but without addition of OX40L and anti-OX40 antibodies (stated in the formula as "OKT3 only") represents the background activation of Jurkat-NFκB-OX40 cells in the absence of OX40L co-stimulation. The luminescence of the OKT3 only condition was subtracted from the sample's signal to obtain the specific signal of the inhibition of the OX40-OX40L pathway induced by the different anti-OX40 antibody treatments.

Plates were incubated for 5 hours at 37° C. and 5% $CO_2$. At the end of the incubation time, 75 μL of Bio-Glo solution were added to the wells and incubated for 15 minutes. Luminescence was measured on Synergy Neo Plate Reader using the following settings: read tape—endpoint; integration time—0.2 seconds; emission—hole; optics position—top; gain 135; read height—6.00 mm.

To assess the binding of the antibodies to OX40 (receptor occupancy), Jurkat-NFκB-OX40 cells were plated at $0.1\times10^6$ cells/well (25 μL) in 96-well U-bottom plates. Anti-OX40 antibodies were prepared 3 times concentrated to reach a final concentration of 200 nM in the wells, with a serial dilution of 1/3 over 11 dilutions. OX40L at 3 different final concentrations (5, 0.3 and 0.07 μg/mL) or medium was added on top of cells (25 μL), as well as 25 μL of each of the treatments. Medium only was added in control wells. Two binding time points were assessed, t=0 hours and t=5 hours. For t=0 hours, plates were directly incubated on ice for 30 minutes, followed by a FACS staining. For t=5 hours, plates were incubated for 5 hours at 37° C. and 5% $CO_2$ before performing the FACS staining. FACS staining was performed on ice. After the incubation with the tested antibodies, cells were washed twice with FACS buffer with 0.05% of sodium azide to avoid internalization. Cells were resuspended with the secondary antibody PE-labeled anti-human IgG Fc and incubated for 30 minutes at 4° C., then washed twice with FACS buffer with 0.05% of sodium azide. Cells were resuspended in DAPI solution (0.1 μg/mL) and acquired on a Cytoflex-S flow cytometer.

The % inhibition was calculated using the following formula using Excel software:

$$\%\text{ inhibition} = \left(1 - \frac{\text{Luminescence sample} - \text{Luminescence } OKT3 \text{ only}}{\text{Luminescence } OX40L\ OKT3 - \text{Luminescence } OKT3 \text{ only}}\right) \times 100$$

Receptor occupancy (RO) % was calculated as follows:

$$RO\,(\text{bound } Ab) = \frac{\text{Geomean } PE\,(\text{Sample}) - \text{Geomean } PE\,(IgG1 + OX40L)}{\text{Geomean } PE\,(\text{Max}) - \text{Geomean } PE\,(IgG1 + OX40L)} \times 100,$$

where Max is defined as the saturating dose of the molecule, which corresponds to the second (next highest) concentration at which the plateau is reached with OX40L at 5 μg/mL and t=5 h.

Maximal inhibition was determined from the previously calculated parameters using JMP software (version 17) and EC50 values were calculated using a logistic 4-parameter non-linear regression model with variable slope in Graphpad prism software (version 10). A one-site binding non-linear regression model from GraphPad Prism (version 10) was applied to the receptor occupancy dataset and Kd were determined.

By applying the "Agonist vs response—Find ECanything" non-linear regression model to the receptor occupancy dataset, the EC20, EC40, EC60, and EC80 of receptor occupancy were determined.

Following the exclusion criteria below, values were set as NQ in the meta-analysis of individual experiments: ECXX was considered NQ when the window of inhibition was lower than 10%, the fitting of the dose-response curve $R2<0.7$, the ECXX values were out of the range of tested concentrations and the maximum inhibition % was lower than 10%. Kd quantification was considered NQ when there was poor fitness of dose-response curve $R2<0.7$ and the Kd values were out of the range of tested concentrations.

Off-Target Assessment

The Retrogenix Cell Microarray Technology platform was used to screen for specific off-target binding interactions of MAB10. 6105 human plasma membrane proteins, secreted proteins, and 400 heterodimers were screened for specific interaction with MAB10.

Results

OX40/OX40L-Induced Cytokine Release in a T Cell Assay

Human IFN-γ, TNF-α, IL-5, IL-13, IL-2, IL-4, IL-31, IL-17a, IL-21, and IL-22 release were quantified in a T cell proliferation assay using OX40L as a co-stimulation factor. All anti-OX40 antibodies inhibit the release of all four cytokines (FIG. 14A-J). MAB10 and MAB1 induce statistically comparable inhibitory potency and have higher inhibitory potency than GBR830, as shown in FIG. 15A-J and Table 17, with associated EC50 between 4.2 and 16.4 nM for MAB10.

MAB10 demonstrates a strong potency to reduce OX40L-induced cytokine production (FIG. 14A-J and FIG. 15A-J). The ability of anti-OX40 antibodies and benchmark antibody AMG451 to inhibit the OX40/OX40L-induced cytokine release was assessed in a T cell proliferation assay. Cytokine release was evaluated for IFN-γ (FIG. 14A), TNF-α (FIG. 14B), IL-5 (FIG. 14C), IL-13 (FIG. 14D), IL-2 (FIG. 14E), IL-4 (FIG. 14F), IL-31 (FIG. 14G), IL-17a (FIG. 14H), IL-21 (FIG. 14I), and IL-22 (FIG. 14J) cytokines using Meso Scale Discovery (MSD) assay. The cytokine release in pg/mL at different concentrations is shown for GBR830, MAB1, MAB10, AMG451 and a control IgG1. Each curve is a nonlinear logistic 4PL model with variable slope and symbols represent Mean+/−SEM for eight individual T cell donors, from two independent experiments.

The half maximum effective concentration (EC50) values in nM for IFN-γ (FIG. 15A), TNF-alpha (FIG. 15B), IL-5 (FIG. 15C), IL-13 (FIG. 15D), IL-2 (FIG. 14E), IL-4 (FIG. 14F), IL-31 (FIG. 14G), IL-17a (FIG. 14H), IL-21 (FIG. 14I), and IL-22 (FIG. 14J) are shown for GBR830, MAB1, MAB10, AMG451. Each symbol represents an EC50 value for one individual donor, among the eight individual T cell donors tested, from two independent experiments. Values were excluded based on goodness of fit ($R^2$>0.7), out-of-range EC50 values or if the curve was not reaching a plateau. EC50 values were compared using a paired One-way ANOVA test followed by Tukey's post-hoc comparison (ns p>0.05, *p<0.05, 0.01<p<0.05, *p<0.01).

TABLE 17

Mean +/− SD in nM of half maximum effective concentration (EC50) values for GBR830, MAB1, MAB10 and AMG451, and fold-difference to GBR830.

| | GBR830 | | MAB1 | | MAB10 | | AMG451 | |
|---|---|---|---|---|---|---|---|---|
| | Mean +/− SD EC50 (nM) | Fold diff to GBR830 | Mean +/− SD EC50 (nM) | Fold diff to GBR830 | Mean +/− SD EC50 (nM) | Fold diff to GBR830 | Mean +/− SD EC50 (nM) | Fold diff to GBR830 |
| IFNγ | 66.7 +/− 1.6 | — | 14.6 +/− 10.5 | 4.6 | 11.8 +/− 7.3 | 5.7 | 10.7 +/− 8.0 | 6.2 |
| IL-5 | 63.6 +/− 2.8 | — | 21.3 +/− 23.5 | 3.0 | 16.4 +/− 16.31 | 3.9 | 18.6 +/− 24.8 | 3.4 |
| IL-8 | 58.25 +/− 334.50 | — | 9.19 +/− 8.22 | 6.3 | 9.55 +/− 7.50 | 6.1 | 4.05 +/− 3.22 | 14.4 |
| IL-10 | 66.78 +/− | — | 28.01 +/− 28.59 | 2.4 | 34.09 +/− 33.39 | 2.0 | 20.31 +/− 26.80 | 3.3 |
| IL-13 | 69.6 +/− 1.8 | — | 6.2 +/− 8.6 | 11.2 | 5.3 +/− 5.9 | 13.1 | 4.0 +/− 4.2 | 17.4 |
| TNF-α | 43.3 +/− 38.1 | — | 4.1 +/− 2.4 | 10.6 | 4.2 +/− 1.8 | 10.3 | 3.9 +/− 3.2 | 11.1 |
| IL-2 | 7.92 +/− 1.30 | — | 2.36 +/− 2.57 | 3.4 | 2.63 +/− 2.17 | 3.0 | 5.87 +/− 3.98 | 1.3 |
| IL-4 | 44.76 +/− 51.60 | — | 2.83 +/− 1.52 | 15.8 | 2.88 +/− 2.64 | 15.5 | 1.77 +/− 1.11 | 25.3 |
| IL-17a | NQ | — | 24.41 +/− 22.57 | — | 23.53 +/− 21.82 | — | 11.73 +/− 13.92 | — |
| IL-21 | 47.27 +/− | — | 2.56 +/− 2.22 | 18.5 | 2.75 +/− 2.74 | 17.2 | 2.75 +/− 2.15 | 17.2 |
| IL-22 | NQ | — | 9.19 +/− 8.99 | — | 7.03 +/− 5.24 | — | 10.38 +/− 16.47 | — |
| IL-31 | 29.87 +/− 41.84 | — | 2.51 +/− 1.28 | 11.9 | 2.00 +/− 2.31 | 14.9 | 1.84 +/− 0.84 | 16.2 |

The comparison between GBR830, MAB1 and MAB10 confirm that enhanced affinity to OX40 in MAB1 and MAB10 binders results in a dramatic increase of potency in blocking T cell proliferation and broader cytokine release inhibition, including Th1, Th2, Th17, and Th22 cytokines, compared to GBR830. In addition, the incorporation of the YTE mutation in MAB10 did not affect the potency, with similar EC50 values in this assay for both MAB10 and MAB1. For all cytokines, the fold differences to GBR830 antibody varies between 2.4/2 to 18.5/17.2-fold for MAB1 and MAB10 respectively.

OX40 Internalization Assay

Figure 24:
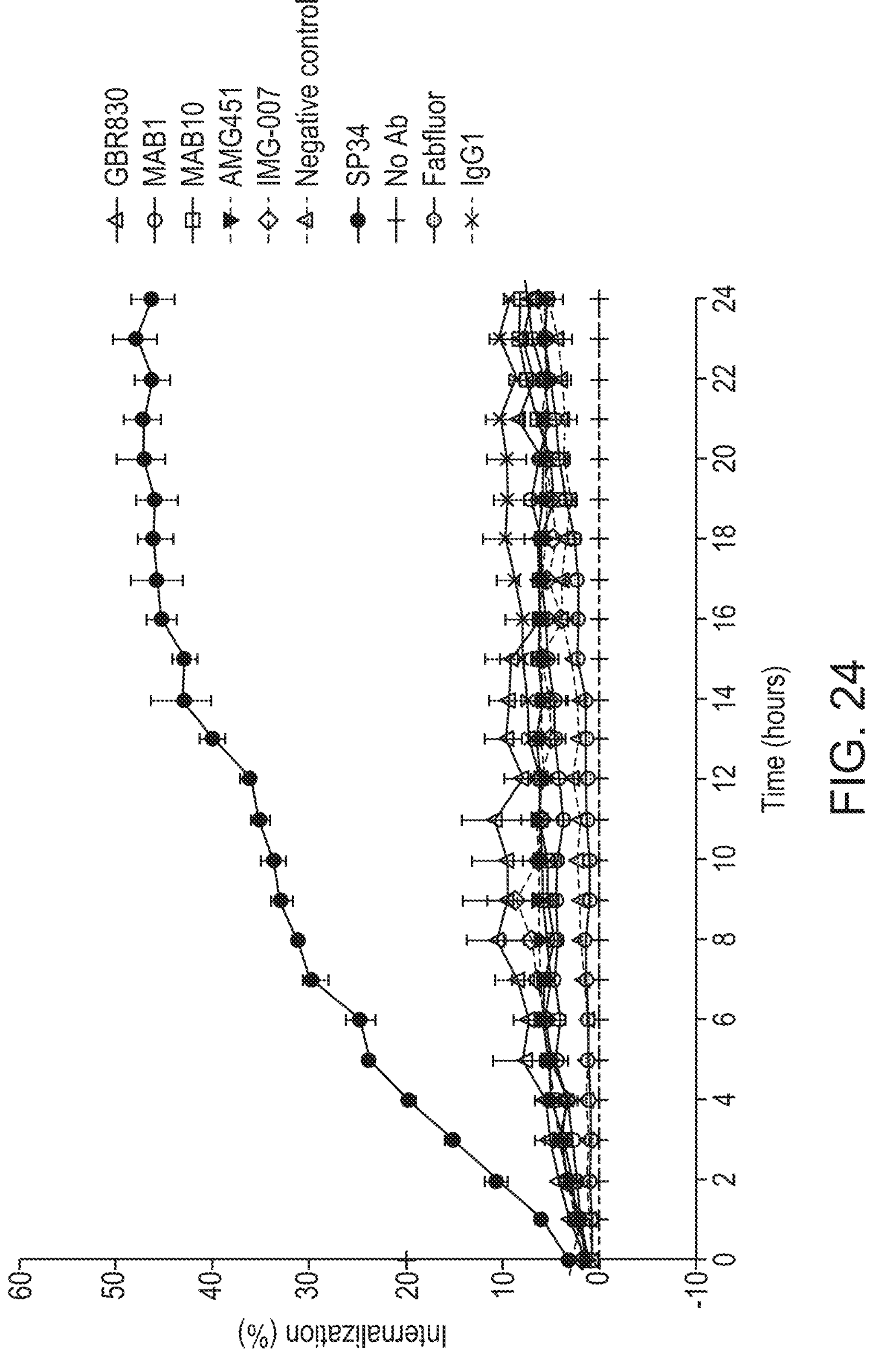
FIG. 24 shows OX40 internalization on activated T cells. Activated T cells were incubated with Fabfluor Red labelled antibodies at 8 μg/mL for 24 hours. Internalization was measured using an Incucyte Live-Cell Analysis System. Dots represent the mean±SEM of 3 activated T cell donors from one experiment.

The internalization of OX40 induced by MAB10, MAB1, GBR830, AMG451, and IMG-007 binding, as well as positive control (SP34), and negative controls was evaluated using activated T cells by live-imaging. MAB10 did not induce OX40 internalization in activated T cells (FIG. 24). MAB1, GBR830, AMG451, and IMG-007 also did not induce OX40 target internalization, as internalization values were below 10% at 8 μg/mL. Negative controls (IgG1, Fabfluor alone, or untreated condition (No Ab)) confirmed that no unspecific internalization occurred during the assay. In contrast, positive control SP34, an antibody targeting CD3 and known to induce OX40 internalization, showed internalization of up to 50% on activated T cells. Thus, the increased affinity for the OX40 target of MAB1 and the Fc region modification in MAB10 did not affect the internalization rate of OX40 in T cells after incubation with MAB10 or MAB1.

Cross Reactivity with Non-Human OX40

The binding of the MAB10 antibody was tested on recombinant OX40 proteins from different species using ELISA. MAB10 demonstrated binding to human, cynomolgus monkey and rabbit OX40 proteins. The calculated EC50 values for human OX40 was 0.0485±0.0017, the cyno OX40 was 0.1792±0.0139, and the rabbit OX40 was 0.3793±0.0173. The calculated EC50 values were 4- or 8-fold lower for the human protein, compared to the cynomolgus monkey and rabbit orthologues. In contrast, no binding of MAB10 to rat or mouse OX40 proteins was observed.

SPR cross reactivity results are presented in Table 18. MAB10 bound to human, cynomolgus monkey, and rabbit OX40. MAB10 exhibited the highest affinity to human OX40 (KD=6.7±0.4 nM) followed by cynomolgus monkey (KD=268 nM) and rabbit OX40 (KD=3305 nM). No binding (NB) was detected for the mouse, or rat OX40, under the tested experimental conditions. Of note, the KD value, obtained in this experiment, for MAB10 binding to huOX40 was consistent with the ELISA assay results.

TABLE 18

SPR cross reactivity binding affinity

| OX40 | ka ($M^{-1}$ $s^{-1}$) ± S.D. | kd ($s^{-1}$) ± S.D. | KD (nM) ± S.D. |
|---|---|---|---|
| Human OX40 | $3 \times 10^5 \pm 4.2 \times 10^4$ | $2.1 \times 10^{-3} \pm 3.7 \times 10^{-4}$ | 6.7 ± 0.4 |
| Cyno OX40 | $2.0 \times 10^5 \pm 2.9 \times 10^3$ | $5.2 \times 10^{-2} \pm 4.2 \times 10^{-4}$ | 268 ± 4 |

TABLE 18-continued

| SPR cross reactivity binding affinity | | | |
|---|---|---|---|
| OX40 | ka ($M^{-1}$ $s^{-1}$) ± S.D. | kd ($s^{-1}$) ± S.D. | KD (nM) ± S.D. |
| Mouse OX40 | NB | NB | NB |
| Rat OX40 | NB | NB | NB |
| Rabbit OX40 | $9.0 \times 10^3 \pm 6.5 \times 10^2$ | $3.0 \times 10^{-2} \pm 1.2 \times 10^{-3}$ | 3305 ± 108 |

Figures 25A, 25B, 25C:
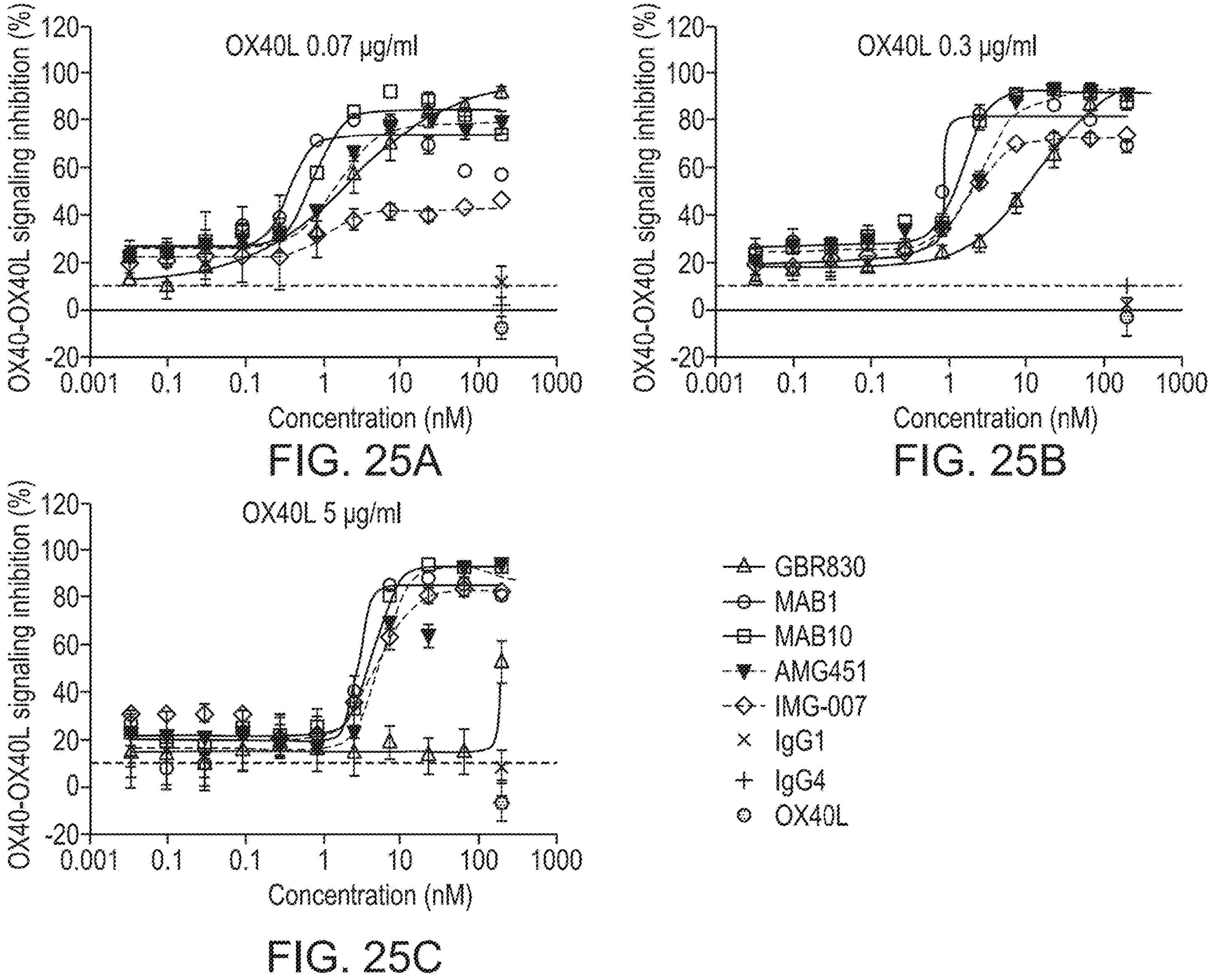
FIG. 25A-C show signaling inhibition with anti-OX40 antibodies on Jurkat-NF-κB-OX40 engineered cells in the presence of OX40L. Graphs show the mean±SEM of 3 independent experiments for the percentage of OX40-OX40L signaling inhibition at different concentrations of the indicated antibodies and different doses of OX40L.

Receptor Occupancy Assessment and Signaling Inhibition in Jurkat-NFκB-OX40 Reporter Cells MAB10 consistently and dose-dependently inhibited the NFκB signaling mediated by OX40L binding to OX40 (FIGS. 25A-C). FIG. 25A shows 0.07 μg/mL OX40L. FIG. 25B shows 0.3 μg/mL OX40L. FIG. 25C shows 5 μg/mL OX40L. The inhibition potency was dependent on the OX40L concentration used, as shown by the increased EC50 at a saturating dose of OX40L of 5 μg/mL, compared to lower concentrations of OX40L. MAB10 showed an average EC50 (inhibition) of 4.59 nM at 5 μg/mL of OX40L, whereas the EC50 was 0.79 nM with 0.07 μg/mL OX40L. The observed inhibition by MAB1 was similar to that of MAB10. GBR830 also inhibited the OX40-OX40L pathway, however, with a higher EC50 than MAB1 and MAB10. GBR830 was also more impacted by the concentration of OX40L, as this molecule only reached a maximum inhibition of 53% for a saturating dose of OX40L, whereas MAB10 had a mean maximum inhibition of 95% under the same conditions.

Figures 26A, 26B, 26C, 26D:
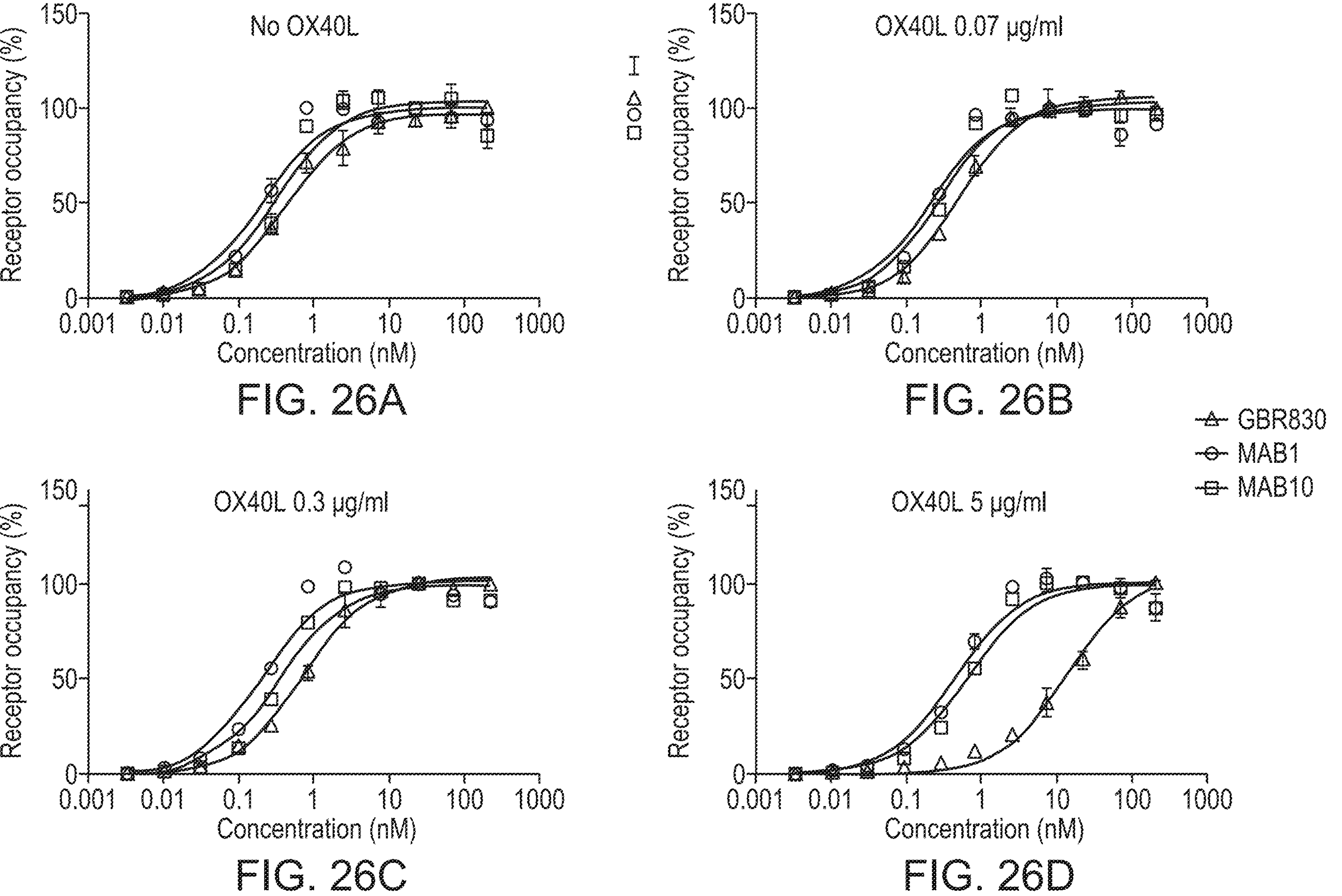
FIG. 26A-D show receptor occupancy in Jurkat-NF-κB-OX40 engineered cells in the presence of OX40L and the indicated antibodies. Graphs show the mean±SEM of 3 independent experiments (singlicate) of the percentage of receptor occupancy at different concentrations of OX40L and in the presence of the indicated antibodies.

The binding of the molecules to the OX40 target was reduced with increasing concentrations of OX40L, i.e., higher concentrations of the indicated antibodies were required to achieve the same binding at higher doses of OX40L (FIG. 26A-D). FIG. 26A shows no OX40L. FIG. 26B shows 0.07 μg/mL OX4L. FIG. 26C shows 0.3 mg/mL OX40L. FIG. 26D shows 5 μg/mL OX40L. The receptor occupancy of GBR83 was most impacted by the concentration of OX40L, whereas MAB1 and MAB10 were only mildly impacted at 5 μg/mL of OX40L.

The data show that MAB10 is capable of inhibiting the binding of OX40L to OX40, and that it outperforms GBR830 in doing so as shown in FIGS. 25B-C.

Off-Target Assessment 6105 human plasma membrane proteins, secreted proteins, and 400 heterodimers were screened for specific interaction with MAB10. MAB10 showed a significant specific interaction with its primary target, TNFRSF4 (OX40), on both fixed and live cell microarrays; no off-target binding was observed. Additionally, it interacted with FCGR3A (Fc gamma receptor IIIa), both alone and as part of a heterodimer with FCER1G or CD247, on fixed cell microarrays, and with FCGR2A and TSLP on live cell microarrays. The interactions with Fc gamma receptors are likely Fc-domain mediated. In a subsequent flow cytometry study, MAB10 exhibited strong binding to TNFRSF4 (OX40) but no significant interaction with TSLP (data not shown).

Example 6: In Vitro Characterization of MAB10 Antibody-Dependent Cell Cytotoxicity Function Materials and Methods Antibody-Dependent Cell Cytotoxicity Assay To evaluate the potential of MAB10 to induce Antibody-Dependent Cell Cytotoxicity (ADCC), a short-term NK-mediated killing assay was performed against OX40-expressing activated and regulatory T cells.

Human PBMC were harvested from buffy coats obtained from Biopole (Switzerland) Transfusion Center using ficoll density gradient isolation. As the assay is performed with autologous cells: naïve T cells were isolated from the PBMC to differentiate them into regulatory T cells using ImmunoCult Human Treg Differentiation Supplement (StemCell Technologies, catalog NO: #10977) and ImmunoCult-XF T Cell Expansion Medium (StemCell Technologies, catalog NO: #10981); PBMC from the same donor were frozen to isolate T cells and NK cells for further activation steps performed during the experiment. Naïve T cells were isolated from PBMCs using the EasySep Human Naïve CD4+ T cell Isolation Kit (StemCell Technologies, catalog NO: #19555) following manufacturer's instructions for 7 days. In parallel, 2 days before the assay, the rest of autologous PBMCs were thawed in pre-warmed complete RPMI medium (RPMI supplemented with 10% heat inactivated fetal calf bovine, 1% Glutamine, 1% Non-essential Amino Acids, 1% Sodium Pyruvate, and 1% Penicillin/Streptomycin) and T cells and NK were isolated, following the manufacturer's protocol. Isolated T cells were resuspended in complete medium at 1 million cells per ml and activated for 2 days with Dynabeads™ (1 million beads per ml). Isolated NK cells were maintained in culture for 2 days at 2 million cells per mL in the presence of 100 Units per mL of recombinant human IL-2. On the day of the assay, ten thousand target cells (activated T cells or regulatory T cells) were co-cultured with fifty thousand NK cells reaching an effector-to-target ratio of 5:1 in 384-well flat bottom plates (ThermoFisher Scientific, catalog NO: 242764). Serial dilutions of GBR830, MAB1, MAB10 and AMG451 starting from 20 nM and diluted by 5-fold, and control antibody were plated shortly after target and effector cells. Plates were then incubated for 4 days at 37° C., 5% $CO_2$. After the incubation, target cell killing was evaluated by measuring the Lactate Dehydrogenase (LDH) release (Promega, catalog NO: G1780) in supernatant. The percentage of ADCC was calculated using the following formula: ADCC (%) (Sample−No Treatment)/(Target only+Lysis buffer−No Treatment)×100, with "No treatment" condition being the spontaneous LDH release induced by Target and Effector cells without treatment and "Target only+Lysis buffer" condition being the maximum LDH release expected in the assay. From those data, percentages of ADCC were plotted using Prism software (GraphPad). Maximum killing was determined using JMP (SAS) software and half maximal effective concentration or EC50 values were calculated from the dose-response curves using a logistic 4 parameter regression model with variable slope. Treatment groups were compared in statistical analyses performed on untransformed Maximum ADCC values, using a paired-one way ANOVA (donor as pairing factor) followed by post-hoc Tukey HSD comparison. Maximum ADCC values are presented in FIG. 4A and B and Mean Maximum ADCC and EC50+/−Standard Deviation are reported in percentages or pM in Tables 19, 20, 21 and 22.

Results

All molecules were tested in an ADCC assay to evaluate their potential to induce the killing of OX40-expressing activated and regulatory T cells. FIG. 16A-B, FIG. 17A-B, and FIG. 18A-B show that all anti-OX40 antibodies induce various level of ADCC on both cell types. Metrics such as Maximum ADCC and EC50 values are summarized in Tables 19 to 22.

On activated T cells, MAB10 elicited considerably less ADCC than AMG451, which demonstrated a 5-fold greater killing capacity (EC50 0.02 nM and 60.29% Maximum ADCC). GBR830, MAB1 and MAB10 showed similar effectiveness in eliminating activated T cells, with comparable subnanomolar EC50 values and Maximum ADCC values around 34.87-45.62%.

On regulatory T cells, MAB10 induced significantly lower ADCC compared to AMG451. Enhanced affinity to OX40 in MAB1 results in an 8-fold increase in the cytotoxic activity against regulatory T cells compared to GBR830. The incorporation of the YTE mutation in MAB10 enhanced its safety profile, as evidenced by statistically lower maximum cytotoxic activity against regulatory T cells relative to GBR830 and MAB1, with respective EC50 values of 2.31 nM compared to 2.5 and 0.28 nM, and 1.6 to 2.3-fold lower maximum ADCC. In contrast, AMG451 exhibits a 46-fold greater potency than MAB10 in the elimination of regulatory T cells through ADCC (EC50 0.05 nM and 85.75% Maximum ADCC).

MAB10 induced significantly lower ADCC on activated or regulatory T cells than AMG451. The ability of anti-OX40 antibodies and benchmark antibody AMG451 to induce the killing of activated (FIG. 16A) or regulatory (FIG. 16B) T cells was assessed in a ADCC assay with a 5:1 Effector-to-target ratio and measured by LDH release after 4.5 hours. At endpoint, LDH release was evaluated from co-culture supernatants and percentages of ADCC were determined. The percentages of ADCC at different concentrations is shown for GBR830, MAB1, MAB10, AMG451 and a control IgG1. Each curve is a nonlinear logistic 4PL model with variable slope and symbols represent Mean+/−SD for eight (FIG. 16A) or six (FIG. 16B) individual donors, from three to four independent experiments.

Figure 17B:
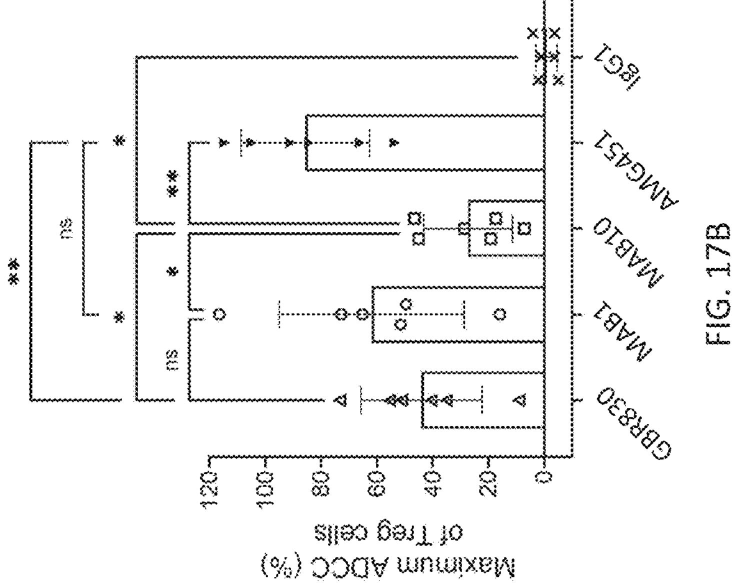
FIG. 17B shows the maximum killing of regulatory T cells through ADCC. Each symbol represents each value for one individual donor, among the eight to six individual donors tested, from three to four independent experiments. Maximum ADCC values were compared using a paired One-way ANOVA test followed by Tukey's post-hoc comparison (ns $p>0.05$, *$p<0.05$, $0.01<p<0.05$, *$p<0.01$).
Figure 17A:
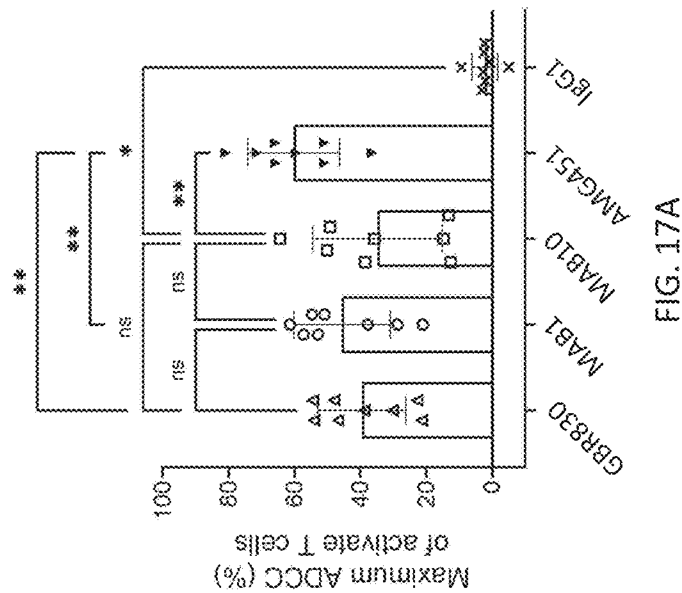
FIG. 17A shows the maximum killing of activated T cells through ADCC.

Maximum ADCC is shown for GBR830, MAB1, MAB10 and AMG451 in FIG. 17A-B. FIG. 17A shows the maximum ADCC of activated T cells. FIG. 17B shows the maximum ADCC of regulatory T cells. Each symbol represents each value for one individual donor, among the eight to six individual donors tested, from three to four independent experiments. Maximum ADCC values were compared using a paired One-way ANOVA test followed by Tukey's post-hoc comparison (ns p>0.05, *p<0.05, 0.01<p<0.05, *p<0.01).

Figure 18B:
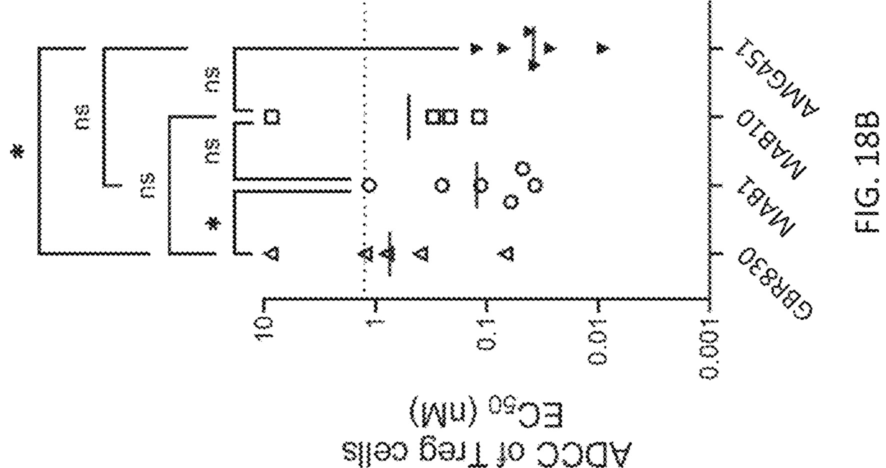
FIG. 18B shows the EC50 (nM) of ADCC with the indicated antibodies against regulatory T cells. Each symbol represents each value for one individual donor, among the eight to six individual donors tested, from three to four independent experiments. EC50 (nM) of ADCC values were compared using a paired One-way ANOVA test followed by Tukey's post-hoc comparison (ns $p>0.05$, *$p<0.05$, $0.01<p<0.05$, *$p<0.01$).
Figure 18A:
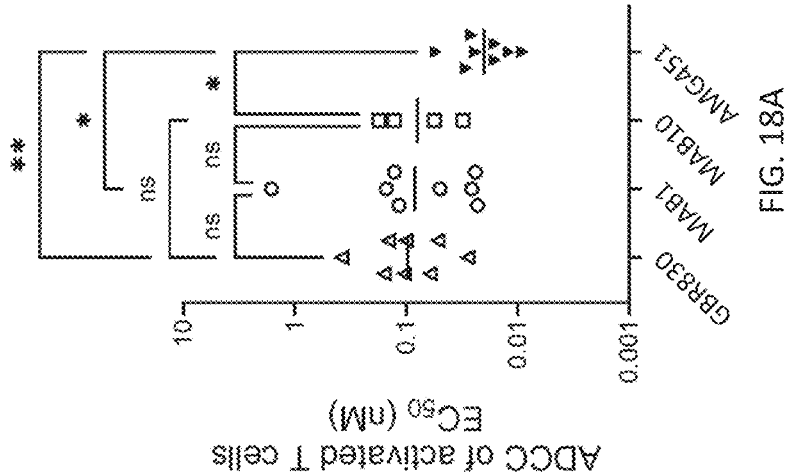
FIG. 18A shows the EC50 (nM) of ADCC with the indicated antibodies against activated T cells.

The half maximum effective concentration (EC50) is shown for GBR830, MAB1, MAB10 and AMG451 in FIG. 18A-B. FIG. 18A shows the EC50 of ADCC with the indicated antibodies against activated T cells. FIG. 18B shows the EC50 of ADCC with the indicated antibodies against regulatory T cells. Each symbol represents each value for one individual donor, among the eight to six individual donors tested, from three to four independent experiments. EC50 of ADCC values were compared using a paired One-way ANOVA test followed by Tukey's post-hoc comparison (ns p>0.05, *p<0.05, 0.01<p<0.05, *p<0.01).

TABLE 19 shows the maximum ADCC values for GBR830, MAB1, MAB10 and AMG451 on activated T cells, and fold-difference to MAB10.

| Antibody | Mean +/− SD Maximum killing (%) | Fold diff to MAB10 |
|---|---|---|
| IgG1 control | 2.27 +/− 3.90 | — |
| GBR830 | 39.58 +/− 13.38 | 1.14 |
| MAB1 | 45.62 +/− 14.61 | 1.31 |
| MAB10 | 34.87 +/− 19.59 | — |
| AMG451 | 60.29 +/− 13.91 | 1.73 |

TABLE 20 shows the maximum ADCC values for GBR830, MAB1, MAB10 and AMG451 on regulatory T cells, and fold-difference to MAB10.

| Antibody | Mean +/− SD Maximum killing (%) | Fold diff to MAB10 |
|---|---|---|
| IgG1 control | −0.83 +/− 3.80 | — |
| GBR830 | 44.06 +/− 21.69 | 1.61 |
| MAB1 | 61.90 +/− 33.15 | 2.27 |
| MAB10 | 27.32 +/− 15.87 | — |
| AMG451 | 85.75 +/− 23.04 | 3.14 |

TABLE 21 shows the mean+/−SD in nM of EC50 values for GBR830, MAB1, MAB10 and AMG451 on activated T cells, and fold-difference to MAB10.

| Antibody | Mean +/− SD EC50 (nM) | Fold diff to MAB10 |
|---|---|---|
| IgG1 control | — | — |
| GBR830 | 0.13 +/− 0.11 | 0.77 |
| MAB1 | 0.27 +/− 0.55 | 0.37 |
| MAB10 | 0.10 +/− 0.07 | — |
| AMG451 | 0.02 +/− 0.01 | 5.00 |

TABLE 22 shows the mean+/−SD in nM of EC50 values for GBR830, MAB1, MAB10 and AMG451 on regulatory T cells, and fold-difference to MAB10.

| Antibody | Mean +/− SD EC50 (nM) | Fold diff to MAB10 |
|---|---|---|
| IgG1 control | — | — |
| GBR830 | 2.25 +/− 3.65 | 1.03 |
| MAB1 | 0.28 +/− 0.43 | 8.25 |
| MAB10 | 2.31 +/− 4.20 | — |
| AMG451 | 0.05 +/− 0.04 | 46.2 |

In sum, in an Fc-mediated assay such as Antibody-Dependent Cell Cytotoxicity assay, MAB10 elicited considerably less ADCC than AMG451, on both OX40-expressing activated and regulatory T cells. GBR830, MAB1 and MAB10 showed similar effectiveness in eliminating activated T cells. Enhanced affinity to OX40 in MAB1 results in an increase in the cytotoxic activity against regulatory T cells compared to GBR830, and the incorporation of the YTE mutation in MAB10 demonstrated statistically lower maximum cytotoxic activity against regulatory T cells relative to GBR830 and MAB1, which may enhance its safety profile in future in-human studies.

Example 7: In Vivo Non-Human Primate Study

Materials and Methods

MAB10 was formulated in buffer (5 mM Histidine, 4% Sucrose, 0.01% polysorbate 20, pH 6.0) at 1.5, 5, and 10 mg/mL concentrations. Cynomolgus monkeys were dosed once subcutaneously. Samples were collected at predetermined intervals for 90 days post-dose.

Animals were assigned to the following groups:

| Group Number | Test Material | Dose Level (mg/kg) | Dose Volume[a] (mL/kg) | Dose Concentration (mg/mL) | Number (Identification of Females) |
|---|---|---|---|---|---|
| 1 | Vehicle control | 0 | 2 | 0 | 3 |
| 2 | MAB10 | 3 | 2 | 1.5 | 3 |
| 3 | MAB10 | 10 | 2 | 5 | 3 |
| 4 | MAB10 | 20 | 2 | 10 | 3 |

[a]Based on the most recent body weight measurement.

Group 1 animals (control) received the vehicle control (5 mM histidine, 4% sucrose, 0.01% polysorbate 20, pH 6.0).

The cynomolgus monkey was chosen as the animal model for this study since MAB10 is a fully humanized anti-OX40 monoclonal antibody which only cross-reacts in non-human primates and not in other laboratory species. In addition, cynomolgus monkey is an accepted nonrodent species for nonclinical toxicity testing by regulatory agencies. The total number of animals used in this study was considered to be the minimum required to properly characterize the effects of the test item. The subcutaneous route of exposure was selected because this is the intended route of human exposure.

Noncompartmental Analysis

A noncompartmental analysis was used for parameter estimation using Phoenix pharmacokinetic software (version 8.3). For MAB10 in serum the extravascular model was used for parameter estimation. All parameters were generated from MAB10 individual concentrations in serum from Day 1. Parameters were estimated using nominal dose levels and nominal sampling times relative to the dose administration. Serum concentration values obtained at the predose time point were used as the concentration at time 0 on Day 1. Concentration values reported as below the limit of quantitation (<375 ng/mL) were treated as 0.

When practical, the terminal elimination phase of each concentration versus time curve was identified using at least the final 3 observed concentration values. The slope of the terminal elimination phase was determined using log linear regression on the unweighted concentration data. Parameters relying on the determination of the terminal elimination phase were reported when RSQadj was ≥0.9.

Results

Figure 19:
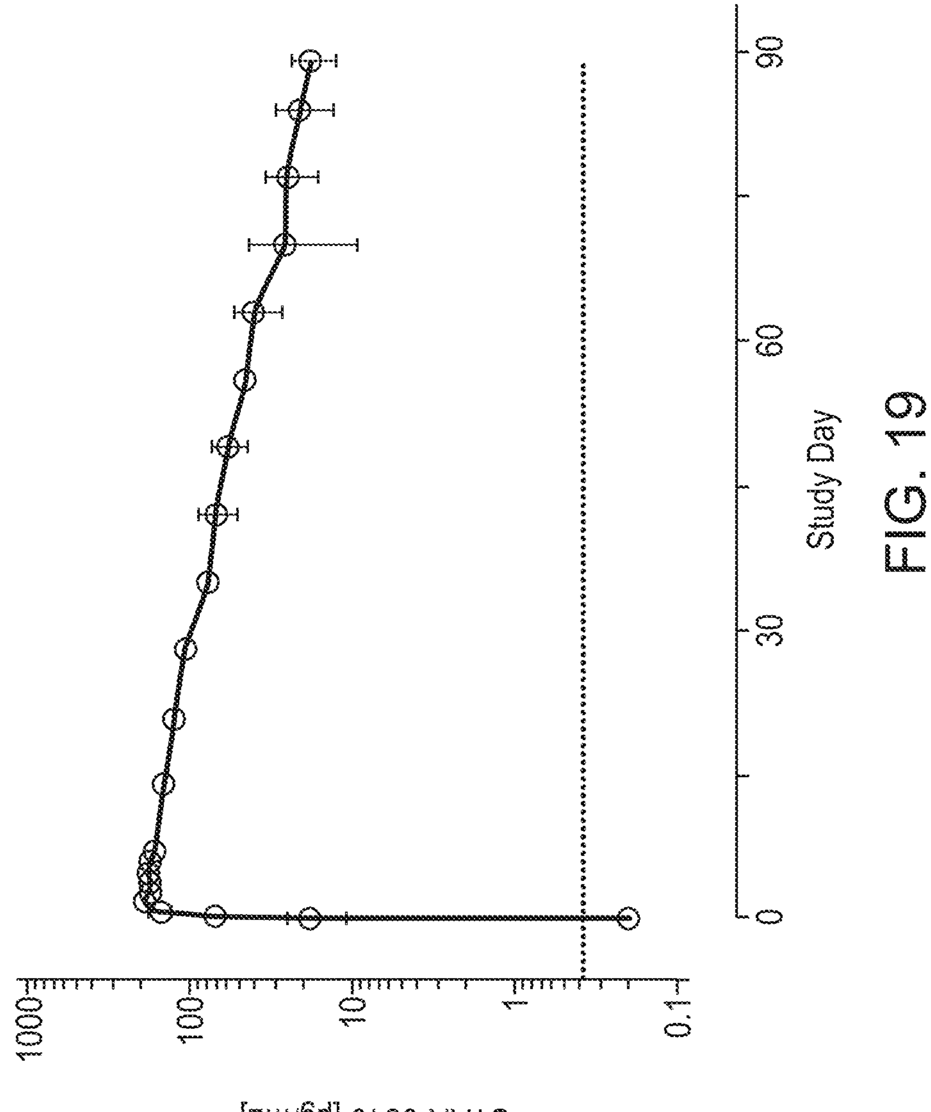
FIG. 19 shows the in vivo pharmacokinetic data from cynomolgus monkeys (n=3) dosed subcutaneously with 20 mg/kg MAB10.

In vivo pharmacokinetic data from cynomolgus monkeys (n=3) dosed subcutaneously with 20 mg/kg MAB10 are provided in FIG. 19. Data represent MAB10 mean concentration (SD) over time. Dotted line represents LLOQ of 0.375 μg/mL; concentrations<LLOQ are plotted as ½ LLOQ. A single subcutaneous administration of MAB10 to cynomolgus monkeys at 3, 10 and 20 mg/kg was well tolerated locally and did not result in any systemic toxicity. MAB10 also exhibited an extended half-life of 26 days (622 hours) in cynomolgus monkey.

NUMBERED EMBODIMENTS

Embodiments disclosed herein include embodiments P1 to P54, as provided in the numbered embodiments of the disclosure:

Embodiment PL. An antibody or antigen binding fragment thereof that binds to OX40 comprising three heavy chain complementarity determining regions (CDRs) (CDR-H1, CDR-H2, and CDR-H3) of a heavy chain variable domain (VH) comprising the amino acid sequence set forth in SEQ ID NO:7 and three light chain complementarity determining regions (CDRs) (CDR-L1, CDR-L2, and CDR-L3) of a light chain variable domain (VL) comprising the amino acid sequence set forth in SEQ ID NO:8, optionally wherein the antibody or antigen binding fragment thereof is an isolated antibody or antigen binding fragment.

Embodiment P2: An antibody or antigen binding fragment thereof that binds to OX40 comprising three heavy chain complementarity determining regions (CDRs) (CDR-H1, CDR-H2, and CDR-H3) of a heavy chain variable domain (VH) comprising the amino acid sequence set forth in SEQ ID NO:7 and three light chain complementarity determining regions (CDRs) (CDR-L1, CDR-L2, and CDR-L3) of a light chain variable domain (VL) comprising the amino acid sequence set forth in SEQ ID NO:12, 15, 18, 21, 24, 27, 30, or 33; optionally wherein the antibody or antigen binding fragment thereof is an isolated antibody or antigen binding fragment.

Embodiment P3. The antibody of Embodiment P1 or P2, wherein:

a. the CDR-H1, CDR-H2, and CDR-H3, and the CDR-L1, CDR-L2, and CDR-L3 are defined according to Kabat;
b. the CDR-H1, CDR-H2, and CDR-H3, and the CDR-L1, CDR-L2, and CDR-L3 are defined according to Chothia;
c. the CDR-H1, CDR-H2, and CDR-H3, and the CDR-L1, CDR-L2, and CDR-L3 are defined according to IMGT;
d. the CDR-H1, CDR-H2, and CDR-H3, and the CDR-L1, CDR-L2, and CDR-L3 are defined according to AbM;
e. the CDR-H1, CDR-H2, and CDR-H3, and the CDR-L1, CDR-L2, and CDR-L3 are defined according to Contact; or
f. the CDR-H1, CDR-H2, and CDR-H3, and the CDR-L1, CDR-L2, and CDR-L3 are defined according to Honneger (AHo).

Embodiment P4: An antibody, or antigen binding fragment thereof, that binds to OX40 comprising:

a. a heavy chain variable region comprising a CDR-H1 comprising the amino acid sequence set forth in SEQ ID NO:1, a CDR-H2 comprising the amino acid sequence set forth in SEQ ID NO:2, a CDR-H3 comprising the amino acid sequence set forth in SEQ ID NO:3; and
b. a light chain variable region comprising a CDR-L1 comprising amino acid sequence set forth in SEQ ID NO:4, a CDR-L2 comprising the amino acid sequence set forth in SEQ ID NO:5, and a CDR-L3 comprising the amino acid sequence set forth in SEQ ID NO:38 or 71, where $X_1$ is F, T, W, or M; where $X_2$ is G, I, V, L, or E; where $X_3$ is A, D, E, L, H, T, or F; and where $X_4$ is W, P, F, Y, or T, optionally wherein the antibody or antigen binding fragment thereof is an isolated antibody or antigen binding fragment.

Embodiment P5: The antibody, or antigen binding fragment thereof, of Embodiment P4, wherein the CDR-L3 comprises the amino acid sequence set forth in SEQ ID NO:38.

Embodiment P6: The antibody, or antigen binding fragment thereof, of Embodiment P4 or P5, wherein $X_1$ is F or T, $X_2$ is L, G, or E, $X_3$ is A, and $X_4$ is W.

Embodiment P7. The antibody, or antigen binding fragment thereof, of any one of Embodiments P4-P6, wherein CDR-L3 comprises the amino acid sequence of SEQ ID NO:6, 11, 14, 17, 20, 23, 26, or 29.

Embodiment P8: An antibody, or antigen binding fragment thereof, that binds to OX40 comprising:

a. a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3; and b. a light chain variable region comprising a CDR-L1 comprising the amino acid sequence set forth in SEQ ID NO:4, a CDR-L2 comprising the amino acid sequence set forth in SEQ ID NO:5, and a CDR-L3 comprising an amino acid sequence as set forth in SEQ ID NOs: 6, 11, 14, 17, 20, 23, 26, 29, or 32.

Embodiment P9. An antibody, or antigen binding fragment thereof, that binds to OX40 comprising:

(a) a heavy chain variable region comprising:

a heavy chain CDR1 comprising the amino acid sequence of SEQ ID NO:1, SEQ ID NO:41, SEQ ID NO:47, SEQ ID NO:53, SEQ ID NO:59, or SEQ ID NO:65;

a heavy chain CDR2 comprising the amino acid sequence of SEQ ID NO:2, SEQ ID NO:42, SEQ ID NO:48, SEQ ID NO:54, SEQ ID NO:60, or SEQ ID NO:66; and a heavy chain CDR3 comprising the amino acid sequence of SEQ ID NO:3, SEQ ID SEQ ID NO:55, SEQ ID NO:61, or SEQ ID NO:67; and (b) comprising a light chain variable region comprising:

a light chain CDR1 comprising the amino acid sequence of SEQ ID NO:4, SEQ ID SEQ ID NO:56, SEQ ID NO:62, or SEQ ID NO:68;

a light chain CDR2 comprising the amino acid sequence of SEQ ID NO:5, SEQ ID SEQ ID NO:57, the amino acid sequence AT, or SEQ ID NO:69; and a light chain CDR3 comprising the amino acid sequence of SEQ ID NO:6, SEQ ID SEQ ID NO:58, or SEQ ID NO:70.

Embodiment P10. The antibody or antigen binding fragment thereof of any one of Embodiments P1-P9, wherein the heavy chain CDR1 comprises the amino acid sequence of SEQ ID NO:1, the heavy chain CDR2 comprises the amino acid sequence of SEQ ID NO:2, the heavy chain CDR3 comprises the amino acid sequence of SEQ ID NO:3, the light chain CDR1 comprises the amino acid sequence of SEQ ID NO:4, the light chain CDR 2 comprises the amino acid sequence of SEQ ID NO:5, and the light chain CDR3 comprise the amino acid sequence of SEQ ID NO:6.

Embodiment P11. The antibody or antigen binding fragment thereof of any one of Embodiments P1-P9, wherein the heavy chain CDR1 comprises the amino acid sequence of SEQ ID NO:41, the heavy chain CDR2 comprises the amino acid sequence of SEQ ID NO:42, the heavy chain CDR3 comprises the amino acid sequence of SEQ ID NO:3, the light chain CDR1 comprises the amino acid sequence of SEQ ID NO:4, the light chain CDR 2 comprises the amino acid sequence of SEQ ID NO:5, and the light chain CDR3 comprise the amino acid sequence of SEQ ID NO:6.

Embodiment P12. The antibody or antigen binding fragment thereof of any one of Embodiments P1-P9, wherein the heavy chain CDR1 comprises the amino acid sequence of SEQ ID NO:47, the heavy chain CDR2 comprises the amino acid sequence of SEQ ID NO:48, the heavy chain CDR3 comprises the amino acid sequence of SEQ ID NO:3, the light chain CDR1 comprises the amino acid sequence of SEQ ID NO:4, the light chain CDR 2 comprises the amino acid sequence of SEQ ID NO:5, and the light chain CDR3 comprise the amino acid sequence of SEQ ID NO:6.

Embodiment P13. The antibody or antigen binding fragment thereof of any one of Embodiments P1-P9, wherein the heavy chain CDR1 comprises the amino acid sequence of SEQ ID NO:53, the heavy chain CDR2 comprises the amino acid sequence of SEQ ID NO:54, the heavy chain CDR3 comprises the amino acid sequence of SEQ ID NO:55, the light chain CDR1 comprises the amino acid sequence of SEQ ID NO:56, the light chain CDR 2 comprises the amino acid sequence of SEQ ID NO:57, and the light chain CDR3 comprise the amino acid sequence of SEQ ID NO:58.

Embodiment P14. The antibody or antigen binding fragment thereof of any one of Embodiments P1-P9, wherein the heavy chain CDR1 comprises the amino acid sequence of SEQ ID NO:59, the heavy chain CDR2 comprises the amino acid sequence of SEQ ID NO:60, the heavy chain CDR3 comprises the amino acid sequence of SEQ ID NO:61, the light chain CDR1 comprises the amino acid sequence of SEQ ID NO:62, the light chain CDR 2 comprises the amino acid sequence AT, and the light chain CDR3 comprise the amino acid sequence of SEQ ID NO:6.

Embodiment P15. The antibody or antigen binding fragment thereof of any one of Embodiments P1-P9, wherein the heavy chain CDR1 comprises the amino acid sequence of SEQ ID NO:65, the heavy chain CDR2 comprises the amino acid sequence of SEQ ID NO:66, the heavy chain CDR3 comprises the amino acid sequence of SEQ ID NO:67, the light chain CDR1 comprises the amino acid sequence of SEQ ID NO:68, the light chain CDR 2 comprises the amino acid sequence of SEQ ID NO:69, and the light chain CDR3 comprise the amino acid sequence of SEQ ID NO:70.

Embodiment P16. The antibody or antigen binding fragment thereof of any one of Embodiments P1-P15, wherein the OX40 is human OX40.

Embodiment P17. The antibody or antigen binding fragment thereof of any one of Embodiments P1-P16, wherein the antibody or antigen binding fragment thereof is an antagonist of OX40.

Embodiment P18. The antibody or antigen binding fragment thereof of any one of Embodiments P1-P17, wherein the antibody or antigen binding fragment thereof is a humanized antibody.

Embodiment P19. The antibody or antigen binding fragment thereof of any one of Embodiments P1-P18, wherein the antibody or antigen binding fragment thereof comprises a heavy chain variable region comprising the amino acid sequence of SEQ ID NO:7.

Embodiment P20. The antibody or antigen binding fragment thereof of any one of Embodiments P1-P19, wherein the antibody or antigen binding fragment thereof comprises a light chain variable region comprising the amino acid sequence of SEQ ID NO:8.

Embodiment P21. The antibody or antigen binding fragment thereof of any one of Embodiments P1-P20, wherein the antibody or antibody or antigen binding fragment thereof comprises a heavy chain variable region comprising the amino acid sequence of SEQ ID NO:7 and a light chain variable region comprising the amino acid sequence of SEQ ID NO:8.

Embodiment P22. The antibody or antigen binding fragment thereof of any one of Embodiments P1-P19, wherein the antibody or antigen binding fragment thereof comprises a heavy chain variable region comprising the amino acid sequence of SEQ ID NO:7 and a light chain variable region comprising an amino acid sequence selected from SEQ ID NO:12, 15, 18, 21, 24, 27, 30, or 33.

Embodiment P23. The antibody or antigen binding fragment thereof any one of Embodiments P1-P22, comprising a heavy chain Fc region comprising an amino acid modification that increases the serum half-life of the antibody or antigen binding fragment thereof.

Embodiment P24. The antibody or antigen binding fragment thereof of any one of Embodiments P1-P23, comprising an IgG1 heavy chain.

Embodiment P25. The antibody or antigen binding fragment thereof of any one of Embodiments P1-P24, wherein the amino acid modification to the Fc region comprises the mutations M252Y, S254T, and T256E as numbered according to EU numbering.

Embodiment P26. The antibody or antigen binding fragment thereof of any one of Embodiments P1-P25, wherein the antibody or antigen binding fragment thereof comprises a heavy chain comprising the amino acid sequence of SEQ ID NO:9.

Embodiment P27. The antibody or antigen binding fragment thereof of any one of Embodiments P1-P25, wherein the antibody or antigen binding fragment thereof comprises a heavy chain comprising the amino acid sequence of SEQ ID NO:73.

Embodiment P28. The antibody or antigen binding fragment thereof of any one of Embodiments P1-P21 or P23-P27, wherein the antibody or antigen binding fragment thereof comprises a light chain comprising the amino acid sequence of SEQ ID NO:10.

Embodiment P29. The antibody or antigen binding fragment thereof of any one of Embodiments P1-P21, P23-P25, P27, or P28, wherein the antibody or antigen binding fragment thereof comprises a light chain comprising the amino acid sequence of SEQ ID NO:10 and a heavy chain comprising the amino acid sequence of SEQ ID NO:73.

Embodiment P30. The antibody or antigen binding fragment thereof of any one of Embodiments P1, P3-P8, P16-P19, P22-P24, or P26 wherein the antibody or antigen binding fragment thereof comprises a heavy chain comprising the amino acid sequence of SEQ ID NO:9 and a light chain comprising the amino acid sequence of SEQ ID NO:10, 13, 16, 19, 22, 25, 28, 31, or 34.

Embodiment P31. The antibody or antigen binding fragment thereof of any one of Embodiments P1, P3-P8, P16-P19, P22-P24, or P27 wherein the antibody or antigen binding fragment thereof comprises a heavy chain comprising the amino acid sequence of SEQ ID NO:73 and a light chain comprising the amino acid sequence of SEQ ID NO:13, 16, 19, 22, 25, 28, 31, or 34.

Embodiment P32. The antibody or antigen binding fragment thereof of any one of Embodiments P1-P31, wherein the antibody increases inhibition of T cell proliferation as compared to telazorlimab.

Embodiment P33. An isolated nucleic acid comprising a nucleotide sequence encoding the heavy chain complementarity determining regions of any one of Embodiments P1-P3, the heavy chain variable region of any one of Embodiments P4-P22, or the heavy chain of any one of Embodiments P23-P27, or P29-P31.

Embodiment P34. An isolated nucleic acid comprising a nucleotide sequence encoding the light chain complementarity determining regions of any one of Embodiments P1-P3, the light chain variable region of any one of Embodiments P4-P22, or the light chain of any one of Embodiments P28-P31.

Embodiment P35. An expression vector comprising the nucleic acid of Embodiment P33.

Embodiment P36. An expression vector comprising the nucleic acid of Embodiment P34.

Embodiment P37. The expression vector of Embodiment P36, further comprising the nucleic acid of Embodiment P33.

Embodiment P38. A host cell comprising the expression vector of Embodiment P35.

Embodiment P39. A host cell comprising the expression vector of Embodiment P36.

Embodiment P40. A host cell comprising the expression vector of Embodiment P37.

Embodiment P41. A host cell comprising the expression vector of Embodiment P35 and the expression vector of Embodiment P36.

Embodiment P42. A method of producing an antibody, or antigen binding fragment thereof, that binds to human OX40, the method comprising:

(a) growing the host cell of Embodiment P40 or Embodiment P41 under conditions so that the host cell expresses a polypeptide or polypeptides comprising the heavy chain or heavy chain variable region and the light chain or light chain variable region, thereby producing the antibody or the antigen-binding fragment of the antibody; and (b) purifying the antibody or the antigen-binding fragment of the antibody.

Embodiment P43. A pharmaceutical composition comprising the antibody or antigen binding fragment of any one of Embodiments P1-P32, and a pharmaceutically acceptable carrier.

Embodiment P44. A method of treating an OX40 mediated disorder in a subject comprising administering to the subject a therapeutically effective amount of the antibody or antigen binding fragment thereof of any one of Embodiments P1-P32, or the pharmaceutical composition of Embodiment P42.

Embodiment P45. A method of reducing or inhibiting T-cell proliferation in a subject in need thereof comprising administering to the subject a therapeutically effective amount of the antibody or antigen binding fragment thereof of any one of Embodiments P1-P32, or the pharmaceutical composition of Embodiment P43.

Embodiment P46. The method of Embodiment P45, wherein the subject has an OX40 mediated disorder.

Embodiment P47. The method of any one of Embodiments P45-P46, wherein the subject is a human.

Embodiment P48. The method of any one of Embodiments P44, P46, or P47, wherein the OX40 mediated disorder is arthritis, rheumatoid arthritis, psoriatic arthritis, asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, prurigo nodularis; vasculitis, surgical adhesions, stroke, Type I Diabetes, Lyme disease, meningoencephalitis, autoimmune uveitis, immune mediated inflammatory disorders of the central and peripheral nervous system such as multiple sclerosis, lupus (such as systemic lupus erythematosus or lupus nephritis) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, chronic spontaneous urticaria (CSU), chronic inducible urticaria (CIU), Wegener's granulomatosis, pancreatitis, trauma (surgery), graft-versus-host disease (GVHD), transplant rejection, cardiovascular disease including ischemic diseases such as myocardial infarction as well as atherosclerosis, intravascular coagulation, bone resorption, osteoporosis, osteoarthritis, periodontitis, hypochlorhydria, hidradenitis suppurativa, alopecia areata, and neuromyelitis optica.

Embodiment P49. The method of any one of Embodiments P44, P46, or P47, wherein the OX40 mediated disorder is Atopic Dermatitis, Prurigo Nodularis, Alopecia Areata, Chronic Spontaneous Urticaria (CSU) and Chronic Inducible Urticaria (CIU), Asthma, Hidradenitis Suppurativa, Lupus Nephritis, Systemic Lupus Erythematosus, Pemphigus Vulgaris, Psoriatic Arthritis, Vasculitis, Hashimoto Thyroiditis, Systemic Sclerosis, Cutaneous Sclerosis, Scleroderma, Chronic Pruritus from Unknown Origin, Ankylosing Spondylitis, Sjogren's Syndrome, Psoriasis, or Vitiligo.

Embodiment P50. The method of any one of Embodiments P44, P46, or P47, wherein the OX40 mediated disorder is atopic dermatitis.

Embodiment P51. The method of any one of Embodiments P44, P46, or P47, wherein the OX40 mediated disorder is chronic spontaneous urticaria.

Embodiment P52. The method of any one of Embodiments P44, P46, or P47, wherein the OX40 mediated disorder is chronic inducible urticaria.

Embodiment P52. The method of any one of Embodiments P44, P46, or P47, wherein the OX40 mediated disorder is asthma.

Embodiment P53. The method of any one of Embodiments P44, P46, or P47, wherein the OX40 mediated disorder is rheumatoid arthritis or systemic lupus erythematosus.

Embodiment P54. The method of any one of Embodiments P44, P46, or P47, wherein the OX40 mediated disorder is alopecia areata, scleroderma, or hidradenitis suppurativa.

INCORPORATION BY REFERENCE

All publications and patents cited throughout the text of this specification (including all patents, patent applications, scientific publications, manufacturer's specifications, instructions, etc.), whether supra or infra, are hereby incorporated by reference in their entirety for all purposes. To the extent the material incorporated by reference contradicts or is inconsistent with this specification, the specification will supersede any such material.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

SEQUENCE LISTING

| SEQ ID NO | Name | Sequence |
|---|---|---|
| 1 | MAB1-11 CDR H1 Kabat | TSGMGVG |
| 2 | MAB1-11 CDR H2 Kabat | HIWWDDDKYYNTALKT |
| 3 | MAB1-11 CDR H3 Kabat | IDWDGFAY |
| 4 | MAB1-11 CDR L1 Kabat | RASSSVSYMH |
| 5 | MAB1-11 CDR L2 Kabat | ATSNRAT |
| 6 | MAB1, 10, and 11 CDR L3 Kabat | QQFGAWPWT |
| 7 | MAB1-11 VH | QVTLKESGPALVKPTQTLTLTCSFSGFSLSTSGMGVGWIRQPPGKALEWI AHIWWDDDKYYNTALKTRLTISKDTSKNQVVLTMTNMDPVDTATYYCARI DWDGFAYWGQGTLVTVSS |
| 8 | MAB1, 10, and 11 VL | EIVLTQSPATLSLSPGERATLSCRASSSVSYMHWYQQKPGQAPRPWIYAT SNRATGIPARFSGSGSGTDYTLTISSLEPEDFAVYYCQQFGAWPWTFGQG TKVEIK |
| 9 | MAB1-9 Heavy Chain | QVTLKESGPALVKPTQTLTLTCSFSGFSLSTSGMGVGWIRQPPGKALEWI AHIWWDDDKYYNTALKTRLTISKDTSKNQVVLTMTNMDPVDTATYYCARI DWDGFAYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLMISRTPEVTCVVVDVSHEDPEVKENWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |
| 10 | MAB1, 10 and 11 Light Chain | EIVLTQSPATLSLSPGERATLSCRASSSVSYMHWYQQKPGQAPRPWIYAT SNRATGIPARFSGSGSGTDYTLTISSLEPEDFAVYYCQQFGAWPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSENRGEC |

-continued

| SEQUENCE LISTING | | |
|---|---|---|
| SEQ ID NO | Name | Sequence |
| 11 | MAB2 CDR L3 Kabat, Chothia, AbM, IMGT | QQFGDPPWT |
| 12 | MAB2 VL | EIVLTQSPATLSLSPGERATLSCRASSSVSYMHWYQQKPGQAPRPWIYAT SNRATGIPARFSGSGSGTDYTLTISSLEPEDFAVYYCQQFGDPPWTFGQG TKVEIK |
| 13 | MAB2 LC | EIVLTQSPATLSLSPGERATLSCRASSSVSYMHWYQQKPGQAPRPWIYAT SNRATGIPARFSGSGSGTDYTLTISSLEPEDFAVYYCQQFGDPPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSENRGEC |
| 14 | MAB3 CDR L3 Kabat, Chothia, AbM, IMGT | QQTIEWPWT |
| 15 | MAB3 VL | EIVLTQSPATLSLSPGERATLSCRASSSVSYMHWYQQKPGQAPRPWIYAT SNRATGIPARFSGSGSGTDYTLTISSLEPEDFAVYYCQQTIEWPWTFGQG TKVEIK |
| 16 | MAB3 LC | EIVLTQSPATLSLSPGERATLSCRASSSVSYMHWYQQKPGQAPRPWIYAT SNRATGIPARFSGSGSGTDYTLTISSLEPEDFAVYYCQQTIEWPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSENRGEC |
| 17 | MAB4 CDR L3 Kabat, Chothia, AbM, IMGT | QQTLLFPWT |
| 18 | MAB4 VL | EIVLTQSPATLSLSPGERATLSCRASSSVSYMHWYQQKPGQAPRPWIYAT SNRATGIPARFSGSGSGTDYTLTISSLEPEDFAVYYCQQTLLFPWTFGQG TKVEIK |
| 19 | MAB4 LC | EIVLTQSPATLSLSPGERATLSCRASSSVSYMHWYQQKPGQAPRPWIYAT SNRATGIPARFSGSGSGTDYTLTISSLEPEDFAVYYCQQTLLFPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC |
| 20 | MAB5 CDR L3 Kabat, Chothia, AbM, IMGT | QQTLHYPWT |
| 21 | MAB5 VL | EIVLTQSPATLSLSPGERATLSCRASSSVSYMHWYQQKPGQAPRPWIYAT SNRATGIPARFSGSGSGTDYTLTISSLEPEDFAVYYCQQTLHYPWTFGQG TKVEIK |
| 22 | MAB5 LC | EIVLTQSPATLSLSPGERATLSCRASSSVSYMHWYQQKPGQAPRPWIYAT SNRATGIPARFSGSGSGTDYTLTISSLEPEDFAVYYCQQTLHYPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC |
| 23 | MAB6 CDR L3 Kabat, Chothia, AbM, IMGT | QQWETWPWT |
| 24 | MAB6 VL | EIVLTQSPATLSLSPGERATLSCRASSSVSYMHWYQQKPGQAPRPWIYAT SNRATGIPARFSGSGSGTDYTLTISSLEPEDFAVYYCQQWETWPWTFGQG TKVEIK |
| 25 | MAB6 LC | EIVLTQSPATLSLSPGERATLSCRASSSVSYMHWYQQKPGQAPRPWIYAT SNRATGIPARFSGSGSGTDYTLTISSLEPEDFAVYYCQQWETWPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC |
| 26 | MAB7 CDR L3 Kabat, Chothia, AbM, IMGT | QQMEFTPWT |
| 27 | MAB7 VL | EIVLTQSPATLSLSPGERATLSCRASSSVSYMHWYQQKPGQAPRPWIYAT SNRATGIPARFSGSGSGTDYTLTISSLEPEDFAVYYCQQMEFTPWTFGQG TKVEIK |

-continued

SEQUENCE LISTING

| SEQ ID NO | Name | Sequence |
|---|---|---|
| 28 | MAB7LC | EIVLTQSPATLSLSPGERATLSCRASSSVSYMHWYQQKPGQAPRPWIYAT SNRATGIPARFSGSGSGTDYTLTISSLEPEDFAVYYCQQMEFTPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC |
| 29 | MAB8 CDR L3 Kabat, Chothia, AbM, IMGT | QQTVAWPWT |
| 30 | MAB8 VL | EIVLTQSPATLSLSPGERATLSCRASSSVSYMHWYQQKPGQAPRPWIYAT SNRATGIPARFSGSGSGTDYTLTISSLEPEDFAVYYCQQTVAWPWTFGQG TKVEIK |
| 31 | MAB8 LC | EIVLTQSPATLSLSPGERATLSCRASSSVSYMHWYQQKPGQAPRPWIYAT SNRATGIPARFSGSGSGTDYTLTISSLEPEDFAVYYCQQTVAWPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSENRGEC |
| 32 | MAB9 CDR L3 Kabat, Chothia, AbM, IMGT | QAASSSSLE |
| 33 | MAB9 VL | EIVLTQSPATLSLSPGERATLSCRASSSVSYMHWYQQKPGQAPRPWIYAT SNRATGIPARFSGSGSGTDYTLTISSLEPEDFAVYYCQAASSSSLEFGQG TKVEIK |
| 34 | MAB9 LC | EIVLTQSPATLSLSPGERATLSCRASSSVSYMHWYQQKPGQAPRPWIYAT SNRATGIPARFSGSGSGTDYTLTISSLEPEDFAVYYCQAASSSSLEFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSFNRGEC |
| 35 | GBR 830 CDR 3 Kabat, Chothia, AbM, IMGT | QQWSSNPWT |
| 36 | GBR 830 VL | EIVLTQSPATLSLSPGERATLSCRASSSVSYMHWYQQKPGQAPRPWIYAT SNRATGIPARFSGSGSGTDYTLTISSLEPEDFAVYYCQQWSSNPWTFGQG TKVEIK |
| 37 | GBR 830 LC | EIVLTQSPATLSLSPGERATLSCRASSSVSYMHWYQQKPGQAPRPWIYAT SNRATGIPARFSGSGSGTDYTLTISSLEPEDFAVYYCQQWSSNPWTFGQG TKVEIKRTVAAPSVFIFPPSDEQLKSGTASVVCLLNNFYPREAKVQWKVD NALQSGNSQESVTEQDSKDSTYSLSSTLTLSKADYEKHKVYACEVTHQGL SSPVTKSENRGEC |
| 38 | Consensus | $QQX_1X_2X_3X_4PWT$ |
| 39 | DNA sequence of MAB1 variable heavy chain (VH) | CAGGTCACACTGAAAGAGTCTGGACCCGCCCTGGTCAAGCCCACCCAGAC ACTGACCCTGACCTGCAGCTTCAGCGGCTTCAGCCTGAGCACAAGCGGCA TGGGCGTGGGCTGGATCAGACAGCCTCCTGGCAAGGCCCTGGAATGGATC GCCCATATTTGGTGGGATGATGATAAATATTATAACACCGCCCTGAAAAC CCGCCTGACCATCAGCAAGGACACCAGCAAGAACCAGGTGGTGCTGACCA TGACCAACATGGACCCCGTGGACACCGCCACCTACTACTGCGCCAGAATC GACTGGGACGGCTTCGCCTATTGGGGCCAGGGAACCCTGGTCACCGTGTC T |
| 40 | DNA sequence of-MAB1 variable light chain (VL) | GAGATCGTGCTGACACAGAGCCCCGCCACCCTGTCTCTGAGCCCTGGCGA AAGAGCCACCCTGAGCTGTAGAGCCAGCAGCAGCGTGTCCTACATGCACT GGTATCAGCAGAAGCCCGGCCAGGCGCCGCGCCCGTGGATTTATGCGACC AGCAATCGGGCCACAGGCATCCCTGCCAGATTTTCTGGCAGCGGCTCCGG CACCGACTACACCCTGACCATCTCCAGCCTGGAACCCGAGGACTTCGCCG TGTACTACTGCCAGCAGTTTGGTGCGTGGCCCTGGACATTTGGCCAGGGC ACCAAGGTGGAAATCAAA |
| 41 | MAB1-11 H1 Chothia | GFSLSTSGM |
| 42 | MAB1-11 H2 Chothia | WWDDD |
| 3 | MAB1-11 H3 Chothia | IDWDGFAY |
| 4 | MAB1-11 L1 Chothia | RASSSVSYMH |
| 5 | MAB1-11 L2 Chothia | ATSNRAT |

-continued

| SEQUENCE LISTING | | |
|---|---|---|
| SEQ ID NO | Name | Sequence |
| 6 | MAB1 L3 Chothia | QQFGAWPWT |
| 47 | MAB1-11 H1 AbM | GFSLSTSGMGVG |
| 48 | MAB1-11 H2 AbM | HIWWDDDKY |
| 3 | MAB1-11 H3 AbM | IDWDGFAY |
| 4 | MAB1-11 L1 AbM | RASSSVSYMH |
| 5 | MAB1-11 L2 AbM | ATSNRAT |
| 6 | MAB1 L3 AbM | QQFGAWPWT |
| 53 | MAB1-11 H1 Contact | STSGMGVG |
| 54 | MAB1-11 H2 Contact | WIAHIWWDDDKY |
| 55 | MAB1-11 H3 Contact | ARIDWDGFA |
| 56 | MAB1-11 L1 Contact | SYMHWY |
| 57 | MAB1-11 L2 Contact | PWIYATSNRA |
| 58 | MAB1 L3 Contact | QQFGAWPW |
| 59 | MAB1-11 H1 IMGT | GFSLSTSGMG |
| 60 | MAB1-11 H2 IMGT | IWWDDDK |
| 61 | MAB1-11 H3 IMGT | ARIDWDGFAY |
| 62 | MAB1-11 L1 IMGT | SSVSY |
| | MAB1-11 L2 IMGT | AT |
| 6 | MAB1 L3 IMGT | QQFGAWPWT |
| 65 | MAB1-11 H1 AHo | FSGFSLSTSGMG |
| 66 | MAB1-11 H2 AHo | IWWDDDKYYNTALKTR |
| 67 | MAB1-11 H3 AHo | IDWDGFA |
| 68 | MAB1-11 L1 AHo | ASSSVSY |
| 69 | MAB1-11 L2 AHo | ATSNRATGIPAR |
| 70 | MAB1 L3 AHo | FGAWPW |
| 71 | | CQQ$X_1X_2X_3X_4$PWTF |
| 72 | OX40 UniProt P43489 | MCVGARRLGR GPCAALLLLG LGLSTVTGLH CVGDTYPSND RCCHECRPGN GMVSRCSRSQ NTVCRPCGPG FYNDVVSSKP CKPCTWCNLR SGSERKQLCT ATQDTVCRCR AGTQPLDSYK PGVDCAPCPP GHFSPGDNQA CKPWTNCTLA GKHTLQPASN SSDAICEDRD PPATQPQETQ GPPARPITVQ PTEAWPRTSQ GPSTRPVEVP GGRAVAAILG LGLVLGLLGP LAILLALYLL RRDQRLPPDA HKPPGGGSFR TPIQEEQADA HSTLAKI |
| 73 | MAB1 Heavy Chain + YTE (MAB10) IgG1 format with M252Y, S254T, and T256E mutations (constant domain shown in bold) | QVTLKESGPALVKPTQTLTLTCSFSGFSLSTSGMGVGWIRQPPGKALEWI AHIWWDDDKYYNTALKTRLTISKDTSKNQVVLTMTNMDPVDTATYYCARI DWDGFAYWGQGTLVTVSS**ASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKD TLYITREPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK** |
| 74 | MAB1 Heavy Chain + LS (MAB11) IgG1 format | QVTLKESGPALVKPTQTLTLTCSFSGFSLSTSGMGVGWIRQPPGKALEWI AHIWWDDDKYYNTALKTRLTISKDTSKNQVVLTMTNMDPVDTATYYCARI |

-continued

SEQUENCE LISTING

| SEQ ID NO | Name | Sequence |
|---|---|---|
| | with M428L and a N434S mutations (constant domain shown in bold) | DWDGFAYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK** |
| 75 | MAB2 L3 Contact | QQFGDPPW |
| 76 | MAB2 L3 AHo | FGDPPW |
| 77 | MAB3 L3 Contact | QQTIEWPW |
| 78 | MAB3 L3 AHo | TIEWPW |
| 79 | MAB4 L3 Contact | QQTLLFPW |
| 80 | MAB4 L3 AHo | TLLFPW |
| 81 | MAB5 L3 Contact | QQTLHYPW |
| 82 | MAB5 L3 AHo | TLHYPW |
| 83 | MAB6 L3 Contact | QQWETWPW |
| 84 | MAB6 L3 AHo | WETWPW |
| 85 | MAB7 L3 Contact | QQMEFTPW |
| 86 | MAB7 L3 AHo | MEFTPW |
| 87 | MAB8 L3 Contact | QQTVAWPW |
| 88 | MAB8 L3 AHo | TVAWPW |
| 89 | MAB9 L3 Contact | QAASSSSL |
| 90 | MAB9 L3 AHo | ASSSSL |

SEQUENCE LISTING

```
Sequence total quantity: 95
SEQ ID NO: 1            moltype = AA  length = 7
FEATURE                 Location/Qualifiers
source                  1..7
                        mol_type = protein
                        organism = synthetic construct
SEQUENCE: 1
TSGMGVG                                                                  7

SEQ ID NO: 2            moltype = AA  length = 16
FEATURE                 Location/Qualifiers
source                  1..16
                        mol_type = protein
                        organism = synthetic construct
SEQUENCE: 2
HIWWDDDKYY NTALKT                                                        16

SEQ ID NO: 3            moltype = AA  length = 8
FEATURE                 Location/Qualifiers
source                  1..8
                        mol_type = protein
                        organism = synthetic construct
SEQUENCE: 3
IDWDGFAY                                                                 8

SEQ ID NO: 4            moltype = AA  length = 10
FEATURE                 Location/Qualifiers
```

```
source                  1..10
                        mol_type = protein
                        organism = synthetic construct
SEQUENCE: 4
RASSSVSYMH                                                     10

SEQ ID NO: 5            moltype = AA  length = 7
FEATURE                 Location/Qualifiers
source                  1..7
                        mol_type = protein
                        organism = synthetic construct
SEQUENCE: 5
ATSNRAT                                                        7

SEQ ID NO: 6            moltype = AA  length = 9
FEATURE                 Location/Qualifiers
source                  1..9
                        mol_type = protein
                        organism = synthetic construct
SEQUENCE: 6
QQFGAWPWT                                                      9

SEQ ID NO: 7            moltype = AA  length = 118
FEATURE                 Location/Qualifiers
source                  1..118
                        mol_type = protein
                        organism = synthetic construct
SEQUENCE: 7
QVTLKESGPA LVKPTQTLTL TCSFSGFSLS TSGMGVGWIR QPPGKALEWI AHIWWDDDKY  60
YNTALKTRLT ISKDTSKNQV VLTMTNMDPV DTATYYCARI DWDGFAYWGQ GTLVTVSS    118

SEQ ID NO: 8            moltype = AA  length = 106
FEATURE                 Location/Qualifiers
source                  1..106
                        mol_type = protein
                        organism = synthetic construct
SEQUENCE: 8
EIVLTQSPAT LSLSPGERAT LSCRASSSVS YMHWYQQKPG QAPRPWIYAT SNRATGIPAR  60
FSGSGSGTDY TLTISSLEPE DFAVYYCQQF GAWPWTFGQG TKVEIK                106

SEQ ID NO: 9            moltype = AA  length = 448
FEATURE                 Location/Qualifiers
source                  1..448
                        mol_type = protein
                        organism = synthetic construct
SEQUENCE: 9
QVTLKESGPA LVKPTQTLTL TCSFSGFSLS TSGMGVGWIR QPPGKALEWI AHIWWDDDKY  60
YNTALKTRLT ISKDTSKNQV VLTMTNMDPV DTATYYCARI DWDGFAYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 10           moltype = AA  length = 213
FEATURE                 Location/Qualifiers
source                  1..213
                        mol_type = protein
                        organism = synthetic construct
SEQUENCE: 10
EIVLTQSPAT LSLSPGERAT LSCRASSSVS YMHWYQQKPG QAPRPWIYAT SNRATGIPAR  60
FSGSGSGTDY TLTISSLEPE DFAVYYCQQF GAWPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 11           moltype = AA  length = 9
FEATURE                 Location/Qualifiers
source                  1..9
                        mol_type = protein
                        organism = synthetic construct
SEQUENCE: 11
QQFGDPPWT                                                      9

SEQ ID NO: 12           moltype = AA  length = 106
FEATURE                 Location/Qualifiers
source                  1..106
                        mol_type = protein
                        organism = synthetic construct
```

```
SEQUENCE: 12
EIVLTQSPAT LSLSPGERAT LSCRASSSVS YMHWYQQKPG QAPRPWIYAT SNRATGIPAR  60
FSGSGSGTDY TLTISSLEPE DFAVYYCQQF GDPPWTFGQG TKVEIK                106

SEQ ID NO: 13          moltype = AA  length = 213
FEATURE                Location/Qualifiers
source                 1..213
                       mol_type = protein
                       organism = synthetic construct
SEQUENCE: 13
EIVLTQSPAT LSLSPGERAT LSCRASSSVS YMHWYQQKPG QAPRPWIYAT SNRATGIPAR  60
FSGSGSGTDY TLTISSLEPE DFAVYYCQQF GDPPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 14          moltype = AA  length = 9
FEATURE                Location/Qualifiers
source                 1..9
                       mol_type = protein
                       organism = synthetic construct
SEQUENCE: 14
QQTIEWPWT                                                          9

SEQ ID NO: 15          moltype = AA  length = 106
FEATURE                Location/Qualifiers
source                 1..106
                       mol_type = protein
                       organism = synthetic construct
SEQUENCE: 15
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT IEWPWTFGQG TKVEIK                106

SEQ ID NO: 16          moltype = AA  length = 213
FEATURE                Location/Qualifiers
source                 1..213
                       mol_type = protein
                       organism = synthetic construct
SEQUENCE: 16
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT IEWPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 17          moltype = AA  length = 9
FEATURE                Location/Qualifiers
source                 1..9
                       mol_type = protein
                       organism = synthetic construct
SEQUENCE: 17
QQTLLFPWT                                                          9

SEQ ID NO: 18          moltype = AA  length = 106
FEATURE                Location/Qualifiers
source                 1..106
                       mol_type = protein
                       organism = synthetic construct
SEQUENCE: 18
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT LLFPWTFGQG TKVEIK                106

SEQ ID NO: 19          moltype = AA  length = 213
FEATURE                Location/Qualifiers
source                 1..213
                       mol_type = protein
                       organism = synthetic construct
SEQUENCE: 19
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT LLFPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 20          moltype = AA  length = 9
FEATURE                Location/Qualifiers
source                 1..9
                       mol_type = protein
                       organism = synthetic construct
SEQUENCE: 20
QQTLHYPWT                                                          9
```

```
SEQ ID NO: 21           moltype = AA  length = 106
FEATURE                 Location/Qualifiers
source                  1..106
                        mol_type = protein
                        organism = synthetic construct
SEQUENCE: 21
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT LHYPWTFGQG TKVEIK                106

SEQ ID NO: 22           moltype = AA  length = 213
FEATURE                 Location/Qualifiers
source                  1..213
                        mol_type = protein
                        organism = synthetic construct
SEQUENCE: 22
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT LHYPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 23           moltype = AA  length = 9
FEATURE                 Location/Qualifiers
source                  1..9
                        mol_type = protein
                        organism = synthetic construct
SEQUENCE: 23
QQWETWPWT                                                          9

SEQ ID NO: 24           moltype = AA  length = 106
FEATURE                 Location/Qualifiers
source                  1..106
                        mol_type = protein
                        organism = synthetic construct
SEQUENCE: 24
EIVLTQSPAT LSLSPGERAT LSCRASSSVS YMHWYQQKPG QAPRPWIYAT SNRATGIPAR  60
FSGSGSGTDY TLTISSLEPE DFAVYYCQQW ETWPWTFGQG TKVEIK                106

SEQ ID NO: 25           moltype = AA  length = 213
FEATURE                 Location/Qualifiers
source                  1..213
                        mol_type = protein
                        organism = synthetic construct
SEQUENCE: 25
EIVLTQSPAT LSLSPGERAT LSCRASSSVS YMHWYQQKPG QAPRPWIYAT SNRATGIPAR  60
FSGSGSGTDY TLTISSLEPE DFAVYYCQQW ETWPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 26           moltype = AA  length = 9
FEATURE                 Location/Qualifiers
source                  1..9
                        mol_type = protein
                        organism = synthetic construct
SEQUENCE: 26
QQMEFTPWT                                                          9

SEQ ID NO: 27           moltype = AA  length = 106
FEATURE                 Location/Qualifiers
source                  1..106
                        mol_type = protein
                        organism = synthetic construct
SEQUENCE: 27
EIVLTQSPAT LSLSPGERAT LSCRASSSVS YMHWYQQKPG QAPRPWIYAT SNRATGIPAR  60
FSGSGSGTDY TLTISSLEPE DFAVYYCQQM EFTPWTFGQG TKVEIK                106

SEQ ID NO: 28           moltype = AA  length = 213
FEATURE                 Location/Qualifiers
source                  1..213
                        mol_type = protein
                        organism = synthetic construct
SEQUENCE: 28
EIVLTQSPAT LSLSPGERAT LSCRASSSVS YMHWYQQKPG QAPRPWIYAT SNRATGIPAR  60
FSGSGSGTDY TLTISSLEPE DFAVYYCQQM EFTPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 29           moltype = AA  length = 9
FEATURE                 Location/Qualifiers
```

```
source                  1..9
                        mol_type = protein
                        organism = synthetic construct
SEQUENCE: 29
QQTVAWPWT                                                               9

SEQ ID NO: 30           moltype = AA  length = 106
FEATURE                 Location/Qualifiers
source                  1..106
                        mol_type = protein
                        organism = synthetic construct
SEQUENCE: 30
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT VAWPWTFGQG TKVEIK                 106

SEQ ID NO: 31           moltype = AA  length = 213
FEATURE                 Location/Qualifiers
source                  1..213
                        mol_type = protein
                        organism = synthetic construct
SEQUENCE: 31
EIVLTQSPAT LSLSPGERAT LSCRASSSVS YMHWYQQKPG QAPRPWIYAT SNRATGIPAR  60
FSGSGSGTDY TLTISSLEPE DFAVYYCQQT VAWPWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 32           moltype = AA  length = 9
FEATURE                 Location/Qualifiers
source                  1..9
                        mol_type = protein
                        organism = synthetic construct
SEQUENCE: 32
QAASSSSLE                                                               9

SEQ ID NO: 33           moltype = AA  length = 106
FEATURE                 Location/Qualifiers
source                  1..106
                        mol_type = protein
                        organism = synthetic construct
SEQUENCE: 33
EIVLTQSPAT LSLSPGERAT LSCRASSSVS YMHWYQQKPG QAPRPWIYAT SNRATGIPAR  60
FSGSGSGTDY TLTISSLEPE DFAVYYCQAA SSSSLEFGQG TKVEIK                 106

SEQ ID NO: 34           moltype = AA  length = 213
FEATURE                 Location/Qualifiers
source                  1..213
                        mol_type = protein
                        organism = synthetic construct
SEQUENCE: 34
EIVLTQSPAT LSLSPGERAT LSCRASSSVS YMHWYQQKPG QAPRPWIYAT SNRATGIPAR  60
FSGSGSGTDY TLTISSLEPE DFAVYYCQAA SSSSLEFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 35           moltype = AA  length = 9
FEATURE                 Location/Qualifiers
source                  1..9
                        mol_type = protein
                        organism = synthetic construct
SEQUENCE: 35
QQWSSNPWT                                                               9

SEQ ID NO: 36           moltype = AA  length = 106
FEATURE                 Location/Qualifiers
source                  1..106
                        mol_type = protein
                        organism = synthetic construct
SEQUENCE: 36
EIVLTQSPAT LSLSPGERAT LSCRASSSVS YMHWYQQKPG QAPRPWIYAT SNRATGIPAR  60
FSGSGSGTDY TLTISSLEPE DFAVYYCQQW SSNPWTFGQG TKVEIK                 106

SEQ ID NO: 37           moltype = AA  length = 213
FEATURE                 Location/Qualifiers
source                  1..213
                        mol_type = protein
                        organism = synthetic construct
SEQUENCE: 37
EIVLTQSPAT LSLSPGERAT LSCRASSSVS YMHWYQQKPG QAPRPWIYAT SNRATGIPAR  60
FSGSGSGTDY TLTISSLEPE DFAVYYCQQW SSNPWTFGQG TKVEIKRTVA APSVFIFPPS  120
```

```
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 38          moltype = AA  length = 9
FEATURE                Location/Qualifiers
source                 1..9
                       mol_type = protein
                       organism = synthetic construct
VARIANT                3
                       note = F, T, W, or M
VARIANT                4
                       note = G, I, V, L, or E
VARIANT                5
                       note = A, D, E, L, H, T, or F
VARIANT                6
                       note = W, P, F, Y, or T
SEQUENCE: 38
QQXXXXPWT                                                          9

SEQ ID NO: 39          moltype = DNA  length = 351
FEATURE                Location/Qualifiers
source                 1..351
                       mol_type = other DNA
                       organism = synthetic construct
SEQUENCE: 39
caggtcacac tgaaagagtc tggacccgcc ctggtcaagc ccacccagac actgaccctg  60
acctgcagct tcagcggctt cagcctgagc acaagcggca tgggcgtggg ctggatcaga  120
cagcctcctg gcaaggccct ggaatggatc gcccatattt ggtgggatga tgataaatat  180
tataacaccg ccctgaaaac ccgcctgacc atcagcaagg acaccagcaa gaaccaggtg  240
gtgctgacca tgaccaacat ggaccccgtg gacaccgcca cctactactg cgccagaatc  300
gactgggacg gcttcgccta ttggggccag ggaaccctgg tcaccgtgtc t           351

SEQ ID NO: 40          moltype = DNA  length = 318
FEATURE                Location/Qualifiers
source                 1..318
                       mol_type = other DNA
                       organism = synthetic construct
SEQUENCE: 40
gagatcgtgc tgacacagag ccccgccacc ctgtctctga gccctggcga aagagccacc  60
ctgagctgta gagccagcag cagcgtgtcc tacatgcact ggtatcagca gaagcccggc  120
caggcgccgc gcccgtggat ttatgcgacc agcaatcggg ccacaggcat ccctgccaga  180
ttttctggca gcggctccgg caccgactac accctgacca tctccagcct ggaacccgag  240
gacttcgccg tgtactactg ccagcagttt ggtgcgtggc cctggacatt tggccagggc  300
accaaggtgg aaatcaaa                                                318

SEQ ID NO: 41          moltype = AA  length = 9
FEATURE                Location/Qualifiers
source                 1..9
                       mol_type = protein
                       organism = synthetic construct
SEQUENCE: 41
GFSLSTSGM                                                          9

SEQ ID NO: 42          moltype = AA  length = 5
FEATURE                Location/Qualifiers
source                 1..5
                       mol_type = protein
                       organism = synthetic construct
SEQUENCE: 42
WWDDD                                                              5

SEQ ID NO: 43          moltype =   length =
SEQUENCE: 43
000

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype = AA  length = 12
FEATURE                Location/Qualifiers
```

```
source                1..12
                      mol_type = protein
                      organism = synthetic construct
SEQUENCE: 47
GFSLSTSGMG VG                                                    12

SEQ ID NO: 48         moltype = AA  length = 9
FEATURE               Location/Qualifiers
source                1..9
                      mol_type = protein
                      organism = synthetic construct
SEQUENCE: 48
HIWWDDDKY                                                        9

SEQ ID NO: 49         moltype =   length =
SEQUENCE: 49
000

SEQ ID NO: 50         moltype =   length =
SEQUENCE: 50
000

SEQ ID NO: 51         moltype =   length =
SEQUENCE: 51
000

SEQ ID NO: 52         moltype =   length =
SEQUENCE: 52
000

SEQ ID NO: 53         moltype = AA  length = 8
FEATURE               Location/Qualifiers
source                1..8
                      mol_type = protein
                      organism = synthetic construct
SEQUENCE: 53
STSGMGVG                                                         8

SEQ ID NO: 54         moltype = AA  length = 12
FEATURE               Location/Qualifiers
source                1..12
                      mol_type = protein
                      organism = synthetic construct
SEQUENCE: 54
WIAHIWWDDD KY                                                    12

SEQ ID NO: 55         moltype = AA  length = 9
FEATURE               Location/Qualifiers
source                1..9
                      mol_type = protein
                      organism = synthetic construct
SEQUENCE: 55
ARIDWDGFA                                                        9

SEQ ID NO: 56         moltype = AA  length = 6
FEATURE               Location/Qualifiers
source                1..6
                      mol_type = protein
                      organism = synthetic construct
SEQUENCE: 56
SYMHWY                                                           6

SEQ ID NO: 57         moltype = AA  length = 10
FEATURE               Location/Qualifiers
source                1..10
                      mol_type = protein
                      organism = synthetic construct
SEQUENCE: 57
PWIYATSNRA                                                       10

SEQ ID NO: 58         moltype = AA  length = 8
FEATURE               Location/Qualifiers
source                1..8
                      mol_type = protein
                      organism = synthetic construct
SEQUENCE: 58
QQFGAWPW                                                         8

SEQ ID NO: 59         moltype = AA  length = 10
```

```
FEATURE                 Location/Qualifiers
source                  1..10
                        mol_type = protein
                        organism = synthetic construct
SEQUENCE: 59
GFSLSTSGMG                                                    10

SEQ ID NO: 60           moltype = AA  length = 7
FEATURE                 Location/Qualifiers
source                  1..7
                        mol_type = protein
                        organism = synthetic construct
SEQUENCE: 60
IWWDDDK                                                       7

SEQ ID NO: 61           moltype = AA  length = 10
FEATURE                 Location/Qualifiers
source                  1..10
                        mol_type = protein
                        organism = synthetic construct
SEQUENCE: 61
ARIDWDGFAY                                                    10

SEQ ID NO: 62           moltype = AA  length = 5
FEATURE                 Location/Qualifiers
source                  1..5
                        mol_type = protein
                        organism = synthetic construct
SEQUENCE: 62
SSVSY                                                         5

SEQ ID NO: 63           moltype =   length =
SEQUENCE: 63
000

SEQ ID NO: 64           moltype =   length =
SEQUENCE: 64
000

SEQ ID NO: 65           moltype = AA  length = 12
FEATURE                 Location/Qualifiers
source                  1..12
                        mol_type = protein
                        organism = synthetic construct
SEQUENCE: 65
FSGFSLSTSG MG                                                 12

SEQ ID NO: 66           moltype = AA  length = 16
FEATURE                 Location/Qualifiers
source                  1..16
                        mol_type = protein
                        organism = synthetic construct
SEQUENCE: 66
IWWDDDKYYN TALKTR                                             16

SEQ ID NO: 67           moltype = AA  length = 7
FEATURE                 Location/Qualifiers
source                  1..7
                        mol_type = protein
                        organism = synthetic construct
SEQUENCE: 67
IDWDGFA                                                       7

SEQ ID NO: 68           moltype = AA  length = 7
FEATURE                 Location/Qualifiers
source                  1..7
                        mol_type = protein
                        organism = synthetic construct
SEQUENCE: 68
ASSSVSY                                                       7

SEQ ID NO: 69           moltype = AA  length = 12
FEATURE                 Location/Qualifiers
source                  1..12
                        mol_type = protein
                        organism = synthetic construct
SEQUENCE: 69
ATSNRATGIP AR                                                 12
```

```
SEQ ID NO: 70            moltype = AA  length = 6
FEATURE                  Location/Qualifiers
source                   1..6
                         mol_type = protein
                         organism = synthetic construct
SEQUENCE: 70
FGAWPW                                                                  6

SEQ ID NO: 71            moltype = AA  length = 11
FEATURE                  Location/Qualifiers
source                   1..11
                         mol_type = protein
                         organism = synthetic construct
VARIANT                  4
                         note = F, T, W, or M
VARIANT                  5
                         note = G, I, V, L, or E
VARIANT                  6
                         note = A, D, E, L, H, T, or F
VARIANT                  7
                         note = W, P, F, Y, or T
SEQUENCE: 71
CQQXXXXPWT F                                                            11

SEQ ID NO: 72            moltype = AA  length = 277
FEATURE                  Location/Qualifiers
source                   1..277
                         mol_type = protein
                         organism = Homo sapiens
SEQUENCE: 72
MCVGARRLGR GPCAALLLLG LGLSTVTGLH CVGDTYPSND RCCHECRPGN GMVSRCSRSQ  60
NTVCRPCGPG FYNDVVSSKP CKPCTWCNLR SGSERKQLCT ATQDTVCRCR AGTQPLDSYK  120
PGVDCAPCPP GHFSPGDNQA CKPWTNCTLA GKHTLQPASN SSDAICEDRD PPATQPQETQ  180
GPPARPITVQ PTEAWPRTSQ GPSTRPVEVP GGRAVAAILG LGLVLGLLGP LAILLALYLL  240
RRDQRLPPDA HKPPGGGSFR TPIQEEQADA HSTLAKI                            277

SEQ ID NO: 73            moltype = AA  length = 448
FEATURE                  Location/Qualifiers
source                   1..448
                         mol_type = protein
                         organism = synthetic construct
SEQUENCE: 73
QVTLKESGPA LVKPTQTLTL TCSFSGFSLS TSGMGVGWIR QPPGKALEWI AHIWWDDDKY  60
YNTALKTRLT ISKDTSKNQV VLTMTNMDPV DTATYYCARI DWDGFAYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLYITREPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                      448

SEQ ID NO: 74            moltype = AA  length = 448
FEATURE                  Location/Qualifiers
source                   1..448
                         mol_type = protein
                         organism = synthetic construct
SEQUENCE: 74
QVTLKESGPA LVKPTQTLTL TCSFSGFSLS TSGMGVGWIR QPPGKALEWI AHIWWDDDKY  60
YNTALKTRLT ISKDTSKNQV VLTMTNMDPV DTATYYCARI DWDGFAYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVLH EALHSHYTQK SLSLSPGK                                      448

SEQ ID NO: 75            moltype = AA  length = 8
FEATURE                  Location/Qualifiers
source                   1..8
                         mol_type = protein
                         organism = synthetic construct
SEQUENCE: 75
QQFGDPPW                                                                8

SEQ ID NO: 76            moltype = AA  length = 6
FEATURE                  Location/Qualifiers
source                   1..6
                         mol_type = protein
                         organism = synthetic construct
```

```
SEQUENCE: 76
FGDPPW                                                          6

SEQ ID NO: 77           moltype = AA  length = 8
FEATURE                 Location/Qualifiers
source                  1..8
                        mol_type = protein
                        organism = synthetic construct
SEQUENCE: 77
QQTIEWPW                                                        8

SEQ ID NO: 78           moltype = AA  length = 6
FEATURE                 Location/Qualifiers
source                  1..6
                        mol_type = protein
                        organism = synthetic construct
SEQUENCE: 78
TIEWPW                                                          6

SEQ ID NO: 79           moltype = AA  length = 8
FEATURE                 Location/Qualifiers
source                  1..8
                        mol_type = protein
                        organism = synthetic construct
SEQUENCE: 79
QQTLLFPW                                                        8

SEQ ID NO: 80           moltype = AA  length = 6
FEATURE                 Location/Qualifiers
source                  1..6
                        mol_type = protein
                        organism = synthetic construct
SEQUENCE: 80
TLLFPW                                                          6

SEQ ID NO: 81           moltype = AA  length = 8
FEATURE                 Location/Qualifiers
source                  1..8
                        mol_type = protein
                        organism = synthetic construct
SEQUENCE: 81
QQTLHYPW                                                        8

SEQ ID NO: 82           moltype = AA  length = 6
FEATURE                 Location/Qualifiers
source                  1..6
                        mol_type = protein
                        organism = synthetic construct
SEQUENCE: 82
TLHYPW                                                          6

SEQ ID NO: 83           moltype = AA  length = 8
FEATURE                 Location/Qualifiers
source                  1..8
                        mol_type = protein
                        organism = synthetic construct
SEQUENCE: 83
QQWETWPW                                                        8

SEQ ID NO: 84           moltype = AA  length = 6
FEATURE                 Location/Qualifiers
source                  1..6
                        mol_type = protein
                        organism = synthetic construct
SEQUENCE: 84
WETWPW                                                          6

SEQ ID NO: 85           moltype = AA  length = 8
FEATURE                 Location/Qualifiers
source                  1..8
                        mol_type = protein
                        organism = synthetic construct
SEQUENCE: 85
QQMEFTPW                                                        8

SEQ ID NO: 86           moltype = AA  length = 6
FEATURE                 Location/Qualifiers
```

```
source                  1..6
                        mol_type = protein
                        organism = synthetic construct
SEQUENCE: 86
MEFTPW                                                                      6

SEQ ID NO: 87           moltype = AA  length = 8
FEATURE                 Location/Qualifiers
source                  1..8
                        mol_type = protein
                        organism = synthetic construct
SEQUENCE: 87
QQTVAWPW                                                                    8

SEQ ID NO: 88           moltype = AA  length = 6
FEATURE                 Location/Qualifiers
source                  1..6
                        mol_type = protein
                        organism = synthetic construct
SEQUENCE: 88
TVAWPW                                                                      6

SEQ ID NO: 89           moltype = AA  length = 8
FEATURE                 Location/Qualifiers
source                  1..8
                        mol_type = protein
                        organism = synthetic construct
SEQUENCE: 89
QAASSSSL                                                                    8

SEQ ID NO: 90           moltype = AA  length = 6
FEATURE                 Location/Qualifiers
source                  1..6
                        mol_type = protein
                        organism = synthetic construct
SEQUENCE: 90
ASSSSL                                                                      6

SEQ ID NO: 91           moltype = AA  length = 4
FEATURE                 Location/Qualifiers
source                  1..4
                        mol_type = protein
                        organism = synthetic construct
SEQUENCE: 91
HRRR                                                                        4

SEQ ID NO: 92           moltype = AA  length = 4
FEATURE                 Location/Qualifiers
source                  1..4
                        mol_type = protein
                        organism = synthetic construct
SEQUENCE: 92
RHRR                                                                        4

SEQ ID NO: 93           moltype = AA  length = 4
FEATURE                 Location/Qualifiers
source                  1..4
                        mol_type = protein
                        organism = synthetic construct
SEQUENCE: 93
HHHR                                                                        4

SEQ ID NO: 94           moltype = AA  length = 4
FEATURE                 Location/Qualifiers
source                  1..4
                        mol_type = protein
                        organism = synthetic construct
SEQUENCE: 94
HHRH                                                                        4

SEQ ID NO: 95           moltype = AA  length = 4
FEATURE                 Location/Qualifiers
source                  1..4
                        mol_type = protein
                        organism = synthetic construct
SEQUENCE: 95
RHHH                                                                        4
```

What is claimed is:

1. An antibody, or antigen binding fragment thereof, that binds to OX40 comprising:

a) a heavy chain variable region comprising a CDR-H1 comprising the amino acid sequence set forth in SEQ ID NO:1, a CDR-H2 comprising the amino acid sequence set forth in SEQ ID NO:2, and a CDR-H3 comprising the amino acid sequence set forth in SEQ ID NO:3; and b) a light chain variable region comprising a CDR-L1 comprising the amino acid sequence set forth in SEQ ID NO:4, a CDR-L2 comprising the amino acid sequence set forth in SEQ ID NO:5, and a CDR-L3 comprising the amino acid sequence set forth in SEQ ID NO:38 or 71, where $X_1$ is F, T, W, or M; where $X_2$ is G, I, V, L, or E; where $X_3$ is A, D, E, L, H, T, or F; and where $X_4$ is W, P, F, Y, or T.

2. The antibody, or antigen binding fragment thereof, of claim 1, wherein the CDR-L3 comprises the amino acid sequence set forth in SEQ ID NO:38.

3. The antibody, or antigen binding fragment thereof, of claim 1, wherein $X_1$ is F, $X_2$ is G, $X_3$ is A, and $X_4$ is W or CDR-L3 comprises the amino acid sequence of SEQ ID NO:6.

4. The antibody, or antigen binding fragment thereof, of claim 1, wherein CDR-L3 comprises the amino acid sequence of SEQ ID NO:11, 14, 17, 20, 23, 26, or 29.

5. The antibody or antigen binding fragment thereof that binds to OX40 of claim 1, wherein the antibody is selected from:

a) an antibody comprising three heavy chain complementarity determining regions (CDRs) (CDR-H1, CDR-H2, and, CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:8;

b) an antibody comprising three heavy chain complementarity determining regions (CDRs) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:12;

c) an antibody comprising three heavy chain complementarity determining regions (CDRs) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:15 d) an antibody comprising three heavy chain complementarity determining regions (DR s) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:18;

e) an antibody comprising three heavy chain complementarity determining regions (DR s) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:21;

f) an antibody comprising three heavy chain complementarity determining regions (CDRs) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:24;

g) an antibody comprising three heavy chain complementarity determining regions (CDRs) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:27; or h) an antibody comprising three heavy chain complementarity determining regions (CDRs) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:30.

6. The antibody or antigen binding fragment thereof that binds to OX40 of claim 5, comprising three heavy chain complementarity determining regions (CDRs) (CDR-H1, CDR-H2, and CDR-H3) of a heavy chain variable domain (VH) comprising the amino acid sequence of SEQ ID NO:7 and three light chain complementarity determining regions (CDRs) (CDR-L1, CDR-L2, and CDR-L3), of a light chain variable domain (VL) comprising the amino acid sequence of SEQ ID NO:8.

7. The antibody or antigen binding fragment of claim 5, wherein:

a) the CDR-H1, CDR-H2, and CDR-H3, and the CDR-L1, CDR-L2, and CDR-L3 are defined according to Kabat;

b) the CDR-H1, CDR-H2, and CDR-H3, and the CDR-L1, CDR-L2, and CDR-L3 are defined according to Chothia;

c) the CDR-H1, CDR-H2, and CDR-H3, and the CDR-L1, CDR-L2, and CDR-L3 are defined according to IMGT;

d) the CDR-H1, CDR-H2, and CDR-H3, and the CDR-L1, CDR-L2, and CDR-L3 are defined according to AbM;

e) the CDR-H1, CDR-H2, and CDR-H3, and the CDR-L1, CDR-L2, and CDR-L3 are defined according to Contact; or f) the CDR-H1, CDR-H2, and CDR-H3, and the CDR-L1, CDR-L2, and CDR-L3 are defined according to Honneger (AHo).

8. The antibody or antigen binding fragment thereof of claim 5, wherein:

the heavy chain CDR-H1 comprises the amino acid sequence of SEQ ID NO:1, the heavy chain CDR-H2 comprises the amino acid sequence of SEQ ID NO:2, the heavy chain CDR-H3 comprises the amino acid sequence of SEQ ID NO:3, the light chain CDR-L1 comprises the amino acid sequence of SEQ ID NO:4, the light chain CDR-L2 comprises the amino acid sequence of SEQ ID NO:5, and the light chain CDR-L3 comprise the amino acid sequence of SEQ ID NO:6.

9. The antibody or antigen binding fragment thereof of claim 5, wherein the antibody or antibody or antigen binding fragment thereof comprises:

(a) a heavy chain variable region comprising the amino acid sequence of SEQ ID NO:7 and/or a light chain variable region comprising the amino acid sequence of SEQ ID NO:8; or (b) a heavy chain variable region comprising the amino acid sequence of SEQ ID NO:7 and a light chain variable region comprising an amino acid sequence selected from SEQ ID NO:12, 15, 18, 21, 24, 27, or 30.

10. The antibody or antigen binding fragment thereof of claim 5, wherein the antibody or antigen binding fragment thereof comprises:

(a) a heavy chain Fc region comprising an amino acid modification that increases the serum half-life of the antibody or antigen binding fragment thereof;

(b) an IgG1 heavy chain; or (c) an IgG1 heavy chain Fc region comprising the mutations M252Y, S254T, and T256E as numbered according to EU numbering.

11. The antibody or antigen binding fragment thereof of claim 5, wherein the antibody or antigen binding fragment thereof comprises:

(a) a heavy chain comprising the amino acid sequence of SEQ ID NO:9 and a light chain comprising the amino acid sequence of SEQ ID NO:10, 13, 16, 19, 22, 25, 28, or 31;

(b) a heavy chain comprising the amino acid sequence of SEQ ID NO:73 and a light chain comprising the amino acid sequence of SEQ ID NO:13, 16, 19, 22, 25, 28, or 31; or (c) a heavy chain comprising the amino acid sequence of SEQ ID NO:73 and a light chain comprising the amino acid sequence of SEQ ID NO:10.

12. An isolated nucleic acid comprising a nucleotide sequence encoding the heavy chain complementarity determining regions and the light chain complementarity determining regions of the antibody or antigen binding fragment thereof of claim 5.

13. An expression vector comprising the nucleic acid of claim 12.

14. A host cell comprising the expression vector of claim 13.

15. A method of producing an antibody, or antigen binding fragment thereof, that binds to human OX40, the method comprising:

(a) growing the host cell of claim 14 under conditions so that the host cell expresses a polypeptide or polypeptides comprising the heavy chain or heavy chain variable region and a polypeptide or polypeptides comprising the light chain or light chain variable region, thereby producing the antibody or the antigen-binding fragment of the antibody; and (b) purifying the antibody or the antigen-binding fragment of the antibody.

16. A pharmaceutical composition comprising the antibody or antigen binding fragment of claim 5, and a pharmaceutically acceptable carrier.

17. The antibody or antigen binding fragment thereof of claim 5, wherein the antibody or antigen binding fragment thereof comprises a heavy chain variable region comprising the amino acid sequence of SEQ ID NO:7 and a light chain variable region comprising the amino acid sequence of SEQ ID NO:8.

18. The antibody or antigen binding fragment thereof of claim 5, wherein the antibody or antigen binding fragment thereof comprises a heavy chain comprising the amino acid sequence of SEQ ID NO:73 and a light chain comprising the amino acid sequence of SEQ ID NO:10.

* * * * *